(12) United States Patent
Irlapati et al.

(10) Patent No.: US 9,790,231 B2
(45) Date of Patent: Oct. 17, 2017

(54) CHROMANE AND CHROMENE DERIVATIVES AND THEIR USE AS CRAC MODULATORS

(71) Applicant: LUPIN LIMITED, Mumbai, Maharashtra (IN)

(72) Inventors: Nageswara Rao Irlapati, Maharashtra (IN); Kiran Chandrashekhar Kulkarni, Maharashtra (IN); Vijay Pandurang Karche, Maharashtra (IN); Gokul Keruji Deshmukh, Maharashtra (IN); Neelima Sinha, Maharashtra (IN); Venkata P. Palle, Maharashtra (IN); Rajender Kumar Kamboj, Maharashtra (IN)

(73) Assignee: LUPIN LIMITED, Mumbai (IN)

( * ) Notice: Subject to any disclaimer, the term of this patent is extended or adjusted under 35 U.S.C. 154(b) by 0 days.

(21) Appl. No.: 14/900,425

(22) PCT Filed: Jun. 23, 2014

(86) PCT No.: PCT/IB2014/062538
§ 371 (c)(1),
(2) Date: Dec. 21, 2015

(87) PCT Pub. No.: WO2014/207648
PCT Pub. Date: Dec. 31, 2014

(65) Prior Publication Data
US 2016/0137659 A1 May 19, 2016

(30) Foreign Application Priority Data

Jun. 24, 2013 (IN) .......................... 2135/MUM/2013
Dec. 17, 2013 (IN) .......................... 3946/MUM/2013

(51) Int. Cl.
| | | |
|---|---|---|
| *A61K 31/352* | (2006.01) | |
| *C07D 311/04* | (2006.01) | |
| *C07D 311/96* | (2006.01) | |
| *C07D 405/04* | (2006.01) | |
| *C07D 405/12* | (2006.01) | |
| *C07D 491/107* | (2006.01) | |
| *C07D 311/22* | (2006.01) | |
| *C07D 311/58* | (2006.01) | |
| *C07D 491/10* | (2006.01) | |
| *C07D 493/10* | (2006.01) | |

(52) U.S. Cl.
CPC ........ *C07D 491/107* (2013.01); *C07D 311/04* (2013.01); *C07D 311/22* (2013.01); *C07D 311/58* (2013.01); *C07D 311/96* (2013.01); *C07D 405/04* (2013.01); *C07D 405/12* (2013.01); *C07D 491/10* (2013.01); *C07D 493/10* (2013.01)

(58) Field of Classification Search
CPC .. C07D 311/04; C07D 311/96; C07D 405/04; C07D 405/12
See application file for complete search history.

(56) References Cited

U.S. PATENT DOCUMENTS

| 6,919,371 B2 * | 7/2005 | O'Connor ............ C07D 311/58 514/337 |
|---|---|---|
| 2010/0152241 A1 | 6/2010 | Whitten |
| 2011/0082165 A1 | 4/2011 | Ellsworth et al. |
| 2012/0088764 A1 | 4/2012 | Cai et al. |
| 2014/0249306 A1 | 9/2014 | Iwaki et al. |
| 2014/0336376 A1 | 11/2014 | Nakagawa et al. |

FOREIGN PATENT DOCUMENTS

| GB | 2497806 A | 6/2013 |
|---|---|---|
| WO | 2005009539 A2 | 2/2005 |
| WO | 2005009954 A2 | 2/2005 |
| WO | 2006034402 A2 | 3/2006 |
| WO | 2006061379 A1 | 6/2006 |
| WO | 2006081389 A1 | 8/2006 |
| WO | 2006081391 A2 | 8/2006 |
| WO | 2006083477 A2 | 8/2006 |
| WO | 2007/042906 A1 | 4/2007 |
| WO | 2007087429 A2 | 8/2007 |
| WO | 2007087441 A2 | 8/2007 |
| WO | 2007087442 A2 | 8/2007 |
| WO | 2007089904 A2 | 8/2007 |
| WO | 2009017819 A1 | 2/2009 |
| WO | 2009035818 A1 | 3/2009 |
| WO | 2009062285 A1 | 5/2009 |
| WO | 2009076454 A2 | 6/2009 |
| WO | 2010025295 A2 | 3/2010 |
| WO | 2010027875 A2 | 3/2010 |
| WO | 2010039238 A1 | 4/2010 |
| WO | 2010128324 A1 | 11/2010 |
| WO | 2010130794 A1 | 11/2010 |
| WO | 2011034962 A2 | 3/2011 |
| WO | 2011048112 A1 | 4/2011 |
| WO | 2011151434 A1 | 12/2011 |
| WO | 2012/028629 A1 | 3/2012 |
| WO | 2012056478 A1 | 5/2012 |
| WO | 2012151355 A1 | 11/2012 |

(Continued)

OTHER PUBLICATIONS

International Search Report for corresponding International Patent Application No. PCT/162014/062538 (mailed Sep. 10, 2014).

(Continued)

*Primary Examiner* — Brian McDowell

(74) *Attorney, Agent, or Firm* — Merchant & Gould P.C.

(57) ABSTRACT

The invention relates to compounds of Formula (I) and their pharmaceutically acceptable salts, wherein the substituents are as described herein, and their use in medicine for the treatment of diseases, disorders associated with the modulation of calcium release-activated calcium (CRAC) channel. The invention also relates to pharmaceutical compositions containing such compounds in treating diseases disorders associated with calcium release-activated calcium (CRAC) channel modulators.

8 Claims, No Drawings

(56) References Cited

FOREIGN PATENT DOCUMENTS

| WO | 2012/170931 A2 | 12/2012 |
| WO | 2013/059666 A1 | 4/2013 |
| WO | 2013059677 A1 | 4/2013 |
| WO | 2013/062028 A1 | 5/2013 |
| WO | 2013065835 A1 | 5/2013 |
| WO | 2013164769 A1 | 11/2013 |
| WO | 2014059333 A1 | 4/2014 |

OTHER PUBLICATIONS

International Search Report and Written Opinion for International Application No. PCT/IB2014/062482, mailed Sep. 26, 2014.
Fabien Vanden Abeele et al.: "Bcl-2-dependent modulation of Ca2+ homeostasis and store-operated channels in prostate cancer cells", Cancer Cell, vol. 1, Mar. 1, 2002, pp. 169-179.
Attila Braun et al.: "Orai1 (CRACM1) is the platelet SOC channel and essential for pathological thrombus formation", Blood, vol. 113, No. 9, Feb. 26, 2009, pp. 2056-2063.
Antonio Di Sabatino et al.: "Targeting Gut T Cell Ca2+ Release-Activated Ca2+ Channels Inhibits T Cell Cytokine Production and T-Box Transcription Factor T-Bet in Inflammatory Bowel Disease", The Journal of Immunology, vol. 183, Jul. 31, 2009, pp. 3454-3462.
Marc Fahrner et al.: "Mechanistic View on Domains Mediating STIM1-Orai Coupling", Immunological Reviews, vol. 231, Issue 1, Sep. 10, 2009, pp. 99-112.
Karen Gilio et al.: "Roles of Platelet STIM1 and Orai1 in Glycoprotein VI- and Thrombin-dependent Procoagulant Activity and Thrombus Formation", Journal of Biological Chemistry, vol. 285, No. 31, Jul. 30, 2010, pp. 23629-23638.
Rajender K. Motiani et al.: "A Novel Native Store-operated Calcium Channel Encoded by Orai3", The Journal of Biological Chemistry, vol. 285, No. 25, Jun. 18, 2010, pp. 19173-19183.
Anant B. Parekh: "Store-operated CRAC channels: function in health and disease", Nature Reviews, Drug Discovery, vol. 9, May 1, 2010, 399-410 pages.
Anant B. Parekh et al.: "Store-Operated Calcium Channels", Physiological Reviews, vol. 85, Issue 2, Apr. 1, 2005, pp. 757-810.
David Varga-Szabo et al.: "The calcium sensor STIM1 is an essential mediator of arterial thrombosis and ischemic brain infarction", The Journal of Experimental Medicine, vol. 205, No. 7, Jun. 16, 2008, pp. 1583-1591.
Peter G. M. Wuts et al.: "Greene's Protective Group in Organic Synthesis", Fourth Edition, John Wiley & Sons, Inc., 2007, 1112 pages.
Shengyu Yang et al.: "Orai1 and STIM1 are Critical for Breast Tumor Cell Migration and Metastasis", Cancer Cell, vol. 15, Feb. 3, 2009, pp. 124-134.
Brynmor Jones et al.: "The Halogenation of Phenolic Ethers and Anilides. Part XVII. An Investigation Into the Additive Effects of Substituents in Benzyl Phenyl Ethers", 1955, pp. 2772-2775.
Yoshikazu Uto et al.: "Synthesis and Evaluation of Novel Stearoyl-CoA Desaturase 1 Inhibitors: 1'-{6-[5-(pyridin-3-ylmethyl)-1,3,4-oxadiazol-2-yl]pyridazin-3-yl}-3, 4-dihydrospiro[chromene-2,4'-piperidine] Analogs", European Journal of Medicinal Chemistry, vol. 45, Issue 11, Nov. 2010, pp. 4788-4796.

* cited by examiner

CHROMANE AND CHROMENE DERIVATIVES AND THEIR USE AS CRAC MODULATORS

RELATED APPLICATIONS

The present application is a National Stage Application of International Patent Application No. PCT/IB2014/062538, filed Jun. 23, 2014, which claims benefit of Indian Provisional Patent Application No. 2135/MUM/2013 filed on Jun. 24, 2013 and 3946/MUM/2013 filed on Dec. 17, 2013 and which applications are incorporated herein by reference. To the extent appropriate, a claim of priority is made to each of the above disclosed applications.

TECHNICAL FIELD OF THE INVENTION

The invention relates to substituted heterocyclic compounds, pharmaceutically acceptable salts thereof and pharmaceutical compositions for the treatment, management, and/or lessening of severity of diseases, disorders, syndromes or conditions associated with the modulation of calcium release-activated calcium (CRAC) channel. The invention also relates to methods of treating, managing and/or lessening the severity of the diseases disorders, syndromes or conditions associated with the modulation of CRAC. The invention also relates to processes for the preparation of the compounds of the invention.

BACKGROUND OF THE INVENTION

Inflammation is the response by the body to infection, irritation or injury; wherein the immune cells of the body are activated in response to any of these stimuli. Inflammation plays a key role in many diseases not only of the immune cells such as allergy, asthma, arthritis, dermatitis, multiple sclerosis, systemic lupus but also organ transplant, diabetes, cardiovascular disease, Alzheimer's disease, Parkinson's disease, inflammatory and/or irritable bowel syndrome (Di Sabatino et. al., J. Immunol., 183, 3454-3462, 2009), psoriasis, and cancer. An initial inflammatory response to pathogens or injury is necessary and required to fight infection or heal the wound, but sustained or persistent inflammation can lead to any of the chronic disorders; characterized by the production of inflammatory cytokines as, specified above.

Inflammation is characterized by the production of different cytokines such as IL-2, IL-4, IL-10, IL-13, IL-17, IL-21, IL-23, IL-28, IFN-γ, TNF-α, etc., that have been implicated in playing a role in different diseases. Any drug which can modulate the production of these cytokines would help to alleviate the disease symptoms and may also cure it.

$Ca^{+2}$ signals have been shown to be essential for diverse cellular functions in different cell types including differentiation, effector functions, and gene transcription in cells of the immune system as well as regulating the cytokine signaling pathway through calcineurin and nuclear factor of activated T cells (NFAT).

In immune cells, sustained $Ca^{+2}$ influx has been shown to be necessary for complete and long-lasting activation of calcineurin-NFAT pathways, essential for cytokine production. Engagement of receptors such as T-cell antigen receptor (TCR), the B-cell antigen receptor (BCR), and the Fc receptors (FcR) on mast cells, macrophages, and NK cells, leads to the tyrosine phosphorylation and activation of phospholipase C-γ (PLC-γ). PLC-γ hydrolyzes phosphatidylinositol-3,4-biphosphate ($PIP_2$) to the second messengers, inositol-1,4,5-triphosphate ($IP_3$) and diacylglycerol (DAG). $IP_3$ binds to $IP_3$ receptors ($IP_3R$) in the membrane of the endoplasmic reticulum (ER) and induces the release of ER $Ca^{+2}$ stores into the cytoplasma. The decrease in the $Ca^{+2}$ concentration in the ER induces store-operated $Ca^{+2}$ entry (SOCE) through plasma membrane $Ca^{+2}$ channels. SOCE through highly $Ca^{+2}$-selective $Ca^{+2}$ release-activated $Ca^{+2}$ (hereinafter, CRAC) channels constitutes the major pathway of intracellular $Ca^{+2}$ entry in T cells, B cells, macrophages, mast cells, and other cell types (Parekh and Putney, Physiol. Rev., 85, 757-810, 2005).

The CRAC channel is comprised of two family proteins, one which functions in sensing $Ca^{+2}$ levels in the ER—the stromal interacting molecules (STIM)-1 and -2 and the other which is a pore-forming protein—Orai1, 2 and 3. The STIM proteins are single transmembrane proteins localized on the ER membrane with their N-termini oriented toward the lumen and containing an EF-hand $Ca^{+2}$ binding motif. Depletion of $Ca^{+2}$ from the ER causes $Ca^{+2}$ to dissociate from STIM, which causes a conformational change that promotes oligomerization and migration of STIM molecules to closely apposed ER-plasma membrane junctions. At the junctions, the STIM oligomers interact with the Orai proteins. In resting cells, Orai channels are dispersed across the plasma membrane and on depletion of $Ca^{+2}$ from the stores, they aggregate in the vicinity of the STIM punctae. The eventual increase in intracellular $Ca^{+2}$ concentration activates the calcineurin-NFAT pathway. NFAT activates transcription of several genes including cytokine genes such as IL-2, etc along with other transcription factors such as AP-1, NFκB and Foxp3 (Fahmer et. al., Immuno. Rev., 231, 99-112, 2009).

The role of CRAC channel in different diseases such as allergy, inflammatory bowel disease, thrombosis and breast cancer has been reported in literature (Parekh, Nat. Rev., 9, 399-410, 2010). It has been reported in the art that STIM1 and Orai1 are essential in in vitro tumor cell migration and in vivo tumor metastasis. Thus the involvement of store operated $Ca^{2+}$ entry in tumor metastasis renders STIM1 and Orai1 proteins potential targets for cancer therapy (Yang et. al., Cancer Cell, 15, 124-134, 2009). Additional literature available on the involvement of CRAC channel in cancer are Abeele et. al., Cancer Cell, 1, 169-179, 2002, Motiani et al., J. Biol. Chem., 285; 25, 19173-19183, 2010.

Recent literature reports the role of STIM1 and Orai1 in collagen dependent arterial thrombosis in mice in vivo and that deficiency in either protects against collagen dependent arterial thrombus formation as well as brain infarction (Varga-Szabo et. al., J. Exp. Med., 205, 1583-1591, 2008; Braun et. al., Blood, 113, 2056-2063, 2009). The role of STIM1-Orai1 mediated SOCE in thrombus formation makes Orai1 a potential target for treatment of thrombosis and related conditions (Gillo et. al., JBC, 285; 31, 23629-23638, 2010).

As the Orai pore channel proteins have been shown to be essential for transmitting the signal induced by the binding of antigens to the cellular receptors on the immune cells, a potential Orai channel interacting drug would be able to modulate the signaling thereby impacting the secretion of the cytokines involved in, as mentioned herein before, inflammatory conditions, cancer, allergic disorders, immune disorders, rheumatoid arthritis, cardiovascular diseases, thrombocytopathies, arterial and/or venous thrombosis and associated or related conditions which can be benefitted by the CRAC channel modulatory properties of the compounds described herein.

Several compounds have been reported in the art as CRAC channel modulators. For Example, patent application publications WO2005009539, WO2005009954, WO2006081391, WO2006081389, WO2006034402, WO2006083477, WO2007087441, WO2007087442, WO2007087429, WO2007089904, WO2009017819, WO2009076454, WO2009035818, US20100152241, WO2010039238, WO2010025295, WO2010027875, WO2011034962, WO2012151355, WO2013059666, WO2013059677, WO2013164769, WO2014059333 disclose the compounds for modulating CRAC channels.

SUMMARY OF THE INVENTION

In accordance with one aspect, the invention provides the compounds having the structure of Formula (I):

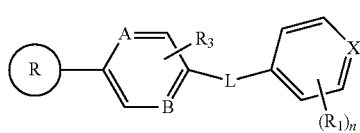

(I)

A and B are independently $CR_3$ or N;
ring R is selected from Formula (i) to (iii):

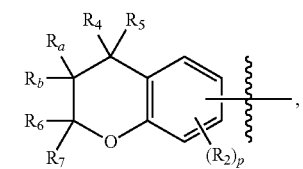

(i)

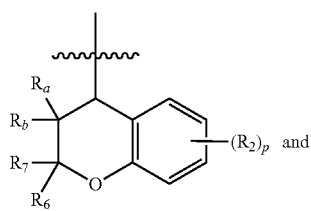

(ii)

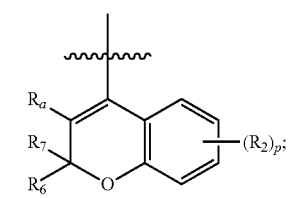

(iii)

L is selected from —$NR_8C(O)$—, —$C(O)NR_8$— and —$NR_8CH_2$—;

X is CR or N where R is selected from hydrogen, halogen or substituted or unsubstituted alkyl;

$R_1$, which may be same or different at each occurrence, is independently selected from halogen, cyano, hydroxyl, substituted or unsubstituted alkyl, substituted or unsubstituted cycloalkyl, substituted or unsubstituted haloalkyl, substituted or unsubstituted alkoxy and substituted or unsubstituted haloalkoxy;

$R_2$, which may be same or different at each occurrence, is independently selected from halogen, cyano, nitro, hydroxyl, substituted or unsubstituted alkyl, substituted or unsubstituted haloalkyl, substituted or unsubstituted alkoxy, substituted or unsubstituted haloalkoxy, —$NR_9R_{10}$ and substituted or unsubstituted cycloalkyl, —$COOR_8$ and $CONR_9R_{10}$;

each of $R_3$ is independently selected from hydrogen, halogen and substituted or unsubstituted alkyl;

$R_4$ and $R_5$, which may be same or different and are independently selected from hydrogen, hydroxyl, substituted or unsubstituted alkyl, substituted or unsubstituted haloalkyl, substituted or unsubstituted alkoxy, substituted or unsubstituted cycloalkyl and —$NR_9R_{10}$; or $R_4$ and $R_5$ together with the carbon atom to which they are attached form oxo (C=O);

one of $R_6$ and $R_7$ is substituted or unsubstituted alkyl, substituted or unsubstituted haloalkyl, substituted or unsubstituted hydroxyalkyl, substituted or unsubstituted cycloalkyl, substituted or unsubstituted alkoxy, substituted or unsubstituted alkoxyalkyl and the other is selected from hydrogen, hydroxyl, substituted or unsubstituted alkyl, substituted or unsubstituted haloalkyl, substituted or unsubstituted hydroxyalkyl, substituted or unsubstituted alkoxy, substituted or unsubstituted alkoxyalkyl, —$NR_9R_{10}$, substituted or unsubstituted cycloalkyl, —$COOR_8$ and —$COR_9R_{10}$; or $R_6$ and $R_7$ together with the carbon atom to which they are attached may form substituted or unsubstituted 3 to 7 membered carbocyclic ring or 4 to 7 membered heterocyclic ring;

$R_8$ is hydrogen or substituted or unsubstituted alkyl;

$R_9$ and $R_{10}$, which may be same or different, are independently selected from hydrogen, substituted or unsubstituted alkyl, substituted or unsubstituted haloalkyl, and substituted or unsubstituted cycloalkyl; or $R_9$ and $R_{10}$, together with the nitrogen atom to which they are attached, may form a substituted or unsubstituted, saturated or unsaturated 5 to 7 membered cyclic ring, wherein the unsaturated cyclic ring may have one or two double bonds;

$R_a$ and $R_b$, which may be same or different and are independently selected from hydrogen, cyano, substituted or unsubstituted hydroxyalkyl, substituted or unsubstituted alkyl, substituted or unsubstituted haloalkyl, substituted or unsubstituted alkoxy, substituted or unsubstituted haloalkoxy, substituted or unsubstituted cycloalkyl, —$NR_9R_{10}$, —$COOR_8$ and —$CONH_2$;

'n' is an integer ranging from 1 to 3, both inclusive; and
'p' is an integer ranging from 0 to 2, both inclusive;
or a pharmaceutically acceptable salt thereof.

According to one embodiment, there are provided compounds having the structure of Formula (II):

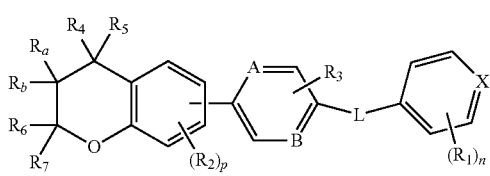

(II)

wherein,
A and B are independently $CR_3$ or N;
L is selected from —NHC(O)—, —C(O)NH— and —$NHCH_2$—;
X is CH or N;
$R_1$, which may be same or different at each occurrence, is independently selected from halogen, substituted or unsubstituted alkyl, substituted or unsubstituted cycloalkyl, substituted or unsubstituted haloalkyl, substituted or unsubstituted alkoxy and substituted or unsubstituted haloalkoxy;

$R_2$ is selected from halogen, substituted or unsubstituted alkyl, substituted or unsubstituted cycloalkyl, substituted or unsubstituted haloalkyl and substituted or unsubstituted alkoxy;

$R_3$ is selected from hydrogen, halogen and substituted or unsubstituted alkyl;

$R_4$ and $R_5$, which may be same or different and are independently selected from hydrogen, hydroxyl, substituted or unsubstituted alkyl, substituted or unsubstituted alkoxy and —$NR_9R_{10}$; or $R_4$ and $R_5$ together with the carbon atom to which they are attached form oxo (C=O);

one of $R_6$ and $R_7$ is substituted or unsubstituted alkyl, substituted or unsubstituted haloalkyl, substituted or unsubstituted hydroxyalkyl and the other is selected from hydrogen, hydroxyl, substituted or unsubstituted alkyl, substituted or unsubstituted haloalkyl, substituted or unsubstituted hydroxyalkyl, substituted or unsubstituted alkoxy, substituted or unsubstituted alkoxyalkyl, —$NR_9R_{10}$, substituted or unsubstituted cycloalkyl, —$COOR_8$, and $CONH_2$; or $R_6$ and $R_7$ together with the carbon atom to which they are attached may form substituted or unsubstituted 3 to 6 membered carbocyclic ring or 4 to 7 membered heterocyclic ring;

$R_8$ is hydrogen or substituted or unsubstituted alkyl;

$R_9$ and $R_{10}$ are independently hydrogen or substituted or unsubstituted alkyl;

$R_a$ and $R_b$ are independently hydrogen or substituted or unsubstituted alkyl;

'n' is an integer ranging from 1 to 2, both inclusive; and

'p' is an integer ranging from 0 to 1, both inclusive;

or a pharmaceutically acceptable salt thereof.

According to another embodiment, there are provided compounds having the structure of Formula (III):

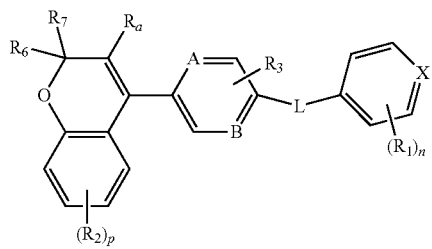

(III)

wherein,

A and B are independently $CR_3$ or N;

L is —NHC(O)— or —C(O)NH—;

X is CH or N;

$R_1$, which may be same or different at each occurrence, is independently selected from halogen, substituted or unsubstituted alkyl, substituted or unsubstituted cycloalkyl, substituted or unsubstituted haloalkyl, substituted or unsubstituted alkoxy and substituted or unsubstituted haloalkoxy;

$R_2$ is selected from halogen, substituted or unsubstituted alkyl, substituted or unsubstituted cycloalkyl, substituted or unsubstituted haloalkyl and substituted or unsubstituted alkoxy;

$R_3$ is selected from hydrogen, halogen and substituted or unsubstituted alkyl;

one of $R_6$ and $R_7$ is substituted or unsubstituted alkyl, substituted or unsubstituted haloalkyl, substituted or unsubstituted hydroxyalkyl and the other is selected from hydrogen, hydroxyl, substituted or unsubstituted alkyl, substituted or unsubstituted haloalkyl, substituted or unsubstituted hydroxyalkyl, substituted or unsubstituted alkoxy, substituted or unsubstituted alkoxyalkyl, —$NR_9R_{10}$, substituted or unsubstituted cycloalkyl, —$COOR_8$, and —$CONH_2$; or $R_6$ and $R_7$ together with the carbon atom to which they are attached may form substituted or unsubstituted 3 to 6 membered carbocyclic ring;

$R_8$ is hydrogen or substituted or unsubstituted alkyl;

$R_9$ and $R_{10}$ are independently hydrogen or substituted or unsubstituted alkyl;

$R_a$ is hydrogen or substituted or unsubstituted alkyl;

'n' is an integer ranging from 1 to 2, both inclusive; and

'p' is an integer ranging from 0 to 1, both inclusive;

or a pharmaceutically acceptable salt thereof.

According to another embodiment, there are provided compounds having the structure of Formula (IV):

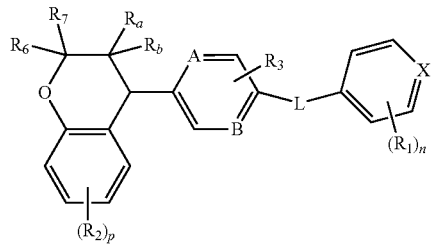

(IV)

wherein,

A and B are independently $CR_3$ or N;

L is —NHC(O)— or —C(O)NH—;

X is CH or N;

$R_1$, which may be same or different at each occurrence, is independently selected from halogen, substituted or unsubstituted alkyl, substituted or unsubstituted cycloalkyl, substituted or unsubstituted haloalkyl, substituted or unsubstituted alkoxy and substituted or unsubstituted haloalkoxy;

$R_2$ is selected from halogen, substituted or unsubstituted alkyl, substituted or unsubstituted cycloalkyl, substituted or unsubstituted haloalkyl and substituted or unsubstituted alkoxy;

$R_3$ is selected from hydrogen, halogen and substituted or unsubstituted alkyl;

one of $R_6$ and $R_7$ is substituted or unsubstituted alkyl, substituted or unsubstituted haloalkyl, substituted or unsubstituted hydroxyalkyl and the other is selected from hydrogen, hydroxyl, substituted or unsubstituted alkyl, substituted or unsubstituted haloalkyl, substituted or unsubstituted hydroxyalkyl, substituted or unsubstituted alkoxy, substituted or unsubstituted alkoxyalkyl, —$NR_9R_{10}$, substituted or unsubstituted cycloalkyl, —$COOR_8$, and —$CONH_2$; or $R_6$ and $R_7$ together with the carbon atom to which they are attached may form substituted or unsubstituted 3 to 6 membered carbocyclic ring;

$R_8$ is hydrogen or substituted or unsubstituted alkyl;

$R_9$ and $R_{10}$ are independently hydrogen or substituted or unsubstituted alkyl;

$R_a$ and $R_b$ are independently hydrogen or substituted or unsubstituted alkyl;

'n' is an integer ranging from 1 to 2, both inclusive; and

'p' is an integer ranging from 0 to 1, both inclusive;

or a pharmaceutically acceptable salt thereof.

It should be understood that the Formula (I), Formula (II), Formula (III) and/or Formula (IV), structurally encompasses all tautomers, stereoisomers, enantiomers and diastereomers, including isotopes wherever applicable and pharmaceutically acceptable salts that may be contemplated from the chemical structure of the genera described herein.

The details of one or more embodiments of the invention set forth in the below are illustrative in nature only and not intended to limit to the scope of the invention. Other features, objects and advantages of the inventions will be apparent from the description and claims.

According to another embodiment there are provided compounds of Formula (I) wherein
L is selected from —NHC(O)—, —C(O)NH— and —NHCH$_2$—.

According to another embodiment there are provided compounds of Formula (I) wherein
X is N or CH.

According to another embodiment there are provided compounds of Formula (I) wherein A and B may be same or different and are independently CR$_3$ or N wherein R$_3$ is hydrogen, halogen or substituted or unsubstituted alkyl.

According to another embodiment there are provided compounds of Formula (I) wherein each of R$_1$ may be same or different and are independently selected from hydrogen, halogen, and substituted or unsubstituted alkyl; and 'n' is 1 or 2.

According to another embodiment there are provided compounds of Formula (I) wherein ring R is Formula (i)

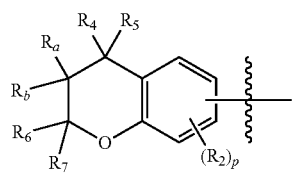

(i)

wherein R$_2$ is halogen or substituted or unsubstituted alkyl; 'p' is 0 to 1; R$_4$ and R$_5$ may be same or different and are independently selected from hydrogen, hydroxyl, substituted or unsubstituted alkyl and —NR$_9$R$_{10}$ or R$_4$ and R$_5$ together with the carbon atom to which they are attached form oxo (C=O); one of R$_6$ and R$_7$ is substituted or unsubstituted alkyl, substituted or unsubstituted hydroxyalkyl and the other is selected from hydrogen, hydroxyl, substituted or unsubstituted alkyl, substituted or unsubstituted hydroxyalkyl, substituted or unsubstituted alkoxyalkyl, substituted or unsubstituted cycloalkyl, —NR$_9$R$_{10}$, —COOH, —COO— alkyl, and CONH$_2$; or R$_6$ and R$_7$ together form substituted or unsubstituted 3 to 6 membered carbocyclic ring or 4 to 7 membered heterocyclic ring; R$_9$ and R$_{10}$ are selected from hydrogen or substituted or unsubstituted alkyl; and R$_a$ and R$_b$ are hydrogen.

According to another embodiment there are provided compounds of Formula (I) wherein ring R is Formula (ii) or Formula (iii)

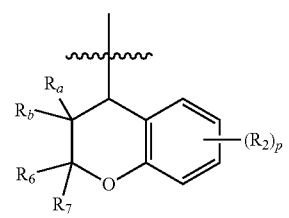

(ii)

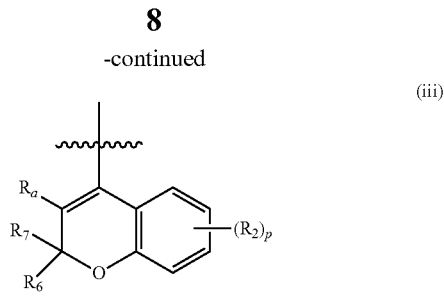

(iii)

wherein R$_2$ is halogen or substituted or unsubstituted alkyl; 'p' is 0 to 1; one of R$_6$ and R$_7$ is substituted or unsubstituted alkyl, substituted or unsubstituted hydroxyalkyl and the other is selected from hydrogen, hydroxyl, substituted or unsubstituted alkyl, substituted or unsubstituted hydroxyalkyl, substituted or unsubstituted alkoxyalkyl, substituted or unsubstituted cycloalkyl, —NR$_9$R$_{10}$, —COOH, —COO-alkyl, and CONH$_2$; or R$_6$ and R$_7$ together form substituted or unsubstituted 3 to 6 membered carbocyclic ring; R$_9$ and R$_{10}$ are hydrogen or substituted or unsubstituted alkyl; and R$_a$ and R$_b$ are hydrogen.

According to another embodiment there are provided compounds of Formula (I) wherein R$_6$ and R$_7$ together with carbon atom to which they are attached to form a ring is selected from

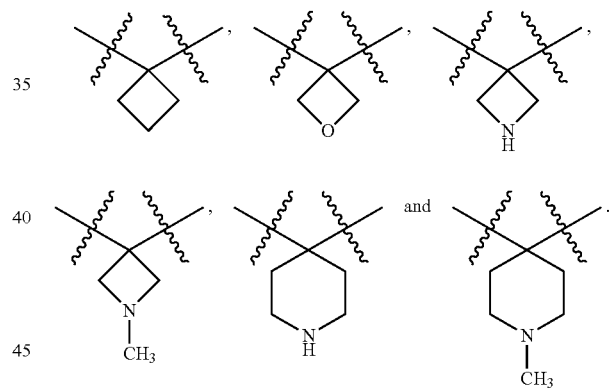

According to another embodiment there are provided compounds of Formula (I)

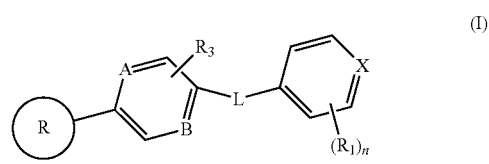

(I)

wherein L is selected from —NHC(O)—, —C(O)NH— and —NHCH$_2$—; X is CH or N; A and B are independently CR$_3$ or N; R$_1$ is halogen, substituted or unsubstituted alkyl or substituted or unsubstituted haloalkyl; 'n' is 1 or 2; R$_3$ is hydrogen or substituted or unsubstituted alkyl; and ring R is Formula (i)

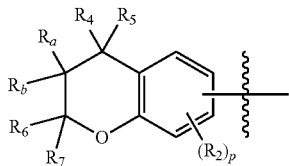

wherein $R_2$ is halogen or substituted or unsubstituted alkyl; 'p' is 0 or 1; $R_4$ and $R_5$, which may be same or different and are independently selected from hydrogen, hydroxyl, —$NR_9R_{10}$ where $R_9$ and $R_{10}$ are hydrogen or substituted or unsubstituted alkyl, or $R_4$ and $R_5$ together form oxo (C=O); one of $R_6$ and $R_7$ is substituted or unsubstituted alkyl or substituted or unsubstituted hydroxyalkyl and the other is selected from hydrogen, hydroxyl, substituted or unsubstituted alkyl, substituted or unsubstituted hydroxyalkyl, substituted or unsubstituted alkoxyalkyl, —C(O)OH, —C(O)Oalkyl, and —CONH$_2$, or $R_6$ and $R_7$ together with the carbon atom to which they are attached may form substituted or unsubstituted 3 to 4 membered carbocyclic ring or 4 to 7 membered heterocyclic ring; and $R_a$ and $R_b$ are hydrogen.

According to another embodiment there are provided compounds of Formula (I)

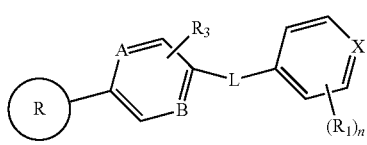

wherein L is —NHC(O)—, —C(O)NH—; X is CH or N; A and B are independently $CR_3$ or N; $R_1$ is halogen, substituted or unsubstituted alkyl or substituted or unsubstituted haloalkyl; 'n' is 1 or 2; $R_3$ is hydrogen or substituted or unsubstituted alkyl; and ring R is Formula (ii) or Formula (iii)

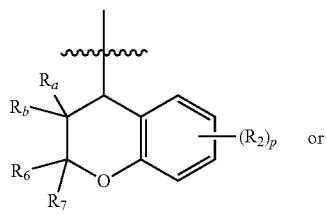

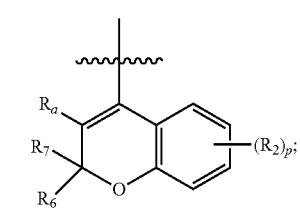

$R_2$ is halogen or substituted or unsubstituted alkyl; 'p' is 0 or 1; one of $R_6$ and $R_7$ is substituted or unsubstituted alkyl or substituted or unsubstituted hydroxyalkyl and the other is selected from hydrogen, hydroxyl, substituted or unsubstituted alkyl, substituted or unsubstituted hydroxyalkyl, substituted or unsubstituted alkoxyalkyl, —C(O)OH, —C(O)Oalkyl, —CONH$_2$, or $R_6$ and $R_7$ together with the carbon atom to which they are attached may form substituted or unsubstituted 3 to 4 membered carbocyclic ring; and $R_a$ and $R_b$, are hydrogen.

In another aspect, the invention provides a pharmaceutical composition comprising at least one compound of Formula (I) and at least one pharmaceutically acceptable excipient.

In another aspect of the invention, there is provided a compound of Formula (I) useful in treating, managing and/or lessening the severity of the diseases, disorders, syndromes or conditions associated with the modulation of CRAC channel.

In another aspect, the invention provides a pharmaceutical composition of a compound of Formula (I) useful in treating, managing and/or lessening the severity of the diseases disorders, syndromes or conditions associated with the modulation of CRAC channel in a subject in need thereof by administering to the subject, one or more compounds described herein in therapeutic effective amount.

In another aspect, the invention provides a method of modulating ion channel activity, for Example, CRAC channel, by administering effective amount of a compound of Formula (I) and/or pharmaceutically acceptable salts.

In another aspect, the invention provides a method of modulating the secretion of cytokines, for Example IL-2, IL-4, IL-10, IL-13, IL-17, IL-21, IL-23, IL-28, IFN-γ and TNF-α and the like, by regulating the cytokine signaling pathway through calcineurin and NFAT cells.

In another aspect, there are provided processes for the preparation of compounds of Formula (II):

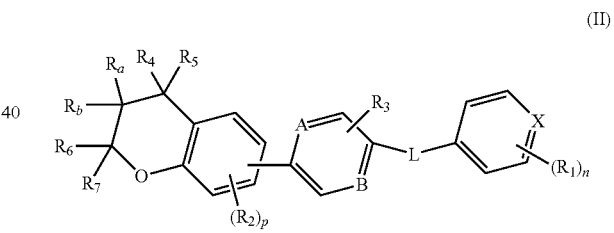

where A, B, L, X, $R_1$, $R_2$, $R_3$, $R_4$, $R_5$, $R_6$, $R_7$, $R_a$, $R_b$ 'n' and 'p' are as described herein above; the process comprising any of the process (A) to (C):

process (A):

reacting compound of Formula (1) where X' is halogen, with compound of Formula (2) where P is pinacolatoboronate to give compound of Formula (II) by using suitable reagents Pd(PPh$_3$)$_2$O$_2$, Pd$_2$dba$_3$, Pd(PPh$_3$)$_4$, or Pd(OAc)$_2$ and a suitable ligand 2,2'-bis(diphenylphosphino)-1,1'-binaphthyl (BINAP), xanthophos, or triphenylphosphine

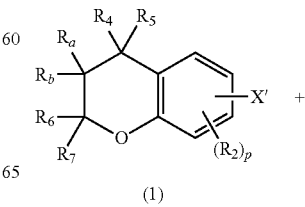

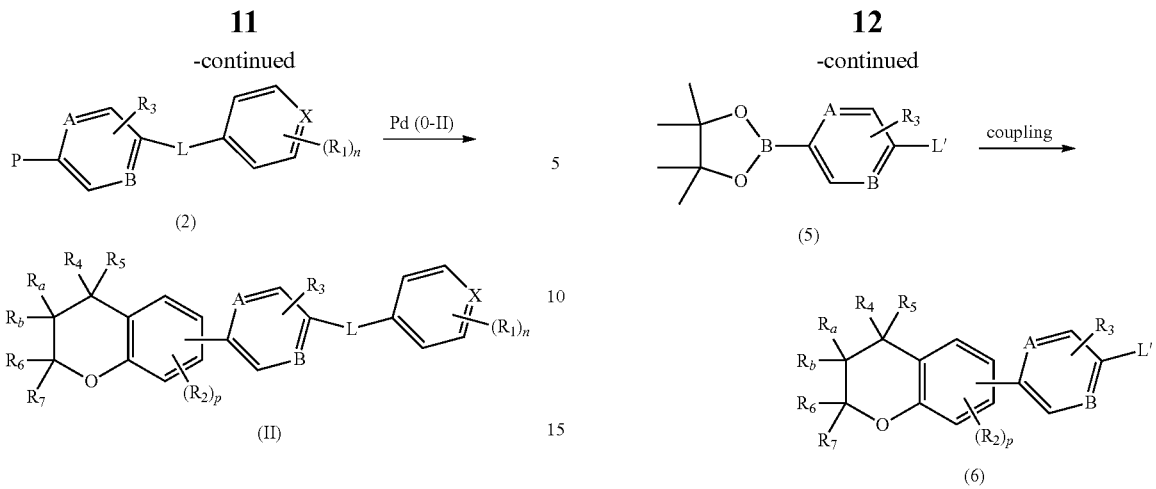

process(B)

reacting a compound of Formula (3) where P is pinacolatoboronate, with compound of Formula (4) where X' is halogen, to give compound of Formula (II) by using suitable reagents Pd(PPh$_3$)$_2$Cl$_2$, Pd$_2$dba$_3$, Pd(PPh$_3$)$_4$, or Pd(OAc)$_2$ and a suitable ligand 2,2'-bis(diphenylphosphino)-1,1'-binaphthyl (BINAP), xanthophos, or triphenylphosphine, b) coupling of compound of Formula (6) with Formula (7) where L" is COOH, COOalkyl, COCl; or NHR$_8$ to give compound of Formula (II) using suitable coupling agent.

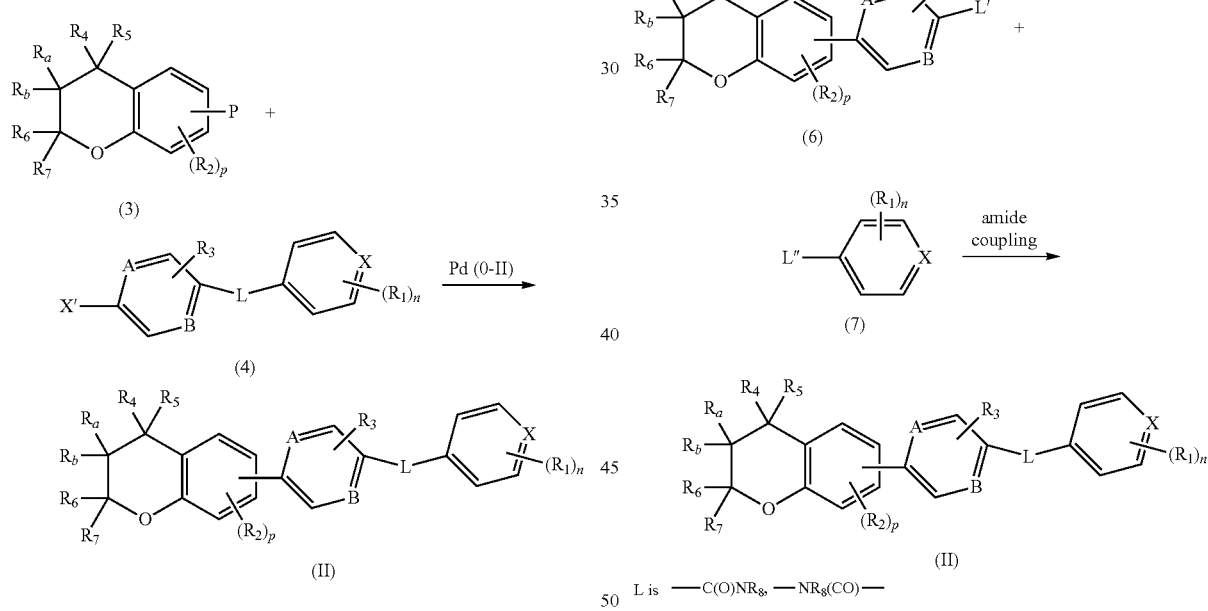

L is —C(O)NR$_8$, —NR$_8$(CO)— process (C), which comprising the step-a and step-b:

a) reacting halo compound of the Formula (1) where X' is halogen with borate compound of the Formula (5) where L' is NHR$_8$; or COOH, COO-alkyl or COCl to give compound of Formula (6)

In another aspect, there are provided processes for the preparation compounds of Formula (III) and (IV);

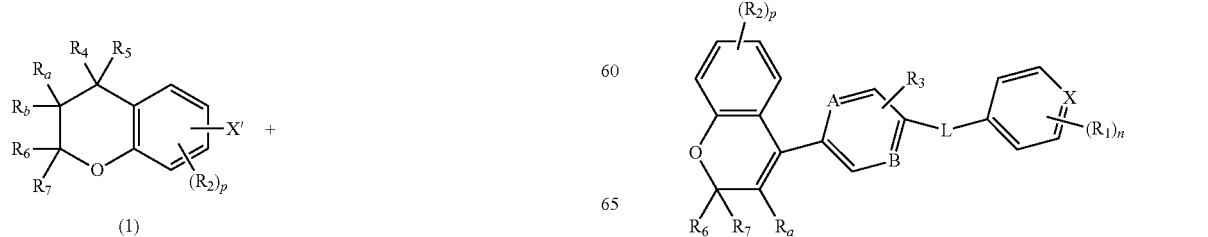

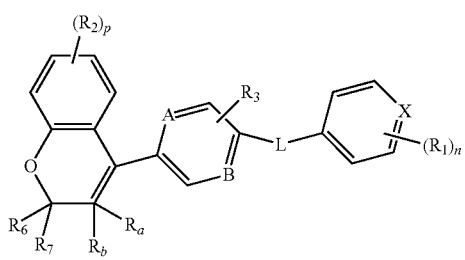

(IV)

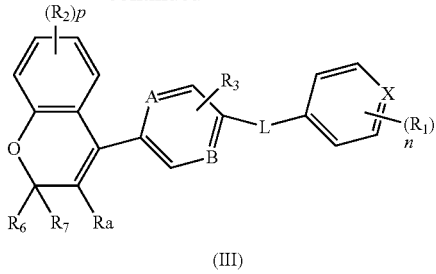

(III)

A, B, L, X, R₁, R₂, R₃, R₄, R₅, R₆, R₇, Rₐ, R_b 'n' and 'p' are as described herein above; the process comprising the steps:

a) reacting of compound of Formula (8) with compound of Formula (2) where P is pinacolatoboronate to give compound of Formula (III) by using suitable reagents

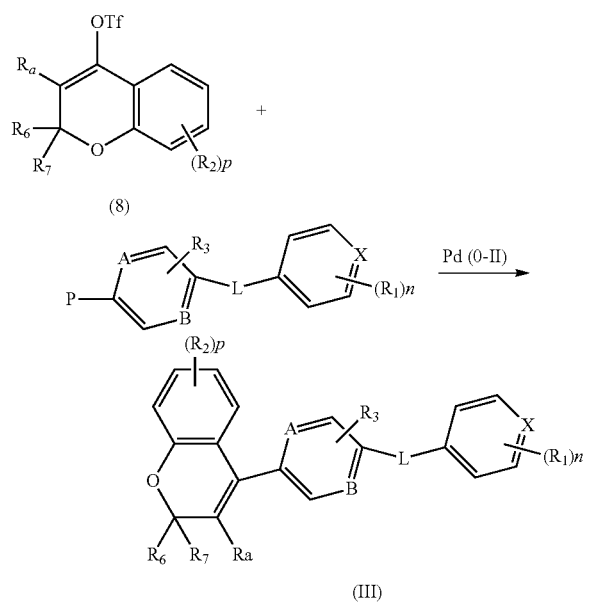

or reacting compound of Formula (9) where P is pinacolatoboronate with compound of Formula (4) where X' is halogen to give compound of Formula (III) by using suitable reagents

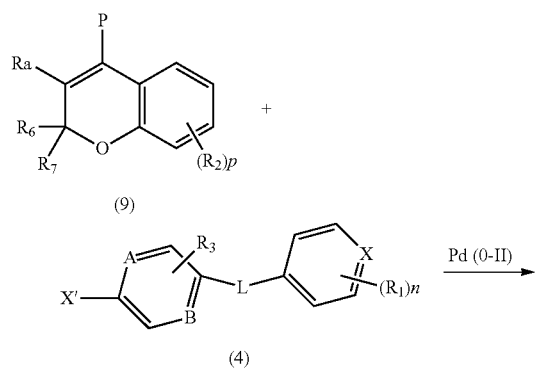

b) reducing a compound of Formula (III) to compound of Formula (IV) using catalyst such as Pd—C, Ra—Ni, Pt—C.

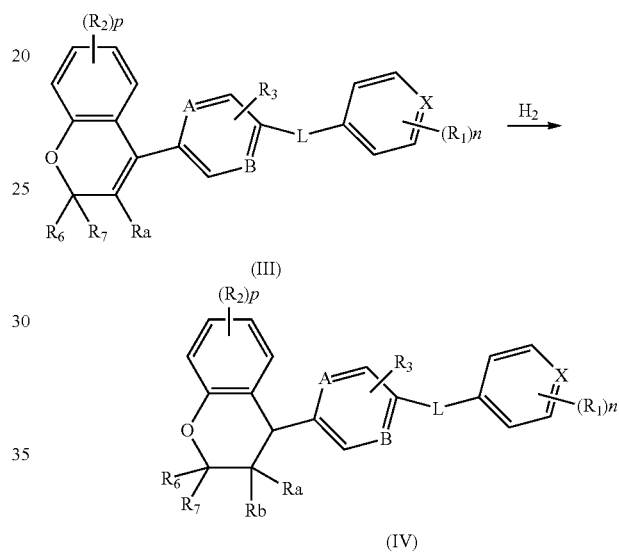

DETAILED DESCRIPTION OF THE INVENTION

Definitions and Abbreviations:

Unless otherwise stated, the following terms used in the specification and claims have the meanings given below.

For purposes of interpreting the specification, the following definitions will apply and whenever appropriate, terms used in the singular will also include the plural and vice versa.

The terms "halogen" or "halo" means fluorine, chlorine, bromine, or iodine.

Unless otherwise stated, in the present application "oxo" means C(=O) group. Such an oxo group may be a part of either a cycle or a chain in the compounds of the invention.

The term "alkyl" refers to an alkane derived hydrocarbon radical that includes solely carbon and hydrogen atoms in the backbone, contains no unsaturation, has from one to six carbon atoms, and is attached to the remainder of the molecule by a single bond, e.g., methyl, ethyl, n-propyl, 1-methylethyl (isopropyl), n-butyl, n-pentyl, 1,1-dimethylethyl (t-butyl) and the like. Unless set forth or recited to the contrary, all alkyl groups described or claimed herein may be straight chain or branched, substituted or unsubstituted.

The term "alkenyl" refers to a hydrocarbon radical containing from 2 to 10 carbon atoms and including at least one carbon-carbon double bond. Non-limiting Examples of alkenyl groups include ethenyl, 1-propenyl, 2-propenyl (allyl), iso-propenyl, 2-methyl-1-propenyl, 1-butenyl, 2-butenyl and the like. Unless set forth or recited to the contrary, all alkenyl groups described or claimed herein may be straight chain or branched, substituted or unsubstituted.

The term "alkynyl" refers to a hydrocarbon radical containing 2 to 10 carbon atoms and including at least one carbon-carbon triple bond. Non-limiting Examples of alkynyl groups include ethynyl, propynyl, butynyl and the like. Unless set forth or recited to the contrary, all alkynyl groups described or claimed herein may be straight chain or branched, substituted or unsubstituted.

The term "alkoxy" refers to an alkyl group attached via an oxygen linkage. Non-limiting Examples of such groups are methoxy, ethoxy and propoxy and the like. Unless set forth or recited to the contrary, all alkoxy groups described or claimed herein may be straight chain or branched, substituted or unsubstituted.

The term "alkoxyalkyl" refers to an alkoxy group as defined above directly bonded to an alkyl group as defined above, e.g., —CH$_2$—O—CH$_3$, —CH$_2$—O—CH$_2$CH$_3$, —CH$_2$CH$_2$—O—CH$_3$ and the like. Unless set forth or recited to the contrary, all alkoxyalkyl groups described or claimed herein may be substituted or unsubstituted.

The term "cycloalkyl" refers to a non-aromatic mono or multicyclic ring system having 3 to 12 carbon atoms, such as cyclopropyl, cyclobutyl, cyclopentyl, cyclohexyl and the like. Examples of multicyclic cycloalkyl groups include, but are not limited to, perhydronapththyl, adamantyl and norbornyl groups, bridged cyclic groups or spirobicyclic groups, e.g., spiro(4,4)non-2-yl and the like. Unless set forth or recited to the contrary, all cycloalkyl groups described or claimed herein may be substituted or unsubstituted.

The term "cycloalkenyl" refers to a non-aromatic mono or multicyclic ring system having 3 to 12 carbon atoms and including at least one carbon-carbon double bond, such as cyclopentenyl, cyclohexenyl, cycloheptenyl and the like. Unless set forth or recited to the contrary, all cycloalkenyl groups described or claimed herein may be substituted or unsubstituted.

The term "cycloalkylalkyl" refers to a cycloalkyl group as defined above, directly bonded to an alkyl group as defined above, e.g., cyclopropylmethyl, cyclobutylmethyl, cyclopentylmethyl, cyclohexylmethyl, cyclohexylethyl, etc. Unless set forth or recited to the contrary, all cycloalkylalkyl groups described or claimed herein may be substituted or unsubstituted.

The term "haloalkyl" refers to an alkyl group as defined above that is substituted by one or more halogen atoms as defined above. Preferably, the haloalkyl may be monohaloalkyl, dihaloalkyl or polyhaloalkyl including perhaloalkyl. A monohaloalkyl can have one iodine, bromine, chlorine or fluorine atom. Dihaloalkyl and polyhaloalkyl groups can be substituted with two or more of the same halogen atoms or a combination of different halogen atoms. Preferably, a polyhaloalkyl is substituted with up to 12 halogen atoms. Non-limiting Examples of a haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl and the like. A perhaloalkyl refers to an alkyl having all hydrogen atoms replaced with halogen atoms.

The term "haloalkoxy" refers to an haloalkyl, defined herein, group attached via an oxygen linkage. Non-limiting Examples of such groups are monohaloalkoxy, dihaloalkoxy or polyhaloalkoxy including perhaloalkoxy. Unless set forth or recited to the contrary, all haloalkoxy groups described or claimed herein may be straight chain or branched, substituted or unsubstituted.

The term "hydroxyalkyl" refers to an alkyl group, as defined above that is substituted by one or more hydroxy groups. Preferably, the hydroxyalkyl is monohydroxyalkyl or dihydroxyalkyl. Non-limiting Examples of a hydroxyalkyl include 2-hydroxyethyl, 3-hydroxypropyl, 2-hydroxypropyl, and the like.

The term "aryl" refers to an aromatic radical having 6- to 14-carbon atoms, including monocyclic, bicyclic and tricyclic aromatic systems, such as phenyl, naphthyl, tetrahydronaphthyl, indanyl, and biphenyl and the like. Unless set forth or recited to the contrary, all aryl groups described or claimed herein may be substituted or unsubstituted.

The term "arylalkyl" refers to an aryl group as defined above directly bonded to an alkyl group as defined above, e.g., —CH$_2$C$_6$H$_5$ and —C$_2$H$_4$C$_6$H$_5$. Unless set forth or recited to the contrary, all arylalkyl groups described or claimed herein may be substituted or unsubstituted.

A "5-7 membered cyclic ring" as used herein refers to a monocyclic, bicyclic heterocyclic ring system. This heterocyclic ring is as described herein.

A "carbocyclic ring" or "carbocycle" as used herein refers to a 3- to 7 membered saturated or partially unsaturated, monocyclic fused bicyclic, spirocyclic ring containing carbon atoms, which may optionally be substituted, for Example, carbocyclic rings include but are not limited to cyclopropyl, cyclobutyl, cyclopentyl, cyclohexyl, cyclopropylene, cyclohexanone, etc.

The term "heterocyclic ring" or "heterocyclyl ring" or "heterocyclyl", unless otherwise specified, refers to substituted or unsubstituted non-aromatic 3- to 15-membered ring which consists of carbon atoms and with one or more heteroatom(s) independently selected from N, O or S. The heterocyclic ring may be a mono-, bi- or tricyclic ring system, which may include fused, bridged or spiro ring systems and the nitrogen, carbon, oxygen or sulfur atoms in the heterocyclic ring may be optionally oxidized to various oxidation states. In addition, the nitrogen atom may be optionally quaternized, the heterocyclic ring or heterocyclyl may optionally contain one or more olefinic bond(s), and one or two carbon atoms(s) in the heterocyclic ring or heterocyclyl may be interrupted with —CF$_2$—, —C(O)—, —S(O)—, S(O)$_2$, —C(=N-alkyl)-, or —C(=N-cycloalkyl), etc. In addition heterocyclic ring may also be fused with aromatic ring. Non-limiting Examples of heterocyclic rings include azetidinyl, benzopyranyl, chromanyl, decahydroisoquinolyl, indanyl, indolinyl, isoindolinyl, isochromanyl, isothiazolidinyl, isoxazolidinyl, morpholinyl, oxazolinyl, oxazolidinyl, 2-oxopiperazinyl, 2-oxopiperidinyl, 2-oxopyrrolidinyl, 2-oxoazepinyl, octahydroindolyl, octahydroisoindolyl, perhydroazepinyl, piperazinyl, 4-piperidonyl, pyrrolidinyl, piperidinyl, phenothiazinyl, phenoxazinyl, quinuclidinyl, tetrahydroisquinolyl, tetrahydrofuryl, tetrahydropyranyl, thiazolinyl, thiazolidinyl, thiamorpholinyl, thiamorpholinyl sulfoxide, thiamorpholinyl sulfone indoline, benzodioxole, tetrahydroquinoline, tetrahydrobenzopyran and the like. The heterocyclic ring may be attached by any atom of the heterocyclic ring that results in the creation of a stable structure. Unless set forth or recited to the contrary, all heterocyclyl groups described or claimed herein may be substituted or unsubstituted; substituents may be on same or different ring atom.

The term "heteroaryl" unless otherwise specified, refers to a substituted or unsubstituted 5- to 14-membered aromatic heterocyclic ring with one or more heteroatom(s) independently selected from N, O or S. The heteroaryl may be a mono-, bi- or tricyclic ring system. The heteroaryl ring may be attached by any atom of the heteroaryl ring that results in the creation of a stable structure. Non-limiting Examples of a heteroaryl ring include oxazolyl, isoxazolyl, imidazolyl, furyl, indolyl, isoindolyl, pyrrolyl, triazolyl, triazinyl, tetrazolyl, thienyl, thiazolyl, isothiazolyl, pyridyl, pyrimidinyl, pyrazinyl, pyridazinyl, benzofuranyl, benzothiazolyl, benzoxazolyl, benzimidazolyl, benzothienyl, carbazolyl, quinolinyl, isoquinolinyl, quinazolinyl, cinnolinyl, naphthyridinyl, pteridinyl, purinyl, quinoxalinyl, quinolyl, isoquinolyl, thiadiazolyl, indolizinyl, acridinyl, phenazinyl, phthalazinyl and the like. Unless set forth or recited to the contrary, all heteroaryl groups described or claimed herein may be substituted or unsubstituted.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure. Unless set forth or recited to the contrary, all heterocyclylalkyl groups described or claimed herein may be substituted or unsubstituted.

The term "heteroarylalkyl" refers to a heteroaryl ring radical directly bonded to an alkyl group. The heteroarylalkyl radical may be attached to the main structure at any carbon atom in the alkyl group that results in the creation of a stable structure. Unless set forth or recited to the contrary, all heteroarylalkyl groups described or claimed herein may be substituted or unsubstituted.

Unless otherwise specified, the term "substituted" as used herein refers to a group or moiety having one or more substituents attached to the structural skeleton of the group or moiety. Such substituents include, but are not limited to hydroxy, halogen, carboxyl, cyano, nitro, oxo (=O), thio (=S), alkyl, haloalkyl, alkenyl, alkynyl, aryl, arylalkyl, cycloalkyl, cycloalkylalkyl, cycloalkenyl, heteroaryl, heterocyclic ring, heterocyclylalkyl, heteroarylalkyl, —C(O)OR$^x$, —C(O)R$^x$, —C(S)R$^x$, —C(O)NR$^x$R$^y$, —NR$^x$C(O)NR$^y$R$^z$, —N(R$^x$)S(O)R$^y$, —N(R$^x$)S(O)$_2$R$^y$, —NR$^x$R$^y$, —NR$^x$(O)R$^y$, —NR$^x$(S)R$^y$, —NR$^x$(S)NR$^y$R$^z$, —S(O)$_2$NR$^x$R$^y$, —OR$^x$, —OC(O)R$^x$, —OC(O)NR$^x$R$^y$, —R$^x$C(O)OR$^y$, —R$^x$C(O)NR$^x$R$^z$, —R$^x$C(O)R$^y$, —SR$^x$, and —S(O)$_2$R$^x$; wherein R$^x$, R$^y$ and R$^z$ are independently selected from hydrogen, halogen, alkyl, haloalkyl, alkenyl, alkynyl, aryl, arylalkyl, cycloalkyl, cycloalkenyl, heteroaryl, heterocyclic ring, heterocyclylalkyl and heteroarylalkyl. The aforementioned "substituted" groups cannot be further substituted. For Example, when the substituent on "substituted alkyl" is "aryl" or "alkenyl", the aryl or alkenyl cannot be substituted aryl or substituted alkenyl, respectively.

The term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. The terms "racemate" or "racemic mixture" refer to a mixture of equal parts of enantiomers.

A "tautomer" refers to a compound that undergoes rapid proton shifts from one atom of the compound to another atom of the compound. Some of the compounds described herein may exist as tautomers with different points of attachment of hydrogen. The individual tautomers as well as mixture thereof are encompassed with compounds of Formula (I).

The term "treating" or "treatment" of a state, disease, disorder, condition or syndrome includes: (a) delaying the appearance of clinical symptoms of the state, disease, disorder, condition or syndrome developing in a subject that may be afflicted with or predisposed to the state, disease, disorder, condition or syndrome but does not yet experience or display clinical or subclinical symptoms of the state, disease, disorder, condition or syndrome; (b) inhibiting the state, disease, disorder, condition or syndrome, i.e., arresting or reducing the development of the disease or at least one clinical or subclinical symptom thereof; c) lessening the severity of a disease disorder or condition or at least one of its clinical or subclinical symptoms thereof; and/or (d) relieving the disease, i.e., causing regression of the state, disorder or condition or at least one of its clinical or subclinical symptoms.

The term "modulate" or "modulating" or "modulation" refers to a decrease or inhibition in the amount, quality, or effect of a particular activity, function or molecule; by way of illustration that block or inhibit calcium release-activated calcium (CRAC) channel. Any such modulation, whether it be partial or complete inhibition is sometimes referred to herein as "blocking" and corresponding compounds as "blockers". For Example, the compounds of the invention are useful as modulators of the CRAC channel.

The term "subject" includes mammals, preferably humans and other animals, such as domestic animals; e.g., household pets including cats and dogs.

A "therapeutically effective amount" means the amount of a compound that, when administered to a subject for treating a disease, disorder, syndrome or condition, is sufficient to cause the effect in the subject which is the purpose of the administration. The "therapeutically effective amount" will vary depending on the compound, the disease and its severity and the age, weight, physical condition and responsiveness of the subject to be treated.

Unless otherwise stated, in the present application "protecting group" refers to the groups intended to protect an otherwise labile group, e.g., an amino group, a carboxy group and the like, under specific reaction conditions. Various protecting groups along with the methods of protection and deprotection are generally known to a person of ordinary skilled in the art. Incorporated herein in this regard as reference is *Greene's Protective Groups in Organic Synthesis,* 4th Edition, John Wiley & Sons, New York. In the invention, preferred amino protecting groups are t-butoxycarbonyl, benzyloxycarbonyl, acetyl and the like; while preferred carboxy protecting groups are esters, amides and the like.

Pharmaceutically Acceptable Salts:

The compounds of the invention may form salts with acid or base. The compounds of invention may be sufficiently basic or acidic to form stable nontoxic acid or base salts, administration of the compound as a pharmaceutically acceptable salt may be appropriate. Non-limiting Examples of pharmaceutically acceptable salts are inorganic, organic acid addition salts formed by addition of acids including hydrochloride salts. Non-limiting Examples of pharmaceutically acceptable salts are inorganic, organic base addition salts formed by addition of bases. The compounds of the invention may also form salts with amino acids. Pharmaceutically acceptable salts may be obtained using standard procedures well known in the art, for Example by reacting a sufficiently basic compound such as an amine with a suitable acid affording a physiologically acceptable anion.

With respect to the overall compounds described by the Formula (I), the invention extends to these stereoisomeric forms and to mixtures thereof. To the extent prior art teaches synthesis or separation of particular stereoisomers, the different stereoisomeric forms of the invention may be separated from one another by a method known in the art, or a given isomer may be obtained by stereospecific or asymmetric synthesis or chiral HPLC (high performance liquid chromatography). Tautomeric forms and mixtures of compounds described herein are also contemplated.

Pharmaceutical Compositions

The invention relates to pharmaceutical compositions containing the compound of Formula (I). In particular, the pharmaceutical compositions contain a therapeutically effective amount of at least one compound of Formula (I) and at least one pharmaceutically acceptable excipient (such as a carrier or diluent). Preferably, the pharmaceutical compositions include the compound(s) described herein in an amount sufficient to modulate the calcium release-activated calcium (CRAC) channel to treat CRAC channel mediated diseases such as inflammatory diseases, autoimmune diseases, allergic disorders, organ transplant, cancer and cardiovascular disorders when administered to a subject.

The compound of the invention may be incorporated with a pharmaceutically acceptable excipient (such as a carrier or a diluent) or be diluted by a carrier, or enclosed within a carrier which can be in the form of a capsule, sachet, paper or other container. The pharmaceutically acceptable excipient includes a pharmaceutical agent that does not itself induce the production of antibodies harmful to the individual receiving the composition, and which may be administered without undue toxicity.

Examples of suitable carriers include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicylic acid, fatty acids, fatty acid amines, fatty acid monoglycerides and diglycerides, pentaerythritol fatty acid esters, polyoxyethylene, hydroxymethylcellulose and polyvinylpyrrolidone.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing procedures known in the art.

The pharmaceutical compositions described herein may be prepared by conventional techniques known in the art. For Example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for Example, in a sachet.

The pharmaceutical compositions may be administered in conventional forms, for Example, capsules, tablets, aerosols, solutions, suspensions or products for topical application.

The route of administration may be any route which effectively transports the active compound of the invention to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment).

Solid oral Formulations include, but are not limited to, tablets, caplets, capsules (soft or hard gelatin), orally disintegrating tablets, dragees (containing the active ingredient in powder or pellet form), troches and lozenges. Tablets, dragees, or capsules having talc and/or a carbohydrate carrier or binder or the like are particularly suitable for oral application. Liquid Formulations include, but are not limited to, syrups, emulsions, suspensions, solutions, soft gelatin and sterile injectable liquids, such as aqueous or non-aqueous liquid suspensions or solutions. For parenteral application, particularly suitable are injectable solutions or suspensions, preferably aqueous solutions with the active compound dissolved in polyhydroxylated castor oil.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

For administration to human patients, the total daily dose of the compounds of the invention depends, of course, on the mode of administration. For Example, oral administration may require a higher total daily dose, than an intravenous (direct into blood). The quantity of active component in a unit dose preparation may be varied or adjusted from 0.1 mg to 10000 mg, more typically 1.0 mg to 1000 mg, and most typically 10 mg to 500 mg, according to the potency of the active component or mode of administration.

Suitable doses of the compounds for use in treating the diseases disorders, syndromes and conditions described herein can be determined by those skilled in the relevant art. Therapeutic doses are generally identified through a dose ranging study in humans based on preliminary evidence derived from the animal studies. Doses must be sufficient to result in a desired therapeutic benefit without causing unwanted side effects for the patient. For Example, the daily dosage of the CRAC channel modulator can range from about 0.1 to about 30.0 mg/kg. Mode of administration, dosage forms, suitable pharmaceutical excipients, diluents or carriers can also be well used and adjusted by those skilled in the art. All changes and modifications are envisioned within the scope of the invention.

Method of Treatment

In a further embodiment, the invention is directed to the treatment or prophylaxis of inflammatory conditions by administering an effective amount of a compound of the invention.

Inflammation is part of the normal host response to infection and injury or exposure to certain substances prone to cause it. Inflammation begins with the immunologic process of elimination of invading pathogens and toxins to repair damaged tissue. Hence, these responses are extremely ordered and controlled. However, excessive or inappropriate inflammation contributes to a range of acute and chronic human diseases and is characterized by the production of inflammatory cytokines, arachidonic acid-derived eicosanoids (prostaglandins, thromboxanes, leukotrienes, and other oxidized derivatives), other inflammatory agents (e.g., reactive oxygen species), and adhesion molecules. As used herein, the term "inflammatory conditions" is defined as a disease or disorder or abnormality characterized by involvement of inflammatory pathways leading to inflammation, and which may result from, or be triggered by, a dysregulation of the normal immune response.

The compound(s) of the invention are useful in treatment of inflammatory conditions including, but not limited to, diseases of many body systems such as (musculoskeletal) arthritis, myositis, rheumatoid arthritis, osteoarthritis, gout, gouty arthritis, acute pseudogout, Reiter's syndrome, ankylosing spondylitis, psoriatic arthritis, dermatomyositis; (pulmonary) pleuritis, pulmonary fibrosis or nodules, restrictive lung disease, chronic obstructive pulmonary disease (COPD), acute respiratory distress syndrome (ARDS), (cardiovascular) aortic valve stenosis, restenosis, arrhythmias, coronary arteritis, myocarditis, pericarditis, Raynaud's phenomenon, systemic vasculitis, angiogenesis, atherosclerosis, ischaemic heart disease, thrombosis, myocardial infarction; (gastrointestinal) dysmotility, dysphagia, inflammatory bowel diseases, pancreatitis, (genitourinary) interstitial cystitis, renal tubular acidosis, urosepsis, (skin) purpura, vasculitis scleroderma, eczema, psoriasis, (neurologic) central nervous system disorders, cranial and peripheral neuropathies, peripheral neuropathy, radiculopathy, spinal cord or cauda equina compression with sensory and motor loss, multiple sclerosis (MS) (mental) cognitive dysfunction, Alzheimer's disease, (neoplastic) lymphoma, inflammation associated with cancer, (ophthalmologic) iridocyclitis, keratoconjunctivitis sicca, uveitis, (hematologic) chronic anemia, thrombocytopenia, (renal) amyloidosis of the kidney, glomerulonephritis, kidney failure and other diseases such as tuberculosis, leprosy, sarcoidosis, syphilis, Sjögren's syndrome, cystitis, fibromyalgia, fibrosis, septic shock, endotoxic shock, surgical complications, systemic lupus erthymotosus (SLE), transplantation associated arteriopathy, graft vs. host reaction, allograft rejection, chronic transplant rejection.

The inflammatory bowel diseases also include Crohn's disease, ulcerative colitis, indeterminate colitis, necrotizing enterocolitis, and infectious colitis.

"Allergic disorders" are defined as disorders/diseases that are caused by a combination of genetic and environmental factors resulting in a hypersensitivity disorder of the immune system. Allergic diseases are characterized by excessive immunoglobulin E (IgE) production, mast cell degranulation, tissue eosinophilia and mucus hypersecretion, resulting in an extreme inflammatory response. These responses also take place during infection with multicellular parasites, and are linked to the production of a characteristic set of cytokines by T helper (Th) 2 cells. For Example asthma is a chronic inflammatory condition of the lungs, characterized by excessive responsiveness of the lungs to stimuli, in the form of infections, allergens, and environmental irritants. Allergic reactions can also result from food, insect stings, and reactions to medications like aspirin and antibiotics such as penicillin. Symptoms of food allergy include abdominal pain, bloating, vomiting, diarrhea, itchy skin, and swelling of the skin during hives. Food allergies rarely cause respiratory (asthmatic) reactions, or rhinitis. Insect stings, antibiotics, and certain medicines produce a systemic allergic response that is also called anaphylaxis. The main therapeutic interest around CRAC in allergic disorders, originates from its role in lymphocytes and mast cells, CRAC activation being a requirement for lymphocyte activation.

The compound(s) of the invention are useful in treatment of allergic disorders including, but not limited to, atopic dermatitis, atopic eczema, Hay fever, asthma, urticaria (including chronic idiopathic urticaria), vernal conjunctivitis, allergic rhinoconjunctivitis, allergic rhinitis (seasonal and perennial), sinusitis, otitis media, allergic bronchitis, allergic cough, allergic bronchopulmonary aspergillosis, anaphylaxis, drug reaction, food allergies and reactions to the venom of stinging insects.

In yet another embodiment, the invention is directed to the treatment of "immune disorders" by administering an effective amount of a compound of the invention.

The compounds of this invention can be used to treat subjects with immune disorders. As used herein, the term "immune disorder" and like terms mean a disease, disorder or condition caused by dysfunction or malfunction of the immune system as a whole or any of its components including autoimmune disorders. Such disorders can be congenital or acquired and may be characterized by the component(s) of the immune system getting affected or by the immune system or its components getting overactive Immune disorders include those diseases, disorders or conditions seen in animals (including humans) that have an immune component and those that arise substantially or entirely due to immune system-mediated mechanisms. In addition, other immune system mediated diseases, such as graft-versus-host disease and allergic disorders, will be included in the definition of immune disorders herein. Because a number of immune disorders are caused by inflammation or lead to inflammation, there is some overlap between disorders that are considered immune disorders and inflammatory disorders. For the purpose of this invention, in the case of such an overlapping disorder, it may be considered either an immune disorder or an inflammatory disorder. An autoimmune disorder is a condition that occurs when the immune system mistakenly attacks and destroys its own body cells, tissues and/or organs. This may result in temporary or permanent destruction of one or more types of body tissue, abnormal growth of an organ, changes in organ function, etc. For Example, there is destruction of insulin producing cells of the pancreas in Type 1 diabetes mellitus. Different autoimmune disorders can target different tissues, organs or systems in an animal while some autoimmune disorders target different tissues, organs or systems in different animals. For Example, the autoimmune reaction is directed against the gastrointestinal tract in Ulcerative colitis and the nervous system in multiple sclerosis whereas in systemic lupus erythematosus (lupus), affected tissues and organs may vary among individuals with the same disease. For Example, one person with lupus may have affected skin and joints whereas another may have affected kidney, skin and lungs.

Specific autoimmune disorders that may be ameliorated using the compounds and methods of this invention include without limitation, autoimmune disorders of the skin (e.g., psoriasis, dermatitis herpetiformis, pemphigus vulgaris, and vitiligo), autoimmune disorders of the gastrointestinal system (e.g., Crohn's disease, ulcerative colitis, primary biliary cirrhosis, and autoimmune hepatitis), autoimmune disorders of the endocrine glands (e.g., Type 1 or immune-mediated diabetes mellitus, Grave's disease. Hashimoto's thyroiditis, autoimmune oophoritis and orchitis, and autoimmune disorder of the adrenal gland), autoimmune disorders of multiple organs (including connective tissue and musculoskeletal system diseases) (e.g., rheumatoid arthritis, systemic lupus erythematosus, scleroderma, polymyositis, dermatomyositis, spondyloarthropathies such as ankylosing spondylitis, and Sjogren's syndrome), autoimmune disorders of the nervous system (e.g., multiple sclerosis, myasthenia gravis, autoimmune neuropathies such as Guillain-Barre, and autoimmune uveitis), autoimmune disorders of the blood (e.g., autoimmune hemolytic anemia, pernicious anemia, and autoimmune thrombocytopenia) and autoimmune disorders of the blood vessels (e.g., temporal arteritis, anti-phospholipid syndrome, vasculitides such as Wegener's granulomatosis, and Behcet's disease).

"Treatment of an immune disorder" herein refers to administering a compound or a composition of the invention alone or in combination with other agents to a subject, who has an immune disorder, a sign or symptom of such a disease or a risk factor towards such a disease, with a purpose to cure, relieve, alter, affect, or prevent such disorder or sign or symptom of such a disease, or the predisposition towards it.

In another embodiment, the invention is directed to the treatment of cancer by administering an effective amount of a compound of the invention.

It has been reported in the art that STIM1 and Orai1 are essential in in vitro tumor cell migration and in vivo tumor metastasis. Thus the involvement of store operated $Ca^{2+}$ entry in tumor metastasis renders STIM1 and Orai1 proteins potential targets for cancer therapy (Yang et. al., Cancer Cell, 15, 124-134, 2009). Additional literature available on the involvement of CRAC channel in cancer are Abeele et. al., Cancer Cell, 1, 169-179, 2002, Motiani et al., J. Biol. Chem., 285; 25, 19173-19183, 2010.

The compound(s) of the invention may be useful in treatment of cancers and/or its metastasis including, but not limited to, breast cancer, lung cancer, pancreatic cancer, ovarian cancer, colon cancer, neck cancer, kidney cancer, bladder cancer, thyroid, blood cancer, skin cancer and the like.

In yet another embodiment, the invention is directed to the treatment or prophylaxis of allergic disorders by administering an effective amount of a compound of the invention.

In yet another embodiment, the invention is directed to the treatment or prophylaxis of cardiovascular diseases or disorders by administering an effective amount of a compound of the invention.

The compounds of this invention can be used to treat subjects with cardiovascular disorders. "Cardiovascular disorder" refers to a structural and functional abnormality of the heart and blood vessels, comprised of diseases including but not limited to, atherosclerosis, coronary artery disease, arrhythmia, heart failure, hypertension, diseases of the aorta and its branches, disorders of the peripheral vascular system, aneurysm, endocarditis, pericarditis, heart valve disease. It may be congenital or acquired. One of the main pathological feature of all these diseases is clogged and hardened arteries, obstructing the blood flow to the heart. The effects differ depending upon which vessels are clogged with plaque. The arteries carrying oxygen rich blood, if clogged, result in coronary artery disease, chest pain or heart attack. If the arteries reaching the brain are affected, it leads to transient ischemic attack or stroke. If the vessels in arms or legs are affected, leads to peripheral vascular disease. Because a number of cardiovascular diseases may also be related to or arise as a consequence of thrombocytopathies, there is some overlap between disorders that are considered under heading cardiovascular disorders and thrmobocytopathies. For the purpose of this invention, in the case of such an overlapping disorder, it may be considered either a cardiovascular disorder or a thrombocytopathy.

STIM1 is located on the endoplasmic reticulum (ER) and functions as a calcium sensor. Orai1 is a pore forming subunit of calcium channel located on the plasma membrane, the depletion of calcium in the endoplasmic reticulum is sensed by STIM1, and calcium enters via Orai1 to refill the endoplasmic reticulum. This pathway of filling the calcium is called store operated calcium entry (SOCE), which plays an important role in calcium homeostasis, cellular dysfunction and has a significant importance in cardiovascular diseases. In cardiomyocytes, calcium is not only involved in excitation-contraction coupling but also acts as a signalling molecule promoting cardiac hypertrophy. Hypertrophic hearts are susceptible to abnormalities of cardiac rhythm and have impaired relaxation. Vascular smooth muscle cells (VSMCs) are responsible for the maintenance of vascular tone. VSMCs disorders, usually manifested as a phenotype change, are involved in the pathogenesis of major vascular diseases such as atherosclerosis, hypertension and restenosis. SOCE was also found increased in metabolic syndrome (MetS) swine coronary smooth muscle cells. The compound of this invention can be used to treat neointimal hyperplasia, occlusive vascular diseases, MetS—which is a combination of medical disorders including coronary artery disease, stroke and type 2 diabetes, abdominal aortic aneurysm, angina, transient ischemic attack, stroke, peripheral artery occlusive disease which includes inflammation, complement activation, fibrinolysis, angiogenesis and/or diseases related to FXII-induced kinin formation such as hereditary angioedema, bacterial infection of the lung, trypanosome infection, hypotensive shock, pancreatitis, chagas disease, thrombocytopenia or articular gout, myocardial infarction, portal vein thrombosis which leads to hypertension, pulmonary hypertension, deep vein thrombosis, jugular vein thrombosis, systemic sepsis, pulmonary embolism, and papilledema, Budd-Chiari syndrome, Paget-Schroetter disease, cerebral venous sinus thrombosis ischemic cardiomyopathy, hypertrophic cardiomyopathy, arrhythmogenic right ventricular cardiomyopathy, Prinzmetal angina, angina pectoris, chronic venous insufficiency, acute coronary syndrome, endocarditis, conceptual apraxia, pulmonary valve stenosis, thrombophlebitis, ventricular tachycardia, temporal arteritis, tachycardia, paroxysmal atrial fibrillation, persistent atrial fibrillation, permanent atrial fibrillation, respiratory sinus arrhythmia, carotid artery dissection, cerebrovascular diseases include, hemorrhagic stroke and ischemic stroke (where the thrombo-inflammatory cascade results in infarct growth), cardiomegaly, endocarditis, pericarditis, pericardial effusion. Valvular heart disease, vascular diseases or vascular inflammation is the result of ruptured atherosclerotic plaque which initiates thrombus formation. Platelet activation play an important role in vascular inflammation leading to myocardial infarction and ischaemic stroke, the compound of this invention will prevent platelet activation and plaque formation and would also be useful to treat all peripheral vascular diseases (PVD), pulmonary thromboembolism, and venous thrombosis.

"Treatment of cardiovascular disorders" herein refers to administering a compound or a composition of the invention alone or in combination with other agents to a subject, who has a cardiovascular disease, a sign or symptom of such a disease or a risk factor towards such a disease, with a purpose to cure, relieve, alter, affect, or prevent such disorder or sign or symptom of such a disease, or the predisposition towards it.

In yet another embodiment, the invention is directed to the treatment of "thrombocytopathies" by administering an effective amount of a compound of the invention.

Thrombocytopathies: The compounds of this invention can be used to treat subjects with thrombocytopathies. Thrombocytopathy is an abnormality of platelets or its functions. It may be congenital or acquired. It may cause a thrombotic or a bleeding tendency or may be part of a wider disorder such as myelodysplasia. Thrombocytopathies include such vascular disorders that arise due to dysfunction of platelets or coagulation system or diseases or complications that arise as a result of partial or complete restriction of blood flow to different organs or systems due to such thrombocytopathies. Thrombocytopathies will thus include without limitation diseases due to superficial vein thrombosis, diseases due to deep vein thrombosis, diseases due to arterial thrombosis, peripheral vascular diseases, thrombophilia, thrombophlebitis, embolisms, thromboembolism, ischemic cardiovascular diseases including but not limited to myocardial ischemia, angina, ischemic cerebrovascular diseases including but not limited to stroke, transient ischemia attack, cerebral venous sinus thrombosis (CYST) and complications arising due to thrmobocytopathies. Besides this, the disorder related to venous or arterial thrombus formation can be inflammation, complement activation, fibrinolysis, angiogenesis and/or diseases related to FXII-induced kinin formation such as hereditary angioedema, bacterial infection of the lung, trypanosome infection, hypotensive shock, pancreatitis, chagas disease, thrombocytopenia or articular gout.

Under normal circumstances, when the endothelial cells lining blood vessels are breached, platelets interact with von Willebrand factor (vWF) via the membrane glycoprotein 1b complex to help seal the breach. Glycoprotein IIb/Ia complex attracts other platelets, which combine to form aggregates. The platelets contain granules which break down to release fibrinogen, vWF, platelet-derived growth factor adenosine 5'-diphosphate (ADP), calcium and 5-hydroxytryptamine (5-HT)-serotonin. All this helps to promote the formation of a haemostatic plug (primary haemostasis). Activated platelets also synthesise thromboxane A2 from arachidonic acid as well as presenting negatively charged phospholipids on the outer leaflet of the platelet membrane bilayer. This negative surface provides binding sites for enzymes and cofactors of the coagulation system. The total effect is therefore to stimulate the coagulation system to form a clot (secondary haemostasis).

Thus physiological platelet activation and thrombus formation are essential to stop bleeding in case of vascular injury, whereas under pathological conditions this may lead to vessel occlusion due to inadequate triggering of the same process in diseased vessels leading to thrombosis, thromboembolism or tissue ischemia of vital organs. A central step in platelet activation is agonist-induced elevation of the intracellular Ca(2+) concentration. This happens on the one hand through the release of Ca(2+) from intracellular stores and on the other hand through Ca(2+) influx from the extracellular space. In platelets, the major Ca(2+) influx pathway is through store operated Ca(2+) entry (SOCE), induced by store depletion. STIM1 is the Ca(2+) sensor in the endoplasmic reticulum (ER) membrane, whereas Orai1 is the major store operated Ca(2+) (SOC) channel in the plasma membrane, which play a key role in platelet SOCE.

"Treatment of thrombocytopathy" herein refers to administering a compound or a composition of the invention alone or in combination with other agents to a subject, who has a thrombocytopathy, a sign or symptom or complication of such a disease or a risk factor towards such a disease, with the purpose to cure, relieve, alter, affect, or prevent such a disorder or sign or symptom, or the predisposition towards it.

General Methods of Preparation

The compounds of the invention, including compounds of general Formula (I) and specific Examples are prepared through the reaction sequences illustrated in synthetic Scheme-1, Scheme-2 and Scheme-3 where A, B, L, $R_1$, $R_2$, $R_3$, $R_4$, $R_5$, $R_6$, $R_7$, $R_a$, $R_b$ 'n' and 'p' are as defined herein above. Starting materials are commercially available or may be prepared by the procedures described herein or by the procedures known in the art. Furthermore, in the following synthetic schemes, where specific acids, bases, reagents, coupling agents, solvents, etc., are mentioned, it is understood that other bases, acids, reagents, coupling agents, solvents etc., known in the art may also be used and are therefore included within the scope of the invention. Variations in reaction conditions and parameterslike temperature, pressure, duration of reaction, etc., which may be used as known in the art are also within the scope of the invention. All the isomers of the compounds described in these schemes, unless otherwise specified, are also encompassed within the scope of this invention.

The compounds obtained by using the general reaction sequences may be of insufficient purity. These compounds can be purified by using any of the methods for purification of organic compounds known in the art, for Example, crystallization or silica gel or alumina column chromatography using different solvents in suitable ratios. Unless mentioned otherwise, room temperature (RT) refers to a temperature in the range of 22° C. to 27° C.

$^1$H-NMR spectra of the compounds of the invention were recorded using a Bruker instrument (model: Avance-III), 400 MHz. Liquid chromatography-mass spectra (LCMS) of the compounds of the invention were recorded using Agilent ion trap model 6320 and Thermo Scientific Single Quad model MSQ plus instruments. IUPAC nomenclature for the compounds of the invention was used according to ChemBioDraw Ultra 12.0 software.

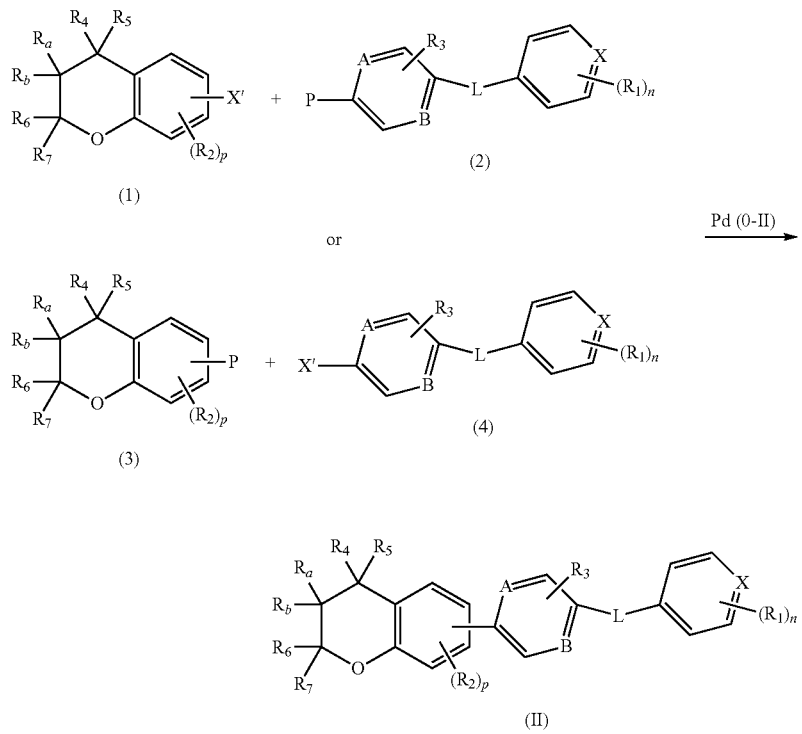

X' is halogen; P is pinacolatoboronate;

The compounds of Formula (II) wherein A, B, X, L, $R_1$, $R_2$, $R_3$, $R_4$, $R_5$, $R_6$, $R_7$, $R_a$, $R_b$, 'n' and 'p' are as defined herein above, is prepared by the reaction of various haloderivatives of Formula (1) with pinacolatoboronate derivative of Formula (2) as depicted in Scheme-1.

Alternatively, the compounds of the Formula (II) can also be prepared by the reaction of the pinacolatoboronate derivatives of the Formula (3) with halo derivatives of the Formula (4) as shown in Scheme 1. The same transformation may also be carried out by other suitable coupling methods known in the art. The compound of Formula (1), (2), (3) and Formula (4) can be prepared by following the methods known in the art.

The said reaction can be mediated by a suitable catalyst known in the art such as $Pd(PPh_3)_2Cl_2$, $Pd(dppf)Cl_2$, $Pd_2dba_3$, $Pd(PPh_3)_4$, $Pd(OAc)_2$ or mixture(s) thereof; a suitable ligand known in the art such as 2,2'-bis(diphenylphosphino)-1,1'-binaphthyl (BINAP), xanthophos, triphenylphosphine or mixture(s) thereof; in the presence of a suitable base, preferably inorganic bases such as alkali-metal carbonates like sodium carbonate, cesium carbonate and phosphates like potassium phosphate or mixture(s) thereof.

Scheme 2

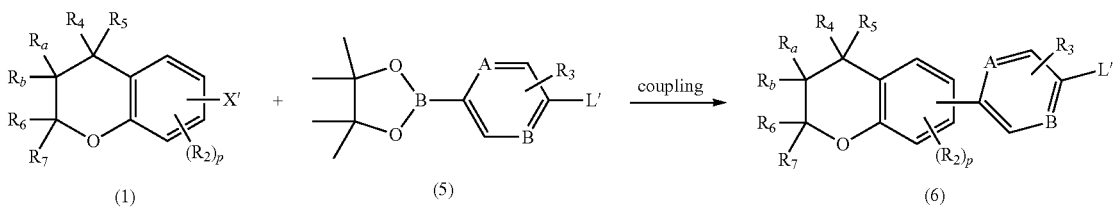

X' is halogen;
L' is either $NHR_8$ or COOH, COOalkyl or COCl
L" is either COOH, COOalkyl, COCl; or $NHR_8$

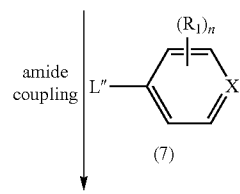

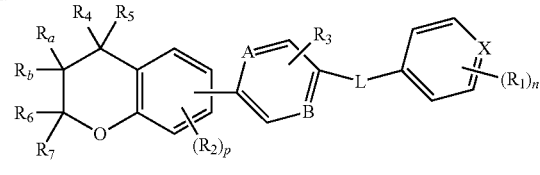

(II)

L is —C(O)NE$_8$, —NR$_8$(CO)—

Alternatively, compound of Formula (II) can be prepared by reacting a halo compound of the Formula (1) with borate compound of the Formula (5) followed by amide coupling reaction using general amide coupling reagents known in the art. The coupling of halo derivatives of the Formula (1) with borate derivatives of the Formula (5) are carried out as per methods known in the art or as described in the Scheme 1.

The compound of the Formula (6) is transformed to compound of Formula (II) using the suitable techniques known in the art. Such reactions are carried out in one or more suitable solvents using suitable base for Examplesodium hydride, triethylamine, N-ethyldiisopropylamine; 4-dialkylaminopyridines like 4-dimethylaminopyridine, pyridine or mixture(s) thereof.

Scheme 3

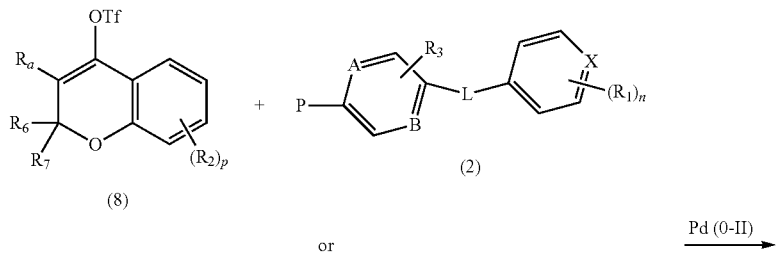

or

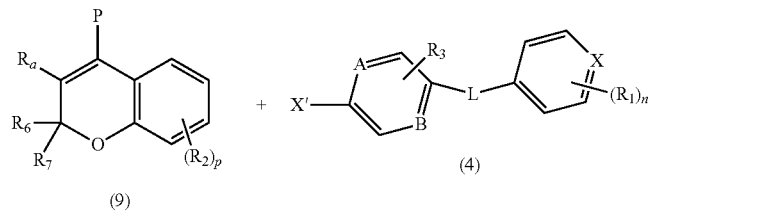

X' is halogen; P is pinacolatoboronate;

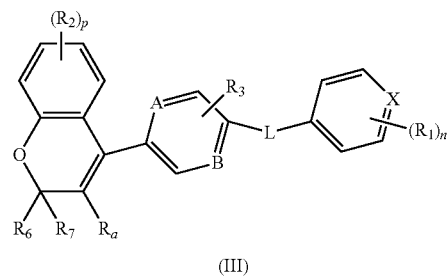

(III)

↓ H$_2$

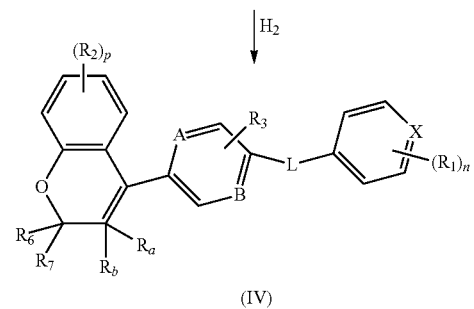

(IV)

R$_b$ is hydrogen;

The compounds of Formula (III) and (IV) wherein A, B, L, X, $R_1$, $R_2$, $R_3$, $R_6$, $R_7$, $R_a$, 'n' and 'p' are as defined herein above, are prepared by the reaction of various triflatederivatives of Formula (8) with borate derivative of Formula (2) as depicted in Scheme-3. Alternatively, compounds of the Formula (III) can also be prepared by the reaction of borate derivatives of the Formula (9) with halo derivatives of the Formula (4). The compound of Formula (2), (4), (8) and (9) are prepared as per the procedure known in the art.

Further, the compounds of the Formula (III) are converted to the compounds of the Formula (IV) under metal catalyzed hydrogenation conditions. The catalyst used for such transformation as known in the art such as Pd—C, Ra—Ni, Pt—C thereof; in presence of suitable solvent such as esters like ethyl acetate, ethers like THF, dioxane or mixture(s) thereof.

EXPERIMENTAL

Intermediates

Intermediate-1a

7-Bromo-2,2,6-trimethylchroman-4-one and

Intermediate-1b 2,2,6-Trimethyl-7-(4,4,5,5-tetramethyl-1,3,2-dioxaborolan-2-yl)chroman-4-one

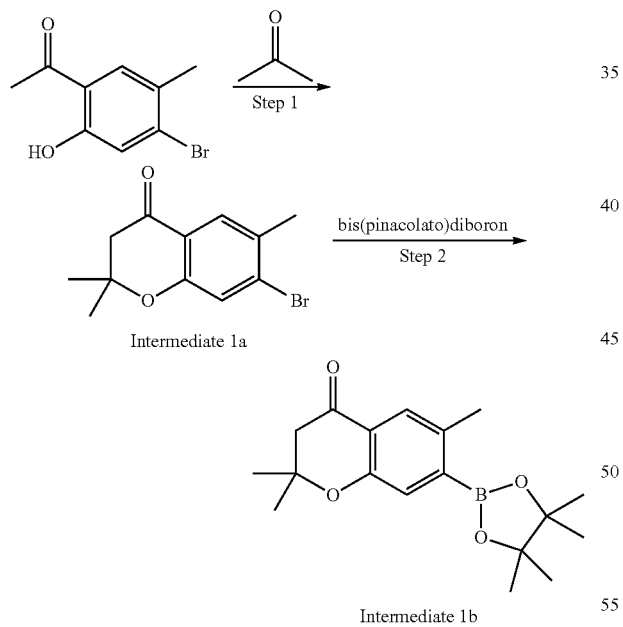

Step-1: 7-bromo-2,2,6-trimethylchroman-4-one: A mixture of 1-(4-bromo-2-hydroxy-5-methylphenyl)ethanone (prepared by following the similar procedure as described in WO2012028629; 2.0 g, 8.73 mmol), propan-2-one (830 μL, 11.35 mmol) and pyrrolidine (505 μL, 6.11 mmol) in methanol (25 mL) was refluxed for 16 h. The reaction was cooled to room temperature and the solvent was evaporated under vacuum. Ethyl acetate (100 mL) was added to the above obtained residue followed by 10% HCl (50 mL). The layers were separated and the aqueous layer was extracted with ethyl acetate (2×50 mL). The combined organic layers were washed with water (50 mL), saturated aqueous $NaHCO_3$ (50 mL) and brine (50 mL) The organic layer was dried ($Na_2SO_4$) and filtered. The filtrate was rotary evaporated and the crude product was purified by flash column chromatography to afford 1.50 g (63%) of the title compound as colorless liquid. $^1$HNMR (400 MHz, $CDCl_3$) δ 7.70 (s, 1H), 7.20 (s, 1H), 2.70 (s, 2H), 2.35 (s, 3H), 1.45 (s, 6H); GC-MS (m/z) 268, 270 [M$^+$, Br$^{79,81}$].

Step-2: 2,2,6-Trimethyl-7-(4,4,5,5-tetramethyl-1,3,2-dioxaborolan-2-yl)chroman-4-one: To a nitrogen purged suspension of potassium acetate (228 mg, 2.32 mmol) in toluene (10 mL) in a microwave vial was added step-1 Intermediate (250 mg, 0.929 mmol) followed by bis(pinacolato)diboron (259 mg, 1.02 mmol). The resulting mixture was thoroughly deoxygenated by purging nitrogen gas for another 10 minutes, and $PdCl_2(dppf)$-$CH_2Cl_2$ adduct (38 mg, 0.046 mmol) was added to the above mixture. The microwave vial was capped and heated at 150° C. for 13 min in a microwave reactor (Biotage). The reaction mixture was cooled to room temperature and filtered through celite. The filtrate was rotary evaporated and the crude product was purified by flash column chromatography (silica gel, ethyl acetate-hexanes system as eluent) to afford 100 mg (34%) of the title compound as white solid. $^1$HNMR (400 MHz, $CDCl_3$) δ 7.62 (s, 1H), 7.35 (s, 1H), 2.71 (s, 2H), 2.46 (s, 3H), 1.44 (s, 6H), 1.35 (s, 12H); ESI-MS (m/z) 317 (MH)$^+$.

Intermediate-2a

7-Bromo-6-ethyl-2,2-dimethylchroman-4-one and

Intermediate-2b

6-Ethyl-2,2-dimethyl-7-(4,4,5,5-tetramethyl-1,3,2-dioxaborolan-2-yl)chroman-4-one

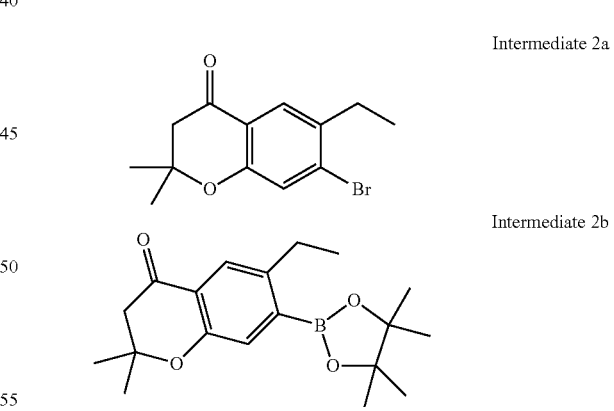

The title compounds were prepared by following the similar procedure as described in Intermediate-1a and Intermediate-1b Intermediate-2a: $^1$H NMR (400 MHz, $CDCl_3$) δ 7.70 (s, 1H), 7.19 (s, 1H), 2.75-2.67 (m, 4H), 1.45 (s, 6H), 1.23 (t, J=7.5 Hz, 3H); GC-MS (m/z) 282,284 [M$^+$, Br$^{79,81}$]

Intermediate-2b: $^1$HNMR (400 MHz, $CDCl_3$) δ 7.65 (s, 1H), 7.35 (s, 1H), 2.84 (q, J=7.5 Hz, 2H), 2.71 (s, 2H), 1.44 (s, 6H), 1.35 (s, 12H), 1.19 (t, J=7.5 Hz, 3H); ESI-MS (m/z) 331 (MH)$^+$

Intermediate-3a

7-Bromo-2,2,8-trimethylchroman-4-one and

Intermediate-3b 2,2,8-Trimethyl-7-(4,4,5,5-tetramethyl-1,3,2-dioxaborolan-2-yl)chroman-4-one

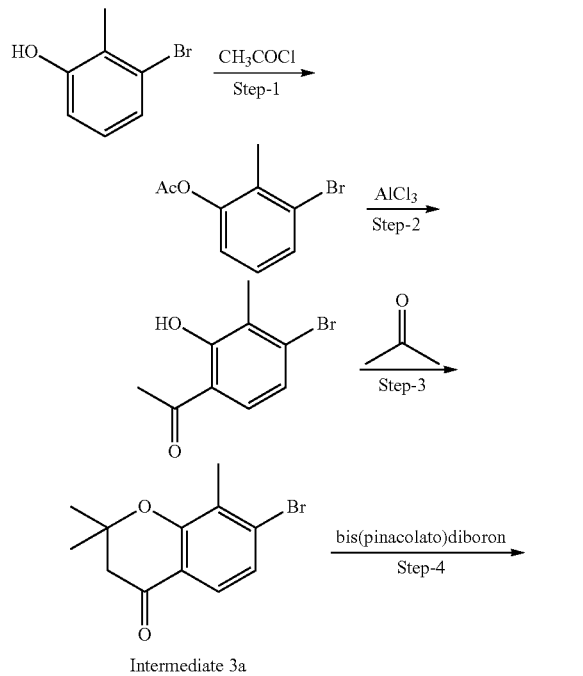

Intermediate 3a

Intermediate 3b

Step-1: 3-Bromo-2-methylphenyl acetate: To the (0° C.) cooled and stirred solution of 3-bromo-2-methylphenol (10.0 g, 53.5 mmol) in DCM (100 mL) was added pyridine (10.8 mL, 134 mmol) followed by drop-wise addition of a solution of acetyl chloride (5.70 mL, 80 mmol) in DCM (30 mL). The resulting mixture was then stirred at room temperature for 18 h. The reaction was then cooled to 0° C. and water (100 mL) was added to the above mixture followed by DCM (50 mL) The layers were separated and the aqueous layer was extracted with DCM (2×100 mL). The combined organic layers were washed with brine (50 mL), dried over $Na_2SO_4$ and filtered. The filtrate was evaporated and the crude product was purified by flash column chromatography (silica gel, 4% ethyl acetate in hexanes system as eluent) to afford 6.50 g (53%) of the title compound as brown oil. $^1$H NMR (400 MHz, CDCl$_3$) δ 7.46 (d, J=8.0, Hz, 1H), 7.11-7.09 (m, 1H), 7.00 (d, J=8.0 Hz, 1H), 2.35 (s, 3H), 2.26 (s, 3H); GC-MS (m/z) 228, 230 [M$^+$, Br$^{79,81}$].

Step-2: 1-(4-Bromo-2-hydroxy-3-methylphenyl)ethanone: A mixture of 3-bromo-2-methylphenyl acetate (6.50 g, 28.4 mmol) and aluminium chloride (4.54 g, 34.1 mmol) was heated at 100° C. for 2 h. The reaction mixture was cooled to 0° C. and aqueous HCl (10%, 50 mL) was added to the above mixture and then continued heating at 120° C. for 2 h. The reaction was then cooled to room temperature and diluted with DCM (200 mL) The layers were separated and the organic layer was washed with water (50 mL), dried ($Na_2SO_4$) and filtered. The filtrate was rotary evaporated and the crude product was purified by flash column chromatography (silica gel, 4% ethyl acetate in hexane system as eluent) to afford 4.0 g (61%) of the title compound as white solid. $^1$HNMR (400 MHz, CDCl$_3$) δ 12.87 (s, 1H), 7.45 (d, J=8.5 Hz, 1H), 7.12 (d, J=8.5 Hz, 1H), 2.63 (s, 3H), 2.36 (s, 3H); GC-MS (m/z) 228, 230 [M$^+$, Br$^{79,81}$].

Step-3: 7-Bromo-2,2,8-trimethylchroman-4-one: To a 0° C. cooled and stirred solution of step 2 Intermediate (2.0 g, 8.73 mmol) in methanol (15 mL) was added acetone (0.96 mL, 13.1 mmol) and pyrrolidine (1.50 mL, 17.4 mmol) sequentially. The resulting mixture was stirred at room temperature for 15 min and then at 75° C. for 18 h. The reaction was cooled to room temperature and the solvent was evaporated under vacuum. Aqueous HCl (10%, 50 mL) was added to the above residue followed by the addition of ethyl acetate (200 mL). The layers were separated and the aqueous layer was extracted with ethyl acetate (2×50 mL). The combined organic layers were washed with water (50 mL), brine (50 mL), dried ($Na_2SO_4$) and filtered. The filtrate was rotary evaporated and the crude product was purified by flash column chromatography (silica gel, 5% ethyl acetate in hexanes system as eluent) to afford 1.50 g (64%) of the title compound as colorless oil. $^1$HNMR (400 MHz, CDCl$_3$) δ 7.58 (d, J=8.0, 1H), 7.19 (d, J=8.0 Hz, 1H), 2.72 (s, 2H), 2.33 (s, 3H), 1.48 (s, 6H); ESI-MS (m/z) 269, 271 [(MH)$^+$, Br$^{79,81}$].

Step-4: 2,2,8-Trimethyl-7-(4,4,5,5-tetramethyl-1,3,2-dioxaborolan-2-yl)chroman-4-one: The title compound was prepared by reacting the step 3 Intermediate with bis(pinacolato)diboron by following the similar procedure as described in step-2 of Intermediate 1. $^1$HNMR (400 MHz, CDCl$_3$) δ 7.69 (d, J=8.0 Hz, 1H), 7.32 (d, J=8.0 Hz, 1H), 2.72 (s, 2H), 2.42 (s, 3H), 1.46 (s, 6H), 1.37 (s, 12H); ESI-MS (m/z) 317 (MH)$^+$.

Intermediate-4a

7-Bromo-2,2,8-trimethylchroman-4-ol and

Intermediate-4b

7-Bromo-2,2,8-trimethylchroman and

Intermediate-4c 4,4,5,5-Tetramethyl-2-(2,2,8-trimethylchroman-7-yl)-1,3,2-dioxaborolane

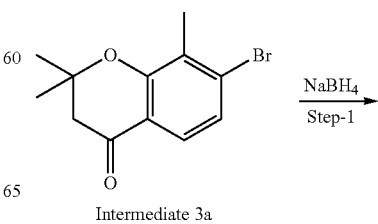

Intermediate 3a

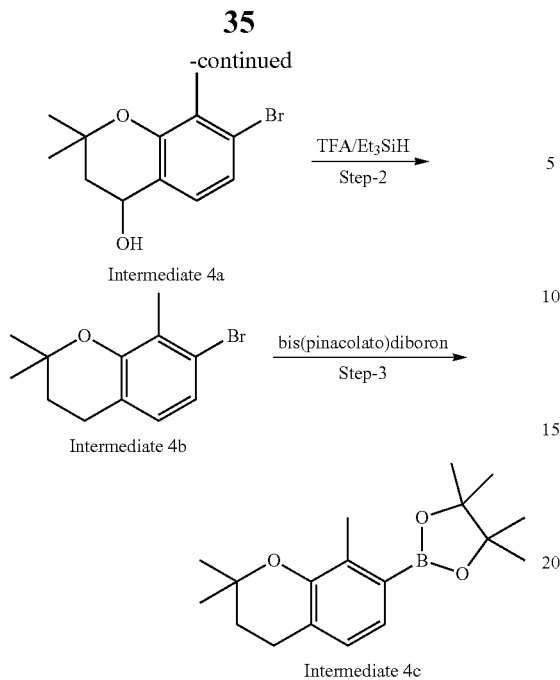

Intermediate 4a

Intermediate 4b

Intermediate 4c

Step-1: 7-Bromo-2,2,8-trimethylchroman-4-ol: To the (0° C.) cooled and stirred solution of Intermediate-3a (2.60 g, 9.66 mmol) in ethanol (30 mL) was added NaBH$_4$ (731 mg, 19.32 mmol) in two portions and the resulting mixture was then stirred at room temperature for 5 h. The reaction was cooled to 0° C. and quenched with ethyl acetate (2 mL). The solvent was evaporated under vacuum and the residue was diluted with ethyl acetate (100 mL). The resulting suspension was filtered and the filtrate was rotary evaporated. The crude product was purified by flash column chromatography (silica gel, 10% ethyl acetate in hexanes system as eluent) to afford 1.20 g (46%) of the title compound as white solid. $^1$HNMR (400 MHz, CDCl$_3$) δ 7.19 (d, J=8.0 Hz, 1H), 7.13 (d, J=8.0 Hz, 1H), 4.86-4.78 (m, 1H), 2.28 (s, 3H), 2.19 (dd, J=13.0, 6.0 Hz, 1H), 1.85 (dd, J=13.0, 6.0 Hz, 1H), 1.67 (d, J=8.0 Hz, 1H), 1.46 (s, 3H), 1.32 (s, 3H); ESI-MS (m/z) 253, 255 [(M-18), Br$^{79,81}$].

Step-2: 7-Bromo-2,2,8-trimethylchroman: To a (0° C.) cooled and stirred solution of step-1 Intermediate, Intermediate-4a, (1.20 g, 4.43 mmol) in DCM (20 mL) was added trifluoroacetic acid (5 mL) followed by the dropwise addition of triethylsilane (1.40 mL, 8.85 mmol). The resulting mixture was then stirred at room temperature for 4 h. The solvent was evaporated under vacuum. The residue was diluted with ethyl acetate (50 mL), cooled to 0° C. and basified with aqueous saturated NaHCO$_3$ solution (25 mL) The layers were separated and the aqueous layer was extracted with ethyl acetate (2×25 mL). The combined organic layers were washed with brine (25 mL), dried (Na$_2$SO$_4$) and filtered. The filtrate was rotary evaporated and the crude product was purified by flash column chromatography (silica gel, 5% ethyl acetate in hexanes system as eluent) to afford 220 mg (19%) of the title compound as white solid. $^1$HNMR (400 MHz, CDCl$_3$) δ 7.02 (d, J=8.0 Hz, 1H), 6.78 (d, J=8.0, Hz, 1H), 2.73 (t, J=6.5 Hz, 2H), 2.27 (s, 3H), 1.79 (t, J=6.5 Hz, 2H), 1.34 (s, 6H); GC-MS (m/z) 254, 256 [(M)$^+$, Br$^{79,81}$].

Step-3: 4,4,5,5-Tetramethyl-2-(2,2,8-trimethylchroman-7-yl)-1,3,2-dioxaborolane: The title compound was prepared from step-2 Intermediate by following the similar procedure as described in step-2 of Intermediate-1. $^1$HNMR (400 MHz, CDCl$_3$) δ 7.23 (d, J=7.5 Hz, 1H), 6.92 (d, J=7.5 Hz, 1H), 2.78 (t, J=7.0 Hz, 2H), 2.39 (s, 3H), 1.79 (t, J=7.0 Hz, 2H), 1.35 (s, 12H), 1.33 (s, 6H); GC-MS (m/z) 302 (M)$^+$.

Intermediate-5a

7-Bromo-2-(((tert-butyldimethylsilyl)oxy)methyl)-2,6-dimethylchroman-4-one and

Intermediate-5b 2-(((tert-Butyldimethylsilyl)oxy)methyl)-2,6-dimethyl-7-(4,4,5,5-tetramethyl-1,3,2-dioxaborolan-2-yl)chroman-4-one

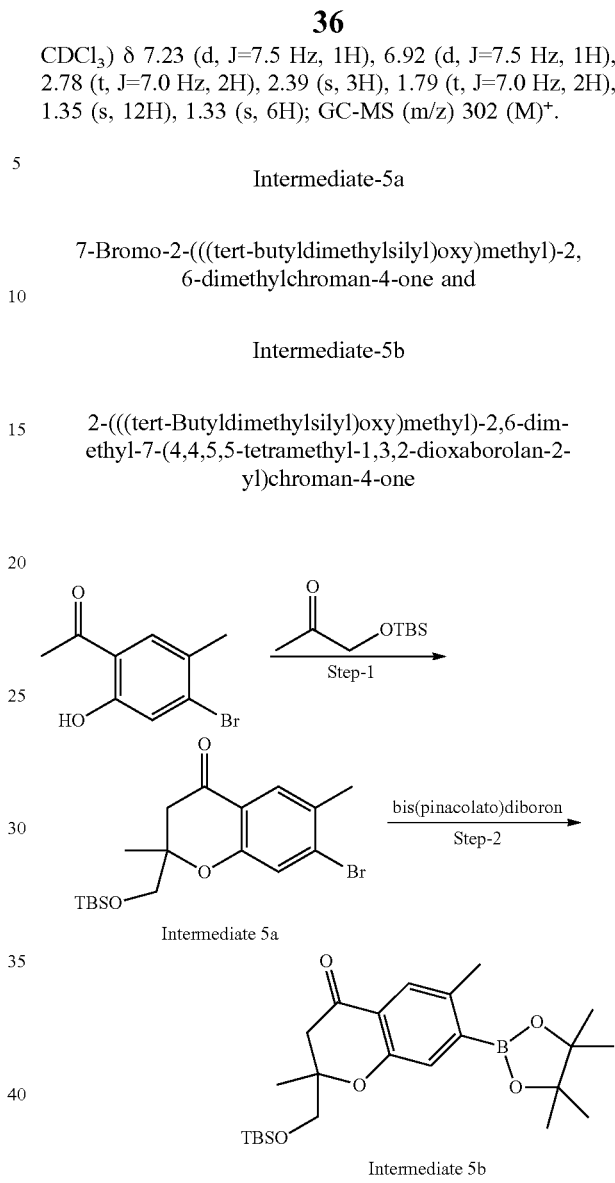

Intermediate 5a

Intermediate 5b

Step-1: 7-bromo-2-(((tert-butyldimethylsilyl)oxy)methyl)-2,6-dimethylchroman-4-one: The title compound was prepared by reacting 1-(4-bromo-2-hydroxy-5-methylphenyl)ethanone with 1-((tert-butyldimethylsilyl)oxy)propan-2-one by following the similar procedure as described in step-1 of the Intermediate-1. $^1$HNMR (400 MHz, CDCl$_3$) δ 7.68 (s, 1H), 7.18 (s, 1H), 3.77 (d, J=10.5 Hz, 1H), 3.60 (d, J=10.5 Hz, 1H), 2.99 (d, J=16.5 Hz, 1H), 2.59 (d, J=16.5 Hz, 1H), 2.35 (s, 3H), 1.35 (s, 3H), 0.86 (s, 9H), 0.05 (s, 3H), 0.02 (s, 3H); ESI-MS (m/z) 399, 401 [(MH)$^+$, Br$^{79,81}$].

Step-2: 2-(((tert-Butyldimethylsilyl)oxy)methyl)-2,6-dimethyl-7-(4,4,5,5-tetramethyl-1,3,2-dioxaborolan-2-yl)chroman-4-one: The title compound was prepared by reacting step-1 Intermediate with bis(pinacolato)diboron by following the similar procedure as described in step-2 of the Intermediate-1. $^1$H NMR (400 MHz, CDCl$_3$) δ 7.61 (s, 1H), 7.33 (s, 1H), 3.77 (d, J=10.5 Hz, 1H), 3.58 (d, J=10.5 Hz, 1H), 3.01 (d, J=16.5 Hz, 1H), 2.58 (d, J=16.5 Hz, 1H), 2.46 (s, 3H), 1.35 (s, 12H), 1.33 (s, 3H), 0.88 (s, 9H), 0.06 (s, 3H), 0.03 (s, 3H); ESI-MS (m/z) 447 (MH)$^+$

Intermediate-6

Methyl-2,6-dimethyl-4-oxo-7-(4,4,5,5-tetramethyl-1,3,2-dioxaborolan-2-yl)chroman-2-carboxylate

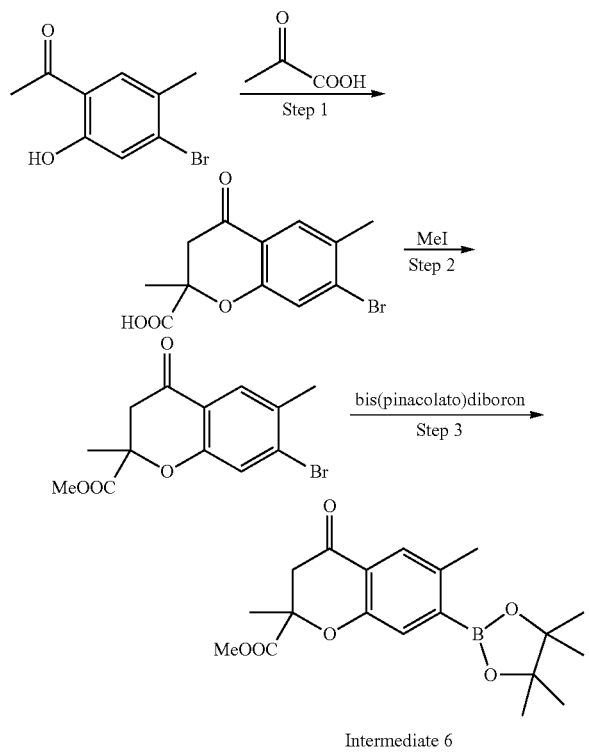

Intermediate 6

Step-1: 7-Bromo-2,6-dimethyl-4-oxochroman-2-carboxylic acid: The title compound was prepared by following the similar procedure as described in step-1 of Intermediate-1. $^1$HNMR (400 MHz, DMSO-d$_6$) δ 7.65 (s, 1H), 7.40 (s, 1H), 3.11 (d, J=16.5 Hz, 1H), 2.99 (d, J=16.5 Hz, 1H), 2.30 (s, 3H), 1.64 (s, 3H); ESI-MS (m/z) 299, 301 [(MH)$^+$, Br$^{79,81}$].

Step-2: Methyl-7-bromo-2,6-dimethyl-4-oxochroman-2-carboxylate: To the (0° C.) cooled and stirred solution of step-1 Intermediate (2.0 g, 6.69 mmol) in DMF (20 mL) was added K$_2$CO$_3$ (1.38 g, 10.03 mmol). The reaction mixture was warmed to room temperature and stirred for 1 h. Iodomethane (544 μL, 8.69 mmol) was added and maintained for another 5 h. The reaction mixture was cooled to 0° C., water (50 mL) was added to the reaction followed by ethyl acetate (100 mL). The layers were separated and aqueous layer was extracted with ethyl acetate (2×50 mL) The combined organic layers were washed with water (2×50 mL), brine (50 mL), dried (Na$_2$SO$_4$) and filtered. The filtrate was rotary evaporated and the crude product was purified by flash column chromatography (silica gel, 20% ethyl acetate in hexane system as eluent) to afford 1.6 g (76%) of the title compound as white semisolid. $^1$HNMR (400 MHz, CDCl$_3$) δ 7.69 (s, 1H), 7.35 (s, 1H), 3.71 (s, 3H), 3.19 (d, J=16.5 Hz, 1H), 2.86 (d, J=16.5 Hz, 1H), 2.36 (s, 3H), 1.73 (s, 3H); ESI-MS (m/z) 313, 315 [(MH)$^+$, Br$^{79,81}$].

Step-3: Methyl-2,6-dimethyl-4-oxo-7-(4,4,5,5-tetramethyl-1,3,2-dioxaborolan-2-yl)chroman-2-carboxylate: The title compound was prepared from step-2 Intermediate by following the similar procedure as described in step-2 of Intermediate-1. $^1$HNMR (400 MHz, CDCl$_3$) δ 7.60 (s, 1H), 7.49 (s, 1H), 3.69 (s, 3H), 3.19 (d, J=16.5 Hz, 1H), 2.86 (d, J=16.5 Hz, 1H), 2.46 (s, 3H), 1.71 (s, 3H), 1.35 (s, 12H); ESI-MS (m/z) 361 (MH)$^+$.

Intermediate-7a tert-Butyl (7-bromo-2,2,6-trimethylchroman-4-yl)carbamate and

Intermediate-7b

7-Bromo-N,N,2,2,6-pentamethylchroman-4-amine

Step-1: 7-Bromo-2,2,6-trimethylchroman-4-one oxime: A mixture of Intermediate-1a (2.10 g, 7.80 mmol) and hydroxylamine hydrochloride (1.62 g, 23.41 mmol) in methanol (5 mL) was heated at 125° C. for 30 min in a microwave reactor (Biotage). The reaction mixture was cooled to room temperature and the solvent was evaporated under vacuum. Water (20 mL) was added to the residue followed by ethyl acetate (50 mL) The layers were separated and aqueous layer was extracted with ethyl acetate (2×30 mL) The combined organic layers were washed with brine (20 mL), dried (Na$_2$SO$_4$) and filtered. The filtrate was rotary evaporated to afford 2.10 g (95%) of the title compound as white solid. $^1$HNMR (400 MHz, CDCl$_3$) δ 7.70 (s, 1H), 7.11 (s, 1H), 2.87 (s, 2H), 2.34 (s, 3H), 1.39 (s, 6H); LC-MS (m/z), 284, 286 [(MH)$^+$, Br$^{79,81}$]

Step-2: 7-Bromo-2,2,6-trimethylchroman-4-amine: To a stirred solution of step-1 Intermediate (300 mg, 1.05 mmol) in acetic acid (10 mL) was added zinc (690 mg, 10.56 mmol) and the resulting mixture was stirred at room temperature for 10 min and then at 110° C. for 6 h. The reaction was cooled to room temperature and filtered through celite bed. The celite cake was washed with acetic acid (20 mL) and the combined filtrates were evaporated under vacuum. The residue was diluted with ethyl acetate (50 mL) and sat. aq. Na₂CO₃ solution (10 mL) was added. The layers were separated and aqueous layer was extracted with ethyl acetate (2×20 mL). The combined organic layers were washed with brine (20 mL), dried (Na₂SO₄) and filtered. The filtrate was rotary evaporated and the crude product was purified by flash column chromatography (silica gel, 5% methanol in dichloromethane system as eluent) to afford 115 mg (40%) of the title compound as white solid. ¹HNMR (400 MHz, CDCl₃) δ 7.33 (s, 1H), 7.00 (s, 1H), 3.95 (dd, J=11.0 & 6.0 Hz, 1H), 2.34 (s, 3H), 2.13-2.05 (m, 1H), 1.71-1.63 (m, 1H), 1.42 (s, 3H), 1.27 (s, 3H); GC-MS (m/z) 269, 271 [M⁺, Br$^{79,81}$]

Step-3: tert-Butyl (7-bromo-2,2,6-trimethylchroman-4-yl)carbamate: To the (0° C.) cooled and stirred solution of step-2 Intermediate (105 mg, 0.389 mmol) in DCM (15 mL) was added BOC₂O (108 μL, 0.46 mmol) followed by triethyl amine (81 μL, 0.58 mmol). The resulting mixture was stirred at room temperature for 18 h. Water (20 mL) was added to the reaction followed by DCM (50 mL). The layers were separated and aqueous layer was extracted with DCM (2×50 mL) The combined organic layers were washed with brine (20 mL), dried (Na₂SO₄) and filtered. The filtrate was rotary evaporated and the crude product was purified by flash column chromatography (silica gel, ethyl acetate-hexanes system as eluent) to afford 120 mg (83%) of the title compound as white solid. ¹HNMR (400 MHz, CDCl₃) δ 7.13 (s, 1H), 7.01 (s, 1H), 4.92-4.85 (m, 1H), 4.64 (d, J=9.0 Hz, 1H), 2.31 (s, 3H), 2.21 (dd, J=13.0, 6.0 Hz, 1H), 1.71-1.62 (m, 1H), 1.52 (s, 9H), 1.41 (s, 3H), 1.30 (s, 3H); GC-MS (m/z) 369, 371 [M⁺, Br$^{79,81}$].

Step-4: 7-Bromo-N,N,2,2,6-pentamethylchroman-4-amine: To the (0° C.) cooled and stirred solution of step-2 Intermediate (300 mg, 1.1 mmol) in methanol (15 mL) was added formaldehyde solution (77 μL, 1.11 mmol, 40% solution in water) followed by acetic acid (6.36 μL, 0.11 mmol). The resulting mixture was stirred for 3 h at room temperature and then sodium cyanoborohydride (209 mg, 3.33 mmol) was added to the above mixture. The reaction was again stirred at room temperature for another 16 h. The solvent was evaporated under vacuum and the crude product was purified by flash column chromatography (silica gel, 10% methanol in DCM) to afford 160 mg (48%) of the title compound as gummy solid. ¹HNMR (400 MHz, DMSO-d₆) δ 7.43 (s, 1H), 6.91 (s, 1H), 3.85 (dd, J=12.0, 6.0 Hz, 1H), 3.44-3.37 (m, 1H), 2.24 (s, 3H), 2.18 (s, 6H), 1.87 (dd, J=12.0, 6.0 Hz, 1H), 1.39 (s, 3H), 1.17 (s, 3H); GC-MS (m/z) 297, 299 [M⁺, Br$^{79,81}$].

Intermediate-8

7-Bromo-2-(((tert-butyldimethylsilyl)oxy)methyl)-2,8-dimethylchroman-4-one

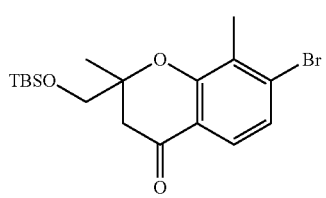

Intermediate 8

The title compound was prepared from the corresponding starting material, by following the similar procedure as described in Intermediate-3a. ¹HNMR (400 MHz, CDCl₃) δ 7.57 (d, J=8.5 Hz, 1H), 7.18 (d, J=8.5 Hz, 1H), 3.79 (d, J=10.5 Hz, 1H), 3.64 (d, J=10.5 Hz, 1H), 2.99 (d, J=16.5 Hz, 1H), 2.61 (d, J=16.5 Hz, 1H), 2.32 (s, 3H), 1.37 (s, 3H), 0.87 (s, 9H), 0.05 (s, 3H), 0.02 (s, 3H); ESI-MS (m/z), 399, 401[(MH)⁺, Br$^{79,81}$].

Intermediate-9

2-(((tert-Butyldimethylsilyl)oxy)methyl)-6-ethyl-2-methyl-7-(4,4,5,5-tetramethyl-1,3,2-dioxaborolan-2-yl)chroman-4-one

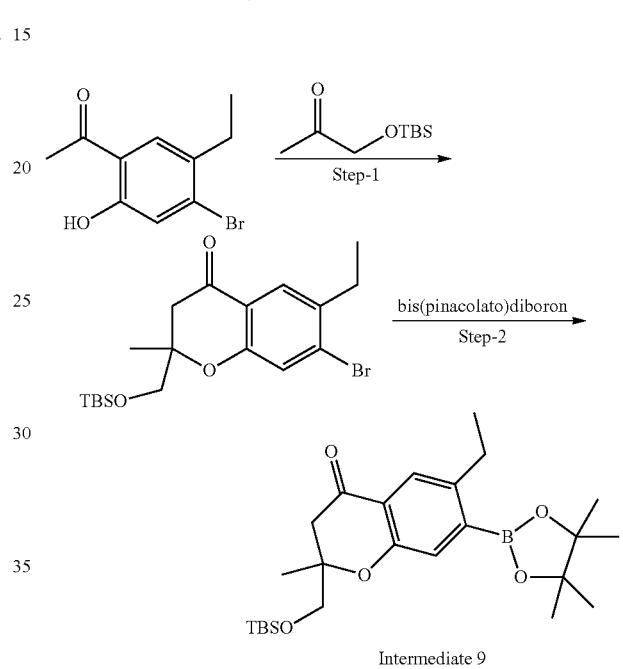

Intermediate 9

The title compound was prepared by following the similar procedure as described in Intermediate-5. ¹HNMR (400 MHz, CDCl₃) δ 7.64 (s, 1H), 7.32 (s, 1H), 3.78 (d, J=10.5 Hz, 1H), 3.58 (d, J=10.5 Hz, 1H), 3.01 (d, J=16.5 Hz, 1H), 2.84 (q, J=7.5 Hz, 2H), 2.59 (d, J=16.5 Hz, 1H), 1.36 (s, 12H), 1.33 (s, 3H), 1.18 (t, J=7.5 Hz, 3H), 0.87 (s, 9H), 0.06 (s, 3H), 0.02 (s, 3H).

Intermediate-10a

7-Bromo-2,2-bis(((tert-butyldimethylsilyl)oxy)methyl)-6-methylchroman-4-one and

Intermediate-10b 2,2-Bis(((tert-butyldimethylsilyl)oxy)methyl)-6-methyl-7-(4,4,5,5-tetramethyl-1,3,2-dioxaborolan-2-yl)chroman-4-one

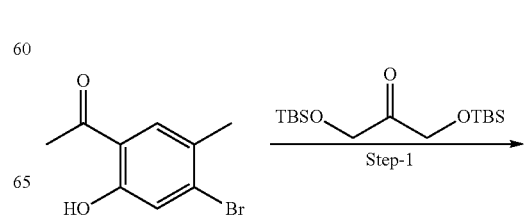

-continued

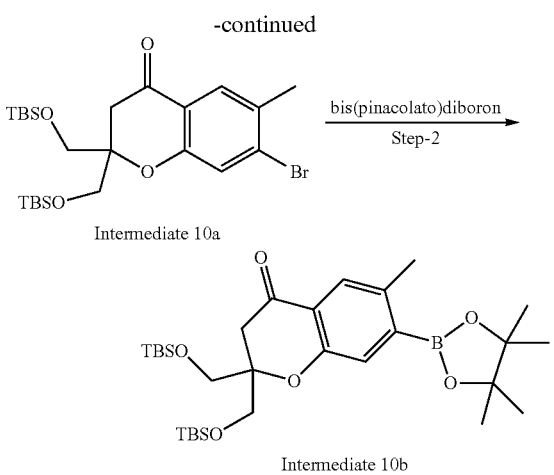

Intermediate 10a

Intermediate 10b

The title compounds were prepared by following the similar procedure as described in Intermediate-5.

Intermediate-10a: $^1$HNMR (400 MHz, CDCl$_3$) δ 7.66 (s, 1H), 7.16 (s, 1H), 3.72 (s, 4H), 2.85 (s, 2H), 2.34 (s, 3H), 0.85 (s, 18H), 0.03 (s, 6H), 0.01 (s, 6H).

Intermediate-10b: $^1$HNMR (400 MHz, CDCl$_3$) δ 7.59 (s, 1H), 7.31 (s, 1H), 3.71 (s, 4H), 2.87 (s, 2H), 2.45 (s, 3H), 1.36 (s, 12H), 0.86 (s, 18H), 0.03 (s, 6H), 0.01 (s, 6H).

Intermediate-11

6-Bromo-5-methylspiro[chroman-2,1'-cyclobutan]-4-one

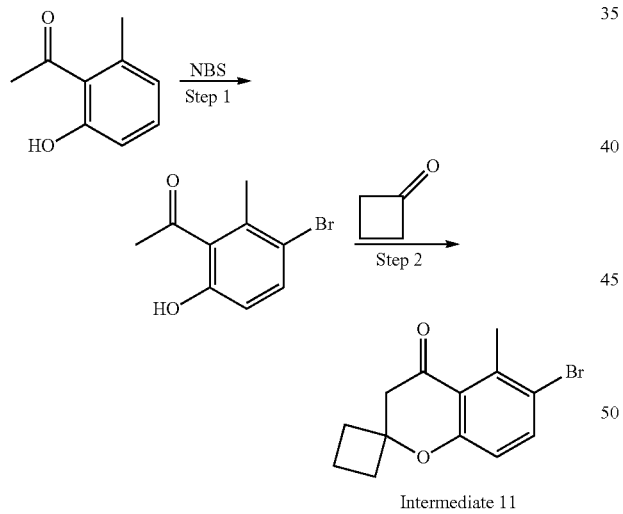

Intermediate 11

Step-1: 1-(3-Bromo-6-hydroxy-2-methylphenyl)ethanone: To a stirred solution of 1-(2-hydroxy-6-methylphenyl)ethanone (prepared by following the similar procedure as reported in *Eur. J. Med. Chem.*, 2010, 45(11), 4788; (200 mg, 1.33 mmol) in acetonitrile (5 mL) was added p-toluenesulfonic acid monohydrate (127 mg, 0.66 mmol) at RT. The resulting mixture was stirred for 5 min then added NBS (237 mg, 1.33 mmol) and further maintained for 2 h at the same temperature. The reaction was then quenched by the addition of Na$_2$S$_2$O$_3$ (10%, 2 mL) followed by the addition of water (5 mL) and diethyl ether (5 mL) The layers were separated and the aqueous layer was extracted with diethyl ether (2×10 mL). The combined organic layers were washed with brine (10 mL), dried (Na$_2$SO$_4$) and filtered. The filtrate was evaporated and the crude product was purified by flash column chromatography (silica gel, 5% ethyl acetate-hexanes system as eluent) to afford 200 mg (65%) of the title compound as white solid. $^1$HNMR (400 MHz, CDCl$_3$) δ 10.76 (s, 1H), 7.55 (d, J=8.0 Hz, 1H), 6.75 (d, J=8.0 Hz, 1H), 2.64 (s, 3H), 2.59 (s, 3H); ESI-MS (m/z) 227, 229 [(M-H), Br$^{79,81}$].

Step-2: 6-Bromo-5-methylspiro[chroman-2,1'-cyclobutan]-4-one: A mixture of Step-1 Intermediate (2.70 g, 11.79 mmol), cyclobutanone (0.8 mL, 11.79 mmol) and pyrrolidine (1.95 mL, 23.57 mmol) in methanol (30 mL) was refluxed for 16 h. The reaction was cooled to RT and the solvent was evaporated under vacuum. Ethyl acetate (100 mL) was added to the above obtained residue and the organic layer was washed with water (50 mL), aqueous hydrochloric acid (2N, 50 mL), saturated aqueous NaHCO$_3$ solution (50 mL), brine (50 mL), dried (Na$_2$SO$_4$) and filtered. The filtrate was evaporated and the crude product was purified by flash column chromatography (silica gel, 5% ethyl acetate in hexanes system as eluent) to afford 153 mg (4%) of the title compound as white solid. $^1$HNMR (400 MHz, CDCl$_3$) δ 7.60 (d, J=8.0 Hz, 1H), 6.75 (d, J=8.0 Hz, 1H), 2.90 (s, 2H), 2.75 (s, 3H), 2.36-2.28 (m, 2H), 2.20-2.13 (m, 2H), 1.96-1.90 (m, 1H), 1.73-1.70 (m, 1H); ESI-MS (m/z) 281, 283 [(MH)$^+$, Br$^{79,81}$].

Intermediate-12a

7-Bromo-6-methylspiro[chroman-2,1'-cyclobutan]-4-one and

Intermediate-12b and

Intermediate-12c

7-Bromo-6-methylspiro[chroman-2,1'-cyclobutane] and

Intermediate-12d

6-Methyl-7-(4,4,5,5-tetramethyl-1,3,2-dioxaborolan-2-yl)spiro[chroman-2,1'-cyclobutan]-4-one

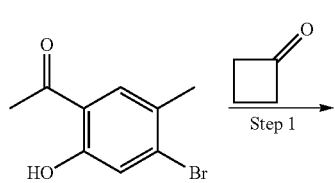

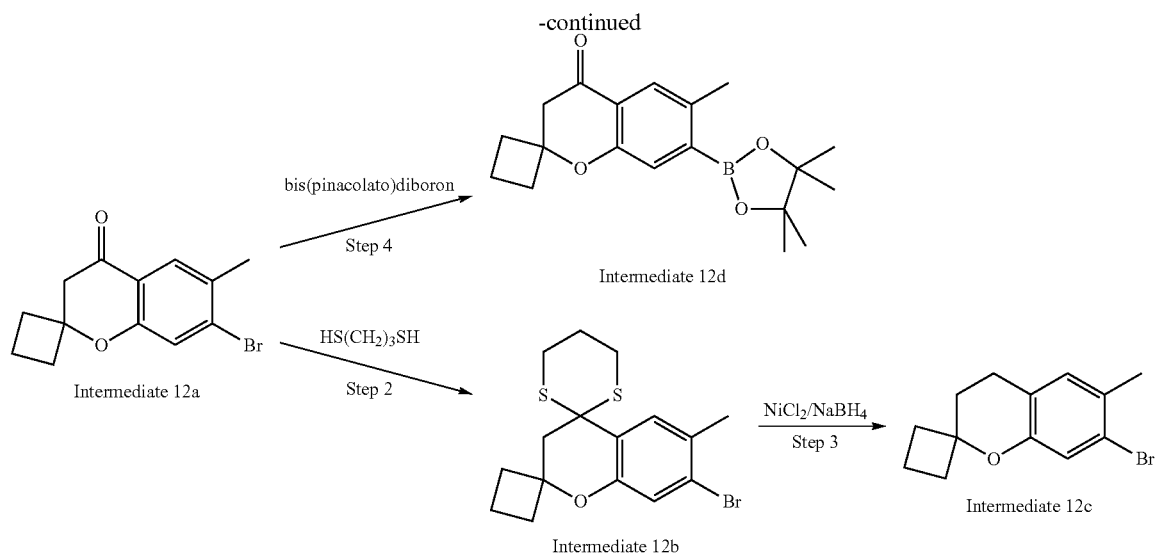

Step-1: 7-Bromo-6-methylspiro[chroman-2,1'-cyclobutan]-4-one: The title compound was prepared by following the similar procedure as described in step-2 of Intermediate-11 by reacting 1-(4-bromo-2-hydroxy-5-methylphenyl)ethanone (prepared by following the similar procedure as described in WO2012028629; 6.0 g, 26.2 mmol) with cyclobutanone (1.97 mL, 26.2 mmol). $^1$HNMR (400 MHz, CDCl$_3$) δ 7.69 (s, 1H), 7.24 (s, 1H), 2.88 (s, 2H), 2.35 (s, 3H), 2.33-2.27 (m, 2H), 2.16-2.12 (m, 2H), 1.97-1.92 (m, 1H), 1.74-1.66 (m, 1H); ESI-MS (m/z) 281, 283 [(MH)$^+$, Br$^{79,81}$].

Step-2: To a stirred solution of step-1 Intermediate (333 mg, 1.18 mmol) in DCM (10 mL) was added propane-1,3-dithiol (119 μL, 1.18 mmol) and boron trifluoride diethyl etherate (15 μL, 0.118 mmol) at RT and continued stirring for 16 h at the same temperature. Water (100 mL) was added to the reaction followed by DCM (10 mL). The layers were separated and the aqueous layer was extracted with DCM (3×10 mL) The combined organic layers were washed with brine (10 mL), dried (Na$_2$SO$_4$) and filtered. The filtrate was rotary evaporated and the crude product was purified by flash column chromatography (silica gel, 5% ethyl acetate in hexanes as eluent) to afford 300 mg (75%) of the title compound as yellow solid. $^1$HNMR (400 MHz, CDCl$_3$) δ 7.65 (s, 1H), 7.08 (s, 1H), 3.29-3.22 (m, 2H), 2.89 (s, 2H), 2.84-2.78 (m, 2H), 2.50-2.44 (m, 2H), 2.34 (s, 3H), 2.25-2.20 (m, 3H), 2.03-2.00 (m, 2H), 1.76-1.72 (m, 1H); ESI-MS (m/z) [(MH)$^+$, Br$^{79,81}$].

Step-3: 7-Bromo-6-methylspiro[chroman-2,1'-cyclobutane]: To a (0° C.) cooled solution of step-2 Intermediate (220 mg, 0.59 mmol) and nickel chloride hexahydrate (1.40 g, 5.92 mmol) in methanol/THF (9 mL, 2:1) was added sodium borohydride (672 mg, 17.77 mmol) in five equal portions. The resulting mixture was continued to stir at 0° C. for 1 h and then filtered through celite bed. The filtrate was rotary evaporated and the crude product was purified by flash column chromatography (silica gel, 2% ethyl acetate in hexanes system as eluent) to afford 50 mg (31%) of the title compound as white solid. $^1$HNMR (400 MHz, CDCl$_3$) δ 7.02 (s, 1H), 6.90 (s, 1H), 2.70 (t, J=6.5 Hz, 2H), 2.33-2.21 (m, 5H), 2.10-2.01 (m, 2H), 1.95 (t, J=6.5 Hz, 2H), 1.92-1.83 (m, 1H), 1.73-1.62 (m, 1H). ESI-MS (m/z) 266, 268 [(MH)$^+$, Br$^{79,81}$].

Step-4: 6-Methyl-7-(4,4,5,5-tetramethyl-1,3,2-dioxaborolan-2-yl)spiro[chroman-2,1'-cyclobutan]-4-one: The title compound was prepared from step-1 Intermediate by following the similar procedure as described in step-2 of Intermediate-1. $^1$HNMR (400 MHz, CDCl$_3$) δ 7.60 (s, 1H), 7.30 (s, 1H), 2.89 (s, 2H), 2.46 (s, 3H), 2.33-2.30 (m, 2H), 2.29-2.27 (m, 2H) 2.33-2.30 (m, 1H), 2.29-2.27 (m, 1H), 1.03 (m, 12H); ESI-MS (m/z) 329 (MH)$^+$.

Intermediate-13a

6-Bromo-7-methylspiro[chroman-2,1'-cyclobutan]-4-one and

Intermediate-13b

6-Bromo-7-methylspiro[chroman-2,1'-cyclobutane]

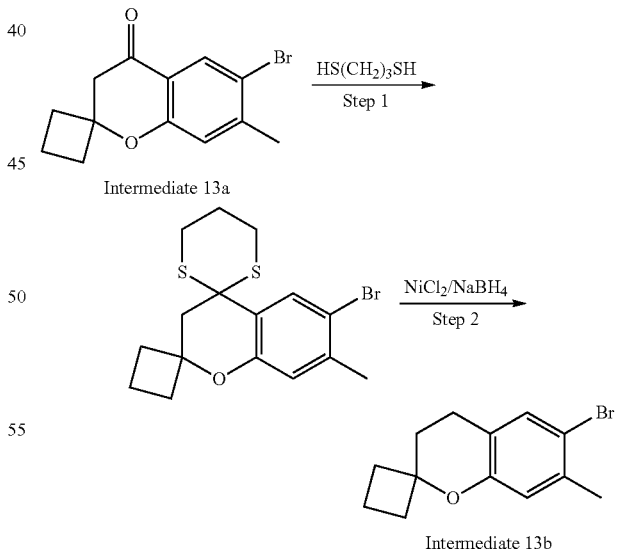

Step-1: The title compound was prepared by reacting 6-Bromo-7-methylspiro[chroman-2,1'-cyclobutan]-4-one (prepared by following the similar procedure as described in WO2007042906; 538 mg, 1.91 mmol) with propane-1,3-dithiol (192 μL, 1.91 mmol) by following the similar procedure as described in step-2 of Intermediate-12. $^1$HNMR (400 MHz, CDCl$_3$) δ 7.94 (s, 1H), 6.76 (s, 1H), 3.27-3.20

(m, 2H), 2.88 (s, 2H), 2.83-2.78 (m, 2H), 2.50-2.45 (m, 2H), 2.32 (s, 3H), 2.23-2.19 (m, 3H), 2.01-1.97 (m, 2H), 1.80-1.70 (m, 1H).

Step-2: 6-Bromo-7-methylspiro[chroman-2,1'-cyclobutane]: To a (0° C.) cooled solution of Step-1 Intermediate (220 mg, 0.59 mmol) and nickel chloride hexahydrate (1.40 g, 5.92 mmol) in methanol/THF (9 mL, 2:1) was added sodium borohydride (672 mg, 17.77 mmol) in five equal portions. The resulting mixture was continued to stir at 0° C. for 1 h and then filtered through celite bed. The filtrate was rotary evaporated and the crude product was purified by flash column chromatography (silica gel, 2% ethyl acetate in hexanes system as eluent) to afford 50 mg (31%) of the title compound as white solid. $^1$HNMR (400 MHz, CDCl$_3$) δ 7.19 (s, 1H), 6.70 (s, 1H), 2.76-2.73 (m, 2H), 2.30 (s, 3H), 2.28-2.23 (m, 2H), 2.08-2.03 (m, 2H), 1.97-1.87 (m, 3H), 1.68-1.63 (m, 1H); GC-MS (m/z) 266, 268 [(M)$^+$, Br$^{79,81}$].

Intermediate-14

7-Bromo-8-methylspiro[chroman-2,1'-cyclobutan]-4-one

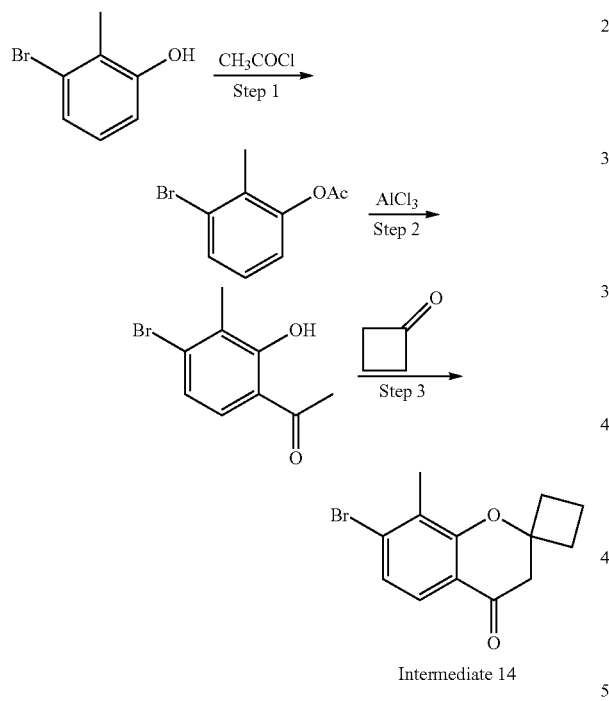

Intermediate 14

Step-1: 3-Bromo-2-methylphenyl acetate: To an ice cooled solution of 3-bromo-2-methylphenol (prepared by following the similar procedure as reported in US20110082165; 4.0 g, 21.39 mmol) and pyridine (1.73 mL, 21.39 mmol) in DCM (20 mL) was added acetyl chloride (1.52 mL, 21.39 mmol) drop-wise and the mixture was then stirred for 16 h at RT. Water (50 mL) was then added to the reaction followed by DCM (50 mL). The layers were separated and the aqueous layer was extracted with DCM (2×50 mL) and the combined organic layers were washed with brine, dried (Na$_2$SO$_4$) and filtered. The filtrate was evaporated and the crude product was purified by flash column chromatography to afford 3.80 g (78%) of the title product as oil. $^1$H NMR (400 MHz, CDCl$_3$) δ 7.46 (d, J=8.0, Hz, 1H), 7.09 (t, J=8.0 Hz, 1H), 7.00 (d, J=8.0, Hz, 1H), 2.35 (s, 3H), 2.27 (s, 3H).

Step-2: 1-(4-Bromo-2-hydroxy-3-methylphenyl)ethanone: A mixture of step-1 Intermediate (3.0 g, 13.10 mmol) and aluminum chloride (2.62 g, 19.64 mmol) in a sealed tube was heated at 110° C. for 3 h. The reaction was then cooled to RT, 10% aqueous hydrochloric acid (5 mL) was added to the reaction and then heated to reflux for another 10 min. The reaction was cooled to RT, DCM (100 mL) was then added followed by water (50 mL) and the layers were separated. The aqueous layer was extracted with DCM (2×50 mL) and the combined organic layers were washed with brine (50 mL), dried (Na$_2$SO$_4$) and filtered. The filtrate was rotary evaporated and the crude product was purified by flash column chromatography (silica gel, 5% ethyl acetate in hexanes system as eluent) to afford 2.20 g (73%) of the title compound as oil. $^1$H NMR (400 MHz, CDCl$_3$) δ 12.87 (s, 1H), 7.45 (d, J=8.5 Hz, 1H), 7.12 (d, J=8.5 Hz, 1H), 2.63 (s, 3H), 2.36 (s, 3H).

Step-3: 7-Bromo-8-methylspiro[chroman-2,1'-cyclobutan]-4-one: The title compound was prepared by reacting step-2 Intermediate with cyclobutanone by following the similar procedure as described for step-2 of Intermediate 11. $^1$H NMR (400 MHz, CDCl$_3$) δ 7.58 (d, J=8.5, Hz, 1H), 7.21 (d, J=8.5 Hz, 1H), 2.90 (s, 2H), 2.37 (s, 3H), 2.30-2.34 (m, 2H), 2.18-2.22 (m, 2H), 2.02-1.90 (m, 1H), 1.75 (m, 1H).

Intermediate-15a

7-Bromo-6-ethylspiro[chroman-2,1'-cyclobutan]-4-one and

Intermediate-15b

6-Ethyl-7-(4,4,5,5-tetramethyl-1,3,2-dioxaborolan-2-yl)spiro[chroman-2,1'-cyclobutan]-4-one

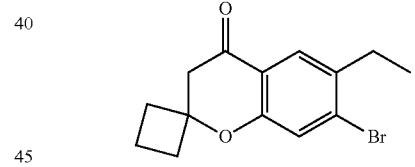

Intermediate 15a

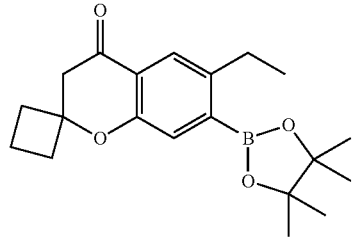

Intermediate 15b

Intermediate-15a: The title compound was prepared from 3-bromo-4-ethylphenol (prepared by following the similar procedure as reported in *J. Chem. Soc.*, 1955, 2772) by following the similar procedure as described in Intermediate-14. $^1$H NMR (400 MHz, CDCl$_3$) δ 7.70 (s, 1H), 7.25 (s, 1H), 2.89 (s, 2H), 2.72 (q, J=7.0 Hz, 2H), 2.39-2.26 (m, 2H), 2.23-2.10 (m, 2H), 1.99-1.87 (m 1H), 1.78-1.66 (m 1H), 1.23 (t, J=7.0 Hz, 3H); GC-MS (m/z) 294, 296 [(M)$^+$, Br$^{79,81}$]

Intermediate-15b: To a nitrogen purged solution of Intermediate-15a, potassium acetate (0.332 g, 3.39 mmol) and bis(pinacolato)diboron (0.645 g, 2.54 mmol) in toluene (10 mL) was added PdCl$_2$(dppf)-CH$_2$Cl$_2$ adduct (0.138 g, 0.169 mmol). The resulting mixture was heated at 150° C. for 30 mins in microwave (Biotage). The reaction mixture was then cooled to rt and filtered through Celite bed. The filtrate was concentrated under vacuum and the crude product was purified by flash column chromatography to give 300 mg (51%) of the desired product as a white solid. $^1$HNMR (400 MHz, CDCl$_3$) δ 7.64 (s, 1H), 7.40 (s, 1H), 2.89 (s, 2H), 2.84 (q, J=7.5 Hz, 2H), 2.38-2.24 (m, 2H), 2.23-2.11 (m, 2H), 1.99-1.85 (m, 1H), 1.77-1.66 (m, 1H), 1.36 (s, 12H), 1.18 (t, J=7.5 Hz, 3H); ESI-MS (m/z) 343 (MH)$^+$.

Intermediate-16a

Spiro[chromene-2,1'-cyclobutan]-4-yl trifluoromethanesulfonate and

Intermediate-16b 4,4,5,5-Tetramethyl-2-(spiro[chromene-2,1'-cyclobutan]-4-yl)-1,3,2-dioxaborolane

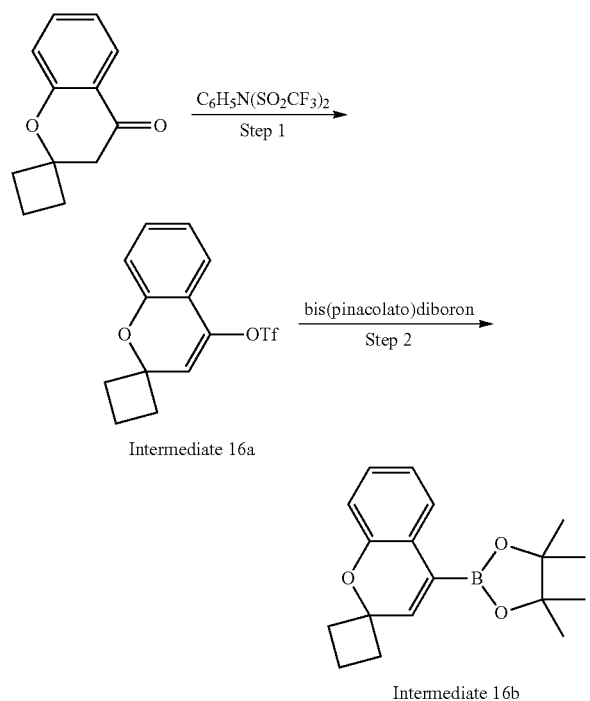

Intermediate 16a

Intermediate 16b

Step-1: Spiro[chromene-2,1'-cyclobutan]-4-yl trifluoromethanesulfonate: To a (−78° C.). cooled and stirred solution of spiro[chroman-2,1'-cyclobutan]-4-one (1.50 g, 7.97 mmol; prepared by following the similar procedure as described in WO2007042906) in THF (30 mL) was added sodium bis(trimethylsilyl)amide (15.9 mL, 15.9 mmol, 1M in THF) followed by 1,1,1-trifluoro-N-phenyl-N-((trifluoromethyl)sulfonyl)methanesulfonimide (5.98 g, 16.74 mmol) in THF (20 mL). The resulting mixture was allowed to warm to room temperature over a period of 3 h. Ice cooled water (20 mL) was added to the reaction followed by ethyl acetate (50 mL) The layers were separated and the aqueous layer was extracted with ethyl acetate (2×50 mL) The combined organic layers were washed with brine (20 mL), dried (Na$_2$SO$_4$) and filtered. The filtrate was rotary evaporated and the crude product was purified by flash column chromatography (silica gel, ethyl acetate-hexanes system as eluent) to afford 1.0 g (39%) of the title compound as colorless oil. $^1$HNMR (400 MHz, CDCl$_3$) δ 7.28-7.23 (m, 2H), 6.96 (t, J=8.0 Hz, 1H), 6.88 (d, J=8.0 Hz, 1H), 5.98 (s, 1H), 2.61-2.53 (m, 2H), 2.39-2.29 (m, 2H), 1.98-1.88 (m, 1H), 1.79-1.69 (m, 1H); ESI-MS (m/z) 321 (MH)$^+$ Step-2: 4,4,5,5-Tetramethyl-2-(spiro[chromene-2,1'-cyclobutan]-4-yl)-1,3,2-dioxaborolane: In a sealed tube, to a nitrogen purged suspension of a potassium acetate (190 mg, 2.02 mmol) in dioxane (10 mL) was added step-1 Intermediate (500 mg, 1.56 mmol) followed by bis(pinacolato) diboron (595 mg, 2.34 mmol). The resulting mixture was thoroughly deoxygenated by purging nitrogen gas for another 10 min and then PdCl$_2$(dppf)-CH$_2$Cl$_2$ adduct (64 mg, 0.07 mmol) was added to the above mixture. The sealed tube was capped and stirred at 100° C. for 16 h. The reaction mixture was cooled back down to room temperature and filtered through celite. The celite cake was washed with ethyl acetate. The filtrate was rotary evaporated and the crude product was purified by flash column chromatography (silica gel, ethyl acetate-hexanes system as eluent) to afford 210 mg (21%) of the title compound as white solid. $^1$HNMR (400 MHz, CDCl$_3$) δ 7.72 (d, J=8.0 Hz, 1H), 7.15-7.06 (m, 1H), 6.93-6.85 (m, 1H), 6.81 (d, J=8.0 Hz, 1H), 6.76 (s, 1H), 2.52-2.40 (m, 2H), 2.29-2.23 (m, 2H), 1.92-1.79 (m, 1H), 1.78-1.73 (m, 1H), 1.36 (s, 12H); ESI-MS (m/z) 299 (MH)$^+$ The following Intermediates (17a-30a) given in Table-1 were prepared from the corresponding starting materials by following the similar procedure as described in Intermediate-16a.

TABLE 1

| Intermediate No: IUPAC name | Structure | $^1$HNMR/ESI-MS |
|---|---|---|
| Intermediate-17a: 5-Methylspiro[chromene-2,1'-cyclobutan]-4-yl trifluoromethanesulfonate | 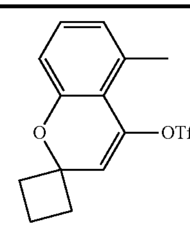 | $^1$HNMR (400 MHz, CDCl$_3$) δ 7.13 (t, J = 8.0 Hz, 1H), 6.80 (d, J = 8.0 Hz, 1H), 6.77 (d, J = 8.0 Hz, 1H), 6.05 (s, 1H), 2.57-2.42 (m, 5H), 2.30-2.24 (m, 2H), 2.00-1.88 (m, 1H), 1.79-1.70 (m, 1H); LC-MS (m/z), 335 (MH)$^+$. |

TABLE 1-continued

| Intermediate No: IUPAC name | Structure | ¹HNMR/ESI-MS |
|---|---|---|
| Intermediate-18a: 6-Methylspiro[chromene-2,1'-cyclobutan]-4-yl trifluoromethanesulfonate | 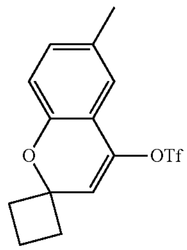 [SMILES: Cc1ccc2c(c1)C(OS(=O)(=O)C(F)(F)F)=CC1(CCC1)O2] | ¹HNMR (400 MHz, CDCl₃) δ 7.07-7.02 (m, 2H), 6.78 (d, J = 8.0 Hz, 1H), 5.96 (s, 1H), 2.59-2.49 (m, 2H), 2.35-2.31 (m, 2H), 2.30 (s, 3H), 1.95-1.87 (m, 1H), 1.78-1.69 (m, 1H). |
| Intermediate-19a: 7-Methylspiro[chromene-2,1'-cyclobutan]-4-yl trifluoromethanesulfonate | 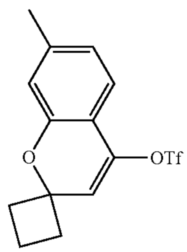 [SMILES: Cc1ccc2c(c1)OC1(C=C2OS(=O)(=O)C(F)(F)F)CCC1] | ¹HNMR (400 MHz, CDCl₃) δ 7.15 (d, J = 8.0 Hz, 1H), 6.68 (dd, J = 2.0 & 8.0 Hz, 1H), 6.64 (d, J = 2.0 Hz, 1H), 5.46 (s, 1H), 2.48-2.42 (m, 2H), 2.30 (s, 3H), 2.22-2.16 (m, 2H), 1.91-1.78 (m, 1H), 1.70-1.65 (m, 1H); ESI-MS (m/z) 335 (MH)⁺. |
| Intermediate-20a: 8-Methylspiro[chromene-2,1'-cyclobutan]-4-yl trifluoromethanesulfonate | 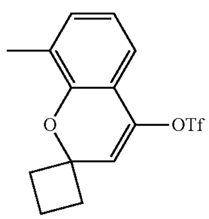 [SMILES: Cc1cccc2c1OC1(C=C2OS(=O)(=O)C(F)(F)F)CCC1] | ¹HNMR (400 MHz, DMSO-d₆) δ 7.23-7.20 (d, J = 8.0 Hz, 1H), 7.01 (d, J = 8.0 Hz, 1H), 6.94 (t, J = 8.0 Hz, 1H), 6.47 (s, 1H), 2.47-2.40 (m, 2H), 2.34-2.28 (m, 2H), 2.19 (s, 3H), 1.85-1.79 (m, 2H); ESI-MS (m/z) 335 (MH)⁺. |
| Intermediate-21a: 2,2-Dimethyl-2H-chromen-4-yl trifluoromethanesulfonate | 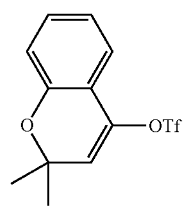 [SMILES: CC1(C)C=C(OS(=O)(=O)C(F)(F)F)c2ccccc2O1] | ¹HNMR (400 MHz, CDCl₃) δ 7.29-7.22 (m, 2H), 6.99-6.94 (m, 1H), 6.88-6.84 (m, 1H), 5.64 (s, 1H), 1.54 (s, 6H). |
| Intermediate-22a: 2,2,6-Trimethyl-2H-chromen-4-yl trifluoromethanesulfonate | 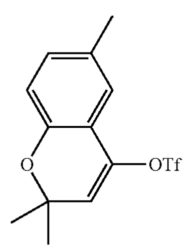 [SMILES: Cc1ccc2c(c1)C(OS(=O)(=O)C(F)(F)F)=CC(C)(C)O2] | ¹HNMR (400 MHz, DMSO-d₆) δ 7.12 (dd, J = 2.0 & 8.0 Hz, 1H), 6.97 (d, J = 2.0 Hz, 1H), 6.81 (d, J = 8.0 Hz, 1H), 6.06 (s, 1H), 2.25 (s, 3H), 1.45 (s, 6H); ESI-MS (m/z) 323 (MH)⁺. |
| Intermediate-23a: 2,2,7-Trimethyl-2H-chromen-4-yl trifluoromethanesulfonate | 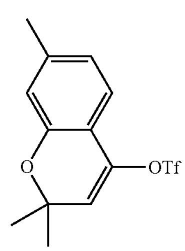 [SMILES: Cc1ccc2c(c1)OC(C)(C)C=C2OS(=O)(=O)C(F)(F)F] | ¹HNMR (400 MHz, CDCl₃) δ 7.14 (d, J = 8.0 Hz, 1H), 6.78 (dd, J = 8.0 & 2.0 Hz, 1H), 6.69 (d, J = 2.0 Hz, 1H), 5.57 (s, 1H), 2.33 (s, 3H), 1.52 (s, 6H); ESI-MS (m/z) 323 (MH)⁺. |

TABLE 1-continued

| Intermediate No: IUPAC name | Structure | 1HNMR/ESI-MS |
|---|---|---|
| Intermediate-24a: 2,2,8-Trimethyl-2H-chromen-4-yl trifluoromethanesulfonate | *structure* | 1HNMR (400 MHz, CDCl$_3$) δ 7.14-7.10 (m, 2H), 6.86 (t, J = 8.0 Hz, 1H), 5.60 (s, 1H), 2.20 (s, 3H), 1.54 (s, 6H); ESI-MS (m/z) 323 (MH)+. |
| Intermediate-25a: 2-(Methoxymethyl)-2-methyl-2H-chromen-4-yl trifluoromethanesulfonate | *structure* | 1HNMR (400 MHz, CDCl$_3$) δ 7.28-7.24 (m, 2H), 6.97 (t, J = 8.0 Hz, 1H), 6.88 (d, J = 8.0 Hz, 1H), 5.68 (s, 1H), 3.59-3.50 (m, 2H), 3.43 (s, 3H), 1.51 (s, 3H); ESI-MS (m/z) 339 (MH)+. |
| Intermediate-26a: 2-(Methoxymethyl)-2,6-dimethyl-2H-chromen-4-yl trifluoromethanesulfonate | *structure* | 1HNMR (400 MHz, CDCl$_3$) δ 7.06 (d, J = 8.0 Hz, 1H), 7.06 (s, 1H), 6.78 (d, J = 8.0 Hz, 1H), 5.66 (s, 1H), 3.57-3.50 (m, 2H), 3.42 (s, 3H), 2.30 (s, 3H), 1.49 (s, 3H); ESI-MS (m/z) 353 (MH)+. |
| Intermediate-27a: 2-(((tert-Butyldimethylsilyl)oxy)methyl)-2-methyl-2H-chromen-4-yl trifluoromethanesulfonate | *structure* | 1HNMR (400 MHz, CDCl$_3$) δ 7.26-7.21 (m, 2H), 6.96-6.92 (m, 1H), 6.83-6.81 (m, 1H), 5.67 (s, 1H), 3.77 (d, J = 12.0 Hz, 1H), 3.65 (d, J = Hz, 1H) 1.48 (s, 3H), 0.85 (s, 9H), 0.05 (s, 3H), 0.03 (s, 3H). |
| Intermediate-28a: 2-(((tert-Butyldimethylsilyl)oxy)methyl)-2,6-dimethyl-2H-chromen-4-yl trifluoromethanesulfonate | *structure* | 1HNMR (400 MHz, DMSO-d$_6$) δ 7.09 (dd, J = 8.0 & 2.0, Hz, 1H), 6.93 (d, J = 2.0, Hz, , 1H), 6.75 (d, J = 8.0 Hz, 1H), 5.91 (s, 1H), 3.68 (s, 2H), 2.23 (s, 3H), 1.37 (s, 3H), 0.75 (s, 9H), −0.01 (s, 3H), −0.07 (s, 3H). |
| Intermediate-29a: 2-(Methoxymethyl)-2,8-dimethyl-2H-chromen-4-yl trifluoromethanesulfonate | *structure* | 1HNMR (400 MHz, CDCl$_3$) δ 7.14-7.10 (m, 2H), 6.90-6.85 (m, 1H), 5.69 (s, 1H), 3.60 (d, J = 9.5 Hz, 1H), 3.51 (d, J = 9.5 Hz, 1H), 3.43 (s, 3H), 2.20 (s, 3H), 1.50 (s, 3H). |

TABLE 1-continued

| Intermediate No: IUPAC name | Structure | ¹HNMR/ESI-MS |
|---|---|---|
| Intermediate-30a: 2-(((tert-Butyldimethylsilyl)oxy)methyl)-2,8-dimethyl-2H-chromen-4-yl trifluoromethanesulfonate | (structure shown) | ¹HNMR (400 MHz, CDCl₃) δ 7.13-7.08 (m, 2H), 6.86-6.82 (m, 1H), 5.67 (s, 1H), 3.77 (d, J = 10.0 Hz, 1H), 3.66 (d, J = 10.0 Hz, 1H), 2.19 (s, 3H), 1.47 (s, 3H), 0.86 (s, 9H), 0.05 (s, 3H), 0.02 (s, 3H). |

Intermediate-18b 4,4,5,5-Tetramethyl-2-(6-methylspiro[chromene-2,1'-cyclobutan]-4-yl)-1,3,2-dioxaborolane

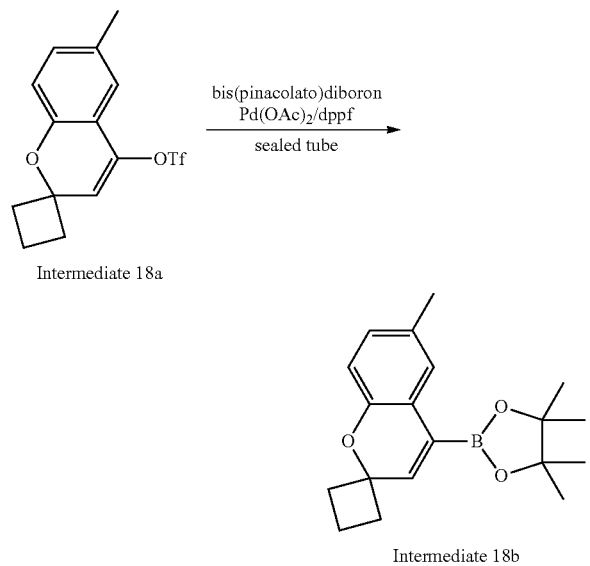

In a sealed tube, to a nitrogen purged suspension of a potassium acetate (572 mg, 5.83 mmol) in dioxane (10 mL) was added Intermediate-18a (1.30 g, 3.89 mmol) followed by bis(pinacolato)diboron (987 mg, 3.87 mmol). The resulting mixture was thoroughly deoxygenated by purging nitrogen gas for another 10 min and then palladium acetate (87 mg, 0.389 mmol) and 1,1'-bis(diphenylphosphino)ferrocene (216 mg, 0.38 mmol) were added to the above mixture. The sealed tube was capped and stirred at 100° C. for 4 h. The reaction mixture was cooled back down to room temperature and filtered through celite. The celite cake was washed with ethyl acetate. The filtrate was rotary evaporated and the crude product was purified by flash column chromatography (silica gel, ethyl acetate-hexanes system as eluent) to afford 1.0 g (82%) of the title compound as white solid. ¹HNMR (400 MHz, CDCl₃) δ 7.50 (d, J=2.0 Hz, 1H), 6.91 (dd, J=8.0 & 2.0, Hz, 1H), 6.75 (s, 1H), 6.72 (d, J=8.0 Hz, 1H), 2.49-2.40 (m, 2H), 2.29 (s, 3H), 2.28-2.21 (m, 2H), 1.91-1.79 (m, 1H), 1.78-1.68 (m, 1H), 1.37 (s, 12H); LC-MS (m/z) 313 (MH)⁺.

The following Intermediates (19b-24b, 26b-30b) given in Table-2 were prepared from the corresponding starting materials by following the similar procedure as described in Intermediate-18b.

TABLE 2

| Intermediate No: IUPAC name | Structure | ¹HNMR/ESI-MS |
|---|---|---|
| Intermediate-19b: 4,4,5,5-Tetramethyl-2-(7-methylspiro[chromene-2,1'-cyclobutan]-4-yl)-1,3,2-dioxaborolane | (structure shown) | ¹HNMR (400 MHz, CDCl₃) δ 7.59 (d, J = 8.0 Hz, 1H), 6.72 (dd, J = 8.0 & 2.0 Hz, 1H), 6.70 (d, J = 2.0 Hz, 1H), 6.65 (s, 1H), 2.50-2.40 (m, 2H), 2.29 (s, 3H), 2.27-2.22 (m, 2H), 1.90-1.83 (m, 1H), 1.78-1.68 (m, 1H), 1.35 (s, 12H); ESI-MS (m/z) 313 (MH)⁺ |

TABLE 2-continued

| Intermediate No: IUPAC name | Structure | ¹HNMR/ESI-MS |
|---|---|---|
| Intermediate-20b: 4,4,5,5-Tetramethyl-2-(8-methylspiro[chromene-2,1'-cyclobutan]-4-yl)-1,3,2-dioxaborolane | 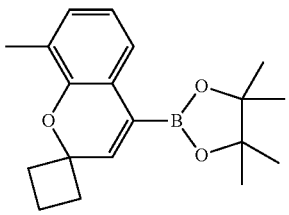 | ¹HNMR (400 MHz, CDCl₃) δ 7.58 (dd, J = 7.5 & 2.0 Hz, 1H), 6.99 (d, J = 7.5, Hz, 1H), 6.80 (t, J = 7.5 Hz, 1H), 6.76 (s, 1H), 2.50-2.40 (m, 2H), 2.32-2.26 (m, 2H), 2.24 (s, 3H), 1.92-1.83 (m, 1H), 1.79-1.72 (m, 1H), 1.36 (s, 12H); ESI-MS (m/z) 313 (MH)⁺ |
| Intermediate-21b: 2-(2,2-Dimethyl-2H-chromen-4-yl)-4,4,5,5-tetramethyl-1,3,2-dioxaborolane | 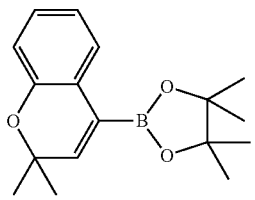 [SMILES: CC1(C)C=C(B2OC(C)(C)C(C)(C)O2)c2ccccc2O1] | ¹HNMR (400 MHz, CDCl₃) δ 7.73 (d, J = 8.0 Hz, 1H), 7.11 (t, J = 8.0 Hz, 1H), 6.89 (t, J= 8.0 Hz, 1H), 6.79 (d, J = 8.0 Hz, 1H), 6.39 (s, 1H), 1.43 (s, 6H), 1.36 (s, 12H); ESI-MS (m/z) 287 (MH)⁺. |
| Intermediate-22b: 4,4,5,5-Tetramethyl-2-(2,2,6-trimethyl-2H-chromen-4-yl)-1,3,2-dioxaborolane | 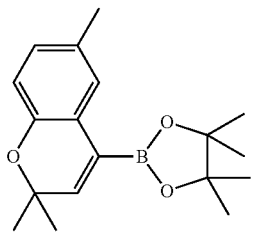 [SMILES: Cc1ccc2c(c1)C(B1OC(C)(C)C(C)(C)O1)=CC(C)(C)O2] | ¹HNMR (400 MHz, CDCl₃) δ 7.50 (d, J = 2.0 Hz 1H), 6.92 (dd, J = 8.0 & 2.0, 1H), 6.69 (d, J = 8.0 Hz, 1H), 6.38 (s, 1H), 2.29 (s, 3H), 1.41 (s, 6H), 1.36 (s, 12H); LC-MS (m/z) 301 (MH)⁺. |
| Intermediate-23b: 4,4,5,5-Tetramethyl-2-(2,2,7-trimethyl-2H-chromen-4-yl)-1,3,2-dioxaborolane | 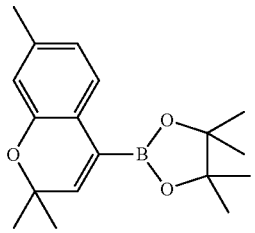 [SMILES: Cc1ccc2c(c1)OC(C)(C)C=C2B1OC(C)(C)C(C)(C)O1] | ¹HNMR (400 MHz, DMSO-d6) δ 7.48 (d, J = 8.0 Hz, 1H), 6.68-6.65 (dd, J = 8.0 & 2.0 Hz, 1H), 6.57 (d, J = 2.0 Hz, 1H), 6.30 (s, 1H), 2.21 (s, 3H), 1.33 (s, 6H), 1.28 (s, 12H); ESI-MS (m/z) 301 (MH)⁺. |
| Intermediate-24b: 4,4,5,5-Tetramethyl-2-(2,2,8-trimethyl-2H-chromen-4-yl)-1,3,2-dioxaborolane | 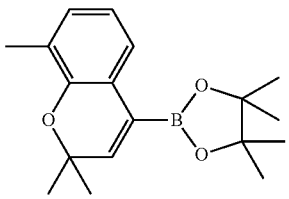 | ¹HNMR (400 MHz, CDCl₃) δ 7.57 (dd, J = 8.0 & 2.0 Hz, 1H), 6.99 (dd, J = 8.0 & 2.0 Hz, 1H), 6.79 (t, J = 8.0 Hz, 1H), 6.38 (s, 1H), 2.19 (s, 3H), 1.42 (s, 6H), 1.35 (s, 12H); ESI-MS (m/z) 301 (MH)⁺. |
| Intermediate-26b: 2-(2-(Methoxy methyl)-2,6-dimethyl-2H-chromen-4-yl)-4,4,5,5-tetramethyl-1,3,2-dioxaborolane | 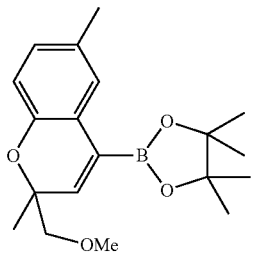 [SMILES: COCC1(C)C=C(B2OC(C)(C)C(C)(C)O2)c2cc(C)ccc2O1] | ¹HNMR (400 MHz, CDCl₃) δ 7.51 (d, J = 2.0 Hz, 1H), 6.94 (dd, J = 8.0 & 2.0 Hz 1H), 6.73 (d, J = 8.0 Hz, 1H), 6.36 (s, 1H), 3.53-3.43 (m, 2H), 3.42 (s, 3H), 2.29 (s, 3H), 1.40 (s, 3H), 1.35 (s, 12H); ESI-MS (m/z) 331 (MH)⁺. |

TABLE 2-continued

| Intermediate No: IUPAC name | Structure | ¹HNMR/ESI-MS |
|---|---|---|
| Intermediate-27b: tert-Butyl dimethyl((2-methyl-4-(4,4,5,5-tetramethyl-1,3,2-dioxaborolan-2-yl)-2H-chromen-2-yl)methoxy)silane | 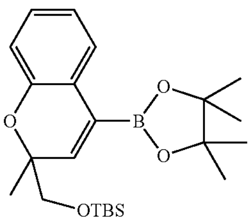 [SMILES: CC1(CO[Si](C)(C)C(C)(C)C)C=C(B2OC(C)(C)C(C)(C)O2)c2ccccc2O1] | ¹HNMR (400 MHz, CDCl₃) δ 7.71 (dd, J = 8.0 & 2.0 Hz, 1H), 7.11-7.07 (m, 1H), 6.88-6.85 (m, 1H), 6.77 (dd, J = 8.0 & 2.0 Hz, 1H), 6.39 (s, 1H), 3.66 (s, 2H), 1.41 (s, 3H), 1.35 (s, 12H), 0.87 (s, 9H), 0.03 (s, 3H), 0.02 (s, 3H); LC-MS (m/z) 417 (MH)⁺. |
| Intermediate-28b: tert-Butyl((2,6-dimethyl-4-(4,4,5,5-tetramethyl-1,3,2-dioxaborolan-2-yl)-2H-chromen-2-yl)methoxy)dimethylsilane | 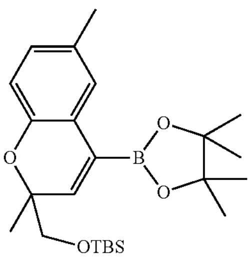 [SMILES: Cc1ccc2c(c1)C(B1OC(C)(C)C(C)(C)O1)=CC(C)(CO[Si](C)(C)C(C)(C)C)O2] | ¹HNMR (400 MHz, CDCl₃) δ 7.48 (d, J = 2.0 Hz, 1H), 6.89 (dd, J = 2.0 & 8.0 Hz, 1H), 6.67 (d, J = 8.0 Hz, 1H), 6.38 (s, 1H), 3.65 (d, J = 2.0 Hz, 2H), 2.28 (s, 3H), 1.39 (s, 3H), 1.35 (s, 12H), 0.88 (s, 9H), 0.03 (s, 3H), 0.01 (s, 3H); ESI-MS (m/z) 431 (MH)⁺. |
| Intermediate-29b: 2-(2-(Methoxymethyl)-2,8-dimethyl-2H-chromen-4-yl)-4,4,5,5-tetramethyl-1,3,2-dioxaborolane | 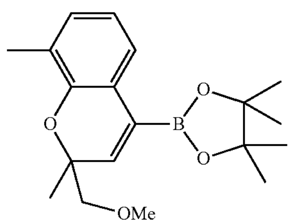 | ¹HNMR (400 MHz, CDCl₃) δ 7.58 (dd, J = 8.0 & 2.0 Hz, 1H), 6.99 (dd, J = 8.0 & 2.0 Hz, 1H), 6.80 (t, J = 8.0 Hz, 1H), 6.39 (s, 1H), 3.51 (d, J = 4.0 Hz, 2H), 3.42 (s, 3H), 2.19 (s, 3H), 1.39 (s, 3H), 1.34 (s, 12H); ESI-MS (m/z) 331 (MH)⁺ |
| Intermediate-30b: tert-Butyl((2,8-dimethyl-4-(4,4,5,5-tetramethyl-1,3,2-dioxaborolan-2-yl)-2H-chromen-2-yl)methoxy)dimethylsilane | 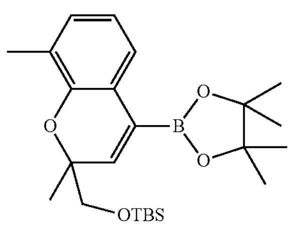 | ¹HNMR (400 MHz, CDCl₃) δ 7.55 (dd, J = 8.0 & 2.0 Hz, 1H), 6.97 (dd, J = 8.0 & 2.0 Hz, 1H), 6.78 (t, J = 8.0 Hz, 1H), 6.39 (s, 1H), 3.67 (d, J = 12.0 Hz, 1H), 3.62 (d, J = 12.0 Hz, 1H), 2.18 (s, 3H), 1.40 (s, 3H), 1.34 (s, 12H), 0.89 (s, 9H), 0.02 (s, 3H), 0.01 (s, 3H). |

Intermediate-31

N-(5-Bromo-4-methylpyridin-2-yl)-2,6-difluorobenzamide

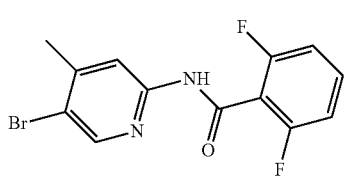

Intermediate 31

The title compound was prepared by following the similar procedure as reported in WO2013164769.

The below Intermediates (32-37) given in Table-3 were prepared from the corresponding starting materials by following the similar procedure as described in WO2012056478.

TABLE 3

| Intermediate No: IUPAC name | Structure |
| --- | --- |
| Intermediate-32: 2,6-Difluoro-N-(4-(4,4,5,5,-tetramethyl-1,3,2-dioxaborolan-2-yl)phenyl) benzamide | 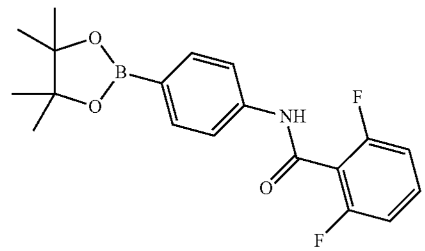 [SMILES: CC1(C)OB(c2ccc(NC(=O)c3c(F)cccc3F)cc2)OC1(C)C] |
| Intermediate-33: 2-Chloro-6-fluoro-N-(4-(4,4,5,5-tetramethyl-1,3,2-dioxaborolan-2-yl)phenyl)benzamide | 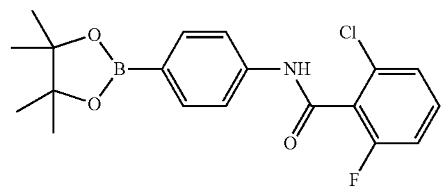 [SMILES: CC1(C)OB(c2ccc(NC(=O)c3c(F)cccc3Cl)cc2)OC1(C)C] |
| Intermediate-34: 2-Fluoro-6-methyl-N-(4-(4,4,5,5-tetramethyl-1,3,2-dioxaborolan-2-yl)phenyl)benzamide | 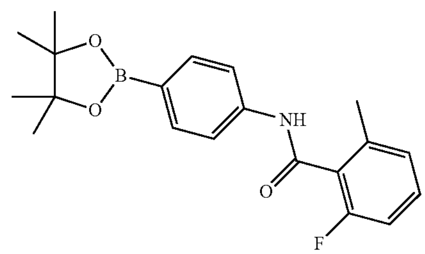 [SMILES: Cc1cccc(F)c1C(=O)Nc1ccc(B2OC(C)(C)C(C)(C)O2)cc1] |
| Intermediate-35: N-(5-Bromopyridin-2-yl)-2,6-difluorobenzamide | 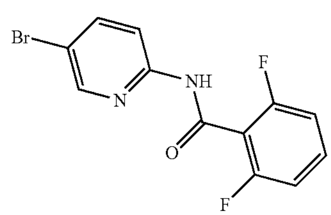 [SMILES: O=C(Nc1ccc(Br)cn1)c1c(F)cccc1F] |
| Intermediate-36: N-(6-Bromopyridin-3-yl)-2,6-difluorobenzamide | 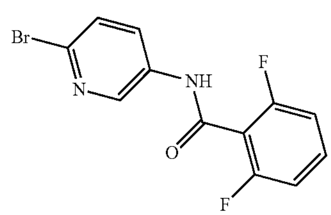 [SMILES: O=C(Nc1ccc(Br)nc1)c1c(F)cccc1F] |
| Intermediate-37: N-(5-Bromopyrazine-2-yl)-2,6-difluorobenzamide | 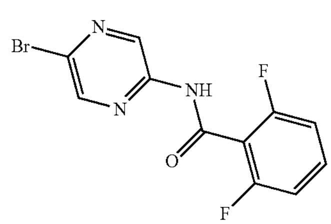 [SMILES: O=C(Nc1cnc(Br)cn1)c1c(F)cccc1F] |

Intermediate-38

N-(2,6-Difluorophenyl)-4-(4,4,5,5-tetramethyl-1,3,2-dioxaborolan-2-yl) benzamide

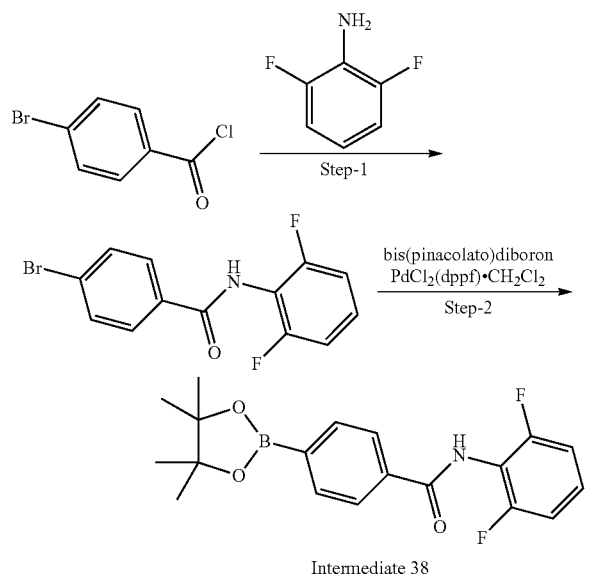

Intermediate 38

Step-1: 4-Bromo-N-(2,6-difluorophenyl)benzamide: To a (0° C.) cooled and stirred solution of 4-bromobenzoyl chloride (1.0 g, 4.56 mmol) in DCM (10 mL) was added dropwise a solution of 2,6-difluoroaniline (0.46 ml, 4.56 mmol) in DCM (2 ml) followed by pyridine (0.48 ml, 5.47 mmol). The resulting mixture was stirred at room temperature overnight. The reaction was diluted with DCM (10 mL), washed with water (10 mL), brine (10 mL), dried (Na$_2$SO$_4$) and filtered. The filtrate was concentrated under vacuum and the crude product was purified by flash column chromatography (silica gel, ethyl acetate-hexane system as eluent) to afford 750 mg (53%) of the title product as a white solid. $^1$HNMR (400 MHz, DMSO) δ 10.25 (s, 1H), 7.93 (d, J=8.5 Hz, 2H), 7.77 (d, J=8.5 Hz, 2H), 7.45-7.38 (m, 1H), 7.23 (t, J=8.0 Hz, 2H), ESI-MS (m/z) 312, 314 [(MH)$^+$ Br$^{79,81}$].

Step-2: N-(2,6-Difluorophenyl)-4-(4,4,5,5-tetramethyl-1,3,2-dioxaborolan-2-yl)benzamide: To a stirred and nitrogen purged solution of step-1 Intermediate (5.40 g, 17.3 mmol) in dioxane (50 mL), 4,4,4',4',5,5,5',5'-octamethyl-2,2'-bi(1,3,2-dioxaborolane) (5.27 g, 20.7 mmol), potassium acetate (5.43 g, 55.4 mmol) and [1,1'-bis(diphenyl phosphino)-ferrocene)dichloro palladium(II) dichloro methane complex (0.706 g, 0.86 mmol) were sequentially added. The resulting mixture was then thoroughly deoxygenated again by subjecting to a vacuum/nitrogen cycle three times and then heated at 100° C. for 6 h under nitrogen atmosphere. The reaction mixture was cooled to room temperature and filtered through celite. The filtrate was concentrated under vacuum and the crude product was purified by flash column chromatography (silica gel, ethyl acetate-hexane system as eluent) to afford 4.80 g (77%) of the Intermediate 6 as a white solid. $^1$HNMR (400 MHz, CDCl$_3$) δ 7.95-7.90 (m, 4H), 7.47 (s, 1H), 7.27-7.23 (m, 1H), 7.01 (t, J=8.0 Hz, 2H); ESI-MS (m/z) 360 (MH)$^+$.

Intermediate-39

5-(4,4,5,5-Tetramethyl-1,3,2-dioxaborolan-2-yl)pyridin-2-amine

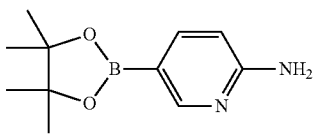 [SMILES: CC1(C)OB(c2ccc(N)nc2)OC1(C)C]

The title compound was prepared by following the similar procedure as reported in US20120088764.

Intermediate-40

N-(2,6-Difluorobenzyl)-4-(4,4,5,5-tetramethyl-1,3,2-dioxaborolan-2-yl)aniline

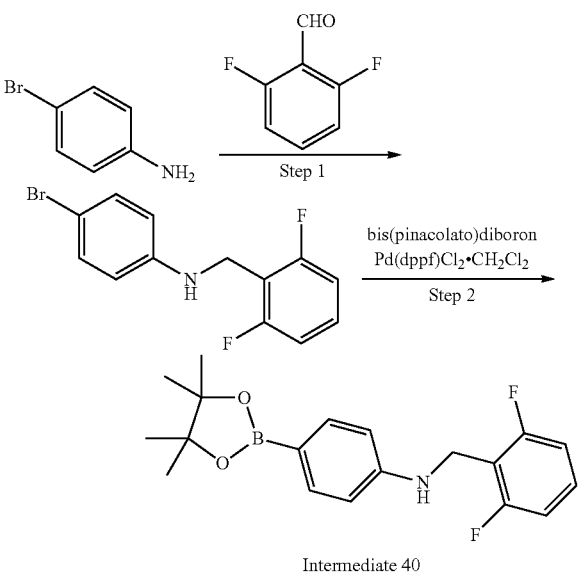

Intermediate 40

Step-1: 4-Bromo-N-(2,6-difluorobenzyl)aniline: To a (0° C.) cooled and stirred solution of 4-bromoaniline (2.0 g, 11.63 mmol) in Methanol (20 mL) was added 2,6-difluorobenzaldehyde (1.27 mL, 11.63 mmol) and acetic acid (600 µL, 11.63 mmol). The resulting mixture was stirred at RT for 30 min. Sodium cyanoborohydride (1.16 g, 18.60 mmol) was added to the above mixture and further stirred for 15 h at the same temperature. The solvent was then evaporated under vacuum and the residue was diluted with water (15 mL) followed by ethyl acetate (20 mL) The layers were separated and the aqueous layer was extracted with ethyl acetate (2×20 mL). The combined organic layers was washed with saturated brine (20 mL) and dried (Na$_2$SO$_4$) and filtered. The filtrate was concentrated under vacuum. The crude product was purified by flash chromatography (silica gel, ethyl acetate-hexanes system as eluent) to give 2.60 g (75%) of the title product as white solid. $^1$HNMR (400 MHz, CDCl$_3$) δ 7.33-7.18 (m, 3H), 6.90 (t, J=8.0 Hz, 2H), 6.61 (d, J=8.5 Hz, 2H), 4.41 (s, 2H); ESI-MS (m/z) 298, 300 [(MH)$^+$, Br$^{79,81}$].

Step-2: N-(2,6-Difluorobenzyl)-4-(4,4,5,5-tetramethyl-1,3,2-dioxaborolan-2-yl)aniline: To a stirred and nitrogen purged solution of Step-1 Intermediate (200 mg, 0.671 mmol), bis(pinacolato)diboron (209 mg, 0.872 mmol) and potassium acetate (132 mg, 1.342 mmol) in 1,4 dioxane (10 mL) was added $PdCl_2$(dppf)-$CH_2Cl_2$ adduct (27 mg, 0.034 mmol). The resulting mixture was stirred at 100° C. for 12 h. The reaction was then cooled back down to RT and filtered through celite. The filtrate was concentrated under vacuum and the crude product was purified by flash column chromatography(silica gel, 12% ethyl acetate in hexanes system as eluent) to give 192 mg (80%) of the title product as white solid. $^1$HNMR (400 MHz, $CDCl_3$) δ 7.64 (d, J=8.0 Hz, 2H), 7.24-7.18 (m, 1H), 6.88 (t, J=8.0 Hz, 2H), 6.71 (d, J=8.0 Hz, 2H), 4.47 (s, 2H), 1.32 (s, 12H).); ESI-MS (m/z) 346 $(MH)^+$.

Intermediate-41

N-(2-Fluoro-6-methylbenzyl)-4-(4,4,5,5-tetramethyl-1,3,2-dioxaborolan-2-yl)aniline Intermediate 41

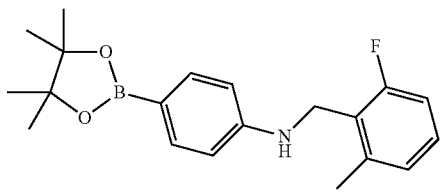

The title compound was prepared by following the similar procedure as described in Intermediate-40. $^1$HNMR (400 MHz, DMSO-$d_6$) δ 7.40 (d, J=8.5 Hz, 2H), 7.28-7.23 (m, 1H), 7.11-6.96 (m, 2H), 6.64 (d, J=8.5 Hz, 2H), 6.18 (t, J=4.5 Hz, 1H), 4.20 (d, J=4.5 Hz, 2H), 2.35 (s, 3H), 1.25 (s, 12H); ESI-MS (m/z) 342 $(MH)^+$ Intermediate-42

5-Bromo-N-(2,6-difluorobenzyl)pyrazin-2-amine

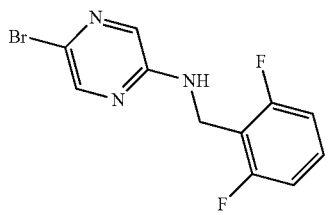 [SMILES: Fc1cccc(F)c1CNc1cnc(Br)cn1]

The title compound was prepared by reacting 2-bromo-5-aminopyrazine with 2,6-difluorobenzaldehyde by following the similar procedure as described in Intermediate-40. $^1$HNMR (400 MHz, DMSO-$d_6$) δ 8.13 (s, 1H), 7.78 (s, 1H), 7.71 (t, J=5.5 Hz, 1H), 7.42-7.39 (m, 1H), 7.09 (t, J=8.0 Hz, 2H), 5.25 (t, J=5.5 Hz, 2H); LC-MS (m/z), 300, 302 [$(MH)^+$, $Br^{79,81}$].

Intermediate-43

5-Bromo-N-(2,6-difluorobenzyl)pyridin-2-amine

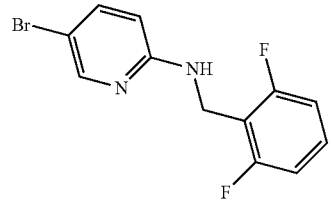 [SMILES: Fc1cccc(F)c1CNc1ccc(Br)cn1]

The title compound was prepared by reacting 2-bromo-5-aminopyridine with 2,6-difluorobenzaldehyde by following the similar procedure as described in Intermediate-40. ESI-MS (m/z) 299, 301 [$(MH)^+$, $Br^{79,81}$].

Intermediate-44

4-Bromo-N-(3-methylpyridin-4-yl)benzamide

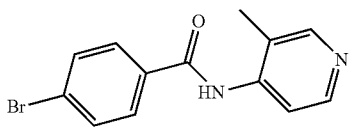 [SMILES: Cc1cnccc1NC(=O)c1ccc(Br)cc1]

To a pre-washed suspension of NaH (0.164 g, 6.83 mmol) in DMF (10 mL) was added drop wise a solution of 3-methylpyridin-4-amine (0.246 g, 2.28 mmol) in DMF (3 mL) at 0° C. After stirring for 15 min, a solution of 4-bromobenzoyl chloride (0.5 g, 2.278 mmol) in $CH_2Cl_2$ (5 mL) was added drop wise and the resulting mixture was stirred at rt for 16 h. The reaction was quenched with cold water and extracted with DCM (2×15 mL). The combined organic layers were washed with water (2×15 mL), brine (15 mL), dried ($Na_2SO_4$) and filtered. The filtrate was rotary evaporated to give 400 mg (63%) of the desired product as a white solid. $^1$HNMR (400 MHz, DMSO-$d_6$) δ 10.04 (s, 1H, $D_2O$ exchangeable), 8.44 (s, 1H), 8.38 (d, J=5.5 Hz, 1H), 7.92 (d, J=8.5 Hz, 2H), 7.78 (d, J=8.5 Hz, 2H), 7.60 (d, J=5.5 Hz, 1H), 2.27 (s, 3H); ESI-MS (m/z) 291, 293 [$(MH)^+$, $Br^{79,81}$]

Intermediate-45

4-Bromo-N-(3,5-difluoropyridin-4-yl)benzamide

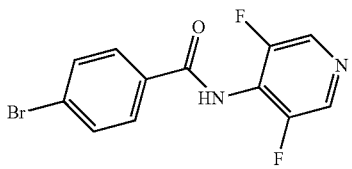 [SMILES: O=C(Nc1c(F)cncc1F)c1ccc(Br)cc1]

The title compound was prepared by reacting 4-bromobenzoyl chloride with 3,5-difluoropyridin-4-amine by following the similar procedure as described in Intermediate-44. $^1$HNMR (400 MHz, $CDCl_3$) δ 8.45 (s, 2H), 7.97 (s, 1H), 7.85 (d, J=8.5 Hz, 2H), 7.68 (d, J=8.5 Hz, 2H); ESI-MS (m/z) 313, 315 [(MH)+, Br$^{79,81}$].

Intermediate-46

2-Fluoro-N-(4-(4,4,5,5-tetramethyl-1,3,2-dioxaborolan-2-yl)phenyl)benzamide

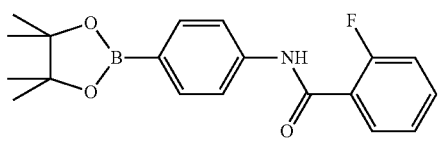 [SMILES: CC1(C)OB(c2ccc(NC(=O)c3ccccc3F)cc2)OC1(C)C]

The title compound was prepared by following the similar procedure as described in Intermediate-32. $^1$HNMR (400 MHz, DMSO-d$_6$) δ 10.56 (s, 1H), 7.79-7.76 (d, J=8.0 Hz, 2H), 7.67 (m, 3H), 7.62-7.54 (m, 1H), 7.43-7.21 (m, 2H), 1.29 (s, 12H); ESI-MS (m/z) 342 [(MH)+].

Intermediate-47

(2,6-Dimethyl-7-(4,4,5,5-tetramethyl-1,3,2-dioxaborolan-2-yl)chroman-2-yl)methanol

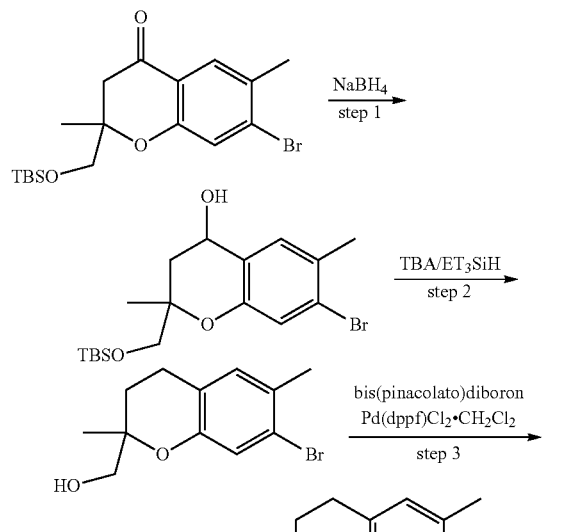

Intermediate 47

Step-1: 7-Bromo-2-(((tert-butyldimethylsilyl)oxy)methyl)-2,6-dimethylchroman-4-ol: The title compound was prepared from Intermediate-5a by following the similar procedure as described in step-1 of Intermediate-4a. $^1$HNMR (400 MHz, CDCl$_3$) δ 7.30 (s, 1H), 7.25 (s, 1H), 3.75 (d, J=10.5 Hz, 1H), 3.66 (d, J=10.5 Hz, 1H), 3.59 (d, J=10.0 Hz, 1H), 3.48 (d, J=10.0 Hz, 1H), 2.31 (s, 3H), 2.17 (t, J=4.5 Hz, 1H), 1.30 (s, 3H), 0.80 (s, 9H), 0.01 (s, 3H), −0.09 (s, 3H); ESI-MS (m/z) 383, 385 [(MH)+, Br$^{79,81}$].

Intermediate-48

6-Bromo-1'-methylspiro[chroman-2,4'-piperidin]-4-one

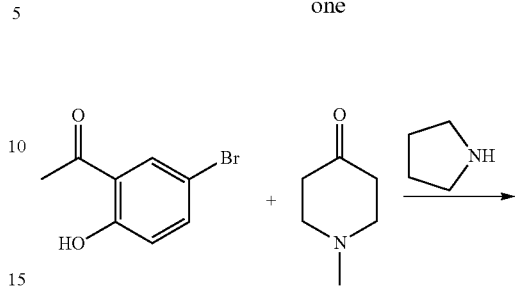

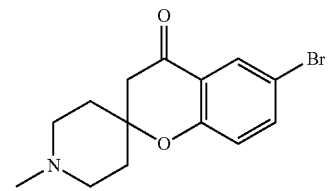

Intermediate 48

A mixture of 1-(5-bromo-2-hydroxyphenyl)ethanone (3.0 g, 13.9 mmol), 1-methylpiperidin-4-one (2.27 mL, 19.5 mmol) and pyrrolidine (2.30 mL, 27.9 mmol) in methanol (100 mL) was refluxed for 16 h. The reaction mass was cooled to room temperature and the solvent was evaporated under vacuum. Ethyl acetate (100 mL) was added to the residue followed by HCl (20 mL, 10%). The layers were separated and aqueous layer was extracted with ethyl acetate (2×50 mL). The combined organic layers were washed with saturated aqueous NaHCO$_3$ (50 mL), brine (50 mL), dried (Na$_2$SO$_4$) and filtered. The filtrate was rotary evaporated and the crude product was purified by flash column chromatography (silica gel, 3% EtOAc in hexane as eluent) to afford 3.0 g (70%) of the title compound as colorless liquid. $^1$HNMR (400 MHz, CDCl$_3$) δ 7.96 (s, 1H), 7.56 (d, J=8.0 Hz, 1H), 6.91 (d, J=8.0 Hz, 1H), 2.71 (s, 2H), 2.61-2.56 (m, 2H), 2.42-2.36 (m, 2H), 2.32 (s, 3H), 2.08-2.00 (m, 2H), 1.79-1.72 (m, 2H); ESI-MS (m/z) 310, 312 [(MH)+, Br$^{79,81}$]

Intermediate-49

7-Bromo-1',6-dimethylspiro[chroman-2,4'-piperidin]-4-one

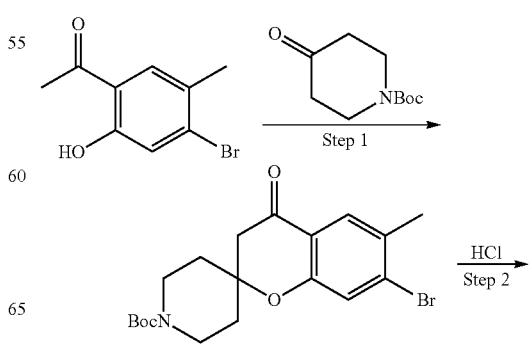

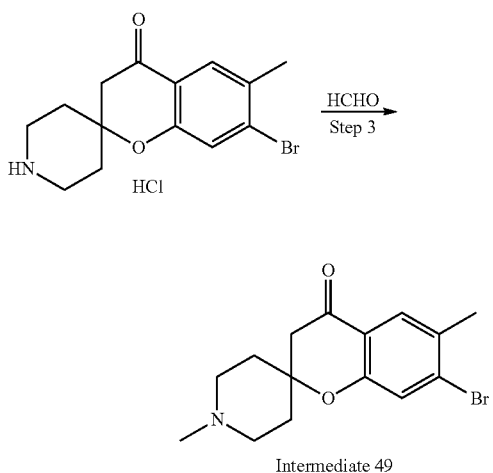

Intermediate 49

Step-1: tert-Butyl 7-bromo-6-methyl-4-oxospiro[chroman-2,4'-piperidine]-1'-carboxylate: The title compound was prepared by following the similar procedure as described in Intermediate-48. $^1$HNMR (400 MHz, CDCl$_3$) δ 7.71 (s, 1H), 7.27 (s, 1H), 3.91-3.87 (m, 2H), 3.24-3.16 (m, 2H), 2.70 (s, 2H), 2.36 (s, 3H), 2.04-1.98 (m, 2H), 1.64-1.59 (m, 2H), 1.47 (s, 9H); ESI-MS (m/z) 310, 312 [(MH-Boc)$^+$, Br$^{79,81}$].

Step-2: 7-Bromo-6-methylspiro[chroman-2,4'-piperidin]-4-one hydrochloride; To the (0° C.) cooled and stirred solution of step-1 Intermediate (500 mg, 1.22 mmol) in dioxane (5 mL) was added dioxane-HCl (10 mL, 4M). The reaction mixture was stirred for 16 h at room temperature. The solvent was removed under vacuum and the residue obtained was washed with hexane (2×10 mL) to afford 300 mg (79%) of the title compound as white solid. $^1$HNMR (400 MHz, DMSO-d$_6$) δ 9.10 (s, 1H, D$_2$O exchangeable), 8.86 (s, 1H, D$_2$O exchangeable), 7.69 (s, 1H), 7.49 (s, 1H), 3.19-3.07 (m, 4H), 2.90 (s, 2H), 2.32 (s, 3H), 2.11-2.07 (m, 2H), 1.91-1.80 (m, 2H); ESI-MS (m/z) 310, 312 [(MH)$^+$, Br$^{79,81}$].

Step-3: 7-Bromo-1',6-dimethylspiro[chroman-2,4'-piperidin]-4-one: To a stirred solution of step-2 Intermediate (300 mg, 0.97 mmol) in methanol (30 mL) was added aqueous solution of formaldehyde (200 μL, 2.90 mmol, 37%), followed by the addition of acetic acid (55 μL, 0.967 mmol). The resulting mixture was stirred at room temperature overnight. Sodium triacetoxyborohydride (410 mg, 1.93 mmol) was then added to the above mixture. The resulting mixture was stirred at rt for 12 h. The solvent was removed under vacuum and the residue was diluted with water (10 mL) and extracted with DCM (2×50 mL). The combined organic layers were washed with brine (20 mL), dried (Na$_2$SO$_4$) and filtered. The filtrate was rotary evaporated to afford 150 mg (48%) of the title compound as white semi-solid. $^1$HNMR (400 MHz, CDCl$_3$) δ 7.74 (s, 1H), 7.27 (s, 1H), 3.19-3.15 (m, 2H), 2.96-2.89 (m, 2H), 2.78 (s, 2H), 2.67 (s, 3H), 2.37 (s, 3H), 2.34-2.24 (m, 2H), 2.18-2.15 (m, 2H); ESI-MS (m/z) 324, 326 [(MH)$^+$, Br$^{79,81}$]

Intermediate-50 tert-Butyl 7'-bromo-6'-methyl-4'-oxospiro[azetidine-3,2'-chroman]-1-carboxylate

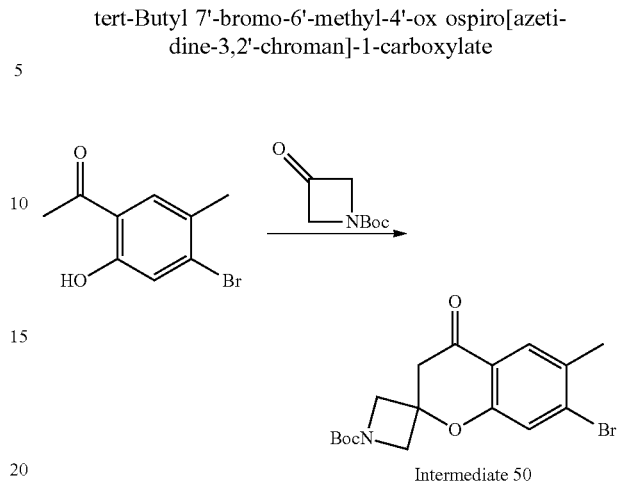

Intermediate 50

The title compound was prepared by following the similar procedure as described in step-1 of Intermediate-49. $^1$HNMR (400 MHz, CDCl$_3$) δ 7.72 (s, 1H), 7.33 (s, 1H), 4.07 (m, 2H), 3.96 (m, 1H), 3.94 (m, 1H), 3.02 (s, 2H), 2.38 (s, 3H), 1.45 (s, 9H); ESI-MS (m/z), 379, 381 [(MH-Boc)$^+$, Br$^{79,81}$].

Intermediate-51

6-Methyl-7-(4,4,5,5-tetramethyl-1,3,2-dioxaborolan-2-yl)spiro[chroman-2,3'-oxetan]-4-one

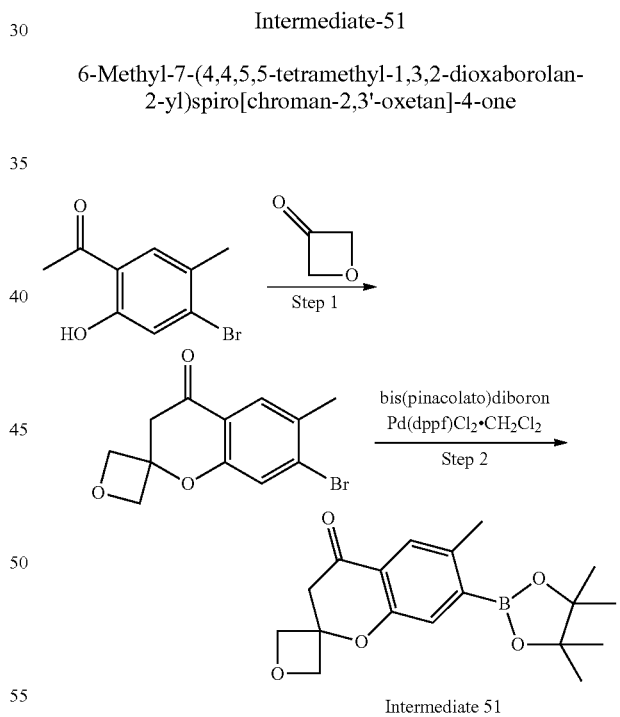

Intermediate 51

Step-1: 7-Bromo-6-ethylspiro[chroman-2,3'-oxetan]-4-one: A stirred mixture of 1-(4-bromo-2-hydroxy-5-methylphenyl)ethanone (2.0 g, 8.73 mmol), oxetan-3-one (1.88 g, 26.2 mmol) and pyrrolidine (1.44 ml, 17.46 mmol) in acetonitrile (10 mL) was heated at 110° C. for 2 h in microwave reactor (Biotage). The reaction was cooled to room temperature and the solvent was evaporated under vacuum. Water (20 mL) was added to the reaction followed by ethyl acetate (50 mL). The layers were separated and aqueous layer was extracted with ethyl acetate (2×50 mL)

The combined organic layers were washed with brine (20 mL), dried ($Na_2SO_4$) and filtered. The filtrate was rotary evaporated and the crude product was purified by flash column chromatography (20% ethyl acetate in hexane system as eluent) to 200 mg (8%) as white solid. $^1$HNMR (400 MHz, $CDCl_3$) δ 7.70 (s, 1H), 7.36 (s, 1H), 4.80 (d, J=7.5 Hz, 2H), 4.60 (d, J=7.5 Hz, 2H), 3.14 (s, 2H), 2.37 (s, 3H); ESI-MS (m/z) 283, 285 (MH)$^+$, Br$^{79,81}$].

Step-2: 6-Ethyl-7-(4,4,5,5-tetramethyl-1,3,2-dioxaborolan-2-yl)spiro[chroman-2,3'-oxetan]-4-one: The title compound was prepared from step-1 Intermediate by following the similar procedure as described in step-2 of Intermediate-1. $^1$HNMR (400 MHz, $CDCl_3$) δ 7.61 (s, 1H), 7.49 (s, 1H), 4.79 (d, J=7.5 Hz, 2H), 4.59 (d, J=7.5 Hz, 2H), 3.14 (s, 2H), 2.47 (s, 3H), 1.37 (s, 12H); ESI-MS (m/z) 331 (MH)$^+$ Intermediate-52

7-Bromo-6-ethylspiro[chroman-2,3'-oxetan]-4-one

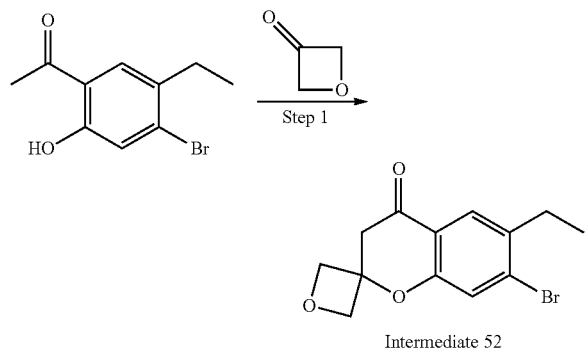

Intermediate 52

7-Bromo-6-ethylspiro[chroman-2,3'-oxetan]-4-one: A solution of 1-(4-bromo-5-ethyl-2-hydroxyphenyl)ethanone (0.5 g, 2.06 mmol), oxetan-3-one (1.81 mL, 30.9 mmol) and pyrrolidine (1.19 mL, 14.4 mmol) was refluxed in IPA (10 mL) for 16 h. The reaction was cooled to rt and the solvent was removed under vacuum. Ethyl acetate (10 mL) was added to the residue. The organic layer was washed with 10% aq HCl (5 mL), followed by saturated $NaHCO_3$ solution (5 mL) The organic layer was dried over anhydrous $Na_2SO_4$ and filtered. The filtrate was rotary evaporated and the crude product was purified by flash chromatography (silica gel, ethyl acetate-hexane system as eluent) to give 80 mg (13%) as a yellow solid. $^1$HNMR (400 MHz, $CDCl_3$) δ 7.70 (s, 1H), 7.36 (s, 1H), 4.81 (d, J=8.0 Hz, 2H), 4.60 (d, J=8.0 Hz, 2H), 3.15 (s, 2H), 2.73 (q, J=7.5 Hz, 2H), 1.23 (t, J=7.5 Hz, 3H); ESI-MS (m/z) 297, 299 (MH)$^+$, Br$^{79,81}$]

EXAMPLES

Example-1

2,6-Difluoro-N-(4-(2,2,6-trimethyl-4-oxochroman-7-yl)phenyl)benzamide

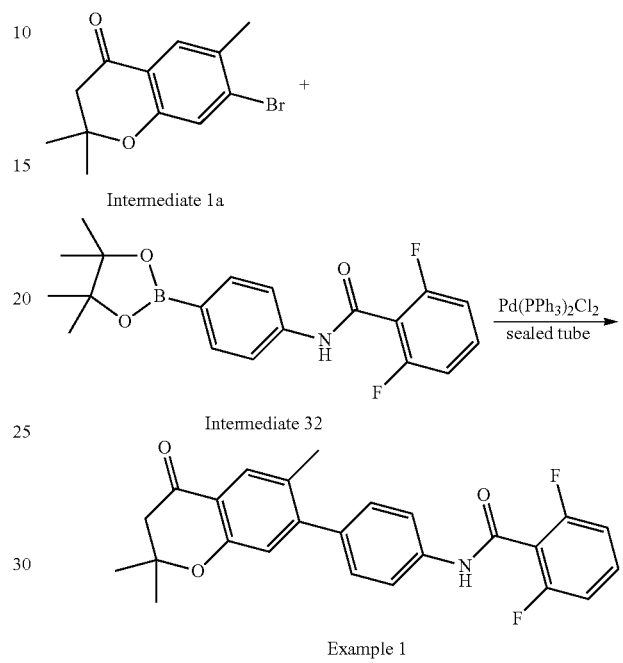

Example 1

In a sealed tube, to a nitrogen purged and stirred solution of aqueous sodium carbonate (315 mg, 2.97 mmol, 2M in water) in dioxane (10 mL) were added Intermediate-1a (400 mg, 1.48 mmol) and Intermediate-32 (534 mg, 1.48 mmol). The resulting mixture was thoroughly deoxygenated by purging nitrogen gas for another 10 minutes, and then bis(triphenylphosphine)palladium(II) chloride (104 mg, 0.14 mmol) was added to the above mixture. The sealed tube was capped and stirred at 100° C. for 16 h. The reaction was cooled to room temperature and filtered through celite. The filtrate was rotary evaporated and the crude product was purified by flash column chromatography to afford 120 mg (19%) of the title compound as white solid. $^1$HNMR (400 MHz, $CDCl_3$) δ 7.83 (s, 1H), 7.75 (s, 1H), 7.73 (d, J=8.0 Hz, 2H), 7.45-7.41 (m, 1H), 7.35 (d, J=8.0 Hz, 2H), 7.03 (t, J=8.0 Hz, 2H), 6.84 (s, 1H), 2.74 (s, 2H), 2.24 (s, 3H), 1.49 (s, 6H); ESI-MS (m/z) 422 (MH)$^+$.

The below Examples (2 to 21) given in Table-4 were prepared by following the similar procedure as described in Example-1 by using the appropriate Intermediates.

TABLE 4

| Example No: IUPAC name | Structure | $^1$HNMR/ESI-MS |
|---|---|---|
| Example-2: N-(4-(6-Ethyl-2,2-dimethyl-4-oxochroman-7-yl)phenyl)-2,6-difluorobenzamide | 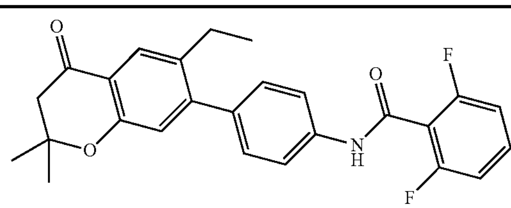 | $^1$HNMR (400 MHz, $CDCl_3$) δ 7.79 (s, 1H), 7.74 (s, 1H), 7.72 (d, J = 8.0 Hz, 2H), 7.48-7.44 (m, 1H), 7.34 (d, J = 8.0 Hz, 2H), 7.04 (t, J = 8.0 Hz, 2H), 6.80 (s, 1H), 2.75 (s, 2H), 2.57 (q, J = 7.5 Hz, 2H), 1.50 (s, 6H), 1.10 (t, J = 7.5 Hz, 3H); ESI-MS (m/z) 436 (MH)$^+$. |

TABLE 4-continued

| Example No: IUPAC name | Structure | ¹HNMR/ESI-MS |
|---|---|---|
| Example-3: N-(2,6-Difluorophenyl)-4-(2,2,6-trimethyl-4-oxochroman-7-yl)benzamide | 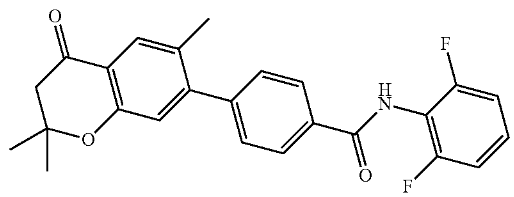 [SMILES: Cc1cc2c(cc1-c1ccc(C(=O)Nc3c(F)cccc3F)cc1)OC(C)(C)CC2=O] | ¹HNMR (400 MHz, CDCl$_3$) δ 8.02 (d, J = 8.0 Hz, 2H), 7.78 (s, 1H), 7.50 (s, 1H), 7.47 (d, J = 8.0 Hz, 2H), 7.30-7.24 (m, 1H), 7.04 (t, J = 8.0 Hz, 2H), 6.85 (s, 1H), 2.76 (s, 2H), 2.22 (s, 3H), 1.50 (s, 6H); ESI-MS (m/z) 422 (MH)$^+$. |
| Example-4: 2,6-Difluoro-N-(5-(2,2,6-trimethyl-4-oxochroman-7-yl)pyrazin-2-yl)benzamide | 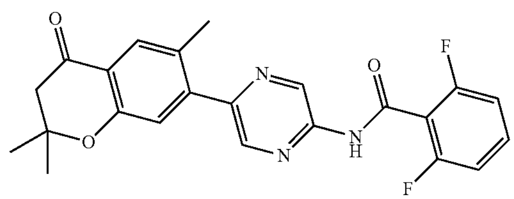 [SMILES: Cc1cc2c(cc1-c1cnc(NC(=O)c3c(F)cccc3F)cn1)OC(C)(C)CC2=O] | ¹HNMR (400 MHz, CDCl$_3$) δ 9.78 (s, 1H), 8.45 (s, 1H), 8.43 (s, 1H), 7.81 (s, 1H), 7.54-7.50 (m, 1H), 7.08 (t, J = 8.0 Hz, 2H), 7.05 (s, 1H), 2.77 (s, 2H), 2.36 (s, 3H), 1.50 (s, 6H); ESI-MS (m/z) 424 (MH)$^+$. |
| Example-5: N-(5-(6-Ethyl-2,2-dimethyl-4-oxochroman-7-yl)pyrazin-2-yl)-2,6-difluorobenzamide | 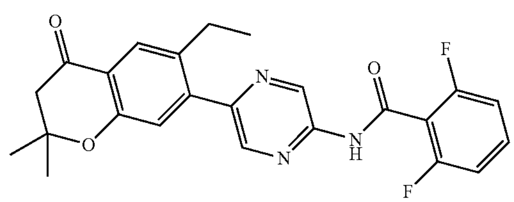 [SMILES: CCc1cc2c(cc1-c1cnc(NC(=O)c3c(F)cccc3F)cn1)OC(C)(C)CC2=O] | ¹HNMR (400 MHz, CDCl$_3$) δ 9.78 (s, 1H), 8.47 (s, 1H), 8.40 (s, 1H), 7.85 (s, 1H), 7.54-7.50 (m, 1H), 7.08 (t, J = 8.0 Hz, 2H), 6.98 (s, 1H), 2.77 (s, 2H), 2.70 (q, J = 7.5 Hz, 2H), 1.50 (s, 6H), 1.14 (t, J = 7.5 Hz, 3H); ESI-MS (m/z) 438 (MH)$^+$. |
| Example-6: 2,6-Difluoro-N-(5-(2,2,6-trimethyl-4-oxochroman-7-yl)pyrazin-2-yl)benzamide | 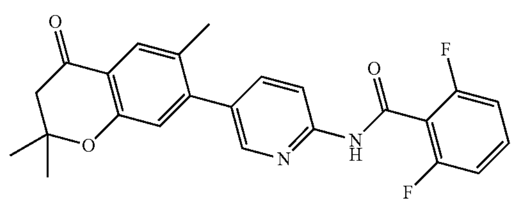 [SMILES: Cc1cc2c(cc1-c1ccc(NC(=O)c3c(F)cccc3F)nc1)OC(C)(C)CC2=O] | 1H NMR (400 MHz, CDCl$_3$) δ 9.10 (s, 1H), 8.54 (d, J = 8.0 Hz, 1H), 8.24 (d, J = 2.0 Hz 1H), 7.84 (dd, J = 2.0 & 8.0 Hz, 1H), 7.79 (s, 1H), 7.48-7.46 (m, 1H), 7.05 (t, J = 8.0 Hz, 2H), 6.83 (s, 1H), 2.77 (s, 2H), 2.25 (s, 3H), 1.50 (s, 6H); ESI-MS (m/z) 423 (MH)$^+$. |
| Example-7: 2,6-Difluoro-N-(5-(2,2,8-trimethylchroman-7-yl)pyrazin-2-yl)benzamide | 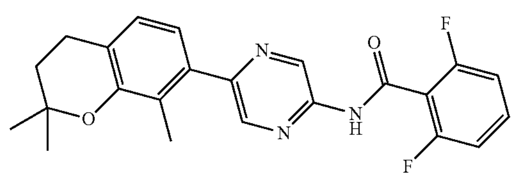 [SMILES: Cc1c(-c2cnc(NC(=O)c3c(F)cccc3F)cn2)ccc2c1OC(C)(C)CC2] | ¹HNMR (400 MHz, CDCl$_3$) δ 9.76 (s, 1H), 8.46 (s, 1H), 8.37 (s, 1H), 7.54-7.47 (m, 1H), 7.11-7.02 (m, 3H), 6.92 (d, J= 8.0 Hz, 1H), 2.85 (t, J = 6.5 Hz, 2H), 2.21 (s, 3H), 1.84 (t, J = 6.5 Hz, 2H), 1.38 (s, 6H); ESI-MS (m/z) 410 (MH)$^+$. |
| Example-8: 2-Chloro-6-fluoro-N-(4-(6-methylspiro[chroman-2,1'-cyclobutan]-7-yl)phenyl)benzamide | 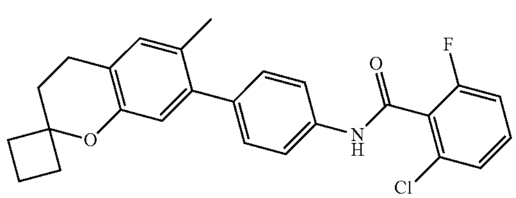 [SMILES: Cc1cc2c(cc1-c1ccc(NC(=O)c3c(F)cccc3Cl)cc1)OC1(CCC1)CC2] | ¹HNMR (400 MHz, CDCl$_3$) δ 7.68 (d, J = 8.5 Hz, 2H), 7.53 (s, 1H), 7.42-7.38 (m, 1H), 7.36 (d, J = 8.5 Hz, 2H), 7.30 (d, J = 8.0 Hz, 1H), 7.13 (t, J = 8.0 Hz, 1H), 6.96 (s, 1H), 6.73 (s, 1H), 2.81 (t, J = 6.5 Hz, 2H), 2.36-2.28 (m, 2H), 2.20 (s, 3H), 2.13-2.09 (m, 2H), 2.01 (t, J = 6.5 Hz, 2H), 1.92-1.89 (m, 1H), 1.72-1.65 (m, 1H); ESI-MS (m/z) 436, 438 [(MH)$^+$, Cl$^{35,37}$]. |
| Example-9: 2-Fluoro-6-methyl-N-(4-(6-methylspiro[chroman-2,1'-cyclobutan]-7-yl)phenyl)benzamide | 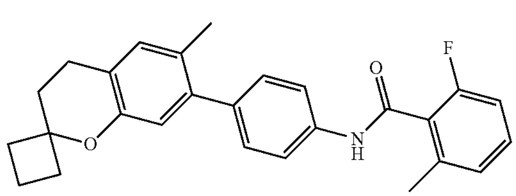 [SMILES: Cc1cc2c(cc1-c1ccc(NC(=O)c3c(C)cccc3F)cc1)OC1(CCC1)CC2] | ¹HNMR (400 MHz, CDCl$_3$) δ 7.67 (d, J = 8.5 Hz, 2H), 7.54 (s, 1H), 7.35 (d, J = 8.5 Hz, 2H), 7.33-7.29 (m, 1H), 7.09 (d, J = 7.5 Hz, 1H), 7.01 (t, J = 8.5 Hz, 1H), 6.96 (s, 1H), 6.74 (s, 1H), 2.81 (t, J = 6.5 Hz, 2H), 2.51 (s, 3H), 2.36-2.28 (m, 2H), 2.20 (s, 3H), 2.13-2.07 (m 2H), 2.01 (t, J = 6.5 Hz, 2H), 1.96-1.84 (m, 1H), 1.75-1.65 (m, 1H); ESI-MS (m/z) 416 (MH)$^+$. |

TABLE 4-continued

| Example No: IUPAC name | Structure | ¹HNMR/ESI-MS |
|---|---|---|
| Example-10: 2-Fluoro-6-methyl-N-(4-(6-methyl-4-oxospiro[chroman-2,1'-cyclobutan]-7-yl)phenyl)benzamide | 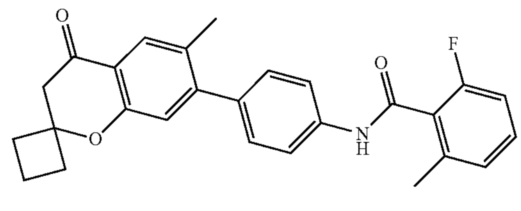 [SMILES: Cc1cc2c(cc1-c1ccc(NC(=O)c3c(C)cccc3F)cc1)OC1(CCC1)CC2=O] | ¹HNMR (400 MHz, CDCl₃) δ 7.75 (s, 1H), 7.73 (d, J = 8.5 Hz, 2H), 7.65 (s, 1H), 7.36 (d, J = 8.5 Hz, 2H), 7.34-7.30 (m, 1H), 7.09 (d, J = 7.0 Hz, 1H), 7.02 (t, J = 8.0 Hz, 1H), 6.89 (s, 1H), 2.92 (s,2H), 2.51 (s, 3H), 2.23-2.17 (m, 2H), 2.24 (s, 3H), 2.23-2.17 (m, 2H), 2.01-1.90 (m, 1H), 1.79-1.70 (m, 1H); ESI-MS (m/z) 430 (MH)⁺ |
| Example-11: 2-Chloro-6-fluoro-N-(4-(6-methyl-4-oxospiro[chroman-2,1'-cyclobutan]-7-yl)phenyl)benzamide | 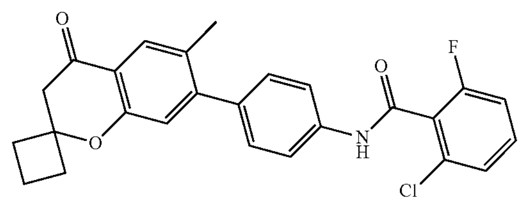 [SMILES: Cc1cc2c(cc1-c1ccc(NC(=O)c3c(F)cccc3Cl)cc1)OC1(CCC1)CC2=O] | ¹HNMR (400 MHz, DMSO-d₆) δ 10.95 (s, 1H), 7.79 (d, J = 8.0 Hz, 2H), 7.63 (s, 1H), 7.61-7.54 (m, 1H), 7.48 (d, J = 8.0 Hz, 1H), 7.40 (m, 3H), 6.89 (s, 1H), 2.98 (s, 2H), 2.32-2.17 (m, 5H), 2.16-2.08 (m, 2H), 1.85-1.72 (m, 2H); ESI-MS (m/z) 450, 452 [(MH)⁺, Cl³⁵,³⁷]. |
| Example-12: 2-Fluoro-N-(4-(6-methyl-4-oxospiro[chroman-2,1'-cyclobutan]-7-yl)phenyl)benzamide | 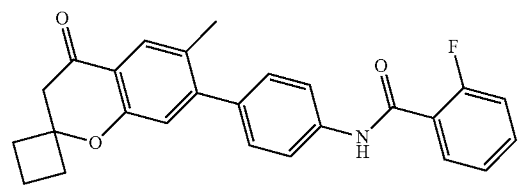 [SMILES: Cc1cc2c(cc1-c1ccc(NC(=O)c3ccccc3F)cc1)OC1(CCC1)CC2=O] | ¹HNMR (400 MHz, DMSO-d₆) δ 10.58 (s, 1H, D₂O exchangeable), 7.82 (d, J = 8.5 Hz, 2H), 7.71-7.61 (m, 1H), 7.63 (s, 1H), 7.62-7.57 (m, 1H), 7.42-7.33 (m, 4H), 6.88 (s, 1H), 2.97 (s, 2H), 2.30-2.18 (m, 5H), 2.17-2.07 (m, 2H), 1.92-1.70 (m, 2H); ESI-MS (m/z) 416 (MH)⁺. |
| Example-13: N-(2,6-Difluorophenyl)-4-(6-methyl-4-oxospiro[chroman-2,1'-cyclobutan]-7-yl)benzamide | 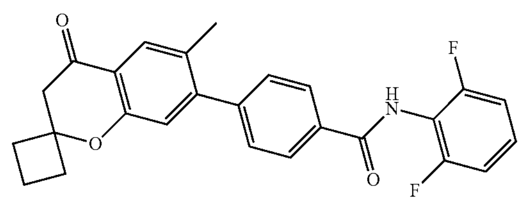 [SMILES: Cc1cc2c(cc1-c1ccc(C(=O)Nc3c(F)cccc3F)cc1)OC1(CCC1)CC2=O] | ¹HNMR (400 MHz, CDCl₃) δ 8.02 (d, J = 8.0 Hz, 2H), 7.78 (s, 1H), 7.50 (s, 1H), 7.47 (d, J = 8.0 Hz, 2H), 7.32-7.23 (m, 1H), 7.04 (t, J = 8.0 Hz, 2H), 6.90 (s, 1H), 2.94 (s, 2H), 2.38-2.33 (m, 2H), 2.28-2.14 (m, 5H), 2.03-1.89 (m, 1H), 1.78-1.73 (m, 1H); ESI-MS (m/z) 434 (MH)⁺. |
| Example-14: 7-(4-((2-Fluoro-6-methylbenzyl)amino)phenyl)-6-methylspiro[chroman-2,1'-cyclobutan]-4-one | 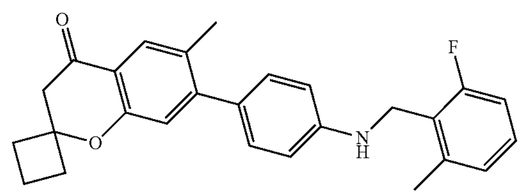 [SMILES: Cc1cc2c(cc1-c1ccc(NCc3c(C)cccc3F)cc1)OC1(CCC1)CC2=O] | ¹HNMR (400 MHz, CDCl₃) δ 7.73 (s, 1H), 7.22 (d, J = 8.0 Hz, 2H), 7.25-7.20 (m, 1H), 7.04 (d, J = 8.0 Hz, 1H), 6.97 (t, J = 8.0 Hz, 1H), 6.88 (s, 1H), 6.76 (d, J = 8.0 Hz, 2H), 4.37 (s, 2H), 3.77 (s, 1H), 2.91 (s, 2H), 2.46 (s, 3H), 2.39-2.31 (m, 2H), 2.28 (s, 3H), 2.23-2.15 (m, 2H), 1.96-1.91 (m, 1H), 1.76-1.69 (m, 1H); ESI-MS (m/z) 416 (MH)⁺. |
| Example-15: 2,6-Difluoro-N-(4-(5-methyl-4-oxospiro[chroman-2,1'-cyclobutan]-6-yl)phenyl)benzamide | 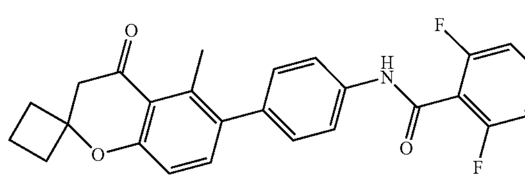 | ¹HNMR (400 MHz, CDCl₃) δ 7.69 (d, J = 8.0 Hz, 2H), 7.67 (s, 1H, D₂O exchangeable), 7.49-7.42 (m, 1H), 7.32 (d, J = 8.0 Hz, 1H), 7.28 (d, J = 8.0 Hz, 2H), 7.04 (t, J = 8.0 Hz, 2H), 6.90 (d, J = 8.0 Hz, 1H), 2.94 (s, 2H), 2.53 (s, 3H), 2.41-2.33 (m, 2H), 2.24-2.06 (m, 2H), 1.75-1.72 (m, 1H), 1.58-1.27 (m, 1H); ESI-MS (m/z) 434 (MH)⁺ |
| Example-16: 2,6-Difluoro-N-(4-(6-methyl-4-oxospiro[chroman-2,1'-cyclobutan]-7-yl)phenyl)benzamide | 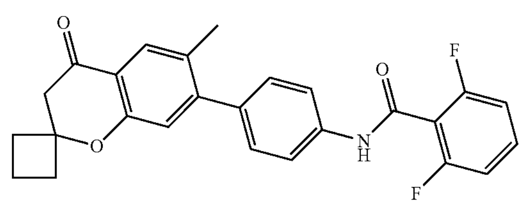 [SMILES: Cc1cc2c(cc1-c1ccc(NC(=O)c3c(F)cccc3F)cc1)OC1(CCC1)CC2=O] | ¹HNMR (400 MHz, CDCl₃) δ 7.78 (s, 1H, D₂O exchangeable), 7.72 (m, 3H), 7.49-7.42 (m, 1H), 7.35 (d, J = 8.0 Hz, 2H), 7.03 (t, J = 8.0 Hz, 2H), 6.88 (s, 1H), 3.48 (s, 2H), 2.39-2.31 (m, 2H), 2.25 (s, 3H), 2.23-2.16 (m, 2H), 1.96-1.93 (m, 1H), 1.74-1.69 (m, 1H); ESI-MS (m/z) 434 (MH)⁺ |

TABLE 4-continued

| Example No: IUPAC name | Structure | ¹HNMR/ESI-MS |
|---|---|---|
| Example-17: 2,6-Difluoro-N-(4-(7-methyl-4-oxospiro[chroman-2,1'-cyclobutan]-6-yl)phenyl)benzamide | 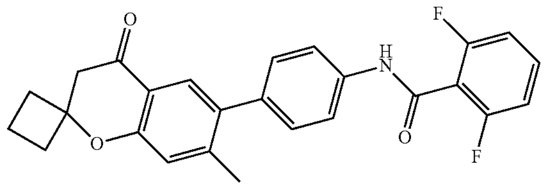 [SMILES: Cc1cc2c(cc1-c1ccc(NC(=O)c3c(F)cccc3F)cc1)C(=O)CC1(CCC1)O2] | ¹HNMR (400 MHz, CDCl₃) δ 7.71-7.68 (m, 4H), 7.49-7.41 (m, 1H), 7.31 (d, J = 8.0 Hz, 2H), 7.04 (t, J = 8.0 Hz, 2H), 6.91 (s, 1H), 2.91 (s, 2H), 2.41-2.33 (m, 2H), 2.30 (s, 3H), 2.23-2.17 (m, 2H), 1.97-1.92 (m, 1H), 1.77-1.70 (m, 1H); ESI-MS (m/z) 434 (MH)⁺ |
| Example-18: 2,6-Difluoro-N-(4-(7-methylspiro[chroman-2,1'-cyclobutan]-6-yl)phenyl)benzamide | 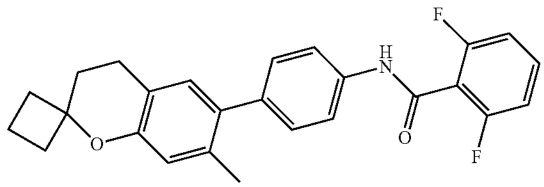 [SMILES: Cc1cc2c(cc1-c1ccc(NC(=O)c3c(F)cccc3F)cc1)CCC1(CCC1)O2] | ¹HNMR (400 MHz, CDCl₃) δ 7.67 (d, J = 8.0 Hz, 2H), 7.63 (s, 1H, D₂O exchangeable), 7.48-7.41 (m, 1H), 7.33 (d, J = 8.0 Hz, 2H), 7.03 (t, J = 8.0 Hz, 2H), 6.92 (s, 1H), 6.73 (s, 1H), 2.79 (t, J = 6.0 Hz, 2H), 2.36-2.26 (m, 2H), 2.22 (s, 3H), 2.13-2.08 (m, 2H), 2.01-1.98 (t, J = 6.0 Hz, 2H), 1.94-1.87 (m, 1H), 1.68-1.57 (m, 1H); ESI-MS (m/z) 420 (MH)⁺ |
| Example-19: 2,6-Difluoro-N-(4-(8-methyl-4-oxospiro[chroman-2,1'-cyclobutan]-7-yl)phenyl)benzamide | 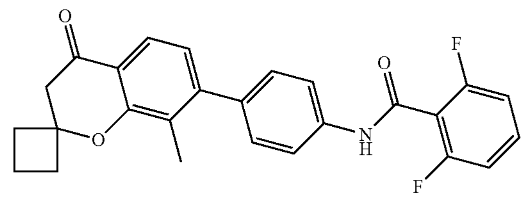 [SMILES: Cc1c(-c2ccc(NC(=O)c3c(F)cccc3F)cc2)ccc2c1OC1(CCC1)CC2=O] | ¹HNMR (400 MHz, DMSO-d₆) δ 10.97 (s, 1H, D₂O exchangeable), 7.80 (d, J = 8.0 Hz, 2H), 7.66-7.58 (m, 2H), 7.39 (d, J = 8.0 Hz, 2H), 7.26 (t, J = 8.0 Hz, 2H), 6.94 (d, J = 8.0 Hz, 1H), 2.99 (s, 2H), 2.29-2.21 (m, 2H), 2.17 (s, 3H), 2.16-2.10 (m, 2H), 1.90-1.74 (m, 2H); ESI-MS (m/z) 434 (MH)⁺ |
| Example-20: N-(4-(6-Ethyl-4-oxospiro[chroman-2,1'-cyclobutan]-7-yl)phenyl)-2,6-difluorobenzamide | 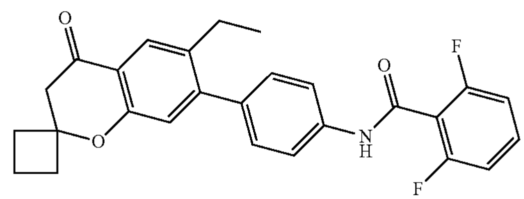 [SMILES: CCc1cc2c(cc1-c1ccc(NC(=O)c3c(F)cccc3F)cc1)OC1(CCC1)CC2=O] | ¹H NMR (400 MHz, CDCl₃) δ 7.79 (s, 1H), 7.72 (m, 3H), 7.50-7.45 (m, 1H), 7.34 (d, J = 8.0 Hz, 2H), 7.05 (t, J = 8.0 Hz, 2H), 6.85 (s, 1H), 2.93 (s, 2H), 2.57 (q, J = 7.0 Hz, 2H), 2.46-2.29 (m, 2H), 2.28-2.14 (m, 2H), 1.96-1.91 (m, 1H), 1.77-1.70 (m, 1H), 1.10 (t, J = 7.0 Hz, 3H); ESI-MS (m/z) 448 (MH)⁺ |
| Example-21: 7-(4-((2,6-Difluorobenzyl)amino)phenyl)-6-methylspiro[chroman-2,1'-cyclobutan]-4-one | 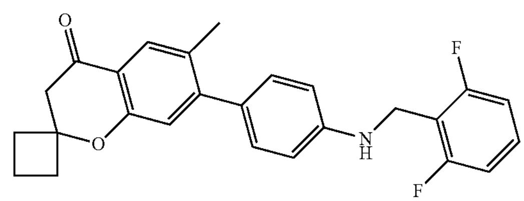 [SMILES: Cc1cc2c(cc1-c1ccc(NCc3c(F)cccc3F)cc1)OC1(CCC1)CC2=O] | ¹HNMR (400 MHz, CDCl₃) δ 7.71 (s, 1H), 7.30-7.22 (m, 1H), 7.18 (d, J = 8.5 Hz, 2H), 6.93 (t, J = 8.0 Hz, 2H), 6.85 (s, 1H), 6.79 (d, J = 8.5 Hz, 2H), 4.49 (s, 2H), 2.90 (s, 2H), 2.38-2.30 (m, 2H), 2.24 (s, 3H), 2.21-2.15 (m, 2H), 1.97-1.90 (m, 1H), 1.79-1.69 (m, 1H); ESI-MS (m/z) 420 (MH)⁺ |

Example-22

2,6-Difluoro-N-(4-(6-methylspiro[chroman-2,1'-cyclobutan]-7-yl)phenyl)benzamide

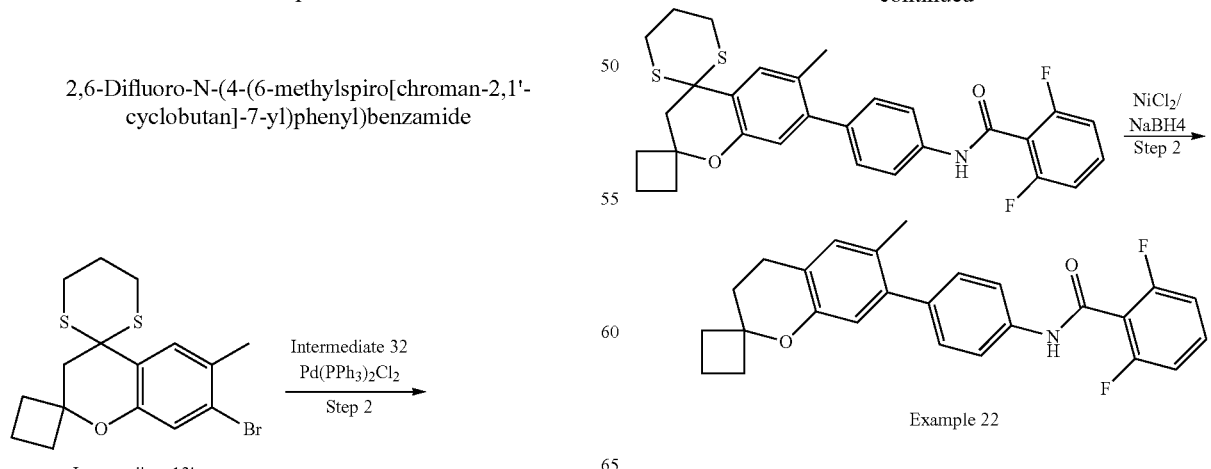

Step-1: Intermediate-12b was reacted with Intermediate-32 by following the similar procedure as described in Example-1 to give step-1 compound. ¹HNMR (400 MHz, CDCl₃) δ 7.67-7.65 (m, 3H), 7.47-7.43 (m, 1H), 7.36 (d, J=8.0 Hz, 2H), 7.04 (t, J=8.0 Hz, 2H), 6.77 (s, 1H), 3.34-3.26 (m, 2H), 2.95 (s, 2H), 2.87-2.81 (m, 2H), 2.53-2.50 (m, 2H), 2.27-2.19 (m, 5H), 2.06-2.01 (m, 3H), 1.80-1.70 (m, 1H); ESI-MS (m/z) 524 (MH)⁺.

Step-2: 2,6-Difluoro-N-(4-(6-methylspiro[chroman-2,1'-cyclobutan]-7-yl)phenyl)benzamide: The title compound was prepared by following the similar procedure as described in step-2 of Intermediate-13b using step-1 Intermediate. ¹HNMR (400 MHz, CDCl₃) δ 7.67 (d, J=8.0 Hz, 2H), 7.64 (s, 1H, D₂O exchangeable), 7.48-7.41 (m, 1H), 7.34 (d, J=8.0 Hz, 2H), 7.05 (t, J=8.0 Hz, 2H), 6.95 (s, 1H), 6.73 (s, 1H), 2.82-2.79 (t, J=6.0 Hz, 2H), 2.36-2.28 (m, 2H), 2.19 (s, 3H), 2.12-2.00 (m, 2H), 2.02-1.99 (t, J=6.0 Hz, 2H), 1.72-1.69 (m, 1H), 1.68-1.59 (m, 1H); ESI-MS (m/z) 420 (MH)⁺.

Example-23

2,6-Difluoro-N-(4-(8-methylspiro[chroman-2,1'-cyclobutan]-7-yl)phenyl)benzamide

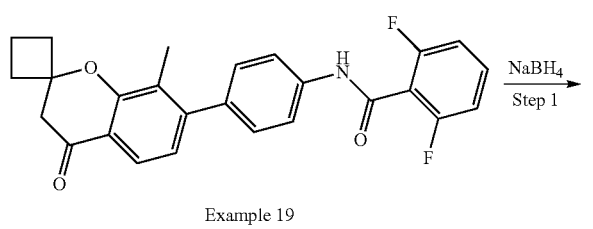

Example 19

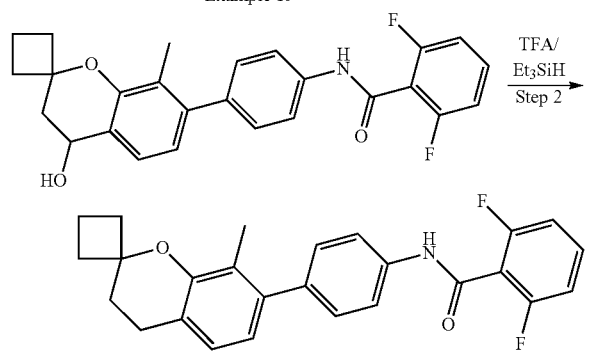

Example 23

Step-1: 2,6-Difluoro-N-(4-(4-hydroxy-8-methylspiro[chroman-2,1'-cyclobutan]-7-yl)phenyl) benzamide: To a (0° C.) cooled and stirred solution of Example-19 (0.28 g, 0.64 mmol) in ethanol (10 mL) was added sodium borohydride (49 mg, 1.29 mmol) portion-wise. The resulting mixture was stirred at RT for 3 h. The reaction was then quenched with ethyl acetate (3 mL) and the solvent was evaporated under vacuum. The crude product was purified by flash column chromatography (silica gel, 30% ethyl acetate in hexanes system as eluent) to afford 100 mg (36%) of the title product as white solid. ¹HNMR (400 MHz, DMSO-d₆) δ 10.89 (s, 1H, D₂O exchangeable), 7.74 (d, J=8.0 Hz, 2H), 7.62-7.58 (m, 1H), 7.30-7.25 (m, 5H), 6.74 (d, J=8.0 Hz, 1H), 5.37 (d, J=4.0 Hz, 1H, D₂O exchangeable), 4.75-4.70 (m, 1H), 3.39-3.32 (m, 2H), 2.33-2.24 (m, 2H), 2.14-2.05 (m, 2H), 2.05 (s, 3H), 1.90-1.68 (m, 2H); ESI-MS (m/z) 436 (MH)⁺

Step-2: 2,6-Difluoro-N-(4-(8-methylspiro[chroman-2,1'-cyclobutan]-7-yl)phenyl)benzamide: To a (0° C.) cooled and stirred solution of step-1 Intermediate (70 mg, 0.16 mmol) in DCM (2 mL) was added trifluoroacetic acid (2 mL). Then triethylsilane (51 µL, 0.32 mmol) was added in drop-wise manner and stirred at RT for 2 h. The reaction mixture was then cooled to 0° C. and basified with aqueous saturated solution of NaHCO₃ (5 mL) The layers were separated and the aqueous layer was extracted with DCM (2×5 mL) The combined organic layers were washed with brine (3 mL), dried (Na₂SO₄) and filtered. The filtrate was concentrated under reduced pressure and the crude product was purified by flash column chromatography (silica gel, 15% ethyl acetate in hexanes system as eluent) to afford 20 mg (29%) of the title product as white solid. ¹HNMR (400 MHz, DMSO-d₆) δ 10.88 (s, 1H, D₂O exchangeable), 7.73 (d, J=8.0 Hz, 2H), 7.64-7.57 (m, 1H), 7.33-7.26 (m, 4H), 6.94 (d, J=8.0 Hz, 1H), 6.66 (d, J=8.0 Hz, 1H), 2.77 (t, J=6.0 Hz, 2H), 2.22-2.14 (m, 2H), 2.11-2.06 (m, 2H), 2.05 (s, 3H), 1.94 (t, J=6.0 Hz, 2H), 1.84-1.68 (m, 2H); ESI-MS (m/z) 420 (MH)⁺.

Example-24

N-(4-(6-Ethylspiro[chroman-2,1'-cyclobutan]-7-yl)phenyl)-2,6-difluorobenzamide

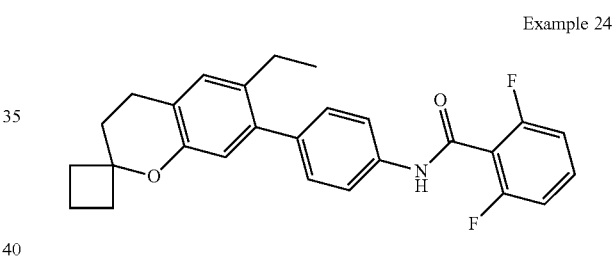

Example 24

The title compound was prepared by following the similar procedure as described in Example-23 using Example-20. ¹H NMR (400 MHz, CDCl₃) δ 7.68-7.65 (m, 3H), 7.47-7.43 (m, 1H), 7.33 (d, J=8.0 Hz, 2H), 7.04 (t, J=8.0 Hz, 2H), 6.98 (s, 1H), 6.69 (s, 1H), 2.83 (t, J=6.0 Hz, 2H), 2.53 (q, J=7.0 Hz, 2H), 2.36-2.28 (m, 2H), 2.13-2.05 (m, 2H), 2.01 (t, J=6.0 Hz, 2H), 1.96-1.85 (m, 1H), 1.74-1.63 (m, 1H), 1.08 (t, J=7.0 Hz, 3H); ESI-MS (m/z) 434 (MH)⁺

Example-25

2,6-Difluoro-N-(4-(4-hydroxy-6-methylspiro[chroman-2,1'-cyclobutan]-7-yl) phenyl)benzamide

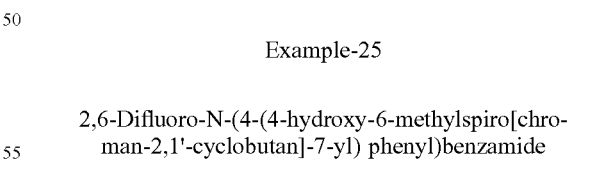

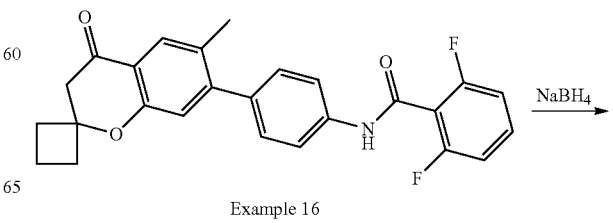

Example 16

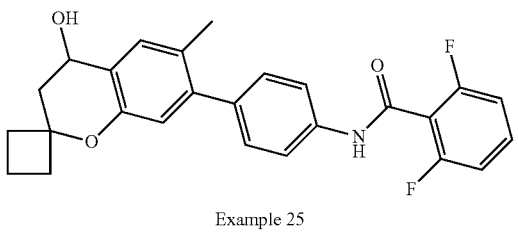

Example 25

The title compound was prepared by following the similar procedure as described in step-1 of Example-23 using Example-16 and sodium borohydride. $^1$HNMR (400 MHz, CDCl$_3$) δ 7.69 (d, J=8.0 Hz, 2H), 7.48-7.43 (m, 1H), 7.36 (d, J=8.0 Hz, 2H), 7.32 (s, 1H), 7.04 (t, J=8.0 Hz, 2H), 6.76 (s, 1H), 4.92-4.89 (m, 1H), 3.53-3.47 (m, 1H), 2.41-2.30 (m, 3H), 2.23 (s, 3H), 2.15-2.06 (m, 2H), 1.97-1.83 (m, 1H), 1.81-1.70 (m, 1H); ESI-MS (m/z) 436 (MH)$^+$.

Example-26

2,6-Difluoro-N-(5-(6-methyl-4-oxospiro[chroman-2,1'-cyclobutan]-7-yl)pyridin-2-yl)benzamide

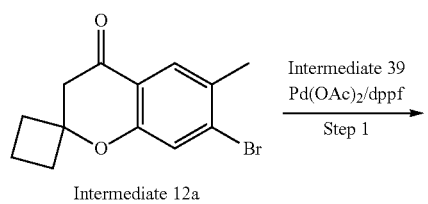

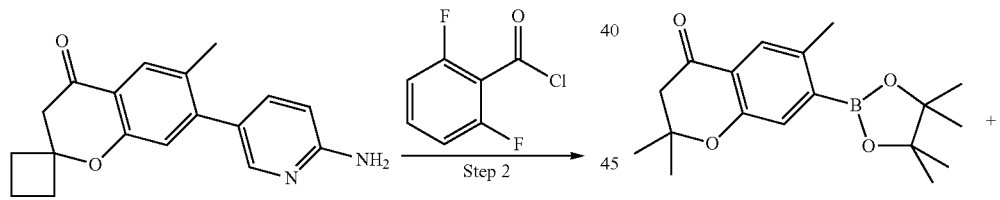

Step-1: 7-(6-Aminopyridin-3-yl)-6-methylspiro[chroman-2,1'-cyclobutan]-4-one: To a nitrogen purged and stirred solution of Intermediate-12a (0.235 g, 0.836 mmol) and Intermediate-39 (0.184 g, 0.836 mmol) in THF (10 mL) was added sodium carbonate (0.177 g, 1.672 mmol) followed by bis(triphenylphosphine)palladium(II) chloride (29 mg, 0.042 mmol). The resulting mixture was thoroughly deoxygenated by purging nitrogen for a period of 5 min and then stirred at 80° C. for 15 h. The reaction was allowed to cool to RT, diluted with ethyl acetate (5 mL) and then filtered through celite bed. The filtrate was concentrated under vacuum and the resultant crude product was purified by flash column chromatography (silica gel, 20% Methanol in DCM system as eluent) to afford 154 mg (61%) of the title product as white solid. $^1$HNMR (400 MHz, DMSO-d$_6$) δ 7.92 (s, 1H), 7.60 (s, 1H), 7.45 (d, J=8.5 Hz, 1H), 6.83 (s, 1H), 6.51 (d, J=8.5 Hz, 1H), 2.94 (s, 2H), 2.30-2.15 (m, 5H), 2.12-2.10 (m 2H), 1.88-1.75 (m, 2H).

Step-2: 2, 6-Difluoro-N-(5-(6-methyl-4-oxospiro[chroman-2,1'-cyclobutan]-7-yl)pyridin-2-yl)benzamide: To a (0° C.) cooled solution of 2,6-difluorobenzoyl chloride (66 μL, 0.52 mmol) in DCM (5 mL) was added step-1 Intermediate (0.154 g, 0.523 mmol) followed by pyridine (51 μL, 0.628 mmol). The resulting mixture was stirred at RT for 3 h and then diluted with DCM (10 mL), washed with aqueous hydrochloric acid (5 mL, 10%), saturated aqueous sodium bicarbonate solution (5 mL), water (5 mL), brine (5 mL), dried (Na$_2$SO$_4$) and filtered. The filtrate was rotary evaporated and the crude product was purified by flash column chromatography (silica gel, 40% ethyl acetate in hexanes system as eluent) to afford 66 mg (30%) of the title product as white solid. $^1$HNMR (400 MHz, CDCl$_3$) δ 8.77 (s, 1H, D$_2$O exchangeable), 8.48 (d, J=8.0 Hz, 1H), 8.21 (d, J=2.0 Hz, 1H), 7.85-7.73 (m, 2H), 7.49-7.47 (m, 1H), 7.05 (t, J=8.0 Hz, 2H), 6.87 (s, 1H), 2.94 (s, 2H), 2.38-2.33 (m, 2H), 2.28-2.14 (m, 5H), 2.03-1.90 (m, 1H), 1.84-1.69 (m, 1H); ESI-MS (m/z) 435 (MH)$^+$.

Example-27

2,6-Difluoro-N-(6-(2,2,6-trimethyl-4-oxochroman-7-yl)pyridin-3-yl)benzamide

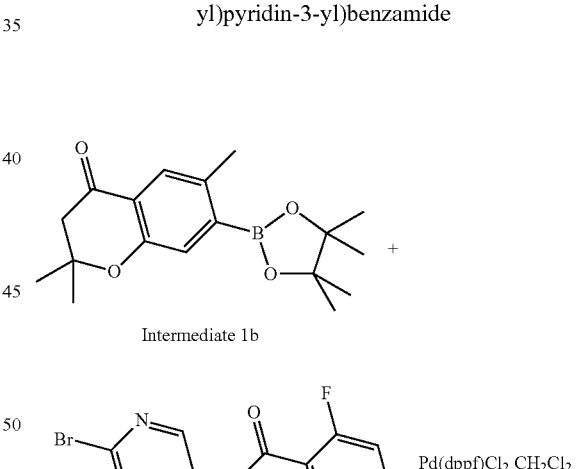

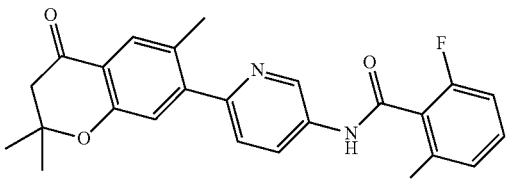

Example 27

To a nitrogen purged and stirred solution of Intermediate-36 (99 mg, 0.32 mmol) in dioxane (5 mL) was added Intermediate-1b (100 mg, 0.32 mmol), aqueous potassium carbonate solution (3 mL) and 1,1'-bis(diphenylphosphino) ferrocenedichloro palladium(II) dichloromethane complex (26 mg, 0.032 mmol) were sequentially added. The resulting mixture was thoroughly deoxygenated by purging nitrogen for a period of 15 minutes and then heated to 130° C. and then maintained for 30 min in microwave (Biotage). The reaction was cooled to room temperature and filtered through celite. The celite cake was washed with ethyl acetate (10 mL) The filtrate was rotary evaporated and the crude product was purified by column chromatography to afford 10 mg (7%) of the title compound as white solid. $^1$H NMR (400 MHz, CDCl$_3$) δ 8.72 (d, J=2.0 Hz, 1H), 8.46 (dd, J=2.0 & 8.0 Hz, 1H), 7.87 (s, 1H), 7.77 (s, 1H), 7.52-7.47 (m, 2H), 7.07 (t, J=8.0 Hz, 2H), 7.02 (s, 1H), 2.75 (s, 2H), 2.32 (s, 3H), 1.48 (s, 6H); LC-MS (m/z) 423 (MH)$^+$.

Example-28

N-(6-(6-Ethyl-2,2-dimethyl-4-oxochroman-7-yl)pyridin-3-yl)-2,6-difluoro benzamide

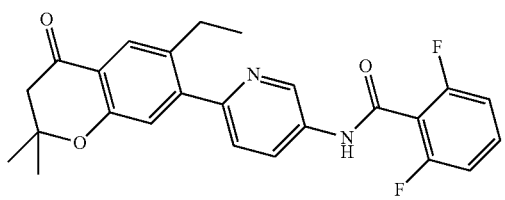

Example 28

The title compound was prepared by following the similar procedure as described in Example-27 by using Intermediate-2b and Intermediate-36. $^1$HNMR (400 MHz, CDCl$_3$) δ 8.75 (d, J=2.0 Hz, 1H), 8.49 (dd, J=2.0 & 8.0 Hz, 1H), 7.99 (s, 1H), 7.82 (s, 1H), 7.54-7.45 (m, 2H), 7.07 (t, J=8.0 Hz, 2H), 6.95 (s, 1H), 2.76 (s, 2H), 2.68 (q, J=7.5 Hz, 2H), 1.48 (s, 6H), 1.10 (t, J=7.5 Hz, 3H); ESI-MS (m/z) 437 (MH)$^+$.

Example-29

2,6-Difluoro-N-(6-(6-methyl-4-oxospiro[chroman-2,1'-cyclobutan]-7-yl)pyridin-3-yl)benzamide

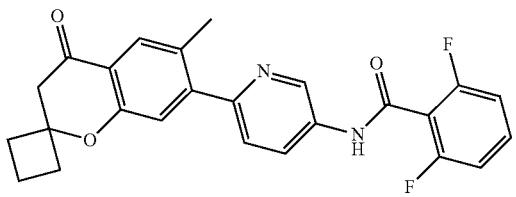 [SMILES: Cc1cc2c(cc1-c1ccc(NC(=O)c3c(F)cccc3F)cn1)OC1(CCC1)CC2=O]

The title compound was prepared by following the similar procedure as described in Example-27 by using Intermediate-12d and Intermediate-36. $^1$HNMR (400 MHz, DMSO-d$_6$) δ 11.21 (s, 1H), 8.92 (d, J=2.5 Hz, 1H), 8.26 (dd, J=8.0 & 2.5 Hz, 1H), 7.70-7.59 (m, 3H), 7.31 (t, J=8.0 Hz, 2H), 7.08 (s, 1H), 2.99 (s, 2H), 2.29 (s, 3H), 2.26-2.19 (m, 2H), 2.16-2.10 (m, 2H), 1.90-1.70 (m, 1H), 0.89-0.76 (m, 1H); ESI-MS (m/z) 435 (MH)$^+$.

Example-30

2,6-Difluoro-N-(4-(2,2,8-trimethyl-4-oxochroman-7-yl)phenyl)benzamide

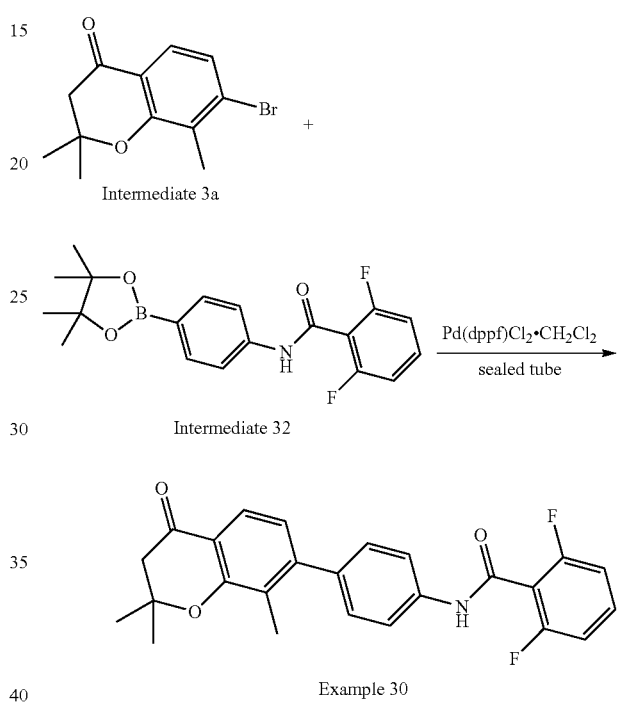

To a stirred and nitrogen purged solution of Intermediate-3a (150 mg, 0.55 mmol) in dioxane (5 mL), in a sealed tube, was added Intermediate-32 (240 mg, 0.66 mmol), aqueous potassium carbonate solution (2 mL, 2M) and PdCl$_2$(dppf)-CH$_2$Cl$_2$ adduct (41 mg, 0.056 mmol) sequentially. The resulting mixture was thoroughly deoxygenated by purging nitrogen gas for another 10 minutes. The sealed tube was capped and stirred at 110° C. for 18 h. The reaction mixture was cooled to room temperature and filtered through celite. The celite bed was washed with ethyl acetate (15 mL) The filtrate was evaporated and the crude product was purified by flash column chromatography (silica gel, 30% ethyl acetate in hexane as eluent) to afford 120 mg (51%) of the title compound as white solid. $^1$HNMR (400 MHz, DMSO-d$_6$) δ 10.96 (s, 1H), 7.79 (d, J=8.0 Hz, 2H), 7.67-7.56 (m, 2H), 7.38 (d, J=8.0 Hz, 2H), 7.28 (t, J=8.0 Hz, 2H), 6.91 (d, J=8.0 Hz, 1H), 2.81 (s, 2H), 2.11 (s, 3H), 1.44 (s, 6H); ESI-MS (m/z) 422 (MH)$^+$.

The below Examples (31-45) given in Table-5 were prepared by following the similar procedure as described in Example-30 by using the appropriate Intermediates.

TABLE 5

| Example No: IUPAC name | Structure | ¹HNMR/ESI-MS |
|---|---|---|
| Example-31: 2,6-Difluoro-N-(5-(2,2,8-trimethyl-4-oxochroman-7-yl)pyrazin-2-yl)benzamide | 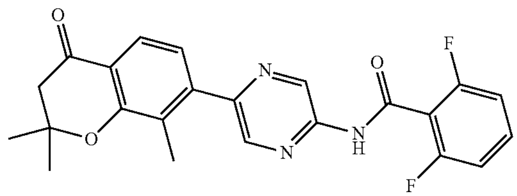 [SMILES: Cc1c(-c2cnc(NC(=O)c3c(F)cccc3F)cn2)ccc2c1OC(C)(C)CC2=O] | ¹HNMR (400 MHz, DMSO-$d_6$) δ 11.84 (s, 1H), 9.52 (s, 1H), 8.66 (s, 1H), 7.70 (d, J = 8.0 Hz, 1H), 7.67-7.59 (m, 1H), 7.28 (t, J = 8.0 Hz, 2H), 7.16 (d, J = 8.0 Hz, 1H), 2.85 (s, 2H), 2.21 (s, 3H), 1.45 (s, 6H); ESI-MS (m/z) 424 (MH)⁺. |
| Example-32: 2,6-Difluoro-N-(4-(4-hydroxy-2,2,8-trimethylchroman-7-yl)phenyl)benzamide | 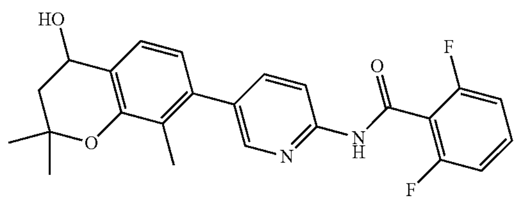 [SMILES: Cc1c(-c2ccc(NC(=O)c3c(F)cccc3F)nc2)ccc2c1OC(C)(C)CC2O] | ¹HNMR (400 MHz, DMSO-$d_6$) δ 10.88 (s, 1H), 7.74 (d, J = 8.0 Hz, 2H), 7.66-7.57 (m, 1H), 7.35-7.26 (m, 5H), 6.74 (d, J = 8.0 Hz, 1H), 5.33 (d, J = 6.0 Hz, 1H, $D_2O$ exchangeable), 4.74-4.68 (m, 1H), 2.12-2.07 (m, 1H), 2.02 (s, 3H), 1.76-1.71 (m, 1H), 1.41 (s, 3H), 1.27 (s, 3H); ESI-MS (m/z) 424 (MH)⁺. |
| Example-33: 7-(4-((2,6-Difluorobenzyl)amino)phenyl)-2,2,6-trimethylchroman-4-one | 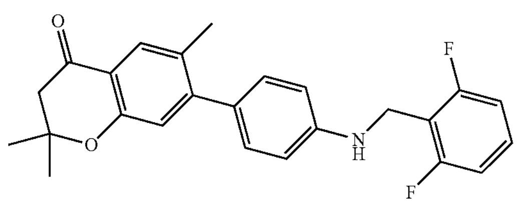 [SMILES: Cc1cc2c(cc1-c1ccc(NCc3c(F)cccc3F)cc1)OC(C)(C)CC2=O] | ¹HNMR (400 MHz, DMSO-$d_6$) δ 7.57 (s, 1H), 7.46-7.38 (m, 1H), 7.17-7.10 (m, 4H), 6.73 (d, J = 8.0 Hz, 2H), 6.71 (s, 1H), 6.29 (t, J = 5.5 Hz, 1H, $D_2O$ exchangeable), 4.30 (d, J = 5.5 Hz, 2H), 2.75 (s, 2H), 2.20 (s, 3H), 1.39 (s, 6H); ESI-MS (m/z) 408 (MH)⁺ |
| Example-34: 7-(5-((2,6-Difluorobenzyl)amino)pyrazin-2-yl)-2,2,6-trimethylchroman-4-one | | 1H NMR (400 MHz, $CDCl_3$) δ 8.19 (s, 1H), 8.12 (s, 1H), 7.76 (s, 1H), 7.34-7.30 (m, 1H), 7.00 (s, 1H), 6.96 (t, J = 8.0 Hz, 2H), 4.76 (d, J = 5.5 Hz, 2H), 2.74 (s, 2H), 2.34 (s, 3H), 1.47 (s, 6H): ESI-MS (m/z) 410 (MH)⁺ |
| Example-35: 7-(6-((2,6-Difluorobenzyl)amino)pyridin-3-yl)-2,2,6-trimethylchroman-4-one | 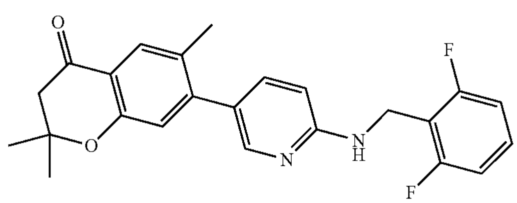 [SMILES: Cc1cc2c(cc1-c1ccc(NCc3c(F)cccc3F)nc1)OC(C)(C)CC2=O] | ¹HNMR (400 MHz, DMSO-$d_6$) δ 8.03 (d, J = 2.5 Hz, 1H), 7.60 (s, 1H), 7.46 (dd, J = 8.5 & 2.5 Hz, 1H), 7.44-7.37 (m, 1H), 7.14-7.09 (m, 3H), 6.78 (s, 1H), 6.59 (d, J = 8.5 Hz, 1H), 4.55 (d, J = 5.5 Hz, 2H), 2.77 (s, 2H), 2.21 (s, 3H), 1.40 (s, 6H): ESI-MS (m/z) 409 (MH)⁺ |
| Example-36: 2,6-Difluoro-N-(5-(6-methyl-4-oxospiro[chroman-2,1'-cyclobutan]-7-yl)pyrazin-2-yl)benzamide | 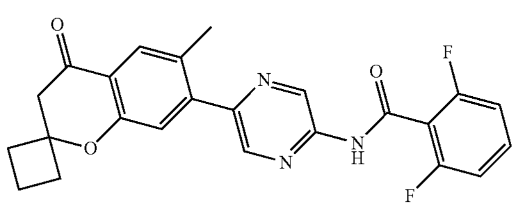 [SMILES: Cc1cc2c(cc1-c1cnc(NC(=O)c3c(F)cccc3F)cn1)OC1(CCC1)CC2=O] | ¹HNMR (400 MHz, $CDCl_3$ δ 9.79 (s, 1H), 8.45 (brs, 1H), 8.44 (s, 1H), 7.80 (s, 1H), 7.54-7.50 (m, 1H), 7.09 (s, 1H), 7.07 (t, J = 8.5 Hz, 2H), 2.95 (s, 2H), 2.36 (s, 3H), 2.35-2.29 (m, 2H), 2.22-2.17 (m, 2H), 2.00-1.89 (m, 1H), 1.76-1.72 (m, 1H); ESI-MS (m/z) 436 (MH)⁺ |
| Example-37: 2,6-Difluoro-N-(6-(2,2,8-trimethyl-4-oxochroman-7-yl)pyridin-3-yl)benzamide | 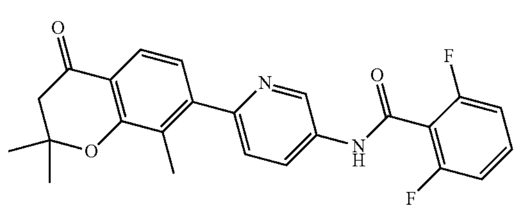 [SMILES: Cc1c(-c2ccc(NC(=O)c3c(F)cccc3F)cn2)ccc2c1OC(C)(C)CC2=O] | ¹HNMR (400 MHz, DMSO-$d_6$) δ 11.21 (s, 1H), 8.94 (d, J = 2.5 Hz, 1H), 8.26 (dd, J = 8.0 & 2.5 Hz, 1H), 7.69-7.62 (m, 2H), 7.59 (d, J = 8.0 Hz, 1H), 7.30 (t, J = 8.0 Hz, 2H), 7.06 (d, J = 8.0 Hz, 1H), 2.83 (s, 2H), 2.17 (s, 3H), 1.44 (s, 6H); ESI-MS (m/z) 423 (MH)⁺. |

TABLE 5-continued

| Example No: IUPAC name | Structure | ¹HNMR/ESI-MS |
|---|---|---|
| Example-38: 7-(5-((2,6-Difluorobenzyl)amino)pyrazin-2-yl)-6-methylspiro[chroman-2,1'-cyclobutan]-4-one | 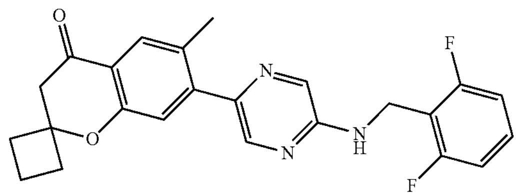 [SMILES: Cc1cc2c(cc1-c1cnc(NCc3c(F)cccc3F)cn1)OC1(CCC1)CC2=O] | ¹HNMR (400 MHz, DMSO-d₆) δ 8.23 (s, 1H), 8.05 (s, 1H), 7.74 (t, J = 5.5 Hz, 1H), 7.59 (s, 1H), 7.47-7.41 (m, 1H), 7.15 (t, J = 8.0 Hz, 2H), 7.06 (s, 1H), 4.58 (d, J = 5.5 Hz, 2H), 2.96 (s, 2H), 2.29 (s, 3H), 2.25-2.18 (m, 2H), 2.15-2.07 (m, 2H), 1.84-1.72 (m, 2H): ESI-MS (m/z) 422 (MH)⁺ |
| Example-39: 7-(6-((2,6-Difluorobenzyl)amino)pyridin-3-yl)-6-methylspiro[chroman-2,1'-cyclobutan]-4-one | 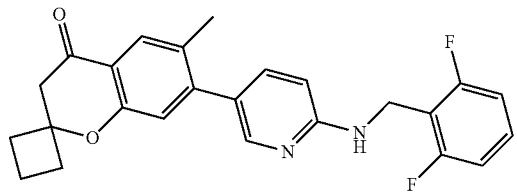 [SMILES: Cc1cc2c(cc1-c1ccc(NCc3c(F)cccc3F)nc1)OC1(CCC1)CC2=O] | ¹HNMR (400 MHz, DMSO-d₆) δ 8.04 (d, J = 2.5 Hz, 1H), 7.59 (s, 1H), 7.47 (dd, J = 8.5 & 2.5 Hz, 1H), 7.44-7.38 (m, 1H), 7.15-7.10 (m, 3H), 6.85 (s, 1H), 6.60 (d, J = 8.5 Hz, 1H), 4.55 (d, J = 5.0 Hz, 2H), 2.95 (s, 2H), 2.27-2.22 (m, 2H), 2.21 (s, 3H), 2.14-2.06 (m, 2H), 1.85-1.71 (m, 2H); ESI-MS (m/z) 421 (MH)⁺ |
| Example-40: 7-(5-((2,6-Difluorobenzyl)amino)pyridin-2-yl)-6-methylspiro[chroman-2,1'-cyclobutan]-4-one | 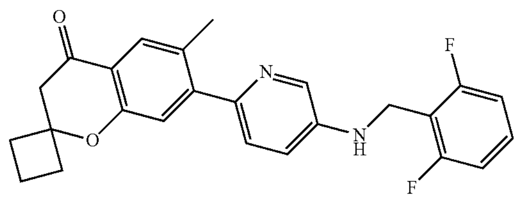 [SMILES: Cc1cc2c(cc1-c1ccc(NCc3c(F)cccc3F)cn1)OC1(CCC1)CC2=O] | ¹HNMR (400 MHz, DMSO-d₆) δ 8.14 (d, 7 = 2.5 Hz, 1H), 7.56 (s, 1H), 7.48-7.41 (m, 1H), 7.36 (d, J = 8.5 Hz, 1H), 7.16 (t, J = 8.0 Hz, 2H), 7.09 (dd, J = 8.5 & 2.5 Hz, 1H), 6.99 (s, 1H), 6.60 (t, J = 5.5 Hz, 1H), 4.36 (d, 7 = 5.5 Hz, 2H), 2.95 (s, 2H), 2.28 (s, 3H), 2.24-2.17 (m, 2H), 2.13-2.06 (m, 2H), 1.86-1.72 (m, 2H); ESI-MS (m/z) 421 (MH)⁺ |
| Example-41: N-(5-(6-Ethyl-4-oxospiro[chroman-2,1'-cyclobutan]-7-yl)pyrazin-2-yl)-2,6-difluorobenzamide | 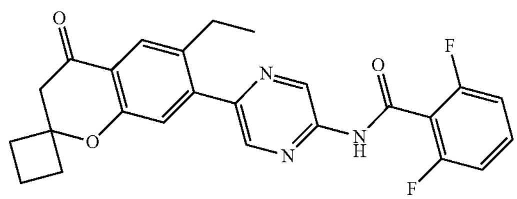 [SMILES: CCc1cc2c(cc1-c1cnc(NC(=O)c3c(F)cccc3F)cn1)OC1(CCC1)CC2=O] | ¹HNMR (400 MHz, CDCl₃) δ 9.78 (s, 1H), 8.47 (s, 1H), 8.40 (s, 1H), 7.84 (s, 1H), 7.52-7.50 (m, 1H), 7.09 (t, J = 8.0 Hz, 2H), 7.03 (s, 1H), 2.95 (s, 2H), 2.70 (q, J = 7.5 Hz, 2H), 2.41-2.33 (m, 2H), 2.27-2.15 (m, 2H), 1.97-1.94 (m, 1H), 1.79-1.71 (m, 1H), 1.14 (t, J = 7.5 Hz, 3H). ESI-MS (m/z) 450 (MH)⁺. |
| Example-42: N-(3,5-Difluoropyridin-4-yl)-4-(6-ethyl-2,2-dimethyl-4-oxochroman-7-yl)benzamide | 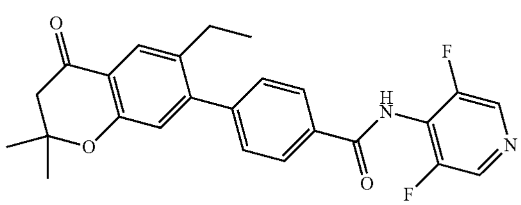 [SMILES: CCc1cc2c(cc1-c1ccc(C(=O)Nc3c(F)cncc3F)cc1)OC(C)(C)CC2=O] | ¹HNMR (400 MHz, DMSO-d6) δ 10.77 (s, 1H, D₂O exchangeable), 8.64 (s, 2H), 8.09 (d, J = 8.0 Hz, 2H), 7.70 (s, 1H), 7.55 (d, J = 8.0 Hz, 2H), 6.82 (s, 1H), 2.83 (s, 2H), 2.56 (q, J = 7.5 Hz, 2H), 1.42 (s, 6H), 1.01 (t, J = 7.5 Hz, 3H); ESI-MS (m/z) 437 (MH)⁺. |
| Example-43: N-(3,5-Difluoropyridin-4-yl)-4-(2,2,6-trimethyl-4-oxochroman-7-yl)benzamide | 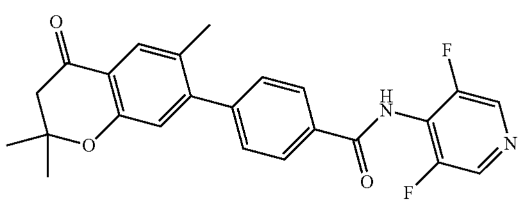 [SMILES: Cc1cc2c(cc1-c1ccc(C(=O)Nc3c(F)cncc3F)cc1)OC(C)(C)CC2=O] | ¹HNMR (400 MHz, CDCl₃) δ 8.44 (s, 2H), 8.03 (d, J = 8.0 Hz, 2H), 7.85 (s, 1H), 7.78 (s, 1H), 7.49 (d, J = 8.0 Hz, 2H), 6.84 (s, 1H), 2.76 (s, 2H), 2.21 (s, 3H), 1.50 (s, 6H); ESI-MS (m/z) 423 (MH)⁺. |
| Example-44: 4-(6-Methyl-4-oxospiro[chroman-2.1'-cyclobutan]-7-yl)-N-(3-methylpyridin-4-yl)benzamide | 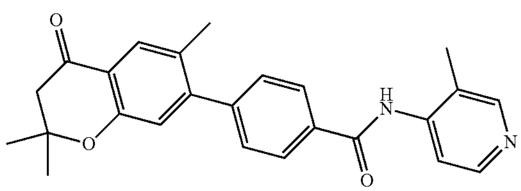 | ¹HNMR (400 MHz, DMSO-d₆) δ 10.05 (s, 1H, D₂O exchangeable), 8.45 (s, 1H), 8.40 (d, J = 5.5 Hz, 1H), 8.06 (d, J = 8.0 Hz, 2H), 7.67 (s, 1H), 7.65 (d, J = 5.5 Hz, 1H), 7.57 (d, 7 = 8.0 Hz, 2H), 6.93 (s, 1H), 3.00 (s, 2H), 2.30 (s, 3H), 2.25-2.23 (m, 2H), 2.21 (s, 3H), 2.17-2.09 (m, 2H), 1.89-1.74 (m, 2H); ESI-MS (m/z) 413 (MH)⁺. |

| Example No: IUPAC name | Structure | ¹HNMR/ESI-MS |
|---|---|---|
| Example-45: Methyl 7-(5-(2,6-difluorobenzamido)pyrazin-2-yl)-2,6-dimethyl-4-oxochroman-2-carboxylate | [Structure] | ¹HNMR (400 MHz, DMSO-d₆) δ 11.86 (s, 1H), 9.51 (s, 1H), 8.70 (s, 1H), 7.69-7.58 (m, 2H), 7.33-7.24 (m, 3H), 3.62 (s, 3H), 3.21 (d, J = 17.0 Hz, 1H), 3.09 (d, J = 17.0 Hz, 1H), 2.33 (s, 3H), 1.70 (s, 3H); ESI-MS (m/z) 468 (MH)⁺ |

Example-46

7-(5-(2,6-Difluorobenzamido)pyrazin-2-yl)-2,6-dimethyl-4-oxochroman-2-carboxamide A solution of Example-45 (130 mg, 0.278 mmol) in methanolic ammonia (5 mL, 7N) was heated at 100° C. for 4 h. The reaction was cooled to room temperature and the solvent was evaporated under vacuum. The crude product was washed with 15% ethyl acetate-hexane to afford 60 mg (47%) of the title compound as white solid. ¹HNMR (400 MHz, DMSO-d₆) δ 11.87 (s, 1H), 9.53 (s, 1H), 8.72 (s, 1H), 7.68-7.61 (m, 3H), 7.42-7.25 (m, 4H), 3.16 (d, J=17.0 Hz, 1H), 2.92 (d, J=17.0 Hz, 1H), 2.34 (s, 3H), 1.61 (s, 3H); ESI-MS (m/z) 453 (MH)⁺.

Example-47

7-(5-(2,6-Difluorobenzamido)pyrazin-2-yl)-2,6-dimethyl-4-oxochroman-2-carboxylic acid To a (0° C.) cooled and stirred solution of Example-45 (130 mg, 0.278 mmol) in THF (5 mL) and water (1 mL) was added lithium hydroxide monohydrate (35 mg, 0.83 mmol). The resulting mixture was stirred at room temperature for 2 h. The solvent was evaporated and the crude product was washed with water (2 mL) to afford 30 mg (24%) of the title compound as pale yellow solid. ¹HNMR (400 MHz, DMSO-d₆) δ 11.85 (s, 1H), 9.52 (s, 1H), 8.66 (s, 1H), 7.69-7.61 (m, 1H), 7.58 (s, 1H), 7.28 (t, J=8.0 Hz, 2H), 7.14 (s, 1H), 3.05 (d, J=16.5 Hz, 1H), 2.82 (d, J=16.5 Hz, 1H), 2.30 (s, 3H), 1.54 (s, 3H); ESI-MS (m/z) 454 (MH)⁺.

Example-48a

N-(4-(6-Ethyl-4-hydroxy-2,2-dimethylchroman-7-yl)phenyl)-2,6-difluorobenzamide and Example-48b N-(4-(6-Ethyl-2,2-dimethylchroman-7-yl)phenyl)-2,6-difluorobenzamide

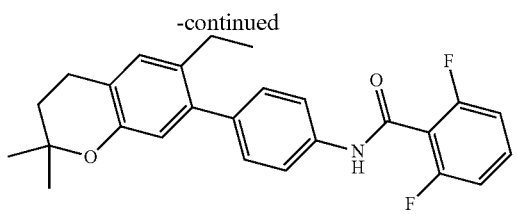

Example 48b

Step-1: N-(4-(6-Ethyl-4-hydroxy-2,2-dimethylchroman-7-yl)phenyl)-2,6-difluorobenzamide: The title compound was prepared by following the similar procedure as described in step-1 of Intermediate-4a by using Example-2. $^1$H NMR (400 MHz, CDCl$_3$) δ 7.69-7.67 (m, 3H), 7.48-7.42 (m, 1H), 7.40 (s, 1H), 7.33 (d, J=8.0 Hz, 2H), 7.04 (t, J=8.0 Hz, 2H), 6.68 (s, 1H), 4.94-4.90 (m, 1H), 2.57 (q, J=7.5 Hz, 2H), 2.23 (dd, J=13.0 & 6.0 Hz, 1H), 1.92 (dd, J=13.0 & 6.0 Hz, 1H), 1.47 (s, 3H), 1.36 (s, 3H), 1.10 (t, J=7.5 Hz, 3H); ESI-MS (m/z) 438 (MH)$^+$.

Step-2: N-(4-(6-Ethyl-2,2-dimethylchroman-7-yl)phenyl)-2,6-difluorobenzamide: The title compound was prepared by following the similar procedure as described in step-2 of Intermediate-4b by using Example-48a. $^1$HNMR (400 MHz, CDCl$_3$) δ 7.67-7.65 (m, 3H), 7.47-7.44 (m, 1H), 7.34 (d, J=8.0 Hz, 2H), 7.06-7.00 (m, 3H), 6.67 (s, 1H), 2.82 (t, J=6.5 Hz, 2H), 2.54 (q, J=7.5 Hz, 2H), 1.85 (t, J=6.5 Hz, 2H), 1.37 (s, 6H), 1.09 (t, J=7.5 Hz, 3H); ESI-MS (m/z) 422 (MH)$^+$.

Example-49

N-(3,5-Difluoropyridin-4-yl)-4-(6-ethyl-2,2-dimethylchroman-7-yl)benzamide

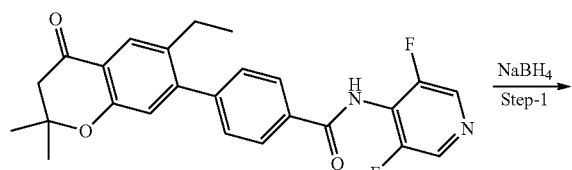

Example 42

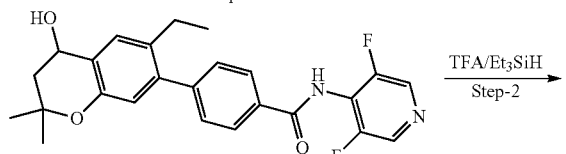

Example 49

The title compound was prepared by following the similar procedure as described for Example-48 by using Example-42. $^1$HNMR (400 MHz, CDCl$_3$) δ 8.45 (s, 2H), 7.98 (d, J=8.0 Hz, 2H), 7.68 (s, 1H), 7.49 (d, J=8.0 Hz, 2H), 7.04 (s, 1H), 6.67 (s, 1H), 2.84 (t, J=6.5 Hz, 2H), 2.52 (q, J=7.5 Hz, 2H), 1.86 (t, J=6.5 Hz, 2H), 1.38 (s, 6H), 1.08 (t, J=7.5 Hz, 3H); ESI-MS (m/z) 423 (MH)$^+$.

Example-50

N-(3,5-Difluoropyridin-4-yl)-4-(2,2,6-trimethylchroman-7-yl)benzamide

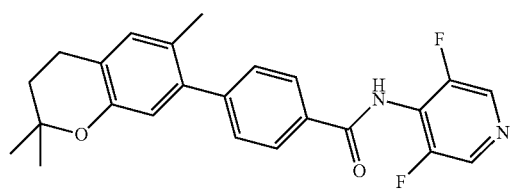

Example 50

The title compound was prepared by following the similar procedure as described for Example-48 by using Example-43. $^1$HNMR (400 MHz, CDCl$_3$) δ 8.44 (s, 2H), 7.98 (d, J=8.0 Hz, 2H), 7.75 (s, 1H), 7.50 (d, J=8.0 Hz, 2H), 7.01 (s, 1H), 6.72 (s, 1H), 2.82 (t, J=6.5 Hz, 2H), 2.20 (s, 3H), 1.85 (t, J=6.5 Hz, 2H), 1.38 (s, 6H); ESI-MS (m/z) 409 (MH)$^+$.

Example-51

2,6-Difluoro-N-(4-(2-(hydroxymethyl)-2,6-dimethyl-4-oxochroman-7-yl)phenyl)benzamide

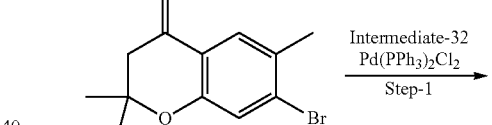

Intermediate 5a

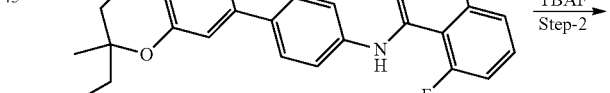

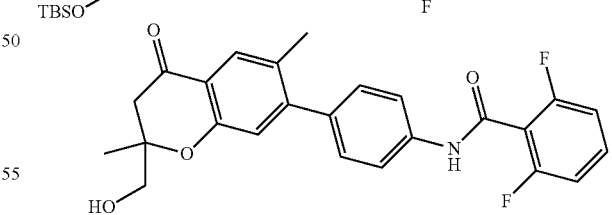

Example 51

Step-1: N-(4-(2-(((tert-Butyldimethylsilyl)oxy)methyl)-2,6-dimethyl-4-oxochroman-7-yl)phenyl)-2,6-difluorobenzamide: The title compound was prepared by reacting Intermediate-5a with Intermediate-32 by following the similar procedure as described in Example-1. $^1$HNMR (400 MHz, CDCl$_3$) δ 7.76-7.70 (m, 3H), 7.49-7.44 (m, 1H), 7.36 (d, J=8.5 Hz, 2H), 7.05 (t, J=8.0 Hz, 2H), 6.82 (s, 1H), 3.81 (d, J=10.5 Hz, 1H), 3.64 (d, J=10.5 Hz, 1H), 3.02 (d, J=16.5 Hz, 1H), 2.64 (d, J=16.5 Hz, 1H), 2.23 (s, 3H), 1.39 (s, 3H), 0.88 (s, 9H), 0.06 (s, 3H), 0.04 (s, 3H); ESI-MS (m/z) 552 (MH)+.

Step-2: 2, 6-Difluoro-N-(4-(2-(hydroxymethyl)-2,6-dimethyl-4-oxochroman-7-yl)phenyl)benzamide: To a solution of step-1 Intermediate (168 mg, 0.305 mmol), in THF (2 mL), a solution of TBAF (457 µL, 0.45 mmol, 1M in THF) was added and the resulting mixture was stirred at room temperature for 16 h. The solvent was removed under vacuum and the crude product was purified by flash column chromatography (50% ethyl acetate-hexanes system as eluent) to afford 10 mg (7%) of the title compound as white solid. $^1$H NMR (400 MHz, CDCl$_3$) δ 7.77 (s, 1H), 7.74-7.72 (m, 3H), 7.51-7.43 (m, 1H), 7.35 (d, J=8.0 Hz, 2H), 7.05 (t, J=8.0 Hz, 2H), 6.86 (s, 1H), 3.81 (d, J=12.0 Hz, 1H), 3.66 (d, J=12.0 Hz, 1H), 3.18 (d, J=16.5 Hz, 1H), 2.54 (d, J=16.5 Hz, 1H), 2.24 (s, 3H), 1.40 (s, 3H); ESI-MS (m/z) 438 (MH)+.

The below Examples (52-58) given in Table-6 were prepared by following the similar procedure as described in Example-51 by using the appropriate Intermediates.

TABLE 6

| Example No: IUPAC name | Structure | $^1$HNMR/ESI-MS |
|---|---|---|
| Example-52: 2,6-Difluoro-N-(5-(2-(hydroxymethyl)-2,6-dimethyl-4-oxochroman-7-yl)pyrazin-2-yl)benzamide | 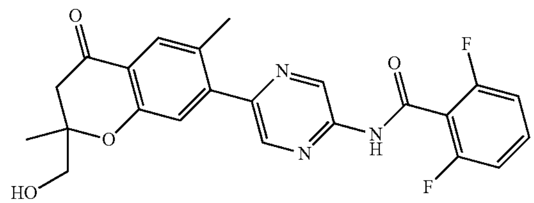 [SMILES: Cc1cc2c(cc1-c1cnc(NC(=O)c3c(F)cccc3F)cn1)OC(C)(CO)CC2=O] | $^1$HNMR (400 MHz, CDCl$_3$) δ 9.79 (s, 1H), 8.46 (s, 1H), 8.44 (s, 1H), 7.82 (s, 1H), 7.55-7.50 (m, 1H), 7.11-7.06 (m, 3H), 3.83 (d, J = 12.0 Hz, 1H), 3.66 (d, J = 12.0 Hz, 1H), 3.20 (d, J = 16.5 Hz, 1H), 2.57 (d, J = 16.5 Hz, 1H), 2.38 (s, 3H), 1.39 (s, 3H); ESI-MS (m/z) 440 (MH)+. |
| Example-53: 2,6-Difluoro-N-(6-(2-(hydroxymethyl)-2,6-dimethyl-4-oxochroman-7-yl)pyridin-3-yl)benzamide | 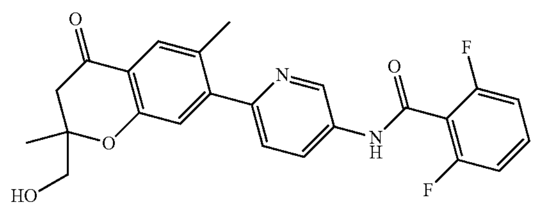 | $^1$HNMR (400 MHz, CDCl$_3$) δ 8.75 (d, J = 2.0 Hz, 1H), 8.50 (dd, J = 2.0 & 8.0 Hz, 1H), 8.16 (s, 1H), 7.78 (s, 1H), 7.54-7.44 (m, 2H), 7.06 (t, J = 8.0 Hz, 2H), 7.03 (s, 1H), 3.79 (d, J = 12.0 Hz, 1H), 3.64 (d, J = 12.0 Hz, 1H), 3.17 (d, J = 16.5 Hz, 1H), 2.55 (d, J = 16.5 Hz, 1H), 2.32 (s, 3H), 1.38 (s, 3H); ESI-MS (m/z) 439 (MH)+. |
| Example-54: 2,6-Difluoro-N-(5-(2-(hydroxymethyl)-2,6-dimethyl-4-oxochroman-7-yl)pyridin-2-yl)benzamide | 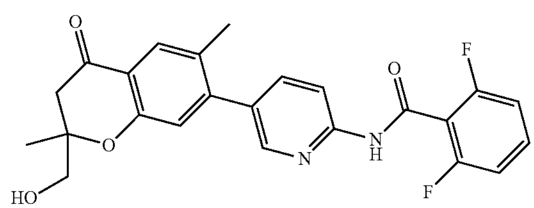 | $^1$HNMR (400 MHz, DMSO-d$_6$) δ 11.51 (s, D$_2$O exchangeable 1H), 8.40 (d, J = 2.0 Hz, 1H), 8.27 (d, J = 8.5 Hz, 1H), 7.94 (dd, J = 2.0 & 8.5 Hz, 1H), 7.65 (s, 1H), 7.62-7.55 (m, 1H), 7.25 (t, J = 8.0 Hz, 2H), 6.90 (s, 1H), 5.22 (t, J = 5.5 Hz, 1H), 3.58 (dd, J = 11.5, 5.5 Hz, 1H), 3.49 (dd, J = 11.5, 5.5 Hz, 1H), 2.97 (d, J = 16.5 Hz, 1H), 2.65 (d, J = 16.5 Hz, 1H), 2.22 (s, 3H), 1.33 (s, 3H); ESI-MS (m/z) 439 (MH)+. |
| Example-55: N-(5-(2,2-Bis(hydroxymethyl)-6-methyl-4-oxochroman-7-yl)pyrazin-2-yl)-2,6-difluorobenzamide | 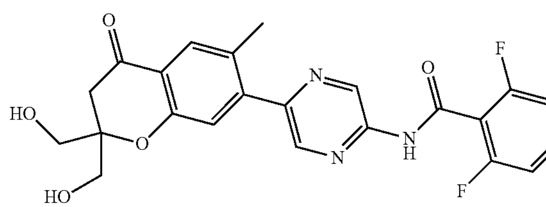 | $^1$HNMR (400 MHz, DMSO-d6) δ 11.83 (s, 1H, D$_2$O exchangeable), 9.51 (s, 1H), 8.67 (s, 1H), 7.67-7.59 (m, 2H), 7.28 (t, J = 8.0 Hz, 2H), 7.12 (s, 1H), 5.11 (t, J = 5.5 Hz, 2H), 3.61-3.52 (m, 4H), 2.85 (s, 2H), 2.31 (s, 3H); ESI-MS (m/z) 456 (MH)+. |
| Example-56: N-(6-(2,2-Bis(hydroxymethyl)-6-methyl-4-oxochroman-7-yl)pyridin-3-yl)-2,6-difluorobenzamide | 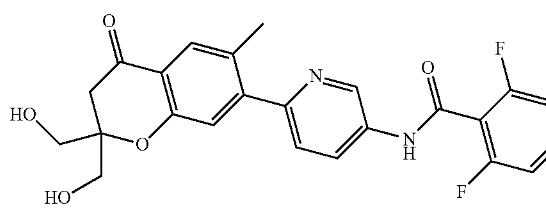 | $^1$HNMR (400 MHz, DMSO-d6) δ 11.21 (s, 1H, D$_2$O exchangeable), 8.92 (d, J = 2.0 Hz, 1H), 8.26 (dd, J = 8.5 & 2.0 Hz, 1H), 7.69-7.60 (m, 2H), 7.59 (s, 1H), 7.31 (t, J = 8.0 Hz, 2H), 6.99 (s, 1H), 5.10 (t, J = 5.5 Hz, 2H), 3.60-3.52 (m, 4H), 2.83 (s, 2H), 2.27 (s, 3H); ESI-MS (m/z) 455 (MH)+. |

TABLE 6-continued

| Example No: IUPAC name | Structure | ¹HNMR/ESI-MS |
|---|---|---|
| Example-57: N-(5-(2,2-Bis(hydroxymethyl)-6-methyl-4-oxochroman-7-yl)pyridin-2-yl)-2,6-difluorobenzamide | 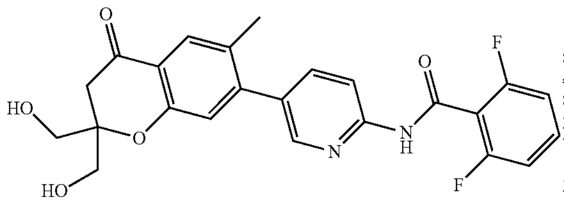 [SMILES: Cc1cc2c(cc1-c1ccc(NC(=O)c3c(F)cccc3F)nc1)OC(CO)(CO)CC2=O] | ¹HNMR (400 MHz, DMSO-d6) δ 11.51 (s, 1H, D₂O exchangeable), 8.39 (d, J = 2.5 Hz, 1H), 8.27 (d, J = 8.5 Hz, 1H), 7.93 (dd, J = 8.5 & 2.5 Hz, 1H), 7.64-7.55 (m, 2H), 7.24 (t, J = 8.0 Hz, 2H), 6.89 (s, 1H), 5.10 (t, J = 5.5 Hz, 2H), 3.61-3.51 (m, 4H), 2.83 (s, 2H), 2.21 (s, 3H); ESI-MS (m/z) 455 (MH)⁺. |
| Example-58: N-(4-(6-Ethyl-2-(hydroxymethyl)-2-methyl-4-oxochroman-7-yl)phenyl)-2,6-difluorobenzamide | 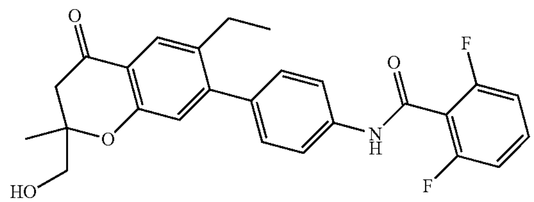 [SMILES: CCc1cc2c(cc1-c1ccc(NC(=O)c3c(F)cccc3F)cc1)OC(C)(CO)CC2=O] | ¹HNMR (400 MHz, CDCl₃) δ 7.81 (s, 1H), 7.73 (d, J = 8.5 Hz, 2H), 7.74-7.72 (brs, 1H) 7.51-7.44 (m, 1H), 7.34 (d, J = 8.5 Hz, 2H), 7.05 (t, J = 8.0 Hz, 2H), 6.82 (s, 1H), 3.81 (d, J = 12.0 Hz, 1H), 3.66 (d, J = 12.0 Hz, 1H), 3.19 (d, J = 16.5 Hz, 1H), 2.61-2.52 (m, 3H), 1.40 (s, 3H), 1.10 (t, J = 7.5 Hz, 3H); ESI-MS (m/z) 452 (MH)⁺. |

Example-59

2,6-Difluoro-N-(4-(2,2,8-trimethylchroman-7-yl)phenyl)benzamide

The title compound was prepared by reacting Intermediate-4b with Intermediate-32 by following the similar procedure as described in Example-30. ¹HNMR (400 MHz, DMSO-d₆) δ 10.88 (s, 1H), 7.73 (J=8.0 Hz, 2H), 7.61 (m, 1H), 7.31-7.24 (m, 4H), 6.97 (d, J=7.5 Hz, 1H), 6.66 (d, J=7.5 Hz, 1H), 2.76 (t, J=6.5 Hz, 2H), 2.01 (s, 3H), 1.78 (t, J=6.5 Hz, 2H), 1.31 (s, 6H); ESI-MS (m/z) 408 (MH)⁺.

Example-60

2,6-Difluoro-N-(4-(4-hydroxy-2,2,6-trimethylchroman-7-yl)phenyl)benzamide

The title compound was prepared by following the similar procedure as described in step-1 of Intermediate-4a by using Example-1. ¹HNMR (400 MHz, CDCl₃) δ 7.68 (d, J=8.5 Hz, 2H), 7.66 (s, 1H, D₂O exchangeable), 7.47-7.34 (m, 1H), 7.37 (s, 1H), 7.35 (d, J=8.5 Hz, 2H), 7.04 (t, J=8.0 Hz, 2H), 6.73 (s, 1H), 4.92-4.88 (m, 1H), 2.24 (s, 3H), 2.23-2.20 (m, 1H) 1.94-1.88 (m, 1H), 1.47 (s, 3H), 1.36 (s, 3H); ESI-MS (m/z) 424 (MH)⁺.

Example-61

2,6-Difluoro-N-(5-(4-hydroxy-6-methylspiro[chroman-2,1'-cyclobutan]-7-yl)pyrazin-2-yl)benzamide The title compound was prepared by following the similar procedure as described in step-1 of Intermediate-4a by using Example-36. ¹HNMR (400 MHz, CDCl₃) δ 9.76 (s, 1H), 8.50 (s, 1H), 8.38 (s, 1H), 7.55-7.48 (m, 1H), 7.37 (s, 1H), 7.07 (t, J=8.0 Hz, 2H), 6.95 (s, 1H), 4.96-4.85 (m, 1H), 2.45-2.24 (m, 7H), 2.21-2.06 (m, 2H), 2.0-1.90 (m, 1H), 1.84-1.74 (m, 1H); ESI-MS (m/z) 438 (MH)⁺

Example-62

N-(4-(4-(Dimethylamino)-2,2,6-trimethylchroman-7-yl)phenyl)-2,6-difluorobenzamide Example 62

The title compound was prepared by reacting Intermediate-7b with Intermediate-32 by following the similar procedure as described in Example-30. $^1$HNMR (400 MHz, DMSO-$d_6$) δ 10.88 (s, 1H), 7.73 (d, J=8.0 Hz, 2H), 7.65-7.56 (m, 1H), 7.39 (s, 1H), 7.33 (d, J=8.0 Hz, 2H), 7.27 (t, J=8.0 Hz, 2H), 6.53 (s, 1H), 3.96-3.91 (m, 1H), 2.22 (s, 6H), 2.16 (s, 3H), 1.91-1.85 (m, 1H), 1.68-1.61 (m, 1H), 1.40 (s, 3H), 1.20 (s, 3H). ESI-MS (m/z) 406 [M-N(Me)$_2$]$^+$.

Example-63

N-(5-(6-Ethyl-2,2-dimethyl-4-oxochroman-7-yl)pyridin-2-yl)-2,6-difluorobenzamide

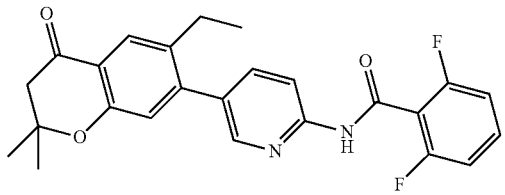 [SMILES: CCc1cc2c(cc1-c1ccc(NC(=O)c3c(F)cccc3F)nc1)OC(C)(C)CC2=O]

The title compound was prepared by reacting Intermediate-2b with Intermediate-35 by following the similar procedure as described in Example-30. $^1$HNMR (400 MHz, CDCl$_3$) δ 9.18 (s, 1H), 8.50 (d, J=8.0 Hz, 1H), 8.11 (d, J=2.0 Hz, 1H), 7.82 (s, 1H), 7.78 (dd, J=2.0 & 8.0 Hz, 1H), 7.45-7.44 (m, 1H), 7.03 (t, J=8.0 Hz, 2H), 6.76 (s, 1H), 2.77 (s, 2H), 2.54 (q, J=7.5 Hz, 2H), 1.51 (s, 6H), 1.11 (t, J=7.5 Hz, 3H); ESI-MS (m/z) 437 (MH)$^+$.

Example-64

N-(3,5-Difluoropyridin-4-yl)-4-(6-methyl-4-oxospiro[chroman-2,1'-cyclobutan]-7-yl)benzamide

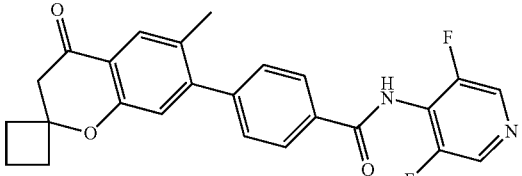

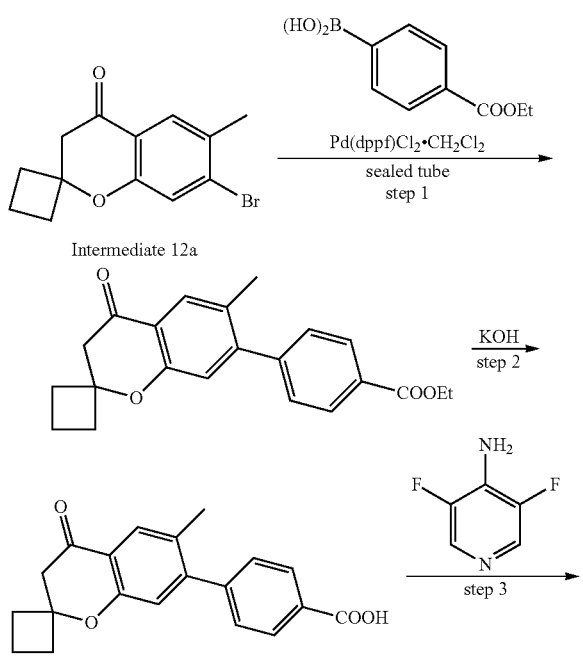

Step-1: Ethyl 4-(6-methyl-4-oxospiro[chroman-2,1'-cyclobutan]-7-yl)benzoate: The title compound was prepared by reacting Intermediate-12a with (4-(ethoxycarbonyl)phenyl)boronic acid by following the similar procedure as described in Example-30. $^1$HNMR (400 MHz, CDCl$_3$) δ 8.12 (d, J=8.0 Hz, 2H), 7.76 (s, 1H), 7.40 (d, J=8.0 Hz, 2H), 6.88 (s, 1H), 4.43 (q, J=7.0 Hz, 2H), 2.93 (s, 2H), 2.40-2.32 (m 2H), 2.23-2.18 (m, 5H), 1.99-1.91 (m, 1H), 1.80-1.69 (m, 1H), 1.44 (t, J=7.0 Hz, 3H); ESI-MS (m/z) 351 (MH)$^+$.

Step-2: 4-(6-Methyl-4-oxospiro[chroman-2,1'-cyclobutan]-7-yl)benzoic acid: To a solution of step-1 Intermediate (2.50 g, 7.13 mmol) in EtOH (25 mL) was added a solution of potassium hydroxide (1.20 g, 21.4 mmol) in water (10 mL). The resulting mixture was stirred at 70° C. for 16 h. The reaction mixture was then cooled to RT, and the solvent was evaporated under vacuum. The residue was dissloved in water, acidified with aqueous HCl (10%, pH=2.0) and then extracted with ethyl acetate (2×50 mL). The combined organic layers were dried over (Na$_2$SO$_4$), and filtered. The filtrate was concentrated to give 1.90 g (78%) of the desired product as a white solid. $^1$HNMR (400 MHz, CDCl$_3$) δ 8.21 (d, J=8.0 Hz, 2H), 7.78 (s, 1H), 7.45 (d, J=8.0 Hz, 2H), 6.90 (s, 1H), 2.95 (s, 2H), 2.43-2.30 (m, 2H), 2.27-2.17 (m, 5H), 1.97-1.94 (m, 1H), 1.78-1.73 (m, 1H); ESI-MS (m/z) 323 (MH)$^+$.

Step-3: N-(3,5-Difluoropyridin-4-yl)-4-(6-methyl-4-oxospiro[chroman-2,1'-cyclobutan]-7-yl)benzamide: To a stirred solution of step-2 Intermediate (0.30 g, 0.93 mmol) in a CH$_2$Cl$_2$ (5 mL) was added dropwise thionyl chloride (3 mL) and the resulting mixture was refluxed for 2 h. The excess thionyl chloride was removed under vacuum to afford the crude acid chloride. To a pre-washed suspension of NaH (67 mg, 2.79 mmol) in DMF (5 mL) was added drop wise a solution of 3,5-difluoropyridin-4-amine (0.121 g, 0.931 mmol) in DMF (3 mL) at 0° C. After stirring for 15 min, an ice-cooled solution of the above prepared acid chloride in CH$_2$Cl$_2$ (5 mL) was added dropwise to the mixture. The resulting mixture was stirred at rt for 16 h. The reaction mixture was quenched with ice-cold water and extracted with CH$_2$Cl$_2$ (2×20 mL) The combined organic layers were washed with 10% aq HCl (10 mL), water (10 mL), dried (Na$_2$SO$_4$) and filtered. The filtrate was rotary evaporated and the crude product was purified by flash column chromatography (silica gel, ethyl acetate-hexane system as eluent) to afford 10 mg (3%) of the desired product as a white solid. $^1$HNMR (400 MHz, DMSO-$d_6$) δ 10.77 (s, 1H), 8.65 (s, 2H), 8.09 (d, J=8.0 Hz, 2H), 7.67 (s, 1H), 7.59 (d, J=8.0 Hz, 2H), 6.95 (s, 1H), 3.00 (s, 2H), 2.29-2.21 (m, 2H), 2.20 (s, 3H), 2.18-2.10 (m, 2H), 1.84-1.74 (m, 2H); ESI-MS (m/z) 467 (MH)$^+$.

The following Examples (65-67) given in Table-7 were prepared by following the similar procedure as described in Example-64 from the appropriate Intermediates.

TABLE 7

| Example No: IUPAC name | Structure | ¹HNMR/ESI-MS |
|---|---|---|
| Example-65: N-(3,5-Dichloropyridin-4-yl)-4-(6-methyl-4-oxospiro[chroman-2,1'-cyclobutan]-7-yl)benzamide | | ¹HNMR (400 MHz, DMSO-$d_6$) δ 10.78 (s, 1H, $D_2O$ exchangeable), 8.77 (s, 2H), 8.10 (d, J = 8.0 Hz, 2H), 7.67 (s, 1H), 7.59 (d, J = 8.0 Hz, 2H), 6.95 (s, 1H), 3.00 (s, 2H), 2.29-2.22 (m, 2H), 2.21 (s, 3H), 2.14-2.13 (m, 2H), 1.88-1.74 (m, 2H); ESI-MS (m/z) 467 (MH)⁺. |
| Example-66: N-(3,5-Difluoropyridin-4-yl)-4-(6-methylspiro[chroman-2,1'-cyclobutan]-7-yl)benzamide | 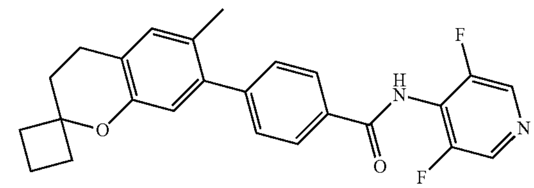 [SMILES: Cc1cc2c(cc1-c1ccc(C(=O)Nc3c(F)cncc3F)cc1)OC1(CCC1)CC2] | ¹HNMR (400 MHz, DMSO-d6) δ 10.70 (s, 1H, $D_2O$ exchangeable), 8.64 (s, 2H), 8.05 (d, J = 8.0 Hz, 2H), 7.51 (d, J = 8.0 Hz, 2H), 7.01 (s, 1H), 6.62 (s, 1H), 2.76 (t, J = 6.5 Hz, 2H), 2.28-2.16 (m, 2H), 2.16 (s, 3H), 2.12-2.03 (m, 2H), 1.95 (t, J = 6.5 Hz, 2H), 1.87-1.75 (m, 1H), 1.75-1.63 (m, 1H); ESI-MS (m/z) 421 (MH)⁺. |
| Example-67: N-(3,5-Dichloropyridin-4-yl)-4-(6-methylspiro[chroman-2,1'-cyclobutan]-7-yl)benzamide | 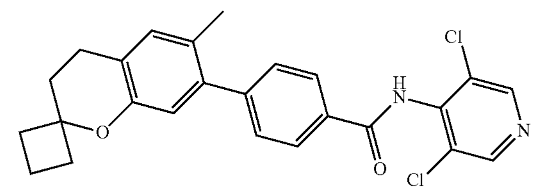 [SMILES: Cc1cc2c(cc1-c1ccc(C(=O)Nc3c(Cl)cncc3Cl)cc1)OC1(CCC1)CC2] | ¹HNMR (400 MHz, DMSO-$d_6$) δ 10.71 (s, 1H, $D_2O$ exchangeable), 8.78 (s, 2H), 8.05 (d, J = 8.0 Hz, 2H), 7.51 (d, J = 8.0 Hz, 2H), 7.01 (s, 1H), 6.63 (s, 1H), 2.76 (t, J = 6.5 Hz, 2H), 2.21-2.15 (m, 2H), 2.14 (s, 3H), 2.10-2.03 (m, 2H), 1.94 (t, J = 6.5 Hz, 2H), 1.86-1.76 (m, 1H), 1.70-1.67 (m, 1H); ESI-MS (m/z) 453 (MH)⁺. |

Example-68

2,6-Difluoro-N-(4-(spiro[chromene-2,1'-cyclobutan]-4-yl)phenyl)benzamide

And

Example-69

2,6-Difluoro-N-(4-(spiro[chroman-2,1'-cyclobutan]-4-yl)phenyl)benzamide

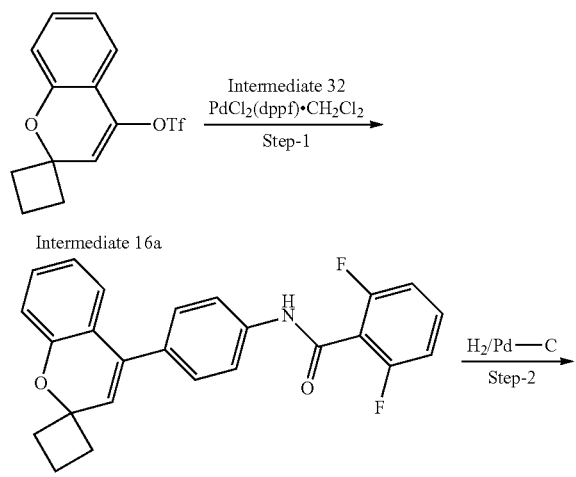

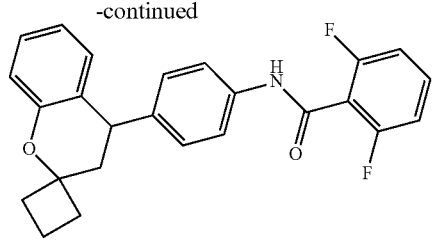

Example 69

Step-1: 2,6-Difluoro-N-(4-(spiro[chromene-2,1'-cyclobutan]-4-yl)phenyl)benzamide: In a sealed tube, to a nitrogen purged suspension of potassium carbonate (5 mL, 2M in water) in dioxane (10 mL) was added Intermediate-16a (300 mg, 0.93 mmol) and Intermediate-32 (330 mg, 0.93 mmol). The resulting mixture was thoroughly deoxygenated by purging nitrogen gas for another 10 minutes and $PdCl_2$(dppf)-$CH_2Cl_2$ adduct (76 mg, 0.094 mmol) was added. The sealed tube was capped and stirred at 100° C. for 16 h. The reaction mixture was cooled to room temperature and filtered through celite. The celite cake was washed with ethyl acetate (25 mL). The filtrate was rotary evaporated and the crude product was purified by flash column chromatography (silica gel, ethyl acetate-hexanes system as eluent) to afford 120 mg (31%) of the title compound as white solid. ¹HNMR (400 MHz, $CDCl_3$) δ 7.71-7.69 (m, 3H), 7.50-7.44 (m, 1H), 7.41 (d, J=8.0 Hz, 2H), 7.19-7.15 (m, 1H), 7.08-7.00 (m, 3H), 6.93 (d, J=8.0, Hz, 1H), 6.84 (t, J=8.0, Hz, 1H), 5.99 (s, 1H), 2.58-2.50 (m, 2H), 2.33-2.27 (m, 2H), 1.98-1.88 (m, 1H), 1.82-1.73 (m, 1H); ESI-MS (m/z) 404 (MH)⁺.

Step-2: 2,6-Difluoro-N-(4-(spiro[chroman-2,1'-cyclobutan]-4-yl)phenyl)benzamide: To a stirred solution of step-1

Intermediate (80 mg, 0.19 mmol) in EtOH (5 mL) was added 10% palladium on carbon (30 mg, 0.28 mmol). The resulting mixture was stirred at room temperature under hydrogen balloon atmosphere for 16 h. The reaction was filtered through celite and the filtrate was evaporated under vacuum. The crude product was purified by flash column chromatography (silica gel, ethyl acetate-hexanes system as eluent) to afford 30 mg (37%) of the title compound as white solid. ¹HNMR (400 MHz, CDCl₃) δ 7.63-7.61 (m, 3H), 7.48-7.41 (m, 1H), 7.25 (d, J=8.0 Hz, 2H), 7.13 (t, J=8.0 Hz, 1H), 7.03 (t, J=8.0 Hz, 2H), 6.87 (d, J=8.0 Hz, 1H), 6.77-6.72 (m 2H), 4.36-4.31 (m, 1H), 2.49-2.46 (m, 1H), 2.36-2.31 (m, 1H), 2.28-2.26 (m, 1H), 2.23-2.15 (m 1H), 2.12-2.04 (m, 2H), 1.98-1.88 (m, 1H) 1.77-1.67 (m, 1H); ESI-MS (m/z) 406 (MH)⁺.

The following Examples (70-92) given in Table-8 were prepared from the corresponding Intermediates by following the similar procedure as described in Example-68 and Example-69.

TABLE 8

| Example No: IUPAC name | Structure | ¹HNMR/ESI-MS |
|---|---|---|
| Example-70: 2,6-Difluoro-N-(5-(spiro[chromene-2,1'-cyclobutan]-4-yl)pyrazin-2-yl)benzamide | | ¹HNMR (400 MHz, CDCl₃) δ 9.76 (s, 1H), 8.57 (s, 1H), 8.37 (s, 1H), 7.53-7.46 (m, 1H), 7.26-7.18 (m, 2H), 7.06 (t, J = 8.0 Hz, 2H), 6.97 (d, J = 8.0 Hz, 1H), 6.91 (t, J = 8.0 Hz, 1H), 6.37 (s, 1H), 2.64-2.50 (m, 2H), 2.43-2.27 (m, 2H), 1.99-1.91 (m 1H), 1.84-1.77 (m 1H); ESI-MS (m/z) 406 (MH)⁺. |
| Example-71: 2,6-Difluoro-N-(6-(spiro[chromene-2,1'-cyclobutan]-4-yl)pyridin-3-yl)benzamide | 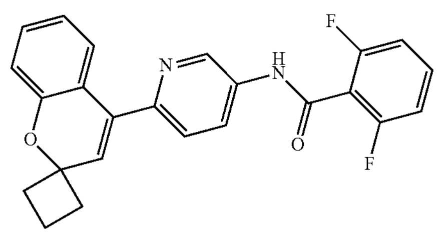 [SMILES: O=C(Nc1ccc(C2=CC3(CCC3)Oc3ccccc32)nc1)c1c(F)cccc1F] | ¹HNMR (400 MHz, CDCl₃) δ 8.75 (s, 1H), 8.47 (d, J = 8.0 Hz, 1H), 8.15 (s, 1H), 7.53-7.43 (m, 2H), 7.20 (d, J = 8.0 Hz, 2H), 7.04 (t, J = 8.0 Hz, 2H), 6.95 (d, J = 8.0 Hz, 1H), 6.88 (t, J = 8.0 Hz, 1H), 6.34 (s, 1H), 2.58-2.51 (m, 2H), 2.37-2.31 (m, 2H), 1.95-1.91 (m, 1H), 1.85-1.76 (m, 1H): ESI-MS (m/z) 405 (MH)⁺. |
| Example-72: 2,6-Difluoro-N-(5-(spiro[chromene-2,1'-cyclobutan]-4-yl)pyridin-2-yl)benzamide | 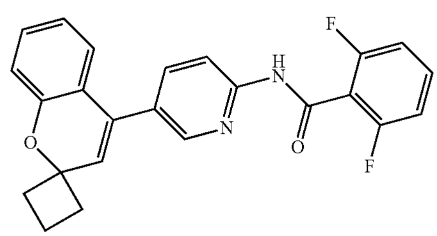 [SMILES: O=C(Nc1ccc(C2=CC3(CCC3)Oc3ccccc32)cn1)c1c(F)cccc1F] | ¹HNMR (400 MHz, DMSO-d6) δ 11.52 (s, 1H), 8.40 (d, J = 2.5 Hz, 1H), 8.26 (d, J = 8.5 Hz, 1H), 7.88 (dd, J = 8.5 & 2.5 Hz, 1H), 7.63-7.55 (m, 1H), 7.28-7.19 (m, 3H), 6.97-6.87 (m, 3H), 6.28 (s, 1H), 2.46-2.38 (m, 2H), 2.34-2.26 (m, 2H), 1.89-1.75 (m, 2H); ESI-MS (m/z) 405 (MH)⁺. |
| Example-73: 2,6-Difluoro-N-(4-(5-methylspiro[chromene-2,1'-cyclobutan]-4-yl)phenyl)benzamide | 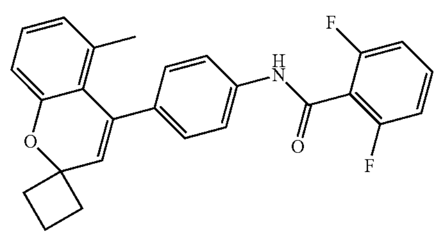 [SMILES: Cc1cccc2c1C(c1ccc(NC(=O)c3c(F)cccc3F)cc1)=CC1(CCC1)O2] | ¹HNMR (400 MHz, CDCl₃) δ 7.67 (s, 1H), 7.64 (d, J = 8.0 Hz, 2H), 7.49-7.42 (m, 1H), 7.28 (d, J = 8.0 Hz, 2H), 7.10 (t, J = 8.0 Hz, 1H), 7.04 (t, J = 8.0 Hz, 2H), 6.89 (d, J = 8.0 Hz, 1H), 6.73 (d, J = 8.0 Hz, 1H), 6.04 (s, 1H), 2.51-2.43 (m, 2H), 2.32-2.14 (m, 2H), 1.94-1.88 (m, 1H), 1.84-1.71 (m, 4H); ESI-MS (m/z), 418 (MH)⁺. |
| Example-74: 2,6-Difluoro-N-(4-(5-methylspiro[chroman-2,1'-cyclobutan]-4-yl)phenyl)benzamide | 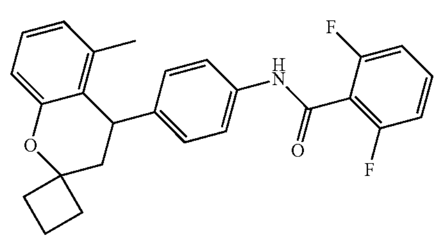 [SMILES: Cc1cccc2c1C(c1ccc(NC(=O)c3c(F)cccc3F)cc1)CC1(CCC1)O2] | ¹HNMR (400 MHz, CDCl₃) δ 7.56 (s, 1H), 7.54 (d, J = 8.0 Hz, 2H), 7.47-7.40 (m, 1H), 7.15-7.07 (m, 3H), 7.02 (t, J = 8.0 Hz, 2H), 6.81 (d, J = 8.0 Hz, 1H), 6.73 (d, J = 8.0 Hz, 1H), 4.23 (t, J = 7.0 Hz, 1H), 2.42-2.37 (m, 1H), 2.30-2.20 (m, 2H), 2.18-2.13 (m, 2H), 1.89 (s, 3H), 1.87-1.78 (m 1H), 1.73-1.66 (m, 1H), 0.90 (t, J = 7.0 Hz, 1H); ESI-MS (m/z), 420 (MH)⁺. |

| Example No: IUPAC name | Structure | ¹HNMR/ESI-MS |
|---|---|---|
| Example-75: 2,6-Difluoro-N-(4-(6-methylspiro[chromene-2,1'-cyclobutan]-4-yl)phenyl)benzamide | 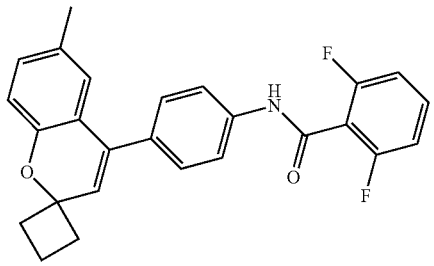 [SMILES: Cc1ccc2c(c1)C(c1ccc(NC(=O)c3c(F)cccc3F)cc1)=CC1(CCC1)O2] | ¹HNMR (400 MHz, DMSO-d$_6$) δ 10.94 (s, 1H), 7.77 (d, J = 8.0 Hz, 2H), 7.66-7.57 (m, 1H), 7.37 (d, J = 8.0 Hz, 2H), 7.28 (t, J = 8.0 Hz, 2H), 6.99 (d, J = 8.0 Hz, 1H), 6.82 (d, J = 8.0 Hz, 1H), 6.76 (s, 1H), 6.13 (s, 1H), 3.35 (s, 3H), 2.42-2.31 (m, 2H), 2.27-2.22 (m, 2H), 1.85-1.72 (m, 2H); ESI-MS (m/z) 418 (MH)$^+$. |
| Example-76: 2,6-Difluoro-N-(5-(6-methylspiro[chromene-2,1'-cyclobutan]-4-yl)pyrazin-2-yl)benzamide | 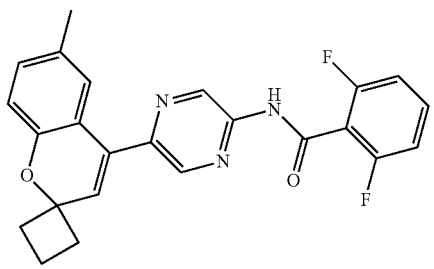 [SMILES: Cc1ccc2c(c1)C(c1cnc(NC(=O)c3c(F)cccc3F)cn1)=CC1(CCC1)O2] | ¹H NMR (400 MHz, DMSO-d$_6$) δ 11.83 (s, 1H), 9.49 (s, 1H), 8.65 (s, 1H), 7.66-7.59 (m, 1H), 7.27 (t, J = 8.0 Hz, 2H), 7.08 (d, J = 2.0 Hz, 1H), 7.01 (dd, J = 8.0 & 2.0 Hz, 1H), 6.83 (d, J = 8.0 Hz, 1H), 6.55 (s, 1H), 2.46-2.35 (m, 2H), 2.34-2.22 (m, 2H), 2.18 (s, 3H), 1.88-1.77 (m, 2H); ESI-MS (m/z) 420 (MH)$^+$. |
| Example-77: 2,6-Difluoro-N-(4-(7-methylspiro[chromene-2,1'-cyclobutan]-4-yl)phenyl)benzamide | 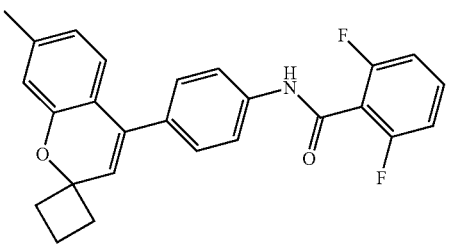 [SMILES: Cc1ccc2c(c1)OC1(C=C2c2ccc(NC(=O)c3c(F)cccc3F)cc2)CCC1] | ¹HNMR (400 MHz, CDCl$_3$) δ 7.69 (d, J = 8.0 Hz, 2H), 7.50-7.44 (m, 1H), 7.40 (d, J = 8.0 Hz, 2H), 7.05 (t, J = 8.0 Hz, 2H), 6.91 (d, J = 8.0 Hz, 1H), 6.77 (s, 1H), 6.67 (d, J = 8.0 Hz, 1H), 5.93 (s, 1H), 2.57-2.48 (m, 2H), 2.32 (s, 3H), 2.31-2.25 (m, 2H), 1.96-1.88 (m, 1H), 1.81-1.72 (m, 1H); ESI-MS (m/z) 418 (MH)$^+$. |
| Example-78: 2,6-Difluoro-N-(4-(8-methylspiro[chromene-2,1'-cyclobutan]-4-yl)phenyl)benzamide | 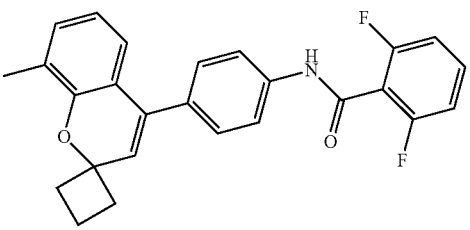 [SMILES: Cc1cccc2c1OC1(C=C2c2ccc(NC(=O)c3c(F)cccc3F)cc2)CCC1] | ¹HNMR (400 MHz, CDCl$_3$) δ 7.69 (d, J = 8.0 Hz, 2H), 7.50-7.44 (m, 1H), 7.40 (d, J = 8.0 Hz, 2H), 7.04 (app t, J = 8.0 Hz, 3H), 6.87 (dd, J = 8.0 & 2.0 Hz, 1H), 6.75 (t, J = 8.0 Hz, 1H), 5.98 (s, 1H), 2.56-2.46 (m, 2H), 2.34-2.31 (m, 2H), 2.30 (s, 3H), 1.99-1.89 (m, 1H), 1.82-1.73 (m, 1H); ESI-MS (m/z) 418 (MH)$^+$. |
| Example-79: N-(4-(2,2-Dimethyl-2H-chromen-4-yl)phenyl)-2,6-difluorobenzamide | 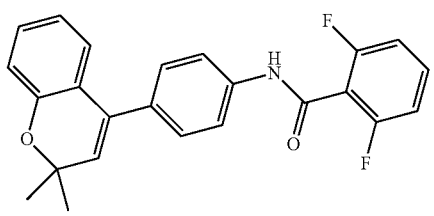 [SMILES: CC1(C)C=C(c2ccc(NC(=O)c3c(F)cccc3F)cc2)c2ccccc2O1] | ¹HNMR (400 MHz, DMSO-d$_6$) δ 10.93 (s, 1H), 7.76 (d, J = 8.0 Hz, 2H), 7.66-7.56 (m, 1H), 7.33 (d, J = 8.0 Hz, 2H), 7.26 (t, J = 8.0 Hz, 2H), 7.20-7.16 (dt, J = 8.0 & 2.0 Hz, 1H), 6.97 (dd, J = 8.0 & 2.0 1H), 6.90-6.82 (m, 2H), 5.76 (s, 1H), 1.44 (s, 6H); ESI-MS (m/z) 392 (MH)$^+$. |
| Example-80: N-(4-(2,2-Dimethylchroman-4-yl)phenyl)-2,6-difluorobenzamide | 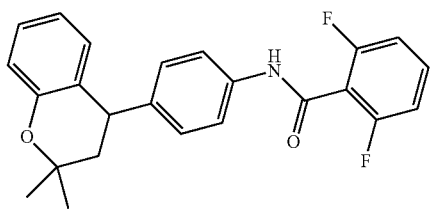 [SMILES: CC1(C)CC(c2ccc(NC(=O)c3c(F)cccc3F)cc2)c2ccccc2O1] | ¹HNMR (400 MHz, DMSO-d$_6$) δ 10.80 (s, 1H), 7.64 (d, J = 8.0 Hz, 2H), 7.62-7.56 (m, 1H), 7.29-7.20 (m, 4H), 7.07 (t, J = 8.0 Hz, 1H), 6.77-6.70 (m, 2H), 6.62 (d, J = 8.0 Hz, 1H), 4.13 (dd, J = 13.0 & 6.0 Hz, 1H), 2.04 (dd, J = 13.0 & 6.0 Hz, 1H), 1.91 (t, J = 13.0 Hz, 1H), 1.41 (s, 3H), 1.30 (s, 3H); ESI-MS (m/z) 394 (MH)$^+$. |

| Example No: IUPAC name | Structure | ¹HNMR/ESI-MS |
|---|---|---|
| Example-81: N-(5-(2,2-Dimethyl-2H-chromen-4-yl)pyrazin-2-yl)-2,6-difluorobenzamide | 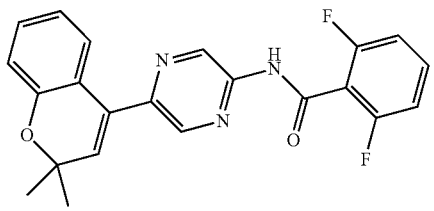 [SMILES: CC1(C)C=C(c2cnc(NC(=O)c3c(F)cccc3F)cn2)c2ccccc2O1] | ¹HNMR (400 MHz, CDCl₃) δ 9.75 (s, 1H), 8.53 (s, 1H), 8.35 (s, 1H), 7.53-7.46 (m, 1H), 7.24-7.20 (m, 2H), 7.06 (t, J = 8.0 Hz, 2H), 6.95-6.89 (m, 2H), 6.01 (s, 1H), 1.54 (s, 6H); ESI-MS (m/z) 394 (MH)⁺. |
| Example-82: N-(5-(2,2-Dimethylchroman-4-yl)pyrazin-2-yl)-2,6-difluorobenzamide | 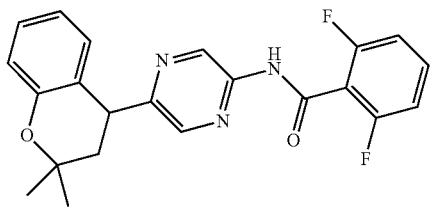 [SMILES: CC1(C)CC(c2cnc(NC(=O)c3c(F)cccc3F)cn2)c2ccccc2O1] | ¹HNMR (400 MHz, CDCl₃) δ 9.65 (s, 1H), 8.58 (s, 1H), 8.04 (s, 1H), 7.51-7.44 (m, 1H), 7.20-7.17 (t, J = 8.0 Hz, 1H), 7.03 (t, J = 8.0 Hz, 2H), 6.89 (d, J = 8.0 Hz, 1H), 6.80 (t, J = 8.0 Hz, 1H), 6.72 (d, J = 8.0 Hz, 1H), 4.41 (t, J = 9.0 Hz, 1H), 2.13 (d, J = 9.0 Hz, 2H), 1.48 (s, 3H), 1.39 (s, 3H); ESI-MS (m/z) 396 (MH)⁺. |
| Example-83: N-(6-(2,2-Dimethyl-2H-chromen-4-yl)pyridin-3-yl)-2,6-difluorobenzamide | 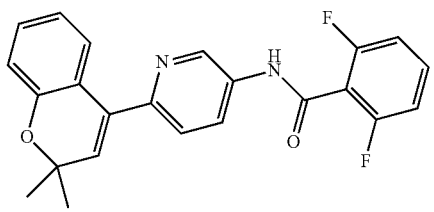 | ¹HNMR (400 MHz, CDCl₃) δ 8.73 (d, J = 2.0 Hz, 1H), 8.46 (d, J = 8.0 Hz, 1H), 8.10 (s, 1H), 7.52-7.45 (m, 2H), 7.22-7.18 (m, 2H), 7.05 (t, J = 8.0 Hz, 2H), 6.93-6.87 (m, 2H), 5.98 (s, 1H), 1.53 (s, 6H); ESI-MS (m/z) 393 (MH)⁺. |
| Example-84: N-(5-(2,2-Dimethyl-2H-chromen-4-yl)-4-methylpyridin-2-yl)-2,6-difluorobenzamide | 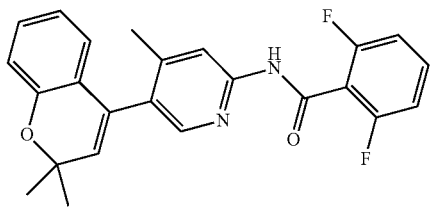 [SMILES: Cc1cc(NC(=O)c2c(F)cccc2F)ncc1C1=CC(C)(C)Oc2ccccc21] | ¹HNMR (400 MHz, DMSO-d₆) δ 11.41 (s, 1H), 8.16 (s, 1H), 8.09 (s, 1H), 7.62-7.54 (m, 1H), 7.23 (t, J = 8.0 Hz, 2H), 7.16 (t, J = 80 Hz, 1H), 6.86 (d, J = 8.0 Hz, 1H), 6.80 (t, J = 8.0 Hz, 1H), 6.55 (d, J = 8.0 Hz, 1H), 5.74 (s, 1H), 2.16 (s, 3H), 1.48 (s, 6H); ESI-MS (m/z) 407 (MH)+. |
| Example-85: 2,6-Dinuoro-N-(4-(2,2,6-trimethyl-2H-chromen-4-yl)phenyl)benzamide | 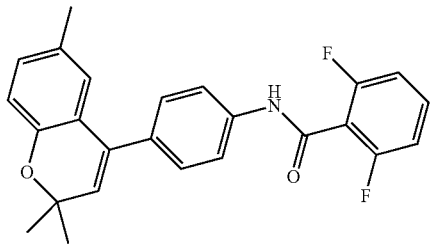 [SMILES: Cc1ccc2c(c1)C(c1ccc(NC(=O)c3c(F)cccc3F)cc1)=CC(C)(C)O2] | ¹HNMR (400 MHz, CDCl₃) δ 7.69 (d, J = 8.0 Hz, 2H), 7.50-7.42 (m, 1H), 7.38 (d, J = 8.0 Hz, 2H), 7.04 (t, J = 8.0 Hz. 2H), 6.98 (dd, J = 2.0 & 8.0 Hz, 1H), 6.82 (d, J = 2.0 Hz 1H), 6.80 (d, J = 8.0 Hz, 1H), 5.61 (s, 1H), 2.22 (s, 3H), 1.49 (s, 6H): ESI-MS (m/z) 406 (MH)⁺. |
| Example-86: 2,6-Difluoro-N-(5-(2,2,6-trimethyl-2H-chromen-4-yl)pyrazin-2-yl)benzamide | 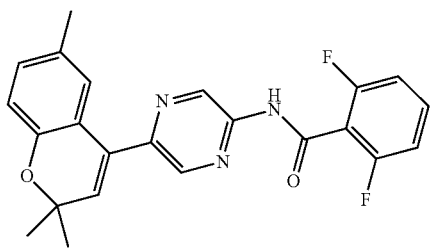 [SMILES: Cc1ccc2c(c1)C(c1cnc(NC(=O)c3c(F)cccc3F)cn1)=CC(C)(C)O2] | ¹HNMR (400 MHz, DMSO-d₆) δ 11.81 (s, 1H), 9.48 (s, 1H), 8.58 (s, 1H), 7.66-7.59 (m, 1H), 7.27 (t, J = 8.0 Hz, 2H), 7.06 (d, J = 2.0 Hz, 1H), 7.01 (dd, J = 8.0 & 2.0 Hz, 1H), 6.78 (d,7 = 8.0 Hz, 1H), 6.14 (s, 1H), 2.18 (s, 3H), 1.45 (s, 6H); ESI-MS (m/z) 408 (MH)⁺. |

TABLE 8-continued

| Example No: IUPAC name | Structure | ¹HNMR/ESI-MS |
|---|---|---|
| Example-87: 2,6-Difluoro-N-(4-(2,2,7-trimethyl-2H-chromen-4-yl)phenyl)benzamide | 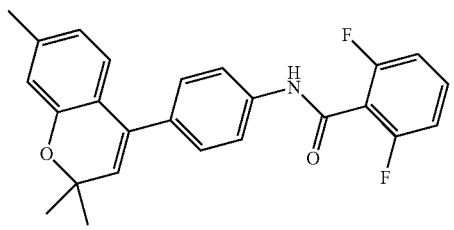 [SMILES: Cc1ccc2c(c1)OC(C)(C)C=C2c1ccc(NC(=O)c2c(F)cccc2F)cc1] | ¹HNMR (400 MHz, DMSO-d6) δ 10.91 (s, 1H), 7.75 (d, J = 8.0 Hz, 2H), 7.64-7.58 (m, 1H), 7.32 (d, J = 8.0 Hz, 2H), 7.27 (t, J = 8.0 Hz, 2H), 6.86 (d, J = 8.0 Hz, 1H), 6.70 (s, 1H), 6.68 (d, J = 8.0 Hz, 1H), 5.68 (s, 1H), 2.25 (s, 3H), 1.42 (s, 6H); ESI-MS (m/z) 406 (MH)⁺. |
| Example-88: 2,6-Difluoro-N-(5-(2,2,7-trimethyl-2H-chromen-4-yl)pyrazin-2-yl)benzamide | 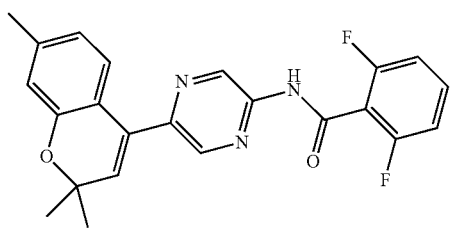 [SMILES: Cc1ccc2c(c1)OC(C)(C)C=C2c1cnc(NC(=O)c2c(F)cccc2F)cn1] | ¹HNMR (400 MHz, DMSO-d6) δ 9.12 (s, 1H), 8.30 (s, 1H), 7.38-7.31 (m, 1H), 7.19 (d, J = 8.0 Hz, 1H), 7.06 (t, J = 8.0 Hz, 2H), 6.71-6.68 (m, 2H), 5.95 (s, 1H), 2.26 (s, 3H), 1.44 (s, 6H); ESI-MS (m/z) 408 (MH)⁺. |
| Example-89: 2,6-Difluoro-N-(5-(2,2,8-trimethyl-2H-chromen-4-yl)pyrazin-2-yl)benzamide | 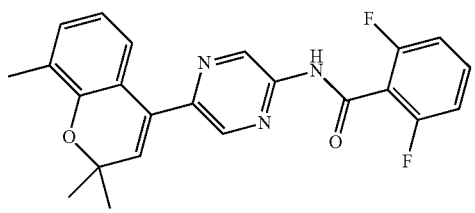 | ¹HNMR (400 MHz, DMSO-$d_6$) δ 11.81 (s, 1H), 9.46 (s, 1H), 8.57 (s, 1H), 7.66-7.60 (m, 1H), 7.27 (t, J = 8.0 Hz, 2H), 7.09 (m, 2H), 6.78 (t, J = 8.0 Hz, 1H), 6.17 (s, 1H), 2.18 (s, 3H), 1.47 (s, 6H); ESI-MS (m/z) 408 (MH)⁺. |
| Example-90: 2,6-Difluoro-N-(4-(2-(methoxymethyl)-2-methyl-2H-chromen-4-yl)phenyl)benzamide | 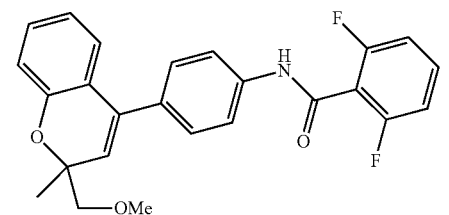 [SMILES: COCC1(C)C=C(c2ccc(NC(=O)c3c(F)cccc3F)cc2)c2ccccc2O1] | ¹HNMR (400 MHz, DMSO-$d_6$) δ 10.94 (s, 1H), 7.76 (d, J = 8.0 Hz, 2H), 7.65-7.58 (m, 1H), 7.33 (d, J = 8.0 Hz, 2H), 7.28 (t, J = 8.0 Hz, 2H), 7.19 (t, J = 8.0 Hz, 1H), 6.98 (d, J = 8.0 Hz, 1H), 6.87 (m, 2H), 5.69 (s, 1H), 3.52-3.45 (m, 2H), 3.31 (s, 3H), 1.39 (s, 3H); ESI-MS (m/z) 422 (MH)⁺. |
| Example-91: 2,6-Difluoro-N-(4-(2-(methoxymethyl)-2,6-dimethyl-2H-chromen-4-yl)phenyl)benzamide | 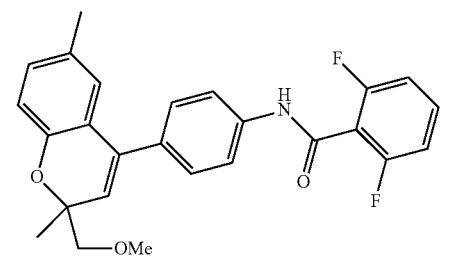 [SMILES: COCC1(C)C=C(c2ccc(NC(=O)c3c(F)cccc3F)cc2)c2cc(C)ccc2O1] | ¹HNMR (400 MHz, CDCl₃) δ 7.71 (s, 1H, D₂O exchangeable), 7.70 (d, J = 8.0 Hz, 2H), 7.50-7.43 (m, 1H), 7.39 (d, J = 8.0 Hz, 2H), 7.05 (t, J = 8.0 Hz, 2H), 6.99 (d, J = 8.0 Hz, 1H), 6.85 (m, 2H), 5.62 (s, 1H), 3.60-3.51 (m, 2H), 3.44 (s, 3H), 2.22 (s, 3H), 1.49 (s, 3H); ESI-MS (m/z) 436 (MH)⁺. |
| Example-92: 2,6-Difluoro-N-(5-(2-(methoxymethyl)-2,6-dimethyl-2H-chromen-4-yl)pyrazin-2-yl)benzamide | 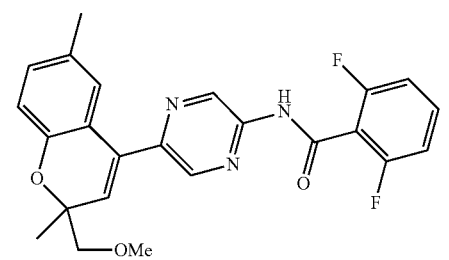 [SMILES: COCC1(C)C=C(c2cnc(NC(=O)c3c(F)cccc3F)cn2)c2cc(C)ccc2O1] | ¹HNMR (400 MHz, DMSO-$d_6$) δ 11.82 (s, 1H), 9.48 (s, 1H), 8.56 (s, 1H), 7.65-7.59 (m, 1H), 7.28 (t, J = 8.0 Hz, 2H), 7.06 (d, J = 2.0 Hz, 1H), 7.01 (dd, J = 8.0 & 2.0 Hz, 1H), 6.79 (d, J = 8.0 Hz, 1H), 6.07 (s, 1H), 3.51 (d, J = 3.5 Hz, 2H), 3.31 (s, 3H), 2.18 (s, 3H), 1.40 (s, 3H); ESI-MS (m/z) 438 (MH)⁺. |

Example-93

2,6-Difluoro-N-(4-(2-(hydroxymethyl)-2-methyl-2H-chromen-4-yl)phenyl)benzamide

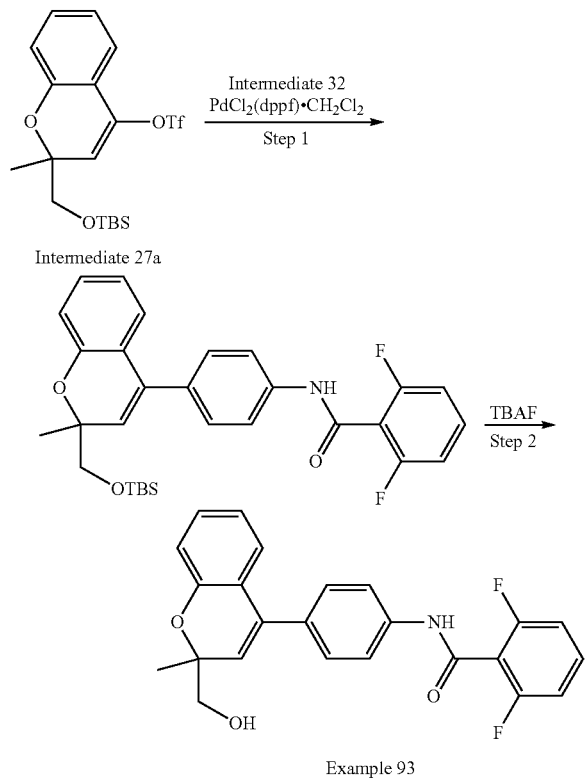

Example 93

Step-1: N-(4-(2-(((tert-Butyldimethylsilyl)oxy)methyl)-2-methyl-2H-chromen-4-yl)phenyl)-2,6-difluorobenzamide: The title compound was prepared by reacting Intermediate-27a with Intermediate-32 by following the similar procedure as described in step-1 of Example-68. $^1$HNMR (400 MHz, CDCl$_3$) δ 7.69 (d, J=8.0 Hz, 3H), 7.46 (t, J=8.0 Hz, 1H), 7.38 (d, J=8.0 Hz, 2H), 7.16 (t, J=8.0 Hz, 1H), 7.06-7.00 (m, 3H), 6.87 (d, J=8.0 Hz, 1H), 6.82 (t, J=8.0 Hz, 1H), 5.64 (s, 1H), 3.77-3.68 (m, 2H), 1.48 (s, 3H), 0.88 (s, 9H), 0.06 (s, 3H), 0.02 (s, 3H); ESI-MS (m/z) 522 (MH)$^+$.

Step-2: 2,6-Difluoro-N-(4-(2-(hydroxymethyl)-2-methyl-2H-chromen-4-yl)phenyl)benzamide: To a (0° C.) cooled and stirred solution of step-1 Intermediate (175 mg, 0.33 mmol) was added a solution of TBAF (0.5 mL, 0.503 mmol, 1M solution in THF) and the resulting mixture was stirred at room temperature for 5 h. The solvent was evaporated under vacuum and the crude product was purified by flash column chromatography (silica gel, ethyl acetate-hexanes system as eluent) to afford 70 mg (45%) of the title compound as white solid. $^1$HNMR (400 MHz, DMSO-d$_6$) δ 10.92 (s, 1H), 7.76 (d, J=8.0 Hz, 2H), 7.63-7.59 (m, 1H), 7.34 (d, J=8.0 Hz, 2H), 7.27 (t, J=8.0 Hz, 2H), 7.17 (t, J=8.0 Hz, 1H), 6.96 (d, J=8.0 Hz, 1H), 6.88-6.82 (m, 2H), 5.71 (s, 1H), 5.05 (t, J=6.0 Hz, 1H), 3.53 (m, 2H), 1.35 (s, 3H); ESI-MS (m/z) 408 (MH)$^+$.

The following Examples (94-97) given in Table-9 were prepared from the corresponding Intermediates by following the similar procedure as described in Example-93.

TABLE 9

| Example No: IUPAC name | Structure | $^1$HNMR/ESI-MS |
|---|---|---|
| Example-94: 2,6-Difluoro-N-(5-(2-(hydroxymethyl)-2-methyl-2H-chromen-4-yl)pyrazin-2-yl)benzamide | 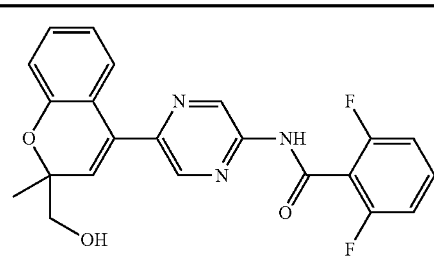 | $^1$HNMR (400 MHz, DMSO-d$_6$) δ 11.83 (s, 1H), 9.47 (s, 1H), 8.61 (s, 1H), 7.66-7.59 (m, 1H), 7.29-7.25 (m, 3H), 7.20 (t, J = 8.0 Hz, 1H), 6.89-6.85 (m, 2H), 6.13 (s, 1H), 5.12 (t, J = 6.0 Hz, 1H,D$_2$O exchangeable ), 3.59-3.55 (m, 2H), 1.38 (s, 3H): ESI-MS (m/z) 410 (MH)$^+$. |
| Example-95: 2,6-Difluoro-N-(4-(2-(hydroxymethyl)-2,6-dimethyl-2H-chromen-4-yl)phenyl)benzamide | 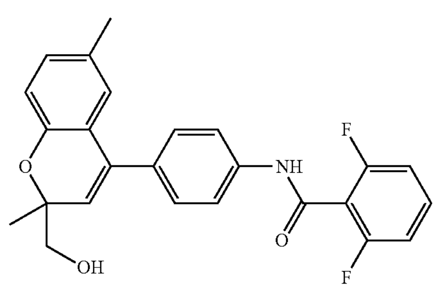 [SMILES: Cc1ccc2c(c1)C(c1ccc(NC(=O)c3c(F)cccc3F)cc1)=CC(C)(CO)O2] | $^1$HNMR (400 MHz, DMSO-d$_6$) δ 10.93 (s, 1H), 7.76 (d, J = 8.0 Hz, 2H), 7.65-7.58 (m, 1H), 7.33 (d, J = 8.0 Hz, 2H), 7.28 (t, J = 8.0 Hz, 2H), 6.97 (d, J = 8.0 Hz, 1H), 6.77-6.75 (m, 2H), 5.69 (s, 1H), 5.04-5.01 (m, 1H), 3.55-3.47 (m, 2H), 2.16 (s, 3H), 1.33 (s, 3H); ESI-MS (m/z) 422 (MH)$^+$. |

TABLE 9-continued

| Example No: IUPAC name | Structure | ¹HNMR/ESI-MS |
|---|---|---|
| Example-96: 2,6-Difluoro-N-(5-(2-(hydroxymethyl)-2,6-dimethyl-2H-chromen-4-yl)pyrazin-2-yl)benzamide | 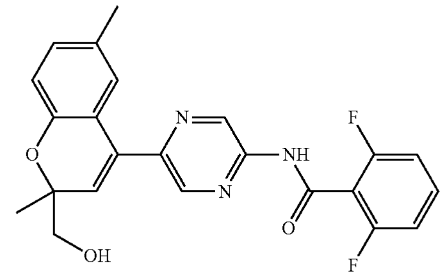 [SMILES: Cc1ccc2c(c1)C(c1cnc(NC(=O)c3c(F)cccc3F)cn1)=CC(C)(CO)O2] | ¹HNMR (400 MHz, DMSO-d6) δ 11.81 (s, 1H), 9.48 (s, 1H), 8.59 (s, 1H), 7.67-7.58 (m, 1H), 7.27 (t, J = 8.0 Hz, 2H), 7.05 (d, J = 2.0 Hz, 1H), 7.00 (dd, J = 8.0 & 2.0 Hz, 1H), 6.78 (d, J = 8.0 Hz, 1H), 6.10 (s, 1H), 5.08 (t, J = 6.0 Hz, 1H), 3.54 (d, J = 6.0 Hz, 2H), 2.18 (s, 3H), 1.35 (s, 3H): ESI-MS (m/z) 424 (MH)⁺. |
| Example-97: 2,6-Difluoro-N-(5-(2-(hydroxymethyl)-2,8-dimethyl-2H-chromen-4-yl)pyrazin-2-yl)(benzamide | 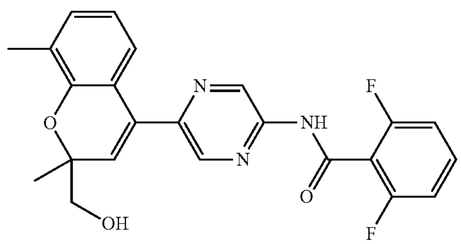 [SMILES: Cc1cccc2c1OC(C)(CO)C=C2c1cnc(NC(=O)c2c(F)cccc2F)cn1] | ¹HNMR (400 MHz, DMSO-d₆) δ 11.81 (s, 1H), 9.46 (s, 1H), 8.58 (s, 1H), 7.67-7.57 (m, 1H), 7.26 (t, J = 8.0 Hz, 2H), 7.10-7.05 (m, 2H), 6.79-6.74 (m, 1H), 6.12 (s, 1H), 5.07 (t, J = 6.0 Hz, 1H), 3.57 (d, J = 6.0 Hz, 2H), 2.18 (s, 3H), 1.38 (s, 3H); ESI-MS (m/z) 424 (MH)⁺ |

The following Examples (98-111) given in Table-10 were prepared from the corresponding Intermediates by following the similar procedure as described in Example-68.

TABLE 10

| Example No: IUPAC name | Structure | ¹HNMR/ESI-MS |
|---|---|---|
| Example-98: 2,6-Difluoro-N(5-(2,2,8-trimethyl-2H-chromen-4-yl)pyridin-2-yl)benzamide | 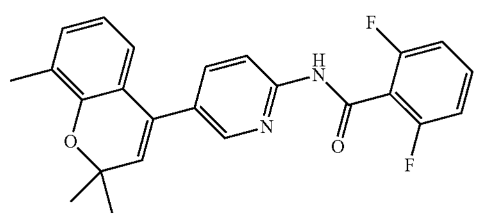 [SMILES: Cc1cccc2c1OC(C)(C)C=C2c1ccc(NC(=O)c2c(F)cccc2F)nc1] | ¹HNMR (400 MHz, DMSO-d₆) δ 11.50 (s, 1H), 8.33 (d, J = 2.5 Hz, 1H), 8.25 (d, J = 8.5 Hz, 1H), 7.82 (dd, J = 8.5 & 2.5 Hz, 1H), 7.62-7.57 (m, 1H), 7.23 (t, J = 8.5 Hz, 2H), 7.11-7.08 (m, 1H), 6.81-6.77 (m, 2H), 5.87 (s, 1H), 2.18 (s, 3H), 1.46 (s, 6H); ESI-MS (m/z) 407 (MH)⁺ |
| Example-99: 2,6-Difluoro-N-(6-(2,2,8-trimethyl-2H-chromen-4-yl)pyridin-3-yl)benzamide | 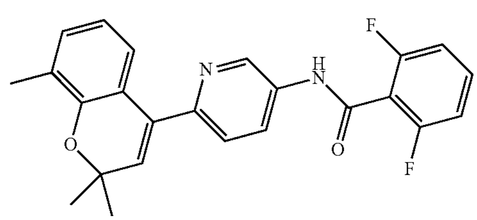 [SMILES: Cc1cccc2c1OC(C)(C)C=C2c1ccc(NC(=O)c2c(F)cccc2F)cn1] | ¹HNMR (400 MHz, DMSO-d₆) δ 11.17 (s, 1H), 8.86 (d, J = 2.5 Hz, 1H), 8.23 (dd, J = 8.5 & 2.5 Hz, 1H), 7.67-7.60 (m, 1H), 7.51 (d, J = 8.5 Hz, 1H), 7.30 (t, J = 8.5 Hz, 2H), 7.06 (t, J = 8.5 Hz, 2H), 6.76 (t, J = 8.5 Hz, 1H), 6.02 (s, 1H), 2.17 (s, 3H), 1.45 (s, 6H); ESI-MS (m/z) 407 (MH)⁺ |
| Example-100: 2,6-Difluoro-N-(5-(8-methylspiro[chromene-2,1'-cyclobutan]-4-yl)pyrazin-2-yl)benzamide | 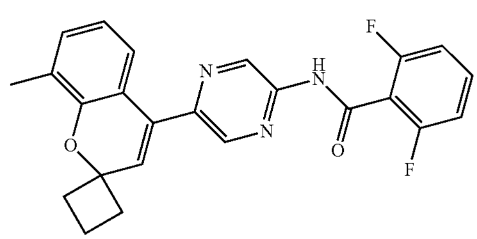 [SMILES: Cc1cccc2c1OC1(C=C2c2cnc(NC(=O)c3c(F)cccc3F)cn2)CCC1] | ¹HNMR (400 MHz, DMSO-d₆) δ 11.82 (s, 1H), 9.47 (s, 1H), 8.64 (s, 1H), 7.69-7.58 (m, 1H), 7.27 (t, J = 8.0 Hz, 2H), 7.15-7.08 (m, 2H), 6.83-6.76 (m, 1H), 6.56 (s, 1H), 2.47-2.38 (m, 2H), 2.37-2.26 (m, 2H), 2.23 (s, 3H), 1.93-1.78 (m, 2H); ESI-MS (m/z) 420 (MH)⁺ |

TABLE 10-continued

| Example No: IUPAC name | Structure | ¹HNMR/ESI-MS |
|---|---|---|
| Example-101: 2,6-Difluoro-N-(5-(8-methylspiro[chromene-2,1'-cyclobutan]-4-yl)pyridin-2-yl)benzamide | 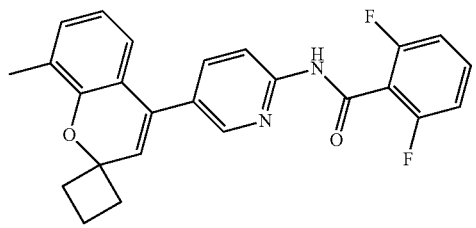 | ¹HNMR (400 MHz, DMSO-d$_6$) δ 11.51 (s, 1H), 8.38 (d, J = 2.5 Hz, 1H), 8.25 (d, J = 8.5 Hz, 1H), 7.86 (dd, J = 8.5 & 2.5 Hz, 1H), 7.63-7.55 (m, 1H), 7.24 (t, J = 8.5 Hz, 2H), 7.10-7.07 (m, 1H), 6.79-6.77 (m, 2H), 6.26 (s, 1H), 2.43-2.37 (m, 2H), 2.32-2.25 (m, 2H), 2.23 (s, 3H), 1.83 (m, 2H); ESI-MS (m/z) 419 (MH)$^+$ |
| Example-102: 2,6-Difluoro-N(6-(8-methylspiro[chromene-2,1'-cyclobutan]-4-yl)pyridin-3-yl)benzamide | 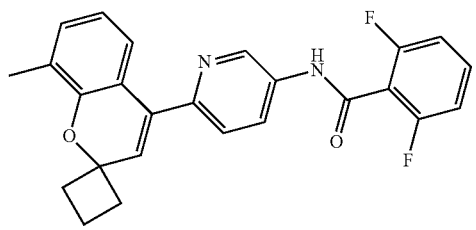 [SMILES: Cc1cccc2c1OC1(C=C2c2ccc(NC(=O)c3c(F)cccc3F)cn2)CCC1] | ¹HNMR (400 MHz, DMSO-d$_6$) δ 11.18 (s, 1H), 8.87 (d, J = 2.5 Hz, 1H), 8.24 (dd, J = 8.5 & 2.5 Hz, 1H), 7.67-7.60 (m, 1H), 7.57 (d, J = 8.5 Hz, 1H), 7.30 (t, J = 8.0 Hz, 2H), 7.12-7.05 (m, 2H), 6.82-6.74 (m, 1H), 6.41 (s, 1H), 2.44-2.33 (m, 2H), 2.31-2.26 (m, 2H), 2.23 (s, 3H), 1.94-1.74 (m, 2H); ESI-MS (m/z) 419 (MH)$^+$ |
| Example-103: 2,6-Difluoro-N-(5-(2-(methoxymethyl)-2,8-dimethyl-2H-chromen-4-yl)pyrazin-2-yl)benzamide | 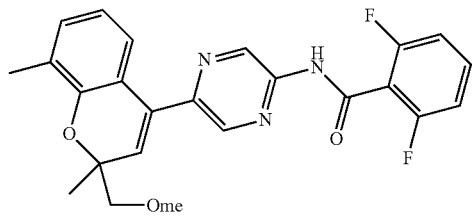 | ¹HNMR (400 MHz, DMSO-d$_6$) δ 11.82 (s, 1H), 9.47 (s, 1H), 8.56 (s, 1H), 7.63-7.58 (m, 1H), 7.27 (t, J = 8.0 Hz, 2H), 7.12-7.08 (m, 2H), 6.81-6.77 (m, 1H), 6.10 (s, 1H), 3.54 (s, 2H), 3.33 (s, 3H), 2.18 (s, 3H), 1.42 (s, 3H); ESI-MS (m/z) 438 (MH)$^+$ |
| Example-104: 2,6-Difluoro-N-(5-(2-(methoxymethyl)-2,8-dimethyl-2H-chromen-4-yl)pyridin-2-yl)benzamide | 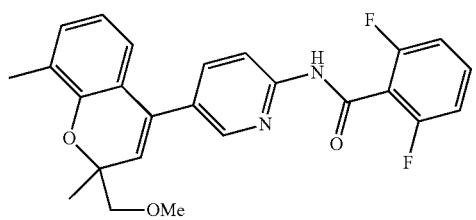 [SMILES: COCC1(C)C=C(c2ccc(NC(=O)c3c(F)cccc3F)nc2)c2cccc(C)c2O1] | ¹HNMR (400 MHz, DMSO-d$_6$) δ 11.51 (s, 1H), 8.32 (d, J = 2.5 Hz, 1H), 8.25 (d, J = 8.5 Hz, 1H), 7.82 (dd, J = 8.5 & 2.5Hz, 1H), 7.62-7.54 (m, 1H), 7.23 (t, J = 8.0 Hz, 2H), 7.12-7.09 (m, 1H), 6.80-6.78 (m, 2H), 5.80 (s, 1H), 3.51 (s, 2H), 3.32 (s, 3H), 2.17 (s, 3H), 1.41 (s, 3H); ESI-MS (m/z) 437 (MH)$^+$ |
| Example-105: 2,6-Difluoro-N-(6-(2-(methoxymethyl)-2,8-dimethyl-2H-chromen-4-yl)pyridin-3-yl)benzamide | 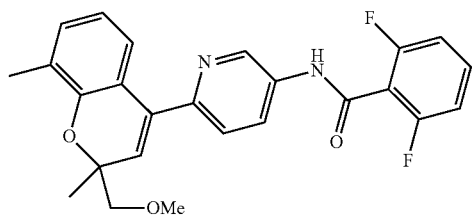 [SMILES: COCC1(C)C=C(c2ccc(NC(=O)c3c(F)cccc3F)cn2)c2cccc(C)c2O1] | ¹HNMR (400 MHz, DMSO-d$_6$) δ 11.18 (s, 1H), 8.86 (d, J = 2.5 Hz, 1H), 8.24 (dd, J = 8.5 & 2.5 Hz, 1H), 7.68-7.58 (m, 1H), 7.50 (d, J = 8.5 Hz, 1H), 7.30 (t, J = 8.0 Hz, 2H), 7.10-7.03 (m, 2H), 6.79-6.74 (m, 1H), 5.96 (s, 1H), 3.51 (s, 2H), 3.32 (s, 3H), 2.17 (s, 3H), 1.40 (s, 3H); ESI-MS (m/z) 437 (MH)$^+$ |
| Example-106: 2,6-Difluoro-N-(5-(6-methylspiro[chromene-2,1'-cyclobutan]-4-yl)pyridin-2-yl)benzamide | 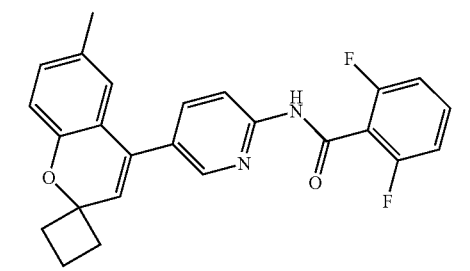 [SMILES: Cc1ccc2c(c1)C(c1ccc(NC(=O)c3c(F)cccc3F)nc1)=CC1(CCC1)O2] | ¹HNMR (400 MHz, DMS-d$_6$) δ 11.52 (s, 1H), 8.39 (d, J = 2.5 Hz, 1H), 8.27 (d, J = 8.5 Hz, 1H), 7.87 (dd, J = 8.5 & 2.5 Hz, 1H), 7.63-7.56 (m, 1H), 7.24 (t, J = 8.0 Hz, 2H), 7.01 (dd, J = 8.0 & 2.0 Hz, 1H), 6.83 (d, J = 8.0 Hz, 1H), 6.75 (d, J = 2.0 Hz, 1H), 6.26 (s, 1H), 2.42-2.34 (m, 2H), 2.29-2.24 (m, 2H), 2.17 (s, 3H), 1.88-1.74 (m, 2H); ESI-MS (m/z) 419 (MH)$^+$ |

TABLE 10-continued

| Example No: IUPAC name | Structure | ¹HNMR/ESI-MS |
|---|---|---|
| Example-107: 2,6-Difluoro-N-(6-(6-methylspiro[chromene-2,1'-cyclobutan]-4-yl)pyridin-3-yl)benzamide | 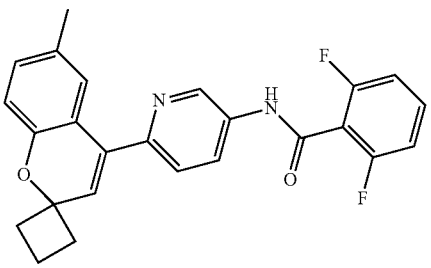 [SMILES: Cc1ccc2c(c1)C(c1ccc(NC(=O)c3c(F)cccc3F)cn1)=CC1(CCC1)O2] | ¹HNMR (400 MHz, DMSO-$d_6$) δ 11.19 (s, 1H), 8.88 (d, J = 2.5 Hz, 1H), 8.26 (dd, J = 8.5 & 2.5 Hz, 1H), 7.68-7.61 (m, 1H), 7.58 (d, J = 8.5 Hz, 1H), 7.30 (t, J = 8.0 Hz, 2H), 7.04 (d, J = 2.0 Hz, 1H), 6.99 (dd, J = 8.0 & 2.0 Hz, 1H), 6.82 (d, J = 8.0 Hz, 1H), 6.39 (s, 1H), 2.44-2.34 (m, 2H), 2.30-2.22 (m, 2H), 2.17 (s, 3H), 1.88-1.74 (m, 2H); ESI-MS (m/z) 419 (MH)⁺ |
| Example-108: N-(5-(2,2-Dimethyl-2H-chromen-4-yl)pyridin-2-yl)-2,6-difluorobenzamide | 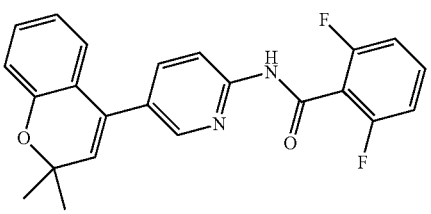 [SMILES: CC1(C)C=C(c2ccc(NC(=O)c3c(F)cccc3F)nc2)c2ccccc2O1] | ¹HNMR (400 MHz, DMSO-$d_6$) δ 11.51 (s, 1H), 8.35 (d, J = 2.5 Hz, 1H), 8.25 (d, J = 8.5 Hz, 1H), 7.84 (dd, J = 8.5 & 2.5 Hz, 1H), 7.63-7.55 (m, 1H), 7.26-7.18 (m, 3H), 6.98-6.95 (m, 1H), 6.91-6.86 (m, 2H), 5.88 (s, 1H), 1.45 (s, 6H); ESI-MS (m/z) 393 (MH)⁺ |
| Example-109: 2,6-Difluoro-N-(5-(7-methylspiro[chromene-2,1'-cyclobutan]-4-yl)pyridin-2-yl)benzamide | 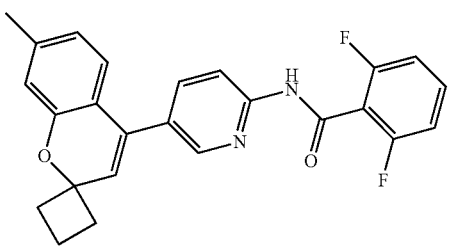 [SMILES: Cc1ccc2c(c1)OC1(C=C2c2ccc(NC(=O)c3c(F)cccc3F)nc2)CCC1] | ¹HNMR (400 MHz, DMSO-$d_6$) δ 11.51 (s, 1H), 8.38 (d, J = 2.5 Hz, 1H), 8.25 (d, J = 8.5 Hz, 1H), 7.86 (dd, J = 8.5 & 2.5 Hz, 1H), 7.65-7.55 (m, 1H), 7.24 (t, J = 8.0 Hz, 2H), 6.84 (d, J = 8.0 Hz, 1H), 6.77 (d, J = 2.0 Hz, 1H), 6.71 (dd, J = 8.0 & 2.0 Hz, 1H), 6.20 (s, 1H), 2.47-2.32 (m, 2H), 2.31 2.22 (m, 5H), 1.88-1.73 (m, 2H); ESI-MS (m/z) 419 (MH)⁺ |
| Example-110: 2,6-Difluoro-N-(6-(7-methylspiro[chromene-2,1'-cyclobutan]-4-yl)pyridin-3-yl)benzamide | 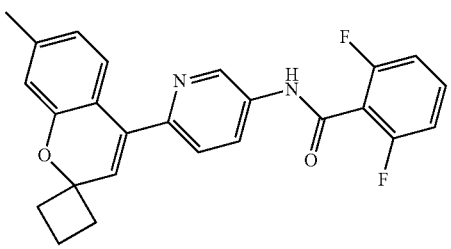 [SMILES: Cc1ccc2c(c1)OC1(C=C2c2ccc(NC(=O)c3c(F)cccc3F)cn2)CCC1] | ¹HNMR (400 MHz, DMSO-$d_6$) δ 11.18 (s, 1H), 8.87 (d, J = 2.5 Hz, 1H), 8.24 (dd, J = 8.5 & 2.5 Hz, 1H), 7.68-7.61 (m, 1H), 7.58 (d, J = 8.5 Hz, 1H), 7.30 (t, J = 8.0 Hz, 2H), 7.16 (d, J = 8.0 Hz, 1H), 6.75 (d, J = 2.0 Hz, 1H), 6.69 (dd, J = 8.0 & 2.0 Hz, 1H), 6.35 (s, 1H), 2.45-2.35 (m, 2H), 2.30-2.27 (m, 2H), 2.27 (s, 3H), 1.89-1.72 (m, 2H); ESI-MS (m/z) 419 (MH)⁺ |
| Example-111: N-(3,5-Difluoropyridin-4-yl)-4-(8-methylspiro[chromene-2,1'-cyclobutan]-4-yl)benzamide | 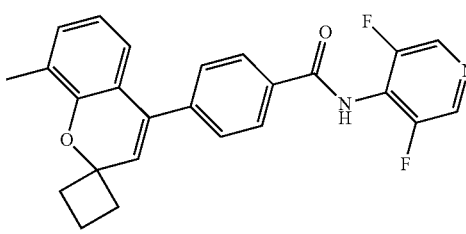 | ¹HNMR (400 MHz, DMSO-d6) δ 10.73 (s, 1H, $D_2O$ exchangeable), 8.64 (s, 2H), 8.09 (J = 8.0 Hz, 2H), 7.56 (J = 8.0 Hz, 2H), 7.11-7.08 (m, 1H), 6.81-6.74 (m, 2H), 6.27 (s, 1H), 2.44-2.37 (m, 2H), 2.34-2.27 (m, 2H), 2.24 (s, 3H), 1.92-1.77 (m, 2H); ESI-MS (m/z) 419 (MH)⁺. |

Example-112

2,6-Difluoro-N-(4-(2-(hydroxymethyl)-2,8-dimethyl-4-oxochroman-7-yl)phenyl)benzamide And

Example-113

2,6-Difluoro-N-(4-(2-(hydroxymethyl)-2,8-dimethyl-chroman-7-yl)phenyl)benzamide

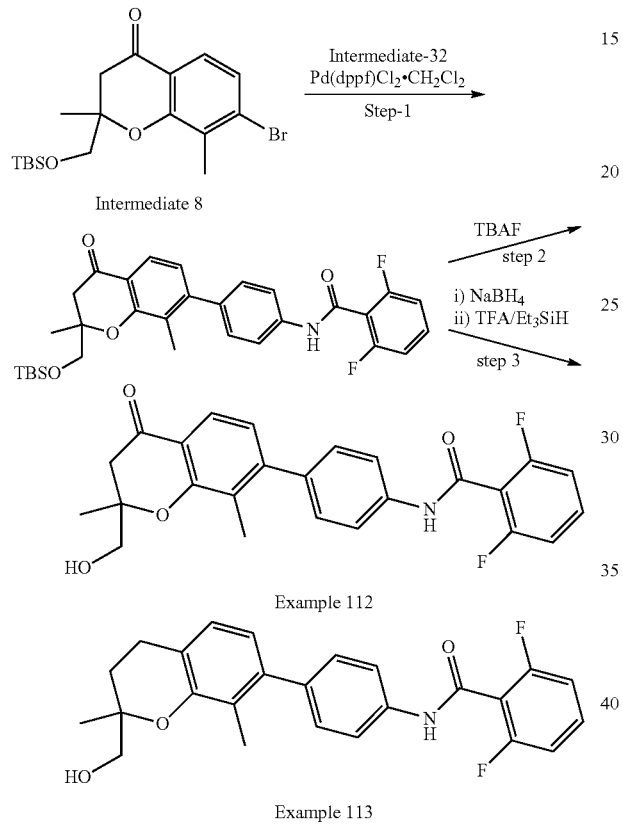

Step-1: N-(4-(2-(((tert-Butyldimethylsilyl)oxy)methyl)-2,8-dimethyl-4-oxochroman-7-yl)phenyl)-2,6-difluorobenzamide: The title compound was prepared by reacting Intermediate-8 with Intermediate-32 by following the similar procedure as described in Example-30. $^1$HNMR (400 MHz, CDCl$_3$) δ 7.79-7.69 (m, 4H), 7.51-7.40 (m, 1H), 7.46 (d, J=8.0 Hz, 2H), 7.05 (t, J=8.0 Hz, 2H), 6.89 (d, J=8.0 Hz, 1H), 3.83 (d, J=10.5 Hz, 1H), 3.68 (d, J=10.5 Hz, 1H), 3.03 (d, J=16.5 Hz, 1H), 2.65 (d, J=16.5 Hz, 1H), 2.16 (s, 3H), 1.41 (s, 3H), 0.88 (s, 9H), 0.07 (s, 3H), 0.04 (s, 3H); ESI-MS (m/z) 552 (MH)$^+$.

Step-2: 2,6-Difluoro-N-(4-(2-(hydroxymethyl)-2,8-dimethyl-4-oxochroman-7-yl)phenyl)benzamide: The title compound was prepared from step-1 Intermediate by following the similar procedure as described in step-2 of Example-51. $^1$HNMR (400 MHz, CDCl$_3$) δ 7.79 (d, J=8.0 Hz, 1H), 7.75-7.71 (m, 3H), 7.51-7.44 (m, 1H), 7.35 (d, J=8.0 Hz, 2H), 7.05 (t, J=8.0 Hz, 2H), 6.94 (d, J=8.0 Hz, 1H), 3.87 (d, J=12.0 Hz, 1H), 3.70 (d, J=12.0 Hz, 1H), 3.19 (d, J=16.5 Hz, 1H), 2.57 (d, J=16.5 Hz, 1H), 2.18 (s, 3H), 1.42 (s, 3H); ESI-MS (m/z) 438 (MH)$^+$.

Step-3: 2,6-Difluoro-N-(4-(2-(hydroxymethyl)-2,8-dimethylchroman-7-yl)phenyl)benzamide: The title compound was prepared from step-1 Intermediate by following the similar procedure as described in Example-48. $^1$H NMR (400 MHz, CDCl$_3$) δ 7.74-7.64 (m, 3H), 7.49-7.42 (m, 1H), 7.34 (d, J=8.0 Hz, 2H), 7.03 (t, J=8.0 Hz, 2H), 6.99 (d, J=8.0 Hz, 1H), 6.79 (d, J=8.0 Hz, 1H), 3.75-3.63 (m, 2H), 3.00-2.78 (m, 2H), 2.12 (s, 3H), 2.10-2.03 (m, 1H), 1.80-1.73 (m, 1H), 1.33 (s, 3H); ESI-MS (m/z) 424 (MH)$^+$

Example-114

2,6-Difluoro-N-(5-(2-(hydroxymethyl)-2,6-dimethyl-chroman-7-yl)pyrazin-2-yl)benzamide

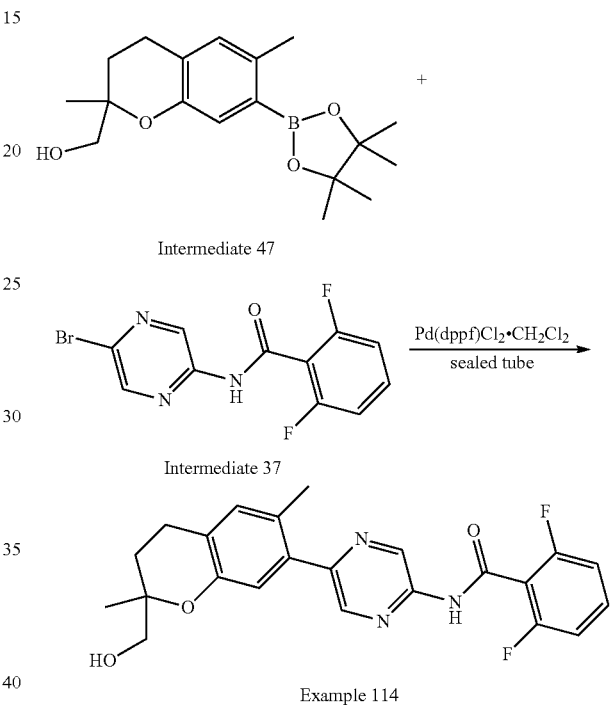

The title compound was prepared by following the similar procedure as described in Example-30 by using Intermediate-47 and Intermediate-37. $^1$HNMR (400 MHz, CDCl$_3$) δ 9.74 (s, 1H), 8.47 (s, 1H), 8.39 (s, 1H), 7.53-7.48 (m, 1H), 7.07 (t, J=8.0 Hz, 2H), 7.04 (s, 1H), 6.93 (s, 1H), 3.71-3.61 (m, 2H), 2.96-2.77 (m, 2H), 2.33 (s, 3H), 2.12-2.03 (m, 1H), 1.81-1.73 (m, 1H), 1.30 (s, 3H); ESI-MS (m/z) 426 (MH)$^+$

Example-115

2,6-Difluoro-N-(5-(2-(methoxymethyl)-2,6-dimethyl-2H-chromen-4-yl)pyridin-2-yl)benzamide

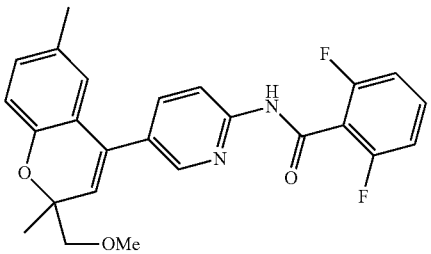 [SMILES: COCC1(C)C=C(c2ccc(NC(=O)c3c(F)cccc3F)nc2)c2cc(C)ccc2O1]

The title compound was prepared by following the similar procedure as described in Example-68 by using Intermediate-26b and Intermediate-35. $^{1}$HNMR (400 MHz, DMSO-$d_6$) δ 11.52 (s, 1H), 8.33 (s, 1H), 8.26 (d, J=8.0 Hz, 1H), 7.84 (d, J=8.0 Hz, 1H), 7.59 (s, 1H), 7.24 (t, J=8.0 Hz, 2H), 7.01 (d, J=8.0 Hz, 1H), 6.82-6.74 (m, 2H), 5.78 (s, 1H), 3.50-3.45 (m, 2H), 3.34 (s, 3H), 2.17 (s, 3H), 1.39 (s, 3H); ESI-MS (m/z) 437 (MH)$^+$.

Example-116

N-(2,6-Difluorophenyl)-4-(6-methylspiro[chroman-2,1'-cyclobutan]-7-yl)benzamide

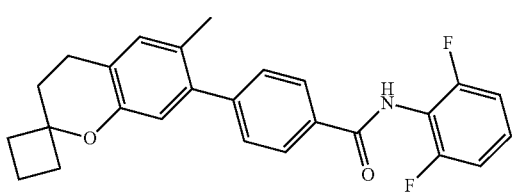 [SMILES: Cc1cc2c(cc1-c1ccc(C(=O)Nc3c(F)cccc3F)cc1)OC1(CCC1)CC2]

The title compound was prepared by following the similar procedure as described in Example-1 by using Intermediate-12c and Intermediate-38. $^{1}$HNMR (400 MHz, CDCl$_3$) δ 7.98 (d, J=8.0 Hz, 2H), 7.48-7.46 (m, 3H), 7.34-7.22 (m, 1H), 7.03 (t, J=8.0 Hz, 2H), 6.99 (s, 1H), 6.75 (s, 1H), 2.83 (t, J=6.0 Hz, 2H), 2.36-2.29 (m, 2H), 2.19 (s, 3H), 2.14-2.11 (m, 2H), 2.02 (t, J=6.0 Hz, 2H), 1.98-1.80 (m, 1H), 1.73-1.66 (m, 1H); LCMS (m/z) 420 (MH)$^+$.

Example-117

2,6-Difluoro-N-(4-(1'-methyl-4-oxospiro[chroman-2,4'-piperidin]-6-yl)phenyl)benzamide

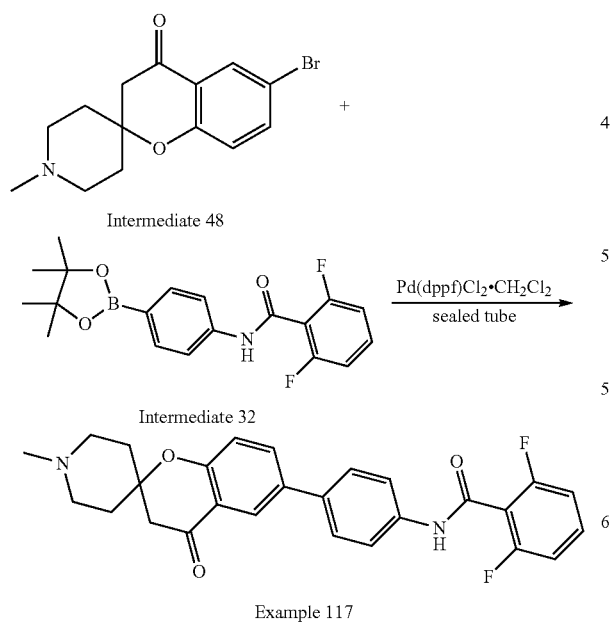

The title compound was prepared by following the similar procedure as described in Example-30 by using Intermediate-48 and Intermediate-32. $^{1}$HNMR (400 MHz, CDCl$_3$) δ 8.10 (s, 1H), 7.77-7.72 (m, 4H), 7.61 (d, J=8.0 Hz, 2H), 7.50-7.41 (m, 1H), 7.10 (d, J=8.0 Hz, 1H), 7.04 (t, J=8.0 Hz, 2H), 2.77 (s, 2H), 2.69-2.66 (m, 2H), 2.53-2.48 (m, 2H), 2.39 (s, 3H), 2.15-2.10 (m, 2H), 1.88-1.82 (m, 2H); ESI-MS (m/z) 463 (MH)$^+$.

Example-118

N-(4-(1',6-Dimethyl-4-oxospiro[chroman-2,4'-piperidin]-7-yl)phenyl)-2,6-difluorobenzamide

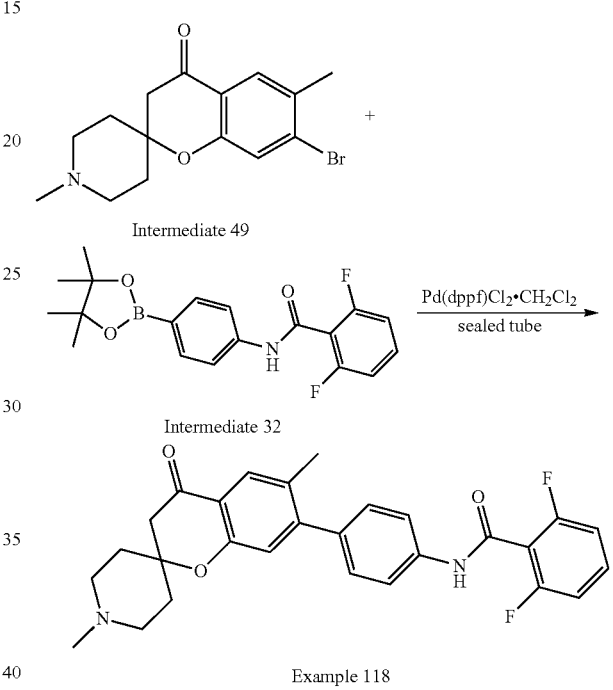

The title compound was prepared by following the similar procedure as described in Example-30 by using Intermediate-49 and Intermediate-32. $^{1}$HNMR (400 MHz, acetone-$d_6$) δ 7.92 (d, J=8.0 Hz, 2H), 7.67 (s, 1H), 7.63-7.56 (m, 1H), 7.43 (d, J=8.0 Hz, 2H), 7.17 (t, J=8.0 Hz, 2H), 6.91 (s, 1H), 2.75 (s, 2H), 2.56-2.51 (m, 2H), 2.41-2.35 (m, 2H), 2.27 (s, 3H), 2.23 (s, 3H), 2.04-1.98 (m, 2H), 1.81-1.74 (m, 2H); ESI-MS (m/z) 477 (MH)$^+$.

Example-119

2,6-Difluoro-N-(4-(6-methyl-4-oxospiro[chroman-2,4'-piperidin]-7-yl)phenyl)benzamide hydrochloride

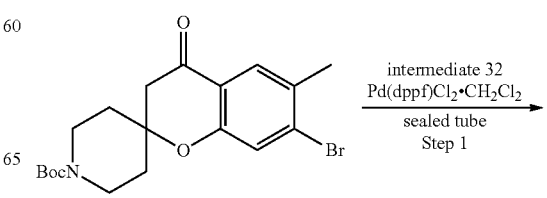

119

-continued

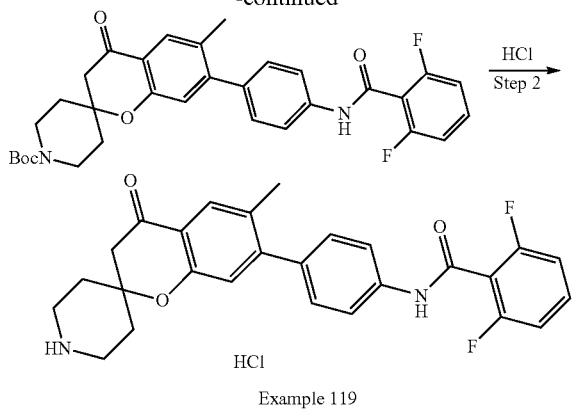

Example 119

Step-1: The title compound was prepared by following the similar procedure as described in Example-30 by using tert-butyl 7-bromo-6-methyl-4-oxospiro[chroman-2,4'-piperidine]-1'-carboxylate (prepared as described in step-1 of Intermediate-49) and Intermediate-32. $^1$HNMR (400 MHz, CDCl$_3$) δ 7.76 (d, J=8.0 Hz, 2H), 7.73 (s, 1H), 7.50-7.44 (m, 1H), 7.36 (d, J=8.0 Hz, 2H), 7.29 (s, 1H), 7.05 (t, J=8.0 Hz, 2H), 6.95 (s, 1H), 3.98-3.81 (m, 2H), 3.30-3.16 (m, 2H), 2.74 (s, 2H), 2.25 (s, 3H), 2.09-2.06 (m, 2H), 1.68-1.62 (m, 2H), 1.60 (s, 9H); ESI-MS (m/z) 463 (MH-Boc)$^+$.

Step-2: 2,6-Difluoro-N-(4-(6-methyl-4-oxospiro[chroman-2,4'-piperidin]-7-yl)phenyl)benzamide hydrochloride: To a (0° C.) cooled and stirred solution of step-1 Intermediate (200 mg, 0.355 mmol) in dioxane (5 mL) was added dioxane-HCl (10 mL, 4M). The reaction mixture was stirred at room temperature for 16 h. The solvent was removed under vacuum and the residue was triturated with hexane (2×10 mL) to afford 100 mg (60%) of the title compound as white solid. $^1$HNMR (400 MHz, DMSO-d$_6$) δ 11.03 (s, 1H), 9.34 (brs, 1H), 9.17 (brs, 1H), 7.80 (d, J=8.0 Hz, 2H), 7.65 (s, 1H), 7.63-7.57 (m, 1H), 7.42 (d, J=8.0 Hz, 2H), 7.27 (t, J=8.0 Hz, 2H), 7.01 (s, 1H), 3.19-3.07 (m, 4H), 2.89 (s, 2H), 2.22 (s, 3H), 2.15-2.11 (m, 2H), 2.00-1.92 (m, 2H); ESI-MS (m/z) 463 (MH)$^+$

Example-120

2,6-Difluoro-N-(4-(6'-methyl-4'-oxospiro[azetidine-3,2'-chroman]-7'-yl)phenyl)benzamide hydrochloride And

Example-121

N-(4-(1,6'-Dimethyl-4'-oxospiro[azetidine-3,2'-chroman]-7'-yl)phenyl)-2,6-difluorobenzamide

120

-continued

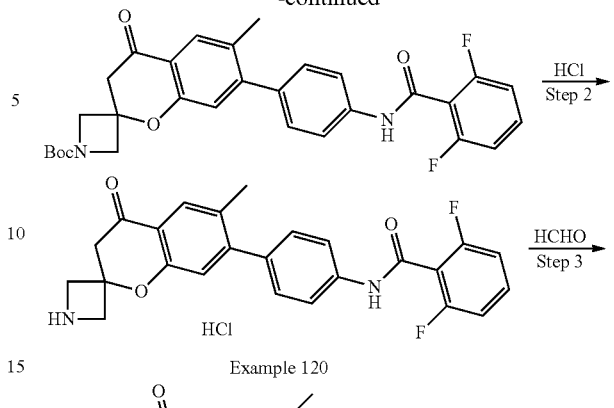

Example 120

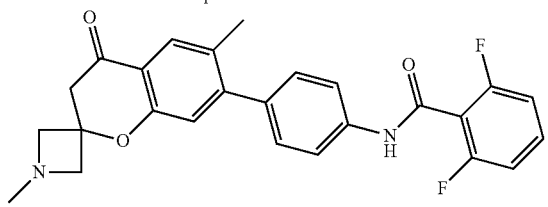

Example 121

Step-1: tert-Butyl 7'-(4-(2,6-difluorobenzamido)phenyl)-6'-methyl-4'-oxospiro[azetidine-3,2'-chroman]-1-carboxylate: The title compound was prepared by following the similar procedure as described in step-1 of Example-119 by using Intermediate-50 and Intermediate-32. $^1$HNMR (400 MHz, CDCl$_3$) δ 7.79-7.73 (m, 4H), 7.35 (d, J=8.0 Hz, 2H), 7.05 (t, J=8.0 Hz, 2H), 6.96 (s, 1H), 4.11 (d, J=9.5 Hz, 2H), 3.98 (d, J=9.5 Hz, 2H), 3.05 (s, 2H), 2.25 (s, 3H), 1.26 (s, 9H). ESI-MS (m/z) 435 (MH-Boc)$^+$.

Step-2: 2,6-Difluoro-N-(4-(6'-methyl-4'-oxospiro[azetidine-3,2'-chroman]-7'-yl)phenyl)benzamide hydrochloride: The title compound was prepared from step-1 Intermediate by following the similar procedure as described in step-2 of Example-119. $^1$HNMR (400 MHz, DMSO-d$_6$) δ 11.01 (s, 1H), 9.48 (brs, 2H), 7.81 (d, J=8.0 Hz, 2H), 7.68 (s, 1H), 7.68-7.54 (m, 1H), 7.42 (d, J=8.0 Hz, 2H), 7.28 (t, J=8.0 Hz, 2H), 6.98 (s, 1H), 4.19-4.11 (m, 4H), 3.30 (s, 2H), 2.24 (s, 3H); ESI-MS (m/z) 435 (MH)$^+$.

Step-3: N-(4-(1,6'-Dimethyl-4'-oxospiro[azetidine-3,2'-chroman]-7'-yl)phenyl)-2,6-difluorobenzamide: The title compound was prepared from step-2 Intermediate by following the similar procedure as described in step-3 of Example-49. $^1$HNMR (400 MHz, CDCl$_3$) δ 7.76 (s, 1H), 7.74 (d, J=8.0 Hz, 2H), 7.49-7.45 (m, 1H), 7.36 (d, J=8.0 Hz, 2H), 7.06 (t, J=8.0 Hz, 2H), 6.94 (s, 1H), 3.52 (d, J=8.0 Hz, 2H), 3.31 (d, J=8.0 Hz, 2H), 3.09 (s, 2H), 2.46 (s, 3H), 2.24 (s, 3H). ESI-MS (m/z) 448 (MH)+,

Example-122

2,6-Difluoro-N-(5-(6-methyl-4-oxospiro[chroman-2,3'-oxetan]-7-yl)pyrazin-2-yl)benzamide

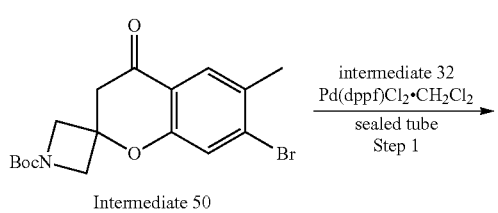

Intermediate 50 intermediate 32
Pd(dppf)Cl$_2$·CH$_2$Cl$_2$
sealed tube
Step 1

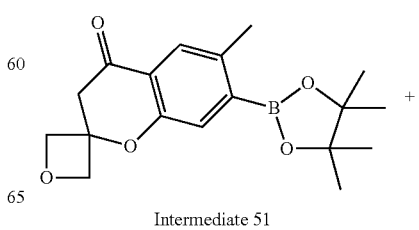

Intermediate 51

+

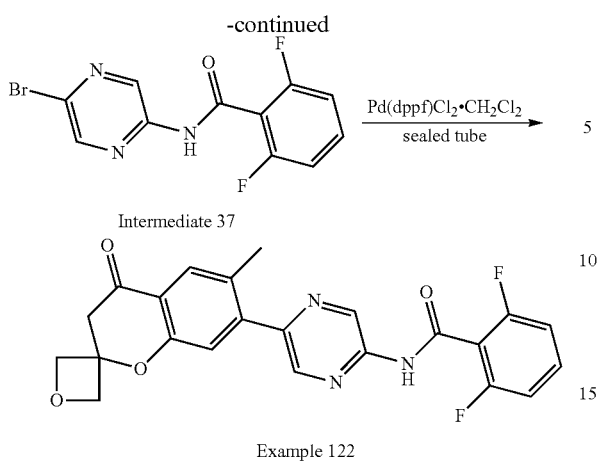

Intermediate 37

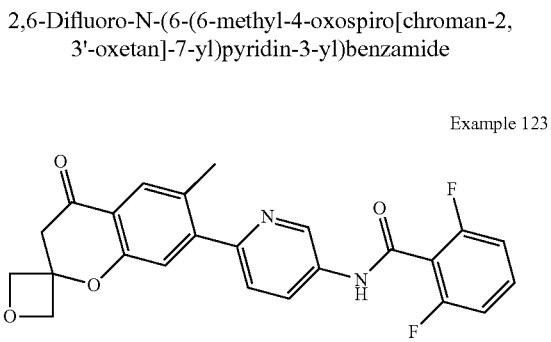

Example 122

The title compound was prepared by following the similar procedure as described in Example-30 by using Intermediate-51 and Intermediate-37. ¹HNMR (400 MHz, CDCl₃) δ 9.80 (s, 1H), 8.49 (s, 1H), 8.45 (s, 1H), 7.81 (s, 1H), 7.58-7.50 (m, 1H), 7.22 (s, 1H), 7.09 (t, J=8.0 Hz, 2H), 4.85 (d, J=7.5 Hz, 2H), 4.64 (d, J=7.5 Hz, 2H), 3.20 (s, 2H), 2.38 (s, 3H); ESI-MS (m/z) 438 (MH)⁺

Example-123

2,6-Difluoro-N-(6-(6-methyl-4-oxospiro[chroman-2, 3'-oxetan]-7-yl)pyridin-3-yl)benzamide Example 123

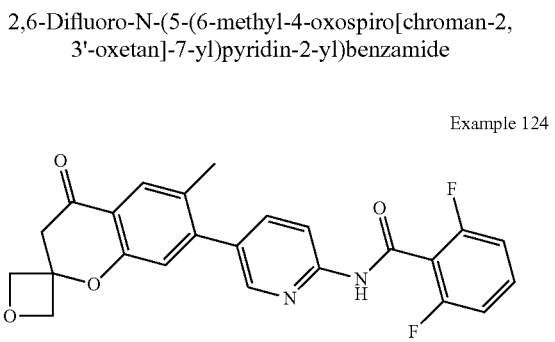

The title compound was prepared by following the similar procedure as described in Example-121 by using Intermediate-51 and Intermediate-36. ¹HNMR (400 MHz, CDCl₃) δ 8.74 (d, J=2.5 Hz, 1H), 8.48 (dd, J=8.5 & 2.5 Hz, 1H), 7.85 (s, 1H), 7.78 (s, 1H), 7.54-7.47 (m, 2H), 7.18 (s, 1H), 7.08 (t, J=8.5 Hz, 2H), 4.84 (d, J=7.0 Hz, 2H), 4.63 (d, J=7.0 Hz, 2H), 3.18 (s, 2H); ESI-MS (m/z) 437 (MH)⁺

Example-124

2,6-Difluoro-N-(5-(6-methyl-4-oxospiro[chroman-2, 3'-oxetan]-7-yl)pyridin-2-yl)benzamide Example 124

The title compound was prepared by following the similar procedure as described in Example-121 by using Intermediate-51 and Intermediate-35. ¹HNMR (400 MHz, CDCl₃) δ 8.73 (s, 1H), 8.51 (d, J=8.5 Hz, 1H), 8.27 (d, J=2.5 Hz, 1H), 7.81 (dd, J=8.5 & 2.5 Hz, 1H), 7.79 (s, 1H), 7.53-7.45 (m, 1H), 7.05 (t, J=8.0 Hz, 2H), 6.99 (s, 1H), 4.85 (d, J=7.5 Hz, 2H), 4.64 (d, J=7.5 Hz, 2H), 3.19 (s, 2H), 2.26 (s, 3H); ESI-MS (m/z) 437 (MH)⁺.

Example-125

N-(4-(6-Ethyl-4-oxospiro[chroman-2,3'-oxetan]-7-yl)phenyl)-2,6-difluorobenzamide Example 125

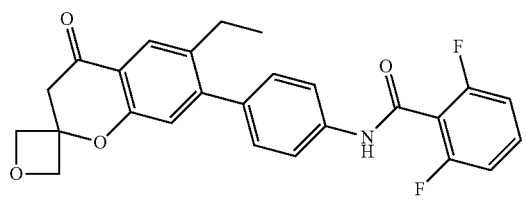

The title compound was prepared by following the similar procedure as described in Example-30 by using Intermediate-52 and Intermediate-32. ¹HNMR (400 MHz, CDCl₃) δ 7.80 (s, 1H), 7.74 (d, J=8.5 Hz, 2H), 7.72 (s, 1H), 7.51-7.45 (m, 1H), 7.34 (d, J=8.5 Hz, 2H), 7.05 (t, J=8.0 Hz, 2H), 6.95 (s, 1H), 4.85 (d, J=7.0 Hz, 2H), 4.63 (d, J=7.0 Hz, 2H), 3.18 (s, 2H), 2.58 (q, J=7.5 Hz, 2H), 1.10 (t, J=7.5 Hz, 3H); ESI-MS (m/z) 450 (MH)⁺.

Biological Assays and Utility:

The CRAC channel modulatory activity of the compounds were thus evaluated by measuring the secretion of IL-2 by antigen stimulated T-cells in vitro. Alternatively, such activity can also be evaluated by assay methods known to one skilled in the art.

In Vitro Assay

Example-126

Inhibition of IL-2 secretion: Jurkat T cells were seeded at a density of 0.5 to 1 million cells per well in RPMI medium. Test compounds from this invention were added to the cells at different concentrations. This was followed by the addition of PHA, a T cell mitogen after 10 minutes. The cells were then incubated for 20 to 24 hours in a CO₂ incubator at 37° C. After incubation with the compounds, cells were centrifuged; the supernatant was collected and processed for ELISA to quantitate the amount of IL-2 secreted. A commercial ELISA kit (R&D Systems, Inc. Minneapolis, Minn., USA) was used to estimate the IL-2 concentrations. Amount of IL-2 secreted by cells stimulated with PHA was considered as a 100% maximal signal and the decrease in amount of IL-2 secreted by cells treated with the test compounds was expressed as percent inhibition of the maximal signal. The dose response data was analyzed using 4-parametric sigmoidal dose response (variable slope) curve-fit.

In the above IL-2 assay, compounds of the invention were found to have IC₅₀ (nM) values as shown below:

| IC$_{50}$ (nM) | Examples |
|---|---|
| <25 nM | 2, 4, 5, 8, 16, 20, 22, 24, 33, 35, 36, 39, 42, 48b, 49, 50, 51, 59, 64, 66, 68, 75, 89, 100, 101, 103, 104, 125 |
| 25.01 nM to 50 nM | 1, 6, 9, 10, 11, 13, 21, 27, 67, 72, 79, 90, 91, 98, 102, 108, 111, 114, 116, 121, 124 |
| 50.01 nM to 100 nM | 7, 17, 18, 23, 41, 54, 58, 62, 76, 77, 81, 87, 93, 95, 120 |
| 100.01 nM to 500 nM | 19, 43, 45, 69, 80, 105, 106, 109 |

Thus, compounds of the invention are shown to inhibit IL-2 secretion.

Example-127

SOCE inhibition: Jurkat E6.1 cells were seeded at a density of 1-2×10$^5$ cells per well in calcium-4 dye prepared in calcium free HBSS (Sigma, USA). Test compounds from this invention were added to the cells at different concentrations. This was followed by the addition of Thapsigargin (TG), a SERCA inhibitor, to empty the stores of calcium. Calcium chloride was added to the cells after 10-30 min to induce calcium influx and the fluorescence was measured for 10 min using the FLIPR-Tetra detection system. Fluorescence was also measured using a plate reader at 485 nm excitation and 520 nm emission (Synergy2, Biotek, USA) after 30-90 minutes of calcium addition. Fluorescence observed in cells treated with Thapsigargin and calcium chloride solution was considered 100% maximal signal and the reduced fluorescent signal observed in the presence of test compounds was expressed as percent inhibition of the maximal signal. The dose response data was analyzed using 4-parametric sigmoidal dose response (variable slope) curve-fit.

In the above SOCE inhibition assay, compounds of the invention showed activity less than <1000 nM against SOCE. Thus, compounds of the invention are shown to have CRAC channel modulation activity by inhibition of SOCE.

Example-128

NFAT Transcriptional Activity: HEK 293 cells were stably co-transfected with a NFAT-FireflyLuciferase and Tk-Renilla Luciferase reporter genes 30,000-80,000 cells were seeded per well. Test compounds from this invention were added to the cells at different concentrations. Thapsigargin (TG) was added after 10 mins and the cells were incubated for 4-8 h. The NFAT-Firefly luciferase and Tk-Renilla luciferase activity was measured using Dual-Glo reagent (Promega USA). The Renilla luciferase activity was used for protein normalization. Luminescence observed in cells treated with thapsigargin was considered 100% maximal signal and the reduced fluorescent signal observed in the presence of test compounds was expressed as percent inhibition of the maximal signal. The data was analyzed using 4-parametric sigmoidal dose response (variable slope) curve-fit.

In the above NFAT transcriptional activity assay, compounds of the invention showed activity less than <1000 nM. Thus, compounds of the invention are shown to inhibit NFAT transcription activity.

Thus, the in vitro screening assays showed that the compounds of invention inhibit CRAC channel activity.

As mentioned hereinbefore, the CRAC channel is involved with numerous biological responses through various Ca$^{2+}$ signaling pathways. The compounds of the invention are therefore useful for the treatment and/or prophylaxis of, although not limited to, inflammatory conditions, cancer, rheumatoid arthritis, allergic disorders, immune disorders, cardiovascular diseases, thrombocytopathies and all related conditions which can be benefitted by the CRAC channel modulatory properties of the compounds described herein.

The compounds of the invention can be administered to a warm-blooded animal, including human being, for the treatment and/or prophylaxis of one or many diseases or disorders mentioned hereinabove which can be benefitted by the CRAC channel modulatory properties of the compounds described herein. The compounds may be Formulated according to the methods known in the art as well as by new methods and may be administered to the body system via gastro-intestinal tract as well as via other routes known to a person skilled in the art. Thus, administration of the compounds of the invention via oral route, parenteral route, inhalation and/or topical applications are within the scope of this application. Any combination of a compound of the invention with excipients and/or other therapeutic agents known in the art for the said conditions, diseases and/or disorders are also encompassed by the invention.

Although certain embodiments and Examples have been described in detail above, those having ordinary skill in the art will clearly understand that many modifications are possible in the embodiments and Examples without departing from the teachings thereof. All such modifications are intended to be encompassed within the below claims of the invention.

The invention claimed is:
1. A compound having the Formula (I):

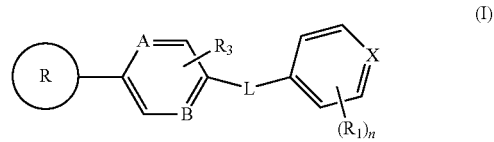

wherein,
A and B are independently CR$_3$ or N;
ring R is Formula (i);

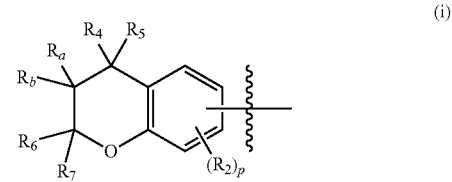

L is selected from —NR$_8$C(O)—, —C(O)NR$_8$—and —NR$_8$CH$_2$—;
X is CR or N where R is selected from hydrogen, halogen or substituted or unsubstituted alkyl;
R$_1$, which may be same or different at each occurrence, is independently selected from halogen, cyano, hydroxyl, substituted or unsubstituted alkyl, substituted or unsubstituted cycloalkyl and haloalkyl;
R$_2$, which may be same or different at each occurrence, is independently selected from halogen, cyano, nitro, hydroxyl, substituted or unsubstituted alkyl, substituted or unsubstituted cycloalkyl, substituted or unsubstituted alkoxy, haloalkyl, —NR$_9$R$_{10}$, —COOR$_8$ and —CONR$_9$R$_{10}$;

each of R$_3$ is independently selected from hydrogen, halogen and substituted or unsubstituted alkyl;

R$_4$ and R$_5$, which may be same or different and are independently selected from hydrogen, hydroxyl, substituted or unsubstituted alkyl, haloalkyl, substituted or unsubstituted alkoxy, substituted or unsubstituted cycloalkyl and —NR$_9$R$_{10}$; or R$_4$ and R$_5$ together with the carbon atom to which they are attached form oxo (C=O);

one of R$_6$ and R$_7$ is alkyl, haloalkyl, hydroxyalkyl, substituted or unsubstituted cycloalkyl, substituted or unsubstituted alkoxy, substituted or unsubstituted alkoxyalkyl and the other is selected from hydrogen, hydroxyl, alkyl, haloalkyl, hydroxyalkyl, substituted or unsubstituted alkoxy, substituted or unsubstituted alkoxyalkyl, —NR$_9$R$_{10}$, substituted or unsubstituted cycloalkyl, —COOR$_8$ and —CONR$_9$R$_{10}$; or R$_6$ and R$_7$ together with the carbon atom to which they are attached may form substituted or unsubstituted 3 to 7 membered carbocyclic ring or 4 to 7 membered heterocyclic ring;

R$_8$ is hydrogen or substituted or unsubstituted alkyl;

R$_9$ and R$_{10}$, which may be same or different, are independently selected from hydrogen, substituted or unsubstituted alkyl, haloalkyl, and substituted or unsubstituted cycloalkyl; or R$_9$ and R$_{10}$, together with the nitrogen atom to which they are attached, may form a substituted or unsubstituted, saturated or unsaturated 5 to 7 membered cyclic ring, wherein the unsaturated cyclic ring may have one or two double bonds;

R$_a$ and R$_b$, which may be same or different and are independently selected from hydrogen, cyano, hydroxyalkyl, substituted or unsubstituted alkyl, haloalkyl, substituted or unsubstituted alkoxy, haloalkoxy, substituted or unsubstituted cycloalkyl, —NR$_9$R$_{10}$, —COOR$_S$ and —CONH$_2$;

'n' is an integer ranging from 1 to 3, both inclusive; and

'p' is an integer ranging from 0 to 2, both inclusive;

or a pharmaceutically acceptable salt thereof.

2. The compound of claim 1 having the structure of Formula (II):

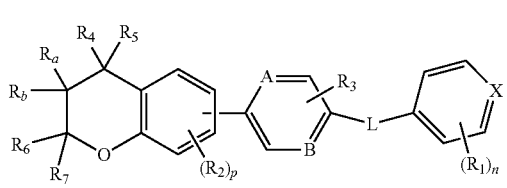

(II)

wherein,
A and B are independently CR$_3$ or N;
L is selected from —NHC(O)—, —C(O)NH— and —NHCH$_2$—;
X is CH or N;
R$_1$, which may be same or different at each occurrence, is independently selected from halogen, substituted or unsubstituted alkyl, substituted or unsubstituted cycloalkyl and haloalkyl;
R$_2$ is selected from halogen, substituted or unsubstituted alkyl, substituted or unsubstituted cycloalkyl, haloalkyl and substituted or unsubstituted alkoxy;

R$_3$ is selected from hydrogen, halogen and substituted or unsubstituted alkyl;

R$_4$ and R$_5$, which may be same or different and are independently selected from hydrogen, hydroxyl, substituted or unsubstituted alkyl, substituted or unsubstituted alkoxy and —NR$_9$R$_{10}$; or R$_4$ and R$_5$ together with the carbon atom to which they are attached form oxo (C=O);

one of R$_6$ and R$_7$ is alkyl, haloalkyl, hydroxyalkyl and the other is selected from hydrogen, hydroxyl, alkyl, haloalkyl, hydroxyalkyl, substituted or unsubstituted alkoxy, substituted or unsubstituted alkoxyalkyl, —NR$_9$R$_{10}$, substituted or unsubstituted cycloalkyl, —COOR$_8$ and —CONH$_2$; or R$_6$ and R$_7$ together with the carbon atom to which they are attached may form substituted or unsubstituted 3 to 6 membered carbocyclic ring or 4 to 7 membered heterocyclic ring;

R$_8$ is hydrogen or substituted or unsubstituted alkyl;

R$_9$ and R$_{10}$ are independently hydrogen or substituted or unsubstituted alkyl;

R$_a$ and R$_b$ are independently hydrogen or substituted or unsubstituted alkyl;

'n' is an integer ranging from 1 to 2, both inclusive; and

'p' is an integer ranging from 0 to 1, both inclusive;

or a pharmaceutically acceptable salt thereof.

3. The compound of claim 1, wherein L is selected from —NHC(O)—, —C(O)NH— and —NHCH$_2$—.

4. The compound of claim 1, wherein ring R is Formula (i)

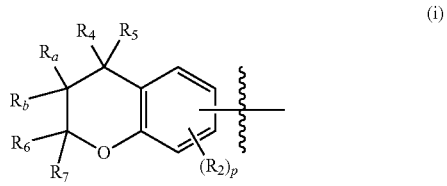

(i)

wherein R$_2$ is halogen or substituted or unsubstituted alkyl; 'p' is 0 to 1; R$_4$ and R$_5$ may be same or different and are independently selected from hydrogen, hydroxyl, substituted or unsubstituted alkyl and —NR$_9$R$_{10}$ or R$_4$ and R$_5$ together with the carbon atom to which they are attached form oxo (C=O); one of R$_6$ and R$_7$ is alkyl, hydroxyalkyl and the other is selected from hydrogen, hydroxyl, alkyl, hydroxyalkyl, substituted or unsubstituted alkoxyalkyl, substituted or unsubstituted cycloalkyl, —NR$_9$R$_{10}$, —COOH, —COO—alkyl, and —CONH$_2$; or R$_6$ and R$_7$ together form substituted or unsubstituted 3 to 6 membered carbocyclic ring or 4 to 7 membered heterocyclic ring; R$_9$ and R$_{10}$ are selected from hydrogen or substituted or unsubstituted alkyl; and R$_a$ and R$_b$ are hydrogen.

5. The compound of claim 1, wherein R$_6$ and R$_7$ together with carbon atom to which they are attached to form a ring which is selected from:

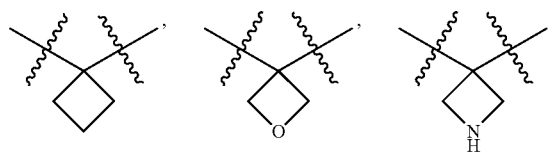

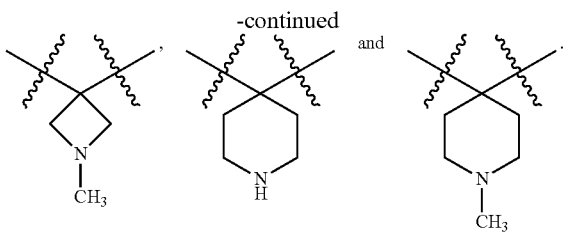

6. The compound of claim 1 having the Formula (I):

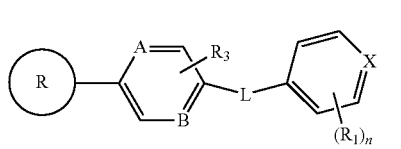

wherein L is selected from —NHC(O)—, —C(O)NH— and —NHCH$_2$—; X is CH or N; A and B are independently CR$_3$ or N; R$_1$ is halogen, substituted or unsubstituted alkyl or haloalkyl; 'n' is 1 or 2; R$_3$ is hydrogen or substituted or unsubstituted alkyl; and ring R is Formula (i)

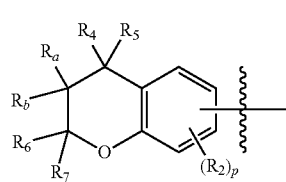

wherein R$_2$ is halogen or substituted or unsubstituted alkyl; 'p' is 0 or 1; R$_4$ and R$_5$, which may be same or different and are independently selected from hydrogen, hydroxyl, —NR$_9$R$_{10}$ where R$_9$ and R$_{10}$ are hydrogen or substituted or unsubstituted alkyl, or R$_4$ and R$_5$ together form oxo (C=O); one of R$_6$ and R$_7$ is alkyl or hydroxyalkyl and the other is selected from hydrogen, hydroxyl, alkyl, hydroxyalkyl, substituted or unsubstituted alkoxyalkyl, —C(O)OH, —C(O)Oalkyl and —CONH$_2$, or R$_6$ and R$_7$ together with the carbon atom to which they are attached may form substituted or unsubstituted 3 to 4 membered carbocyclic ring or 4 to 7 membered heterocyclic ring; and R$_a$ and R$_b$ are hydrogen.

7. A compound which is selected from:
2,6-Difluoro-N-(4-(2,2,6-trimethyl-4-oxochroman-7-yl) phenyl)benzamide,
N-(4-(6-Ethyl-2,2-dimethyl-4-oxochroman-7-yl)phenyl)-2,6-difluorobenzamide,
N-(2,6-Difluorophenyl)-4-(2,2,6-trimethyl-4-oxochroman-7-yl)benzamide,
2,6-Difluoro-N-(5-(2,2,6-trimethyl-4-oxochroman-7-yl)pyrazin-2-yl)benzamide,
N-(5-(6-Ethyl-2,2-dimethyl-4-oxochroman-7-yl)pyrazin-2-yl)-2,6-difluorobenzamide,
2,6-Difluoro-N-(5-(2,2,6-trimethyl-4-oxochroman-7-yl)pyrazin-2-yl)benzamide,
2,6-Difluoro-N-(5-(2,2,8-trimethylchroman-7-yl)pyrazin-2-yl)benzamide,
2-Chloro-6-fluoro-N-(4-(6-methylspiro[chroman-2,1'-cyclobutan]-7-yl)phenyl)benzamide,
2-Fluoro-6-methyl-N-(4-(6-methylspiro[chroman-2,1'-cyclobutan]-7-yl)phenyl)benzamide,
2-Fluoro-6-methyl-N-(4-(6-methyl-4-oxospiro[chroman-2,1'-cyclobutan]-7-yl)phenyl)benzamide,
2-Chloro-6-fluoro-N-(4-(6-methyl-4-oxospiro[chroman-2,1'-cyclobutan]-7-yl)phenyl)benzamide,
2-Fluoro-N-(4-(6-methyl-4-oxospiro[chroman-2,1'-cyclobutan]-7-yl)phenyl)benzamide,
N-(2,6-Difluorophenyl)-4-(6-methyl-4-oxospiro[chroman-2,1'-cyclobutan]-7-yl)benzamide,
7-(4-((2-Fluoro-6-methylbenzyl)amino)phenyl)-6-methylspiro[chroman-2,1'-cyclobutan]-4one,
2,6-Difluoro-N-(4-(5-methyl-4-oxospiro[chroman-2,1'-cyclobutan]-6-yl)phenyl)benzamide,
2,6-Difluoro-N-(4-(6-methyl-4-oxospiro[chroman-2,1'-cyclobutan]-7-yl)phenyl)benzamide,
2,6-Difluoro-N-(4-(7-methyl-4-oxospiro[chroman-2,1'-cyclobutan]-6-yl)phenyl)benzamide,
2,6-Difluoro-N-(4-(7-methylspiro[chroman-2,1'-cyclobutan]-6-yl)phenyl)benzamide,
2,6-Difluoro-N-(4-(8-methyl-4-oxospiro[chroman-2,1'-cyclobutan]-7-yl)phenyl)benzamide,
N-(4-(6-Ethyl-4-oxospiro[chroman-2,1'-cyclobutan]-7-yl)phenyl)-2,6-difluorobenzamide,
7-(4-(2,6-Difluorobenzyl)amino)phenyl)-6-methylspiro[chroman-2,1'-cyclobutan]-4-one,
2,6-Difluoro-N-(4-(6-methylspiro[chroman-2,1'-cyclobutan]-7-yl)phenyl)benzamide,
2,6-Difluoro-N-(4-(8-methylspiro[chroman-2,1'-cyclobutan]-7-yl)phenyl)benzamide,
N-(4-(6-Ethylspiro[chroman-2,1'-cyclobutan]-7-yl)phenyl)-2,6-difluorobenzamide,
2,6-Difluoro-N-(4-(4-hydroxy-6-methylspiro[chroman-2,1'-cyclobutan]-7-yl) phenyl)benzamide,
2,6-Difluoro-N-(5-(6-methyl-4-oxospiro[chroman-2,1'-cyclobutan]-7-yl)pyridin-2yl)benzamide,
2,6-Difluoro-N-(6-(2,2,6-trimethyl-4-oxochroman-7-yl)pyridin-3-yl)benzamide,
N-(6-(6-Ethyl-2,2-dimethyl-4-oxochroman-7-yl)pyridin-3-yl)-2,6-difluoro benzamide,
2,6-Difluoro-N-(6-(6-methyl-4-oxospiro[chroman-2,1'-cyclobutan]-7-yl)pyridin-3yl)benzamide,
2,6-Difluoro-N-(4-(2,2, 8-trimethyl-4-oxochroman-7-yl) phenyl)benzamide,
2,6-Difluoro-N-(5-(2,2,8-trimethyl-4-oxochroman-7-yl) pyrazin-2-yl)benzamide,
2,6-Difluoro-N-(4-(4-hydroxy-2,2, 8-trimethylchroman-7-yl)phenyl)benzamide,
7-(4-((2, 6-Difluorobenzyl)amino)phenyl)-2,2, 6-trimethylchroman-4-one,
7-(5-((2, 6-Difluorobenzyl)amino)pyrazin-2-yl)-2,2, 6-trimethylchroman-4-one,
7-(6-((2, 6-Difluorobenzyl)amino)pyridin-3 -yl)-2,2,6-trimethylchroman-4-one,
2,6-Difluoro-N-(5-(6-methyl-4-oxospiro[chroman-2,1'-cyclobutan]-7-yl)pyrazin-2-yl)benzamide,
2,6-Difluoro-N-(6-(2,2,8-trimethyl-4-oxochroman-7-yl)pyridin-3-yl)benzamide,
7-(5-((2,6-Difluorobenzyl)amino)pyrazin-2-yl)-6-methylspiro[chroman-2,1'-cyclobutan]-4-one,
7-(6-((2,6-Difluorobenzyl)amino)pyridin-3-yl)-6-methylspiro[chroman-2,1'-cyclobutan]-4-one,
7-(5-((2,6-Difluorobenzyl)amino)pyridin-2-yl)-6-methylspiro[chroman-2,1'-cyclobutan]-4-one,
N-(5-(6-Ethyl-4-oxospiro [chroman-2,1'-cyclobutan]-7-yl)pyrazin-2-yl)-2,6-difluoro benzamide, N-(3,5-Difluoropyridin-4-yl)-4-(6-ethyl-2,2-dimethyl-4-oxochroman-7-yl)benzamide,
N-(3,5-Difluoropyridin-4-yl)-4-(2,2,6-trimethyl-4-oxochroman-7-yl)benzamide,
4-(6-Methyl-4-oxospiro [chroman-2,1'-cyclobutan]-7-yl)-N-(3-methylpyridin-4-yl)benzamide,
Methyl 7-(5-(2,6-difluoro benzamido)pyrazin-2-yl)-2,6-dimethyl-4-oxochroman-2-carboxylate,
7-(5 -(2,6-Difluorobenzamido)pyrazin-2-yl)-2,6-dimethyl-4-oxochroman-2-carboxamide,
7-(5-(2,6-Difluorobenzamido)pyrazin-2-yl)-2,6-dimethyl-4-oxochroman-2-carboxylic acid,
N-(4-(6-Ethyl-4-hydroxy-2,2-dimethylchroman-7-yl)phenyl)-2,6-difluoro benzamide,
N-(4-(6-Ethyl-2,2-dimethylchroman-7-yl)phenyl)-2,6-difluorobenzamide,
N-(3,5-Difluoropyridin-4-yl)-4-(6-ethyl-2,2-dimethylchroman-7-yl)benzamide,
N-(3,5-Difluoropyridin-4-yl)-4-(2,2,6-trimethylchroman-7-yl)benzamide,
2,6-Difluoro-N-(4-(2-(hydroxymethyl)-2,6-dimethyl-4-oxochroman-7-yl)phenyl) benzamide,
2,6-Difluoro-N-(5-(2-(hydroxymethyl)-2,6-dimethyl-4-oxochroman-7-yl)pyrazin-2-yl)benzamide,
2,6-Difluoro-N-(6-(2-(hydroxymethyl)-2,6-dimethyl-4-oxochroman-7-yl)pyridin-3-yl)benzamide,
2,6-Difluoro-N-(5-(2-(hydroxymethyl)-2,6-dimethyl-4-oxochroman-7-yl)pyridin-2-yl)benzamide,
N-(5-(2,2-Bis(hydroxymethyl)-6-methyl-4-oxochroman-7-yl)pyrazin-2-yl)-2,6-difluorobenzamide,
N-(6-(2,2-Bis(hydroxymethyl)-6-methyl-4-oxochroman-7-yl)pyridin-3-yl)-2,6-difluorobenzamide,
N-(5-(2,2-Bis(hydroxymethyl)-6-methyl-4-oxochroman-7-yl)pyridin-2-yl)-2,6-difluorobenzamide,
N-(4-(6-Ethyl-2-(hydroxymethyl)-2-methyl-4-oxochroman-7-yl)phenyl)-2,6-difluorobenzamide,
2,6-Difluoro-N-(4-(2,2,8-trimethylchroman-7-yl)phenyl)benzamide,
2,6-Difluoro-N-(4-(4-hydroxy-2,2,6-trimethylchroman-7-yl)phenyl)benzamide,
2,6-Difluoro-N-(5-(4-hydroxy-6-methylspiro[chroman-2,1'-cyclobutan]-7-yl)pyrazin-2-yl)benzamide,
N-(4-(4-(Dimethylamino)-2,2,6-trimethylchroman-7-yl)phenyl)-2,6-difluoro benzamide,
N-(5-(6-Ethyl-2,2-dimethyl-4-oxochroman-7-yl)pyridin-2-yl)-2,6-difluorobenzamide,
N-(3,5-Difluoropyridin-4-yl)-4-(6-methyl-4-oxospiro[chroman-2,1'-cyclobutan]-7-yl)benzamide,
N-(3,5-Dichloropyridin-4-yl)-4-(6-methyl-4-oxospiro[chroman-2,1'-cyclobutan]-7-yl)benzamide,
N-(3,5-Difluoropyridin-4-yl)-4-(6-methylspiro[chroman-2,1'-cyclobutan]-7-yl)benzamide,
N-(3,5-Dichloropyridin-4-yl)-4-(6-methylspiro[chroman-2,1'-cyclobutan]-7-yl)benzamide,
2,6-Difluoro-N-(4-(2-(hydroxymethyl)-2,8-dimethyl-4-oxochroman-7-yl)phenyl)benzamide,
2,6-difluoro-N-(4-(2-(hydroxymethyl)-2,8-dimethylchroman-7-yl) phenyl)benzamide,
2,6-Difluoro-N-(5-(2-(hydroxymethyl)-2,6dimethylchroman-7-yl)pyrazin-2-yl)benzamide,
N-(2,6-Difluorophenyl)-4-(6-methylspiro[chroman-2,1'-cyclobutan]-7-yl)benzamide,
2,6-Difluroro-N-(4-(1'-methyl-4-oxospiro[chroman-2,4'-piperidin]-6-yl)phenyl)benzamide,
N-(4-(1',6-Dimethyl-4-oxospiro[chroman-2,4'-piperiden]-7-yl)phenyl)-2,6-difluorobenzamide,
2,6-Difluoro-N-(4-(6methyl-4-oxospiro[chroman-2,4'-piperidin]-7-yl)phenyl)benzamide hydrochloride,
2,6-Difluoro-N-(4-(6'-methyl-4'-oxospiro[azetidine-3,2'-chroman]-7'-yl)phenyl)benzamide hydrochloride,
N-(4-(1,6'-Dimethyl-4'-oxospiro[azetidine-3,2'-chroman]-7'-yl)phenyl)-2,6-difluorobenzamide,
2,6-Difluoro-N-(5-(6-methyl-4-oxospiro[chroman-2,3'-oxetan]-7-yl)pyrazin-2-yl)benzamide,
2,6-Difluoro-N-(6-(6-methyl-4-oxospiro[chroman-2,3'-oxetan]-7-yl)pyridin-3-yl)benzamide,
2,6-Difluoro-N-(5-(6-methyl-4-oxospiro[chroman-2,3'-oxetan]-7-yl)pyridin-2-yl)benzamide and
N-(4-(6-Ethyl-4-oxospiro[chroman-2,3'-oxetan]-7-yl)phenyl)-2,6-difluorobenzamide or a pharmaceutically acceptable salt thereof.

8. A pharmaceutical composition comprising one or more compounds of Formula (I) according to claim 1 and one or more pharmaceutically acceptable excipients.

* * * * *